(12) United States Patent
Von Moger et al.

(10) Patent No.: US 11,160,947 B2
(45) Date of Patent: Nov. 2, 2021

(54) NASAL MASK SYSTEM

(71) Applicant: ResMed Pty Ltd, Bella Vista (AU)

(72) Inventors: Lochlan Von Moger, Sydney (AU); Matthew Eves, Sydney (AU); Memduh Guney, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 1567 days.

(21) Appl. No.: 14/402,008

(22) PCT Filed: Apr. 12, 2013

(86) PCT No.: PCT/AU2013/000383
§ 371 (c)(1),
(2) Date: Nov. 18, 2014

(87) PCT Pub. No.: WO2013/170290
PCT Pub. Date: Nov. 21, 2013

(65) Prior Publication Data
US 2015/0151071 A1    Jun. 4, 2015

Related U.S. Application Data

(60) Provisional application No. 61/648,807, filed on May 18, 2012.

(51) Int. Cl.
*A61M 16/08* (2006.01)
*A61M 16/06* (2006.01)
(Continued)

(52) U.S. Cl.
CPC ........ *A61M 16/0816* (2013.01); *A61M 16/06* (2013.01); *A61M 16/0622* (2014.02);
(Continued)

(58) Field of Classification Search
CPC ................ A61M 16/20; A61M 16/208; A61M 16/0611; A61M 16/0616; A61M 16/0633;
(Continued)

(56) References Cited

U.S. PATENT DOCUMENTS

| 3,824,999 A | 7/1974 | King |
| 4,944,310 A | 7/1990 | Sullivan |

(Continued)

FOREIGN PATENT DOCUMENTS

| AU | 2003203836 | 11/2003 | |
| AU | WO 2010139014 A1 * | 12/2010 | ............ A61M 16/06 |

(Continued)

OTHER PUBLICATIONS

Extended European Search Report issued in corresponding European Application No. 13 79 1477.6 dated May 13, 2016.
(Continued)

*Primary Examiner* — Kendra D Carter
*Assistant Examiner* — Elliot S Ruddie
(74) *Attorney, Agent, or Firm* — Nixon & Vanderhye P.C.

(57) ABSTRACT

A swivel elbow and connector assembly for a patient interface system includes a ring (128) configured to be sealingly secured in an aperture of the patient interface system and an elbow (125) swivably secured in the ring (128). The ring (128) includes a first side (128(1)) in an interior of the patient interface system and a second side (128(2)) at an exterior of the patient interface system when the ring (128) is secured in the aperture. The ring (128) comprises a first flange on the first side and a second flange on the second side, the first and second flanges defining a channel (128(3)) that sealingly engages the aperture of the patient interface system. An inner surface (128(4)) of the ring (128) is partially spherical and an outer surface (125(3)) of the elbow (125) is partially spherical and the elbow (125) and the ring (128) form a ball and socket connection.

25 Claims, 99 Drawing Sheets

US 11,160,947 B2

Page 2

(51) Int. Cl.
*A61M 16/20* (2006.01)
*A61M 39/10* (2006.01)
*A61M 16/10* (2006.01)

(52) U.S. Cl.
CPC .... *A61M 16/0666* (2013.01); *A61M 16/0683* (2013.01); *A61M 16/0825* (2014.02); *A61M 16/0875* (2013.01); *A61M 16/208* (2013.01); *A61M 39/1055* (2013.01); *A61M 16/0611* (2014.02); *A61M 16/0616* (2014.02); *A61M 16/0633* (2014.02); *A61M 16/107* (2014.02); *A61M 2205/42* (2013.01); *A61M 2207/00* (2013.01); *A61M 2210/0618* (2013.01)

(58) Field of Classification Search
CPC ............ A61M 16/107; A61M 39/1055; A61M 2016/0027; A61M 2016/003; A61M 2205/3334; A61M 2205/42; A61M 2205/52; A61M 2207/00; A61M 2207/10; A61M 2210/0618; A61M 16/0825; A61M 16/0816; A61M 16/0003; A61M 16/0622; A61M 39/00; A61M 16/0066; A61M 16/06; A61M 16/0683; A61M 16/0875
USPC .................................................... 128/207.13
See application file for complete search history.

(56) References Cited

U.S. PATENT DOCUMENTS

| | | | | |
|---|---|---|---|---|
| 5,284,160 A * | 2/1994 | Dryden | ................. | A61M 16/08 128/203.12 |
| 5,921,239 A | 7/1999 | McCall et al. | | |
| 6,532,959 B1 | 3/2003 | Berthon-Jones | | |
| 6,581,594 B1 | 6/2003 | Drew et al. | | |
| 7,318,437 B2 | 1/2008 | Gunaratnam et al. | | |
| 2003/0196662 A1* | 10/2003 | Ging | ..................... | A61M 16/06 128/204.15 |
| 2005/0150497 A1* | 7/2005 | Eifler | .................... | A61M 16/06 128/206.21 |
| 2006/0076017 A1 | 4/2006 | Walker et al. | | |
| 2007/0277828 A1 | 12/2007 | Ho et al. | | |
| 2008/0110464 A1* | 5/2008 | Davidson | .......... | A61M 16/0622 128/206.26 |
| 2008/0210241 A1 | 9/2008 | Schullz et al. | | |
| 2009/0044808 A1* | 2/2009 | Guney | .............. | A61M 16/0605 128/206.24 |
| 2009/0050156 A1 | 2/2009 | Ng et al. | | |
| 2009/0078259 A1 | 3/2009 | Kooij et al. | | |
| 2010/0000534 A1 | 1/2010 | Kooij et al. | | |
| 2010/0083969 A1* | 4/2010 | Crumblin | .............. | A61M 16/06 128/206.21 |
| 2010/0229866 A1 | 9/2010 | Sullivan | | |
| 2010/0307502 A1 | 12/2010 | Rummery et al. | | |
| 2011/0114096 A1 | 5/2011 | Matula, Jr. et al. | | |
| 2011/0232645 A1 | 9/2011 | Smith | | |
| 2011/0232649 A1 | 9/2011 | Collazo et al. | | |
| 2011/0240031 A1 | 10/2011 | Jaffre et al. | | |

FOREIGN PATENT DOCUMENTS

| | | | |
|---|---|---|---|
| CN | 101485914 A | 7/2009 | |
| CN | 101653636 A | 2/2010 | |
| CN | 102458548 A | 5/2012 | |
| DE | 297 23 101 U1 | 5/1998 | |
| EP | 1 334 742 A2 | 8/2003 | |
| EP | 2 022 528 A2 | 2/2009 | |
| JP | 2009-527260 A | 7/2009 | |
| JP | 2012-528608 A | 11/2012 | |
| JP | 2015-516241 A | 6/2015 | |
| WO | WO 1998/04310 | 2/1998 | |
| WO | WO 1998/34665 | 8/1998 | |
| WO | WO 2000/78381 | 12/2000 | |
| WO | WO 2004/096332 | 11/2004 | |
| WO | 2005/079726 | 9/2005 | |
| WO | WO 2006/074513 | 7/2006 | |
| WO | WO 2007/104045 | 9/2007 | |
| WO | WO 2009/052560 | 4/2009 | |
| WO | WO 2010/135785 | 12/2010 | |
| WO | WO 2010/139014 | 12/2010 | |
| WO | 2011/059346 | 5/2011 | |
| WO | 2011/060479 A1 | 5/2011 | |
| WO | WO-2012122601 A1 * | 9/2012 ........ A61M 16/0683 | |
| WO | WO 2013/006899 | 1/2013 | |
| WO | WO 2013/071359 | 5/2013 | |
| WO | 2013/170290 A1 | 11/2013 | |

OTHER PUBLICATIONS

Patent Examination Report No. 1 issued in corresponding Australian Patent Application No. 2013262459 dated Jun. 28, 2016.
Notification of the Second Office Action dated Oct. 18, 2016 issued in Chinese Application No. 201380038166.6 with English translation (20 pages).
First Examination Report dated Nov. 24, 2016 issued in New Zealand Application No. 720554 (2 pages).
Further Examination Report dated Jan. 12, 2017 issued in New Zealand Application No. 630695 (2 pages).
Office Action dated Jan. 30, 2017 issued in Japanese Application No. 2015-511862 with English translation (7 pages).
Office Action dated Apr. 27, 2017 issued in Chinese Application No. 201380038166.6 with English translation (17 pages).
Communication dated Oct. 5, 2017 issued in European Application No. 13791477.6 (4 pages).
Decision of Rejection dated Sep. 25, 2017 issued in Japanese Application No. 2015-511862 with English translation (8 pages).
Communication Granting Extension of Time dated Oct. 30, 2017 issued in New Zealand Application No. 630695 (1 page).
Notice of Opposition to Grant of Patent (Section 21), dated Oct. 27, 2017, filed by Fisher & Paykel Healthcare Limited in New Zealand Application No. 630695 (2 pages).
Decision of Rejection dated Oct. 23, 2017 issued in Chinese Application No. 201380038166.6 with English translation (20 pages).
Deadline for Counterstatement dated Jan. 15, 2018 issued in New Zealand Application No. 630695 (2 pages).
Amended Notice of Opposition to Grant of Patent (Section 21), with no markups, dated Dec. 22, 2017 filed by Fisher & Paykel Healthcare Limited in New Zealand Application No. 630695 (2 pages).
Amended Notice of Opposition to Grant of Patent (Section 21), with markups, dated Dec. 22, 2017 filed by Fisher & Paykel Healthcare Limited in New Zealand Application No. 630695 (2 pages).
Statement of Case dated Dec. 22, 2017 filed by Fisher & Paykel Healthcare Limited in New Zealand Application No. 630695 (29 pages).
Pre-Appeal Examination Report dated Feb. 16, 2018 issued in Japanese Application No. 2015-511862 with English translation (18 pages).
Office Action dated Apr. 2, 2018 issued in Japanese Application No. 2017-88002 with English translation (15 pages).
Office Action dated Jun. 6, 2018 issued in European Application No. 13791477.6 (5 pages).
Office Action dated Jul. 23, 2018 issued in Japanese Application No. 2017-088002 with English translation (10 pages).
International Search Report issued in PCT Appln. No. PCT/AU2013/000383, dated Jun. 11, 2013.
Written Opinion of the International Preliminary Examining Authority issued in PCT Appln. No. PCT/AU2013/000383, dated Dec. 18, 2013.
Written Opinion of the International Preliminary Examining Authority issued in PCT/AU2013/000383, dated Mar. 11, 2014.
Notification of Transmittal of International Preliminary Report on Patentability issued in PCT/AU2013/000383, dated Sep. 1, 2014.
U.S. Appl. No. 61/443,623 filed Feb. 16, 2011.
Two (2) Photos of Aloha Nasal Pillow System (released in Mar. 2012).
Three (3) Photos of Weinmann SomnoPlus Mask (released in 1999).

(56) References Cited

OTHER PUBLICATIONS

First Office Action issued in corresponding Chinese Application No. 201380038166.6 dated Feb. 1, 2016 with English translation thereof.
First Examination Report issued in corresponding New Zealand Application No. 630695 dated Sep. 10, 2015.
Examination Decision on Request for Reexamination dated Feb. 26, 2019 in Chinese Application No. 201380038166.6, with English Translation (34 pages).
Notice of Reasons for Rejection dated Apr. 22, 2019 in Japanese Application No. 2015-511862, with English translation, 6 pages.
Notice of Reasons for Rejection dated Nov. 24, 2020 in Japanese Application No. 2019-050919, with English translation, 7 pages.
Extended European Search Report dated Mar. 5, 2021 in European Application No. 20197536.4, 10 pages.

* cited by examiner

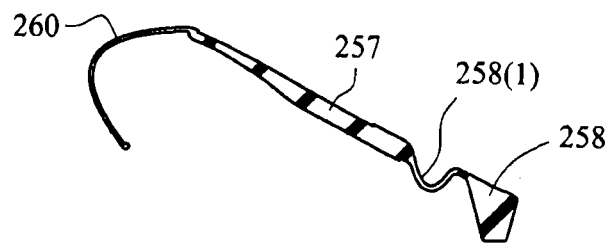
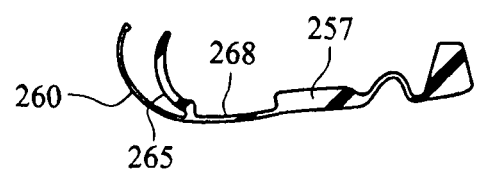
FIG. 3-23
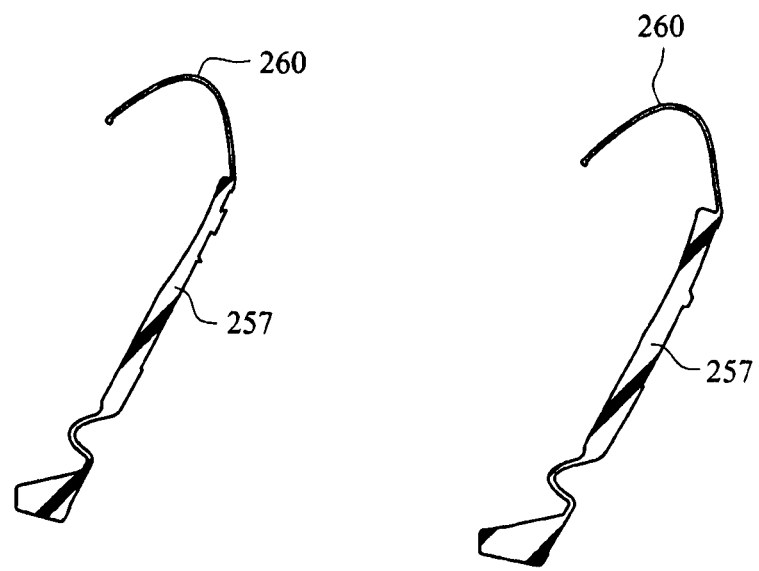
FIG. 3-24     FIG. 3-25

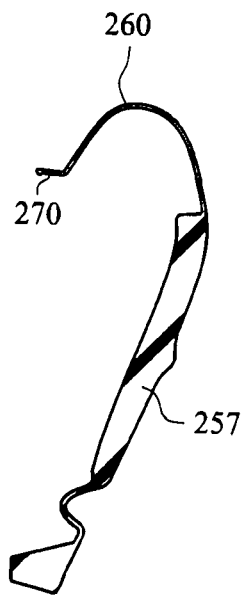
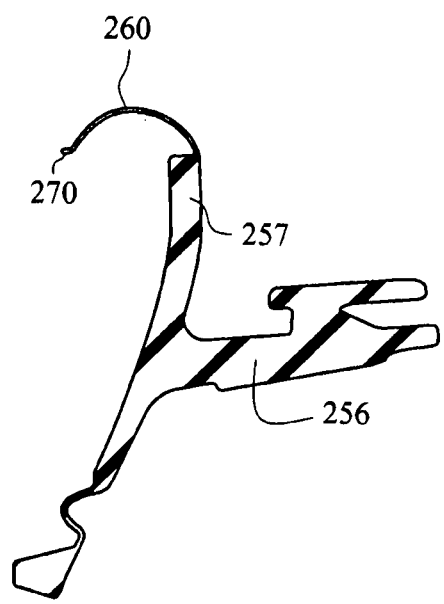
FIG. 3-26  FIG. 3-27
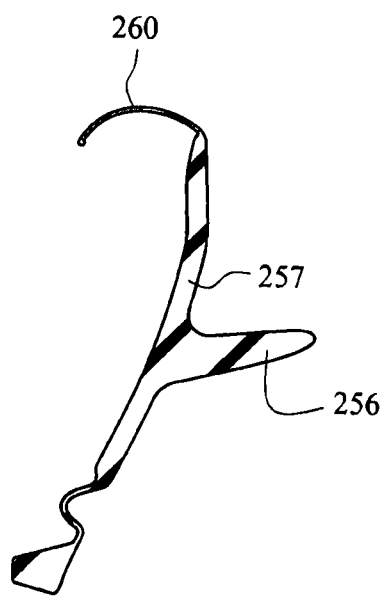
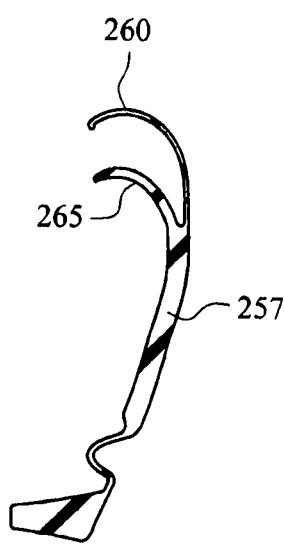
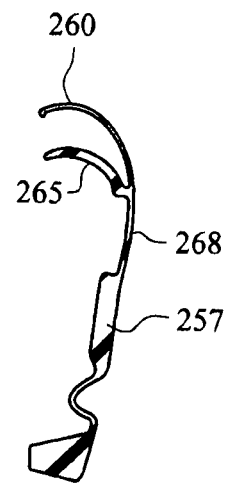
FIG. 3-28  FIG. 3-29  FIG. 3-30

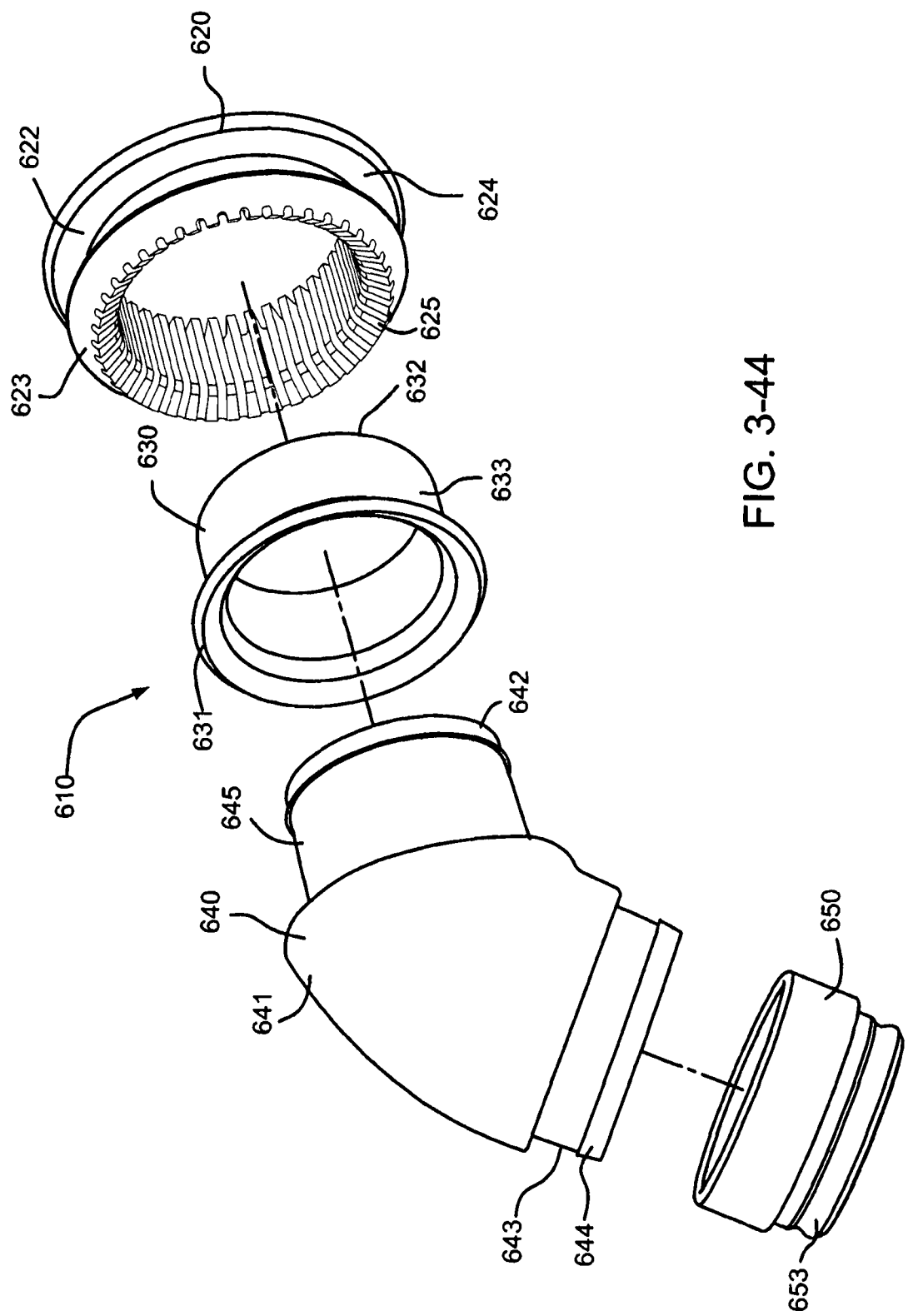

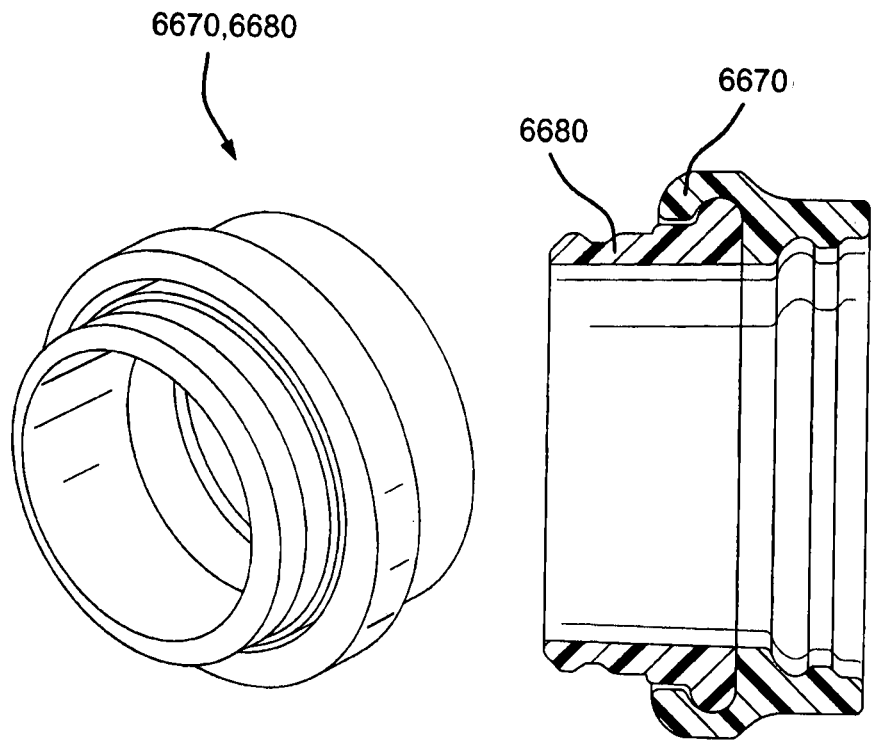
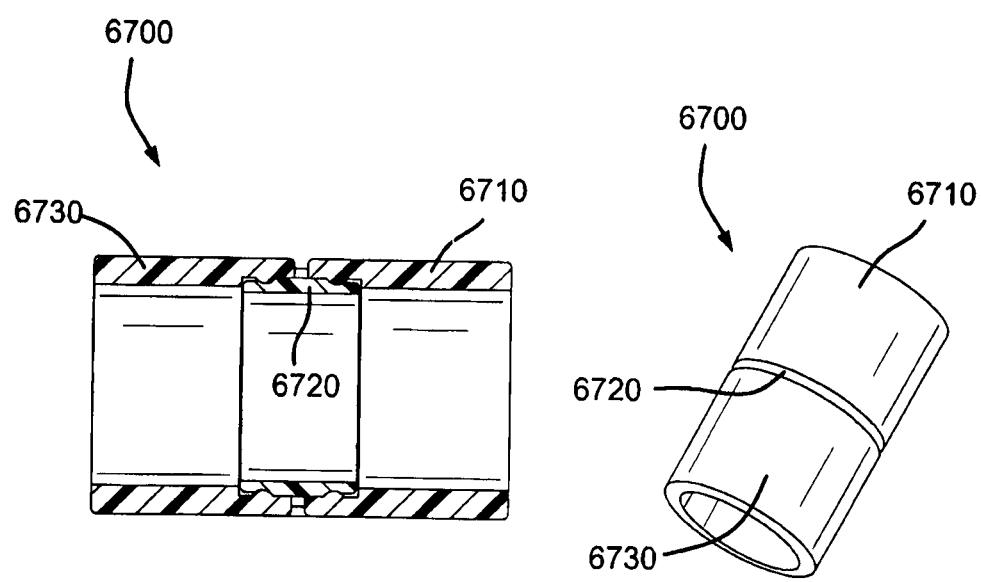

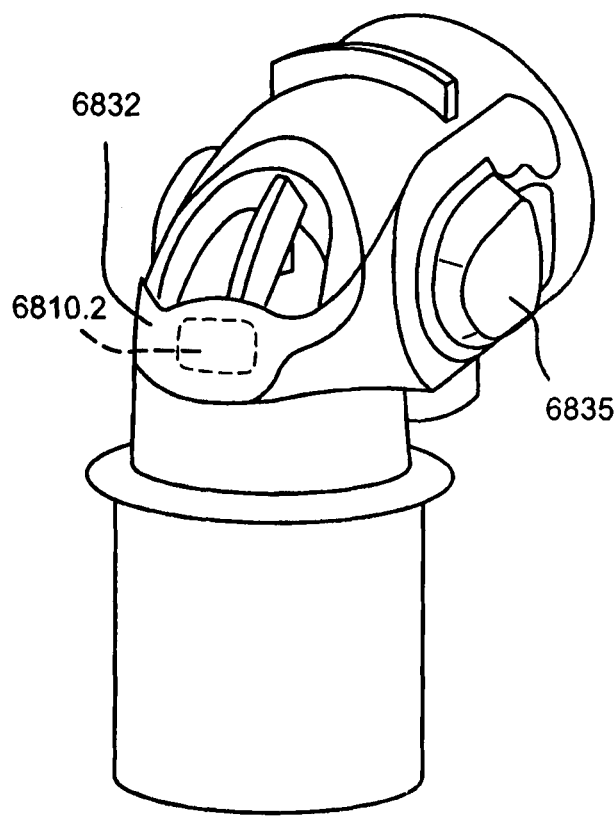
FIG. 3-110A
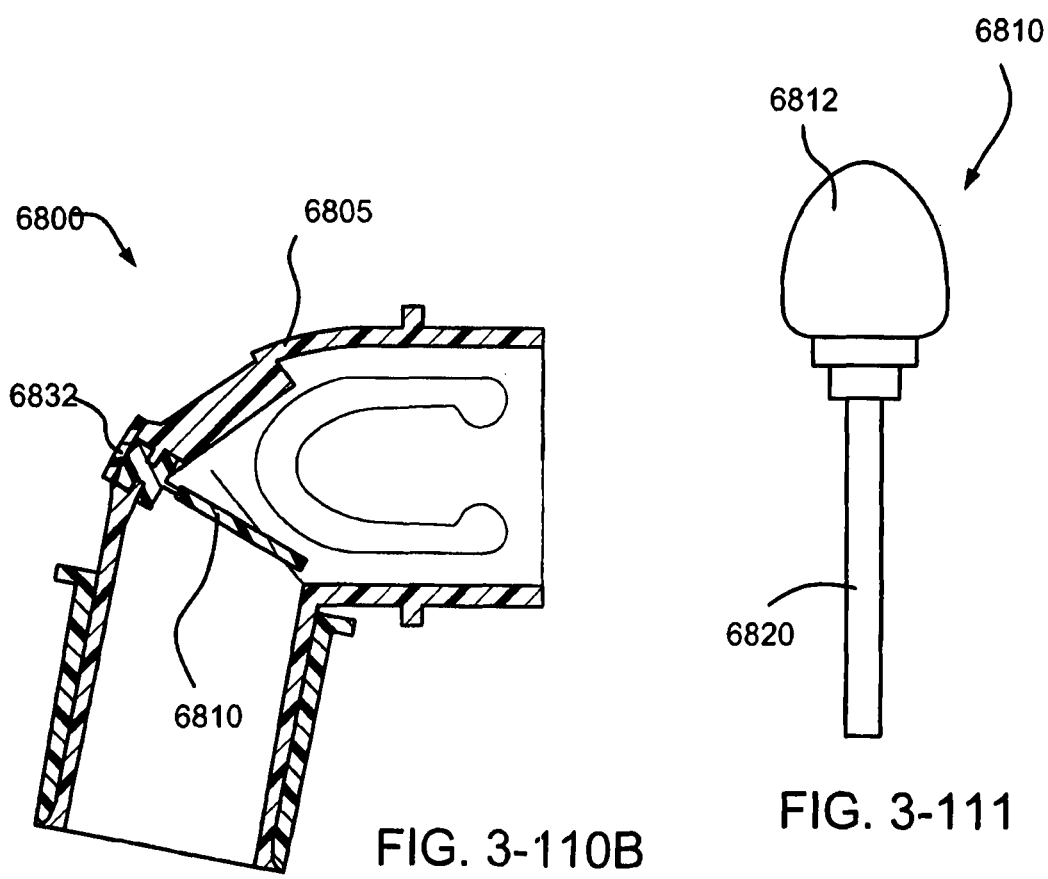
FIG. 3-110B
FIG. 3-111

NASAL MASK SYSTEM

1 CROSS-REFERENCE TO RELATED APPLICATIONS

This application is the U.S. national phase of International Application No. PCT/AU2013/000383 filed Apr. 12, 2013, which designated the U.S. and claims the benefit of U.S. Provisional Application No. 61/648,807, filed May 18, 2012, the contents of each of which is incorporated herein by reference in its entirety.

BACKGROUND OF TECHNOLOGY

2.1 (1) Field of Technology

The present technology relates to treatment of respiratory disorders, and to procedures to prevent respiratory disorders. In particular, the present technology relates to medical devices, and their use for treating respiratory disorders and for preventing respiratory disorders. More particularly, the present technology relates to a nasal mask system used for treatment, e.g., of Sleep Disordered Breathing (SDB) with Continuous Positive Airway Pressure (CPAP) or Non-Invasive Positive Pressure Ventilation (NIPPV).

The present technology also relates to apparatus to deliver breathable gas to a patient including a positive airway pressure (PAP) device, an air delivery conduit or tube, and a patient interface. The patient interface contacts the patient's face in use to deliver pressurized breathable gas to the patient from the PAP device.

2.2 (2) Description of the Related Art

The respiratory system of the body facilitates gas exchange. The nose and mouth form the entrance to the airways of a patient.

The airways consist of a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnoea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnoea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnoea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnoea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

2.2.1 Systems

One known product used for treating sleep disordered breathing is the S9 Sleep Therapy System, manufactured by ResMed.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, NMD and Chest Wall disorders.

2.2.3 Patient Interface

The application of a supply of air at positive pressure to the entrance of the airways of a patient, e.g., while a patient sleeps, is facilitated by the use of a patient interface, such as a nasal mask, full-face mask or nasal pillows.

Known patient interface devices suffer from being one or more of obtrusive, aesthetically undesirable, poorly fitting, difficult to use and uncomfortable, especially when worn for long periods of time or when a patient is unfamiliar with a system.

2.2.3.1 Seal-Forming Portion

Patient interfaces typically include a seal-forming portion.

A range of patient interface seal-forming portion technologies are disclosed in the following patent applications, assigned to ResMed Limited: WO 1998/004,310; WO 2006/074,513; WO 2010/135,785.

2.2.3.2 Positioning and Stabilising

A seal-forming portion, of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses.

2.2.3.3 Vent Technologies

Some forms of patient interface systems may include a vent to allow the washout of exhaled carbon dioxide.

ResMed Limited has developed a number of mask vent technologies. See WO 1998/034,665; WO 2000/078,381; U.S. Pat. No. 6,581,594; US Patent Application; US 2009/0050156; US Patent Application 2009/0044808.

3 BRIEF SUMMARY OF TECHNOLOGY

An aspect of the present technology relates to an elbow and a connector assembly adapted to receive gases from a flow generator and deliver the gases to a patient interface.

An aspect of the present technology relates to an elbow and a connector adapted to vent gases from a patient interface.

As aspect of the present technology is to have multiple functions in one part or component and/or manufactured together, e.g., quick release button(s)/member(s)/actuator(s), baffle and swivel all formed together, so patient is not required to disassemble; this may increase potential for reduced overall part costs.

An aspect of the present technology relates to a multi-axis elbow assembly that allows movement of a connected tube in two separate planes while substantially isolating drag forces from the tube.

Another aspect of the present technology relates to a method for manufacturing an elbow for a patient interface assembly, comprising providing a skeleton, e.g., of rigid or semi-rigid material and adapted to communicate air flow under pressure between an air delivery conduit and a mask; separately molding an anti-asphyxia valve (AAV) with a pull tab; and assembling the skeleton and the AAV by pulling the pull tab from inside the skeleton and through an opening in the skeleton to position, retain and/or seal the AAV relative to the skeleton. The method may include removing at least a portion of the pull tab once pulled through such that an outer flange of the AAV sits flush with an exterior elbow surface. The method may further comprise providing a flexible component to secure the AAV in position. The flexible component may form one or more release buttons or actuators on the elbow.

Another aspect of the present technology relates to an elbow for a patient interface assembly, comprising a skeleton or frame, e.g., of rigid or semi-rigid material, and adapted to communicate air flow under pressure between an air delivery conduit and a mask; an anti-asphyxia valve (AAV) with a pull tab, whereby to assembly the AAV to the skeleton, the pull tab is inserted or guided inside the skeleton and pulled through an opening in the skeleton to position, retain and/or seal the AAV relative to the skeleton. At least a portion of an outer flange of the AAV, once the pull tab is pulled through, sits flush with an exterior elbow surface. The elbow may include a flexible component to secure the AAV in position and/or to form one or more release buttons or actuators on the elbow, the release buttons adapted to remove the elbow from a frame.

Another aspect of the technology relates to a swivel elbow and connector assembly for a patient interface for delivering pressurized breathable gas to a patient from a PAP device. According to one aspect, the swivel elbow and connector assembly is connected to a flexible patient interface structure, e.g. a cushion, through an aperture in the patient interface structure. According to another aspect, the swivel elbow and connector assembly includes a connector, for example a ring, which is attachable to and detachable from the patient interface structure at the aperture. The connector includes a plurality of slots for venting gases from the interior of the patient interface structure to the exterior of the patient interface structure.

Yet another aspect of the technology relates to a swivel elbow connected to the connector and slots to permit venting of gases between the ring and the swivel elbow. According to another aspect, the swivel elbow is connected to the connector and the slots permit venting of gases between the connector and the patient interface structure, e.g. cushion, and no venting occurs between the connector and the swivel elbow.

A further aspect of the technology relates to a swivel elbow and anti-asphyxia valve assembly having a diffuse vent. A still further aspect of the technology relates to a swivel elbow and anti-asphyxia valve assembly having a diffuse vent that may be molded in one piece. An even further aspect of the technology relates to a swivel elbow and anti-asphyxia valve assembly having a diffuse vent that may have engagement portions that, when pressed, permit engagement and disengagement of the swivel elbow and anti-asphyxia valve assembly from a patient interface, e.g. a mask.

According to an example of the technology, a swivel elbow and connector assembly for a patient interface system comprises a ring configured to be sealingly secured in an aperture of the patient interface system, the ring including a first side in an interior of the patient interface system and a second side at an exterior of the patient interface system when the ring is secured in the aperture, the ring comprising a plurality of vents configured to permit flow of gases from the interior to the exterior of the patient interface system; and an elbow swivelably secured in the ring. The ring comprises a first flange on the first side and a second flange on the second side, the first and second flanges defining a channel that sealingly engages the aperture of the patient interface system and the second flange comprises an angled surface that directs the flow of gases from the plurality of vents at an angle to the longitudinal axis of the ring.

According to another example of the technology, a patient interface system for delivering a flow of breathable gas to a user comprises a patient interface structure configured to sealingly engage the face of the user, the patient interface structure comprising an aperture; and a swivel elbow and connector assembly as disclosed herein.

According to another example of the technology, an elbow for delivering gases to a patient interface comprises a first connecting portion, a second connecting portion and a venting portion. The first connecting portion is adapted to receive a tube connection, the second connecting portion is adapted to receive a patient interface assembly, and the venting portion is proximal to the second connecting portion. The venting portion may be diffused about the perimeter of the second connecting portion. The elbow may further comprise a baffle to separate the venting portion from an incoming air stream from the first connecting portion.

According to still another example of the technology, a swivel elbow and anti-asphyxia valve assembly for a patient interface assembly comprises a first component including a first connection portion configured to be sealingly secured in an aperture of the patient interface system, a second connection portion configured to be connected to a swivel or a delivery conduit, one or more first supports between the first connection portion and the second connection portion, and a first aperture and a second aperture are provided between the one or more first supports; and a second component including a valve member, engagement members, and a flexible member, the valve member being between the one or more first supports of the first component and movable between a first position in which the valve member occludes the first aperture and a second position in which the valve member does not occlude the first aperture, the engagement members being configured to engage the one or more first supports when pressed by a user of the patient interface system, and the flexible member being connected to the engagement members and sealing the second aperture.

Another aspect of the present technology is directed towards providing medical devices used in the diagnosis, treatment or prevention of respiratory disorders having one or more of improved comfort, cost, efficacy, ease of use and manufacturability.

Another aspect of the present technology relates to apparatus used in diagnosis, treatment or prevention of a respiratory disorder.

Another aspect of the present technology relates to methods used in diagnosis, treatment or prevention of a respiratory disorder.

One aspect of the present technology is a patient interface that is one or more of comfortable, effective, simple to use, unobtrusive and with a wide fit range.

An aspect of one form of the present technology is a patient interface that avoids a jetting effect of nasal pillows or prongs, and/or a feeling of discomfort from locating a portion of a mask within a nasal cavity of a patient.

An aspect of one form of the present technology is a nasal mask that is easy to put on, and may avoid a need for headgear straps to interfere with, or cross the ears in use, and may avoid interfering or crossing the ears while putting on or removing.

Another aspect of one form of the present technology is a method of putting on or removing a mask.

In one form of the present technology, a small, unobtrusive nasal mask is provided.

In one form of the present technology, a nasal mask is provided that does not form a seal on a lower lip, or a chin of a patient.

In one form of the present technology, a patient interface is provided that does not exert a rearward force on the mandible, e.g. the patient interface does not push on the mandible from the anterior towards the posterior.

In one form of the present technology, a patient interface is provided that does not comprise a rigid shell or rigid frame.

In one form of the present technology, a patient interface is provided that comprises a plenum chamber constructed from a flexible or semi-rigid material, for example a flexible rubber of a suitable thickness (e.g. silicone with a type A hardness in the range of about 35 to about 45, and about 1.5 mm to about 3 mm thick).

In one form of the technology, a nasal mask is provided that does not require engagement or disengagement of a clip to don or remove the mask.

An aspect of one form of the present technology is a patient interface comprising a seal-forming portion having a first sealing region that is constructed to have little nor no resistance to compression, and a second sealing region that is constructed to substantially resist a compressive force (e.g. as a result of headgear tension). In an example in use, the first sealing region is arranged to overlay a portion of the cartilaginous framework of the nose, and the second sealing region is arranged to overlay a portion of a bone region the face. In an example, the bone region of the face is a region adjacent the ala, and optionally adjacent to the alar crest point.

According to one form of the present technology, a patient interface is provided that comprises: (i) a seal-forming portion that in use overlays at least part of a top lip region of a patient's face, and a portion of the cartilaginous framework of the nose; and (ii) a seal positioning and stabilising structure that may be donned and removed without interfering with the ears of the patient.

Another aspect of one form of the present technology is a patient interface having a seal-forming portion associated with a two point connection with a seal positioning and stabilising structure. In an example, the patient interface does not comprise a forehead support. In an additional or alternative example, the seal positioning and stabilising structure comprises a non-rigid or flexing connection element.

Another aspect of one form of the present technology is a patient interface that is moulded or otherwise constructed with a clearly defined perimeter shape which is intended to match that of an intended wearer in use.

Another aspect of one form of the present technology is a patient interface that is constructed and arranged so that while forming a seal on at least part of the cartilaginous framework of the nose, it avoids or reduces a tendency to restrict nasal air flow therethrough.

According to one form of the present technology, a patient interface is provided that comprises a first superior sealing portion that in use overlays a portion of the cartilaginous framework of the nose, and a second inferior sealing portion that in use overlays a portion of the upper lip and wherein in use, a relatively larger portion of a headgear sealing force is directed towards the portion of the upper lip and the underlying maxilla, teeth or gum than is directed towards the cartilaginous framework of the nose.

Another aspect of one form of the present technology is a patient interface that is constructed and arranged to avoid or reduce a tendency to put unnecessary pressure on the nasal septum.

According to one form of the present technology, a patient interface is provided that in use forms a seal on a portion of an upper lip of a patient, and which comprises a plenum chamber having a wall and wherein a first portion of the wall that is constructed to be located adjacent the septum in use has a relatively less stiff spring constant that portions of the wall that are adjacent to said first portion.

Another aspect of one form of the present technology is a patient interface that while forming a seal on a portion of the cartilaginous framework of the nose, provides an effective or improved seal on the region of the nose near a junction between the greater alar cartilage and the lateral cartilage.

According to one form of the present technology, a patient interface is provided that comprises a sealing flange that defines a generally T-shaped, or three lobed orifice. In an example, the sealing flange includes a membrane and a sealing flap that protrudes from the edge of the membrane along its inner perimeter in each side of nose region. The edge of the membrane along its inner perimeter along with the edge of each sealing flap along its inner perimeter cooperate to define an orifice into the plenum chamber. In an example, such orifice includes a general T-shape, or three lobed orifice, including an upper orifice portion (along vertical axis v as viewed in FIG. 3-20) and a lower orifice portion (along horizontal axis h as viewed in FIG. 3-20) that extends generally transverse to the upper orifice portion.

According to one form of the present technology, an inner edge of a sealing flange is spring biased towards the face of a wearer in use, e.g. with respect to a middle portion of the sealing flange.

Another aspect of one form of the present technology is a nasal mask that is constructed and arrange to pivot or rotate about a top lip region upon adjustment of a headgear tension.

Another aspect of one form of the present technology is a method of manufacturing a patient interface.

Another aspect of one form of the present technology is a device for preventing, treating or ameliorating one or more of OSA, CSA, OHS, COPD, NMD and chest-wall disorders.

Another aspect of the present technology is a mask system that can accommodate a wide range of different facial shapes including faces with high and low nose bridge regions, and narrow and wide noses. Another aspect of the present technology is a mask system with a wide fit range.

Another aspect of one form of the present technology is a mask system that is small and unobtrusive, and yet is stable on the face while a patient is sleeping.

One aspect of the present technology is a mask that is constructed and arranged to seal at its upper extent on a region of the nose that is generally above or superior to the pronasale, or tip of the nose.

One aspect of one form of the present technology is a mask that is constructed and arranged to seal at its upper extent at locations that are generally below or inferior to the nasal bones.

In one form of the present technology, a mask is provided that is constructed and arranged to have a seal forming portion that overlays a portion of the upper or superior lip, and that overlays a portion of the cartilaginous framework of the nose, e.g., without overlaying the nasal bones.

In one form of the present technology a mask is provided that is constructed and arranged to have a first seal forming portion that overlays a portion of the upper or superior lip, and a second seal-forming portion that overlays of the cartilaginous framework of the nose, e.g., without overlaying the nasal bones.

In one form of the present technology a mask is provided that is constructed and arranged to have a first seal forming portion that is substantially in compression, or subject to bending forces in use, and a second seal-forming portion that is substantially in tension in use.

In one form of the present technology a mask is provided that is constructed and arranged to have a first seal forming portion that is relatively stiff before use, and a second seal-forming portion that is relatively floppy before use.

Another aspect of one form of the present technology is a mask system with an improved sealing cuff. In an example, the mask system includes a facial flap comprising a relatively thin member formed of a flexible, e.g., and at least semi-resilient, material. In an example, the mask system further comprises, in at least some regions, a back-up band.

Another aspect of the present technology is a mask that is formed, moulded or otherwise constructed with a clearly defined perimeter shape which is intended to match that of an intended wearer.

A further aspect of the present technology is a cushion for a mask that seals at its upper extent in a region of the nose that is generally superior to or above the pronasale or tip of the nose, and extends across the alar or flares of the patient's nose.

A further aspect of the present technology is a cushion for a mask that seals at its upper extent in a region of the nose that is generally superior to or above the pronasale or tip of the nose, and extends across the alar or flares of the patient's nose, e.g., not extending over or across the nasal bones of the patient's nose.

One aspect of one form of the present technology is a cushion for a mask that seals at its upper extent in a region of the nose that is generally close to the junction between bone and cartilage on a range of people with larger noses, and which avoids impinging on the sight of people with smaller noses.

In one form of the present technology, a mask system is provided that does not require a rigid frame or skeleton, and which seals at its upper extent in a region of the nose that is generally above or superior to the pronasale, or tip of the nose.

One aspect of the present technology is a cushion for a mask that includes a sealing membrane and a backup band or undercushion, in at least some regions.

Another aspect of the present technology is a cushion for a nasal mask that includes an undercushion or backup band in the region of the top lip.

Another aspect of one form of the present technology is a cushion for a nasal mask that includes an undercushion or backup band in the region of the top lip, and no undercushion or backup band in the sides of the nose or ridge of the nose regions to avoid relatively high sealing forces on the sides of the nose or ridge of the nose regions as these relatively high sealing forces may cause occlusion of the nasal airway.

Another aspect of the present technology includes a cushion for a nasal mask, the cushion having a sealing region, a side wall region and an attachment region, wherein the sealing region is adapted to form a seal with a patient, the side wall region connects the sealing region and attachment region, and the attachment region is adapted to connect or otherwise attach to an air delivery system.

Another aspect of the present technology includes a cushion for a nasal mask, the cushion having a sealing region and an attachment region, wherein the attachment region comprises a decoupling element.

Another aspect of the present technology includes a cushion for a nasal mask, the cushion having a sealing region and an attachment region, wherein the attachment region comprises a decoupling element, the decoupling element comprising a relatively thinner wall section. For example, the relatively thinner wall section may be 50-85% thinner.

Another aspect of the present technology includes a cushion for a nasal mask, the cushion comprising headgear connectors integrally formed with a side wall, e.g., wherein the side wall is constructed of a flexible elastomer or rubber.

Another aspect of the present technology includes a cushion for a nasal mask, the cushion comprising headgear connectors, the headgear connectors constructed and arranged to position a portion of a sealing region superior to or above the pronasale or tip of the patient's nose.

Another aspect of the present technology includes a cushion for a nasal mask, the cushion having a nose ridge region, the nose ridge region having a dip or curvature, e.g. a local saddle region, adapted to conform to, or be complementary to the nose ridge of the patient.

A further aspect of the present technology includes a cushion for a nasal mask, the cushion having a nose ridge region, the nose ridge region having a relatively longer membrane length when compared to other regions of the cushion, the relatively longer membrane length adapted to engage a greater fit range of patient's nose ridge heights.

Another aspect of the present technology includes a cushion for a nasal mask, the cushion having a sides of the nose region, the sides of the nose region having a raised portion, the raised portion having a greater height when compared to the nose ridge region, the raised portion adapted to engage with the sides of the patient's nose and ensure engagement with tall nose ridges as well as flat nose ridges.

Another aspect of the present technology includes a cushion for a nasal mask, the cushion having a corners of the nose region, generally corresponding to the region of the face between and including the subalare and the alar crest, the corners of the nose region having the greatest height when compared to all other regions of the cushion, wherein the corners of the nose region anchors the cushion in position. The height of the corners of the nose region may be arranged to ensure seal in the corners of the nose, as this is a particularly difficult area of the face to seal on.

Another aspect of the present technology includes a cushion for a nasal mask, the cushion having a top lip region, the top lip region configured to conform to the curvature of a patient's top lip region. The top lip region may be generally rounded, extending from a trough or dip and continuing up to the sides of the nose region. The membrane at the top lip region may stretch across a patient's top lip to ensure a seal with the patient's top lip.

Another aspect of the present technology relates to a nasal mask system including a cushion assembly including a sealing region that provides a single orifice adapted to surround both nares of the patient's nose and a headgear assembly including a pair of side straps and a rear strap. The side straps are adapted to extend along sides of the patient's face between the patient's eyes and ears and engage respective headgear connectors provided to the cushion assembly to provide a two-point connection with the cushion assembly. The rear strap extends between the side straps and is adapted to engage along the back or posterior of the patient's head along, below or inferior to the occipital bone.

Another aspect of the present technology relates to a nasal mask system including a cushion assembly including a sealing region having a nose ridge region, sides of nose region, corners of nose region, and a top lip region adapted to seal around both nares of the patient's nose. The nose ridge region is adapted to be positioned and seal along a nasal cartilage region which is above or superior to the pronasale and below or inferior to a nasal bone region of the patient's nasal bridge. In one form, the sealing region includes a membrane seal that extends around an entire perimeter of the sealing region and an undercushion that is only provided in the top lip and corners of nose regions.

Another aspect of the present technology relates to a nasal mask system including a cushion assembly including a sealing region adapted to seal around both nares of the patient's nose, an attachment region adapted to receive an elbow assembly, and a side wall region extending between the sealing region and the attachment region. The sealing region has a nose ridge region, sides of nose region, corners of nose region, and a top lip region. The side wall region includes an area adjacent the top lip region of the sealing region that includes a thickness that is less than corresponding thicknesses adjacent the nose ridge, sides of nose, and corners of nose regions of the sealing region.

Another aspect of the present technology relates to a nasal mask system including a cushion assembly including a sealing region having a nose ridge region, sides of nose region, corners of nose region, and a top lip region adapted to seal around both nares of the patient's nose. The sides of nose region includes a portion adapted to be positioned and seal along a region adjacent the junction between the nasal greater alar cartilage and the lateral nasal cartilage of the patient's nose.

Another aspect of the present technology relates to a patient interface for applying a supply of air at positive pressure to the entrance of a patient's airways. The patient interface includes a nasal mask and a positioning and stabilising structure. The nasal mask has a seal forming portion constructed and arranged to form a seal on a portion of an upper lip of a patient, and to form a seal on a portion of a cartilaginous framework of the patient's nose. The nasal mask further has a plenum chamber that receives in use a portion of the patient's nose including the pronasale. The positioning and stabilising structure includes a pair of side straps that provide a two-point connection to the nasal mask and being constructed and arranged to be donned or removed without the side straps passing inferior to the patient's ears.

Another aspect of the present technology relates to a method for fitting a patient interface to a patient. The method includes positioning a sealing region of the patient interface with respect the patient's nose such that the sealing region surrounds both nares and engaging headgear straps of the patient interface with the patient's head without passing straps inferior to the patient's ears.

Another aspect of the present technology relates to a nasal mask for delivery of a supply of air to the entrance of a patient's airways. The nasal mask includes a superior sealing portion and an inferior sealing portion. The superior sealing portion is constructed and arranged to be located on a portion of the cartilaginous framework of the nose, and to form a seal therewith without exerting a sealing force that would restrict a flow of air through the nasal cavity. The inferior sealing portion is constructed and arranged to be located in part on a portion of an upper lip of a patient and to direct a sealing force to a portion of a maxilla bone of the patient.

Another aspect of the present technology relates to a nasal mask defining a breathing chamber for delivery of a supply of gas at positive pressure to the airways of a patient. The nasal mask includes a vent ad a cushion. The vent is adapted to exhaust breathable gas and is adapted to be sufficiently rigid to avoid collapse. The cushion includes a sealing cuff and headgear connectors. The sealing cuff comprises a membrane seal and an undercushion. The membrane seal extends about a perimeter of the cushion including a nose ridge region of the cushion and a side of the nose region of the cushion, and the undercushion is located in a top lip region of the cushion and does not extend to the nose ridge region of the cushion or the side of the nose region of the cushion. The headgear connectors are formed with a side wall of the cushion.

Another aspect of the present technology relates to a patient interface for applying a supply of air at positive pressure to the entrance of a patient's airways. The patient interface includes a nasal mask and a positioning and stabilising structure. The nasal mask has a seal forming portion constructed and arranged to form a seal on a portion of an upper lip of a patient, and to form a seal on a portion of a cartilaginous framework of the patient's nose. The nasal mask further has a plenum chamber that receives in use a portion of the patient's nose including the pronasale. The positioning and stabilising structure provides a sealing vector oriented at an angle with respect to a Frankfort horizontal direction. The positioning and stabilising structure includes a two-point connection to the nasal mask.

Another aspect of the present technology relates to a patient interface for applying a supply of air at positive pressure to the entrance of a patient's airways. The patient interface includes a nasal mask and a positioning and stabilising structure. The nasal mask has a seal forming portion constructed and arranged to form a seal on a portion of an upper lip of a patient, and to form a seal on a portion of a cartilaginous framework of the patient's nose. The nasal mask further has a plenum chamber that receives in use a portion of the patient's nose including the pronasale. The positioning and stabilising structure provides a sealing vector oriented at an angle with respect to a Frankfort horizontal direction. The nasal mask does not include a forehead support.

Another aspect of the present technology relates to a patient interface for applying a supply of air at positive pressure to the entrance of a patient's airways. The patient interface includes a nasal mask and a positioning and stabilising structure. The nasal mask has a seal forming portion constructed and arranged to form a seal on a portion of an upper lip of a patient, and to form a seal on a portion of a cartilaginous framework of the patient's nose. The nasal mask further has a plenum chamber that receives in use a portion of the patient's nose including the pronasale. The positioning and stabilising structure provides a sealing vector oriented at an angle with respect to a Frankfort horizontal direction. The positioning and stabilising structure includes a pair of side straps adapted to extend towards and over a crown of the patient's head.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000. The PAP device 4000, humidifier 5000 and air circuit 4170 may be connected to a patient interface 3000 in accordance with the present technology.

4.2 Therapy

4.2.1 Respiratory System

4.2.2 Facial Anatomy

Figure 1A:
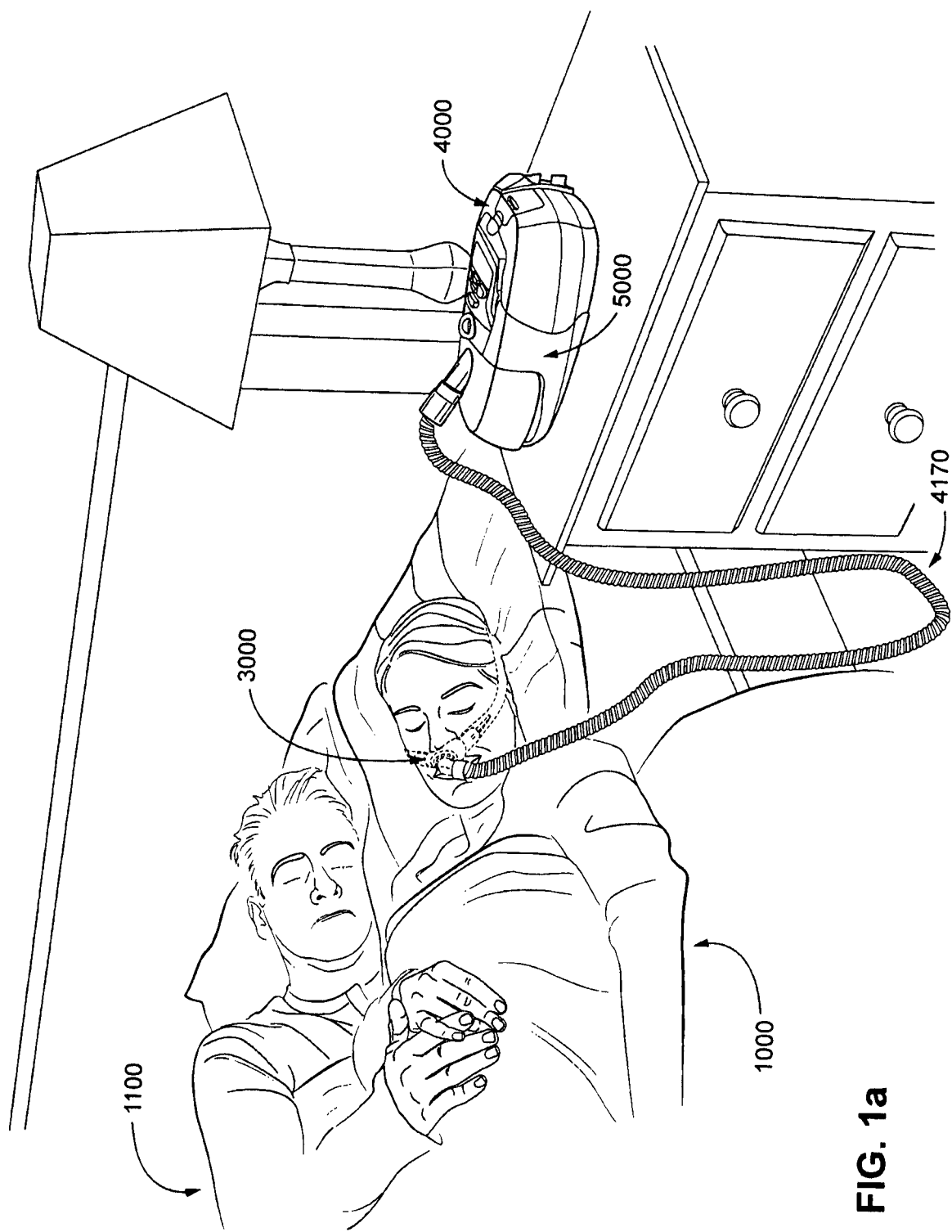
Figure 2A:
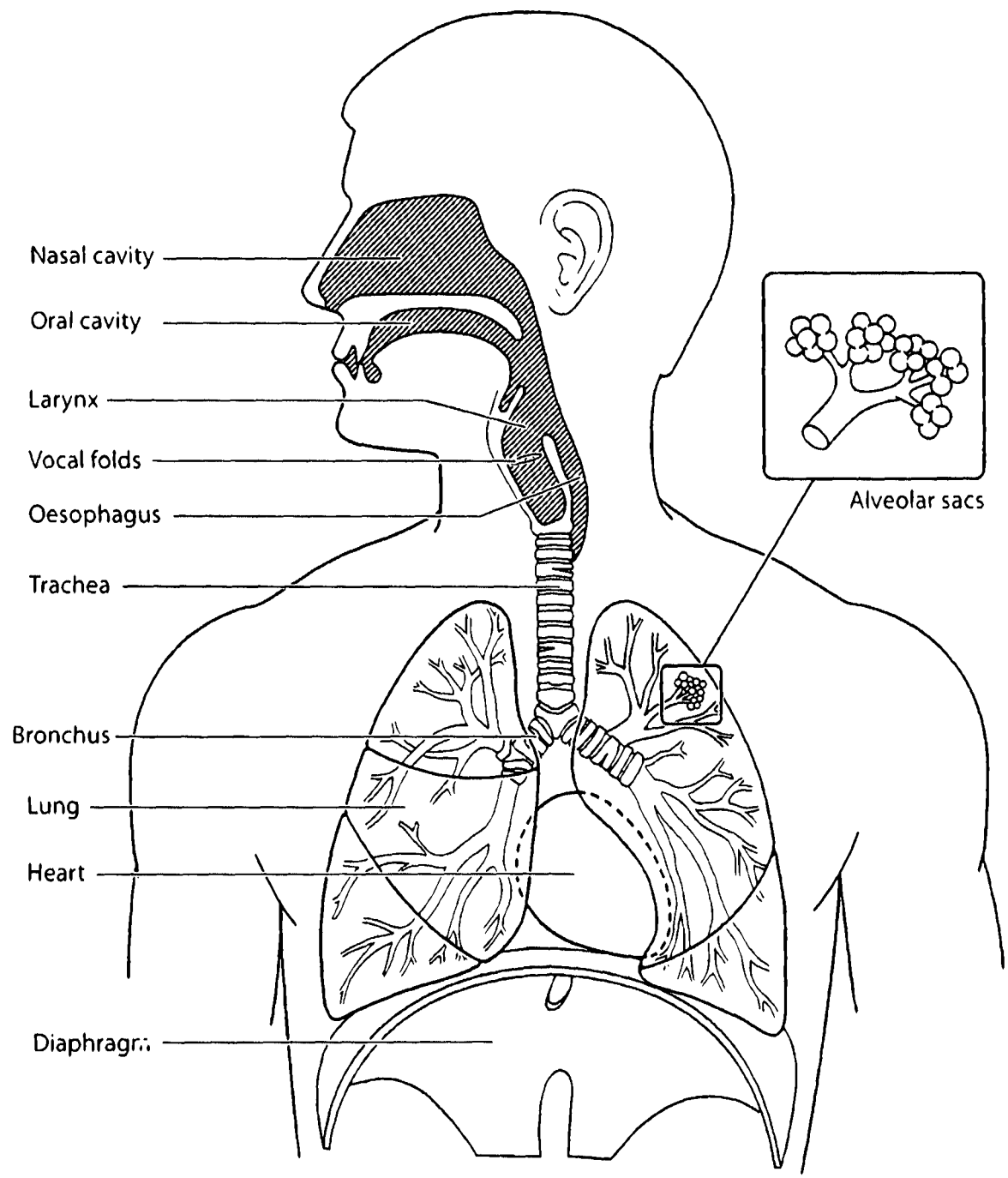
FIG. 2a shows an overview of a human respiratory system including the nasal and oral cavities, the larynx, vocal folds, oesophagus, trachea, bronchus, lung, alveolar sacs, heart and diaphragm.
Figure 2B:
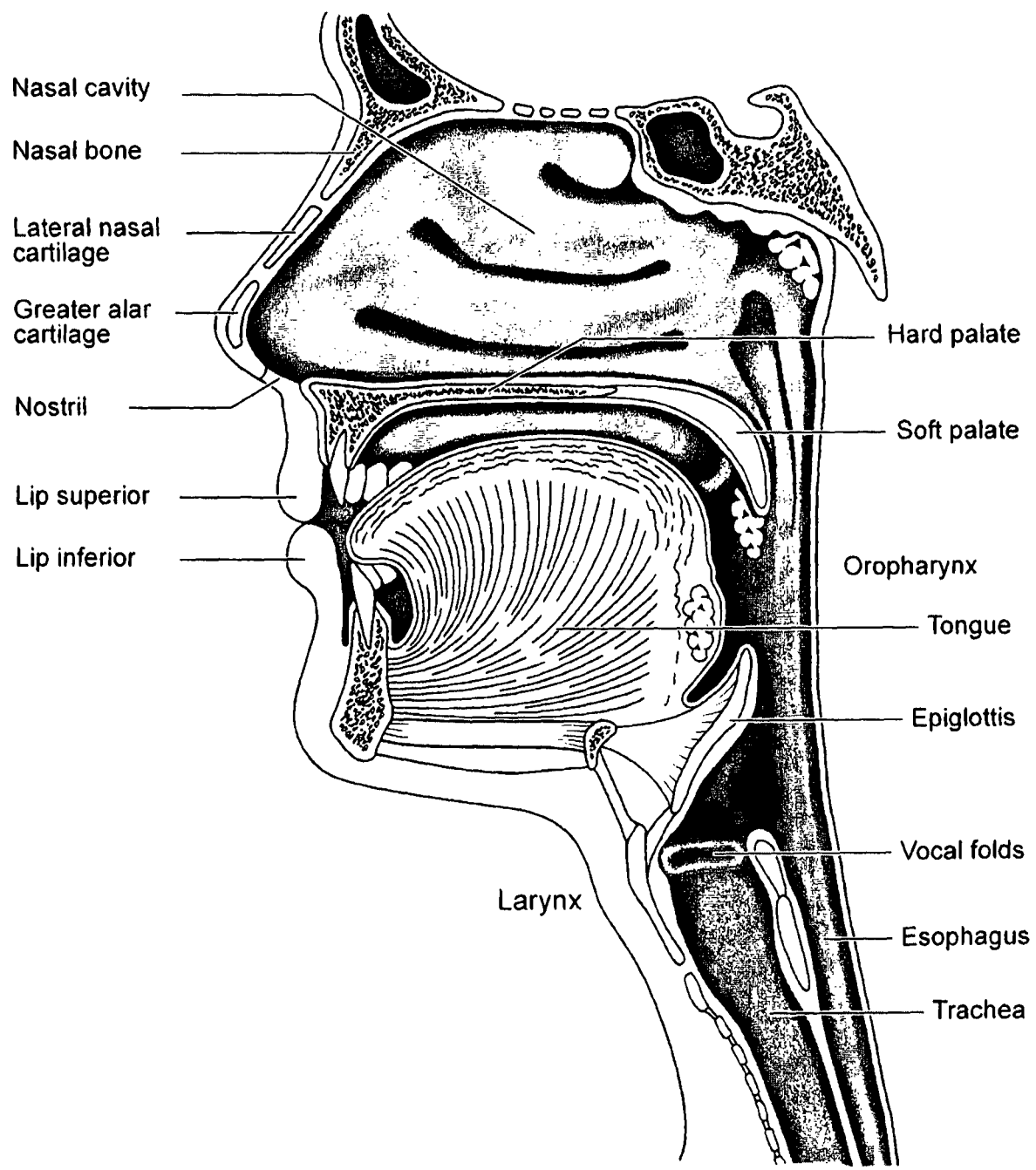
FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
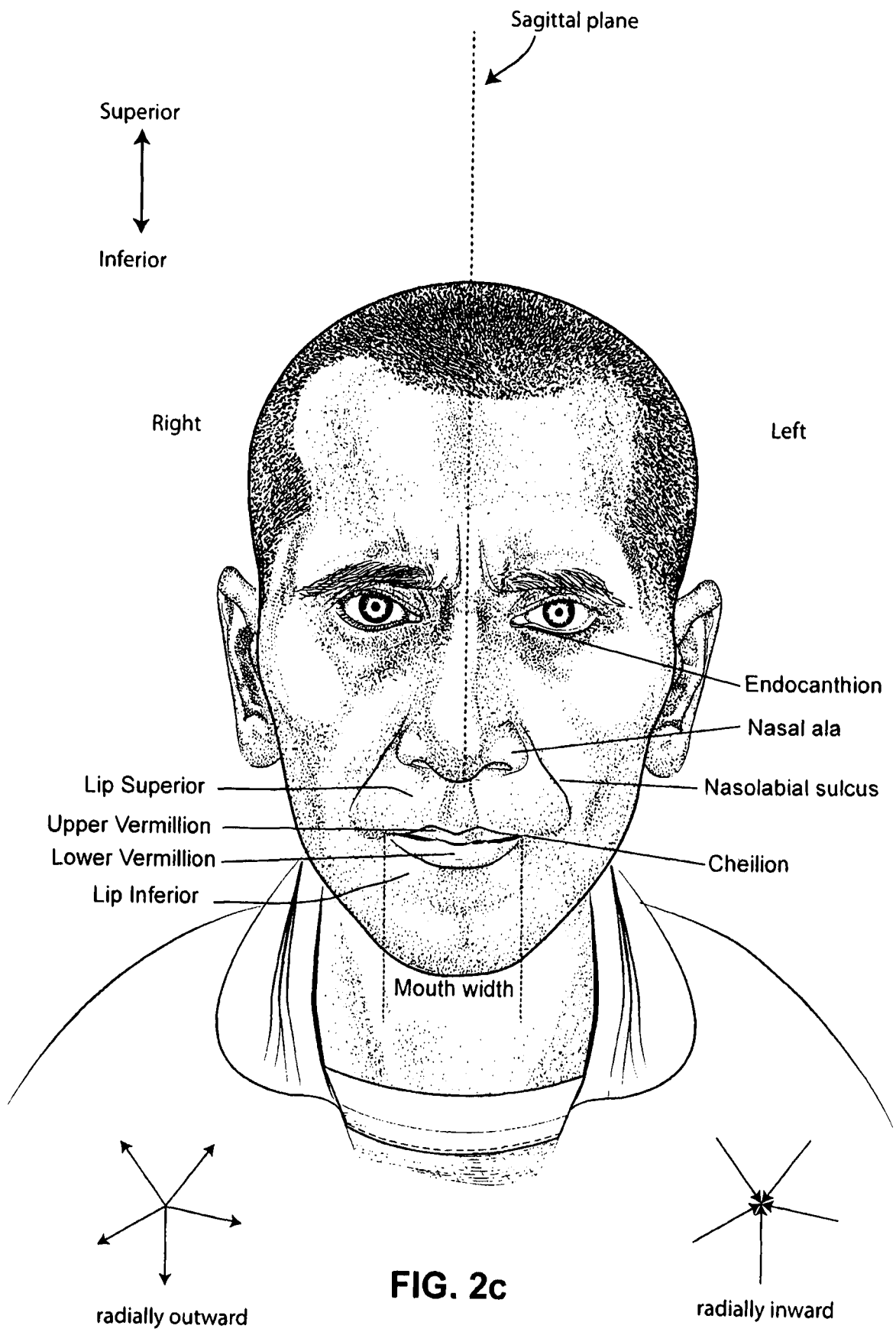

FIG. 2c is a front view of a face with several features of surface anatomy identified including the lip superior, upper vermillion, lower vermilion, lip inferior, mouth width, endocanthion, a nasal ala, nasolabial sulcus and cheilion.

Figure 2D:
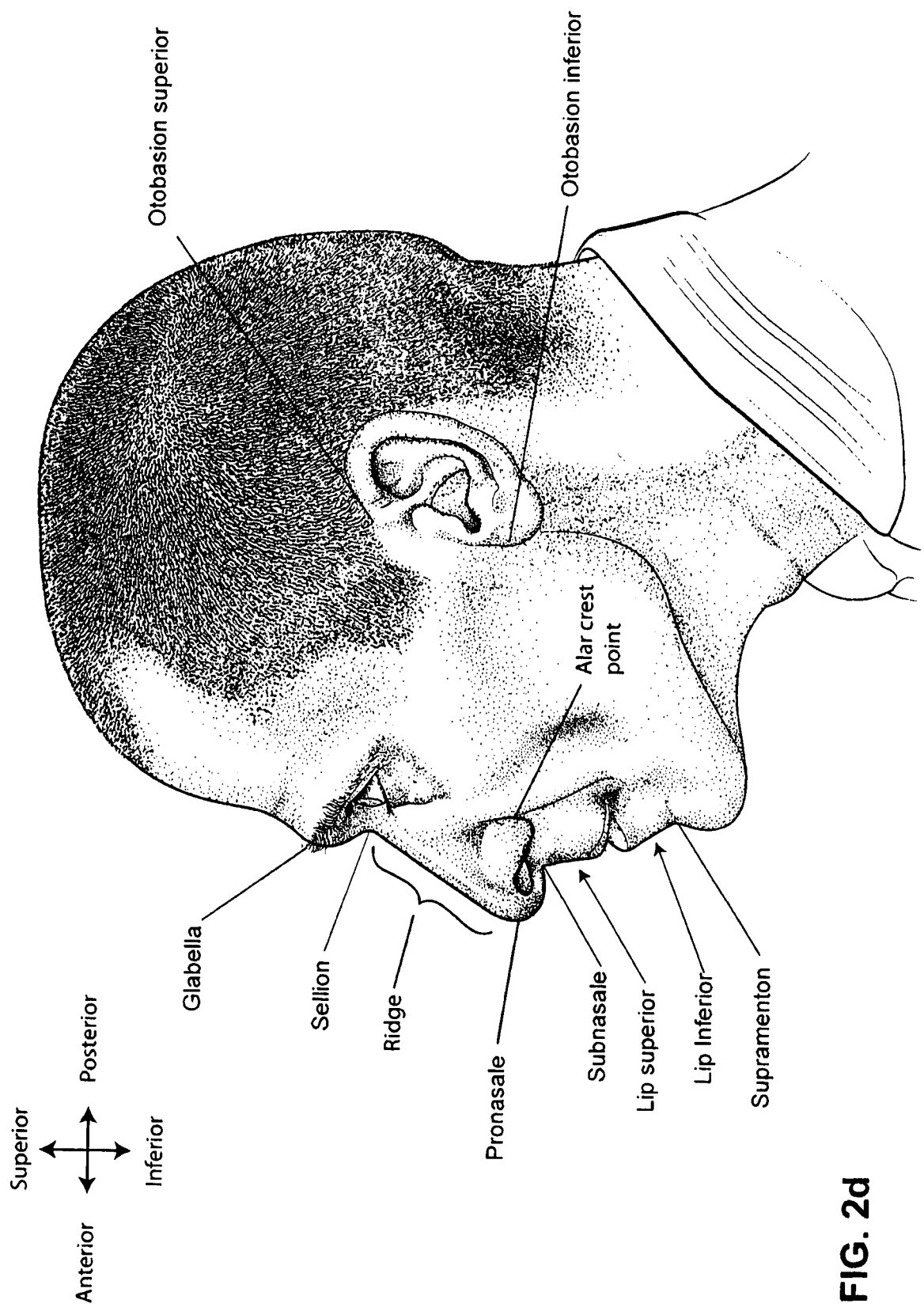

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

Figure 2E:
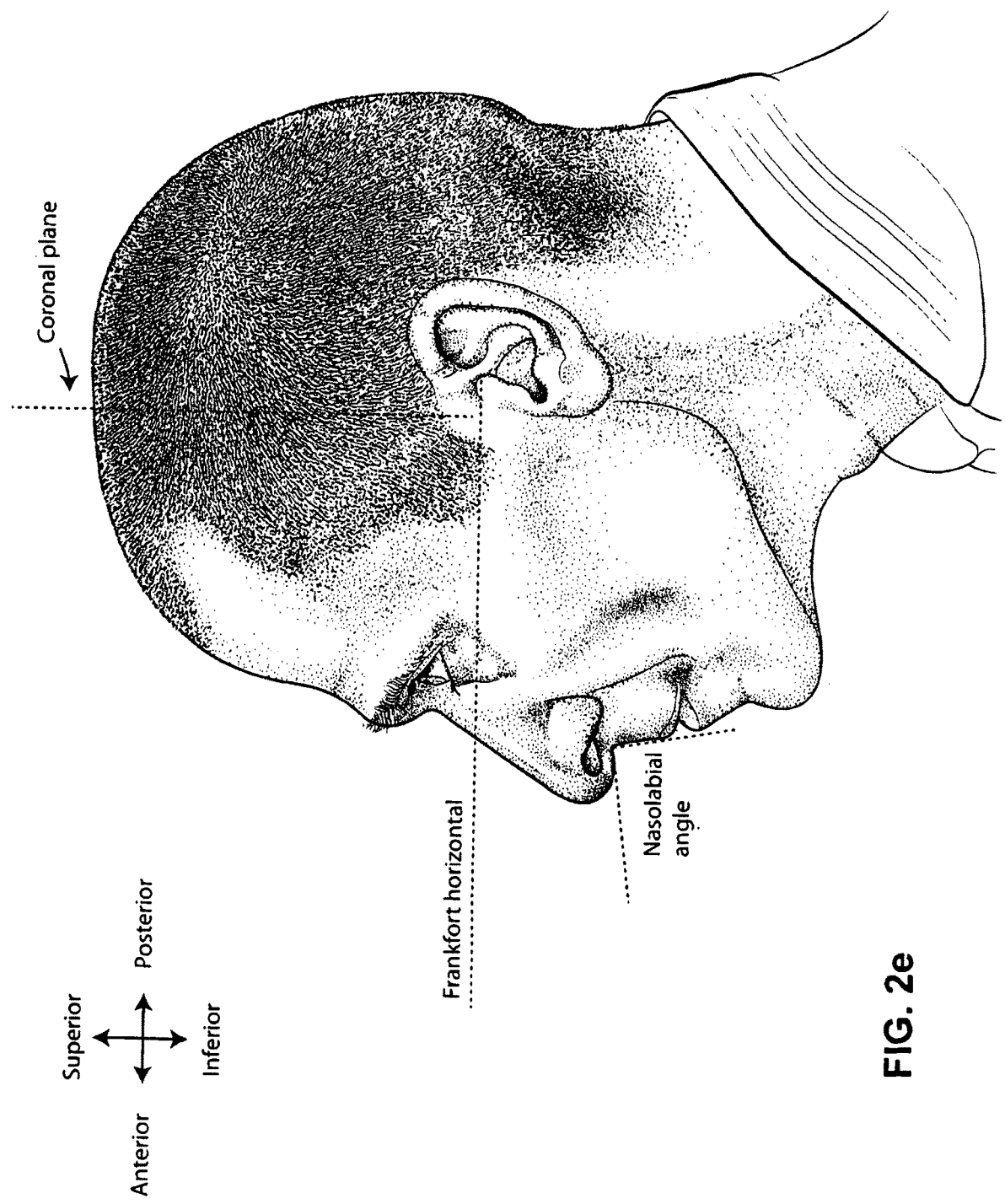

FIG. 2e is a further side view of a head. The approximate locations of the Frankfort horizontal and nasolabial angle are indicated.

Figure 2F:
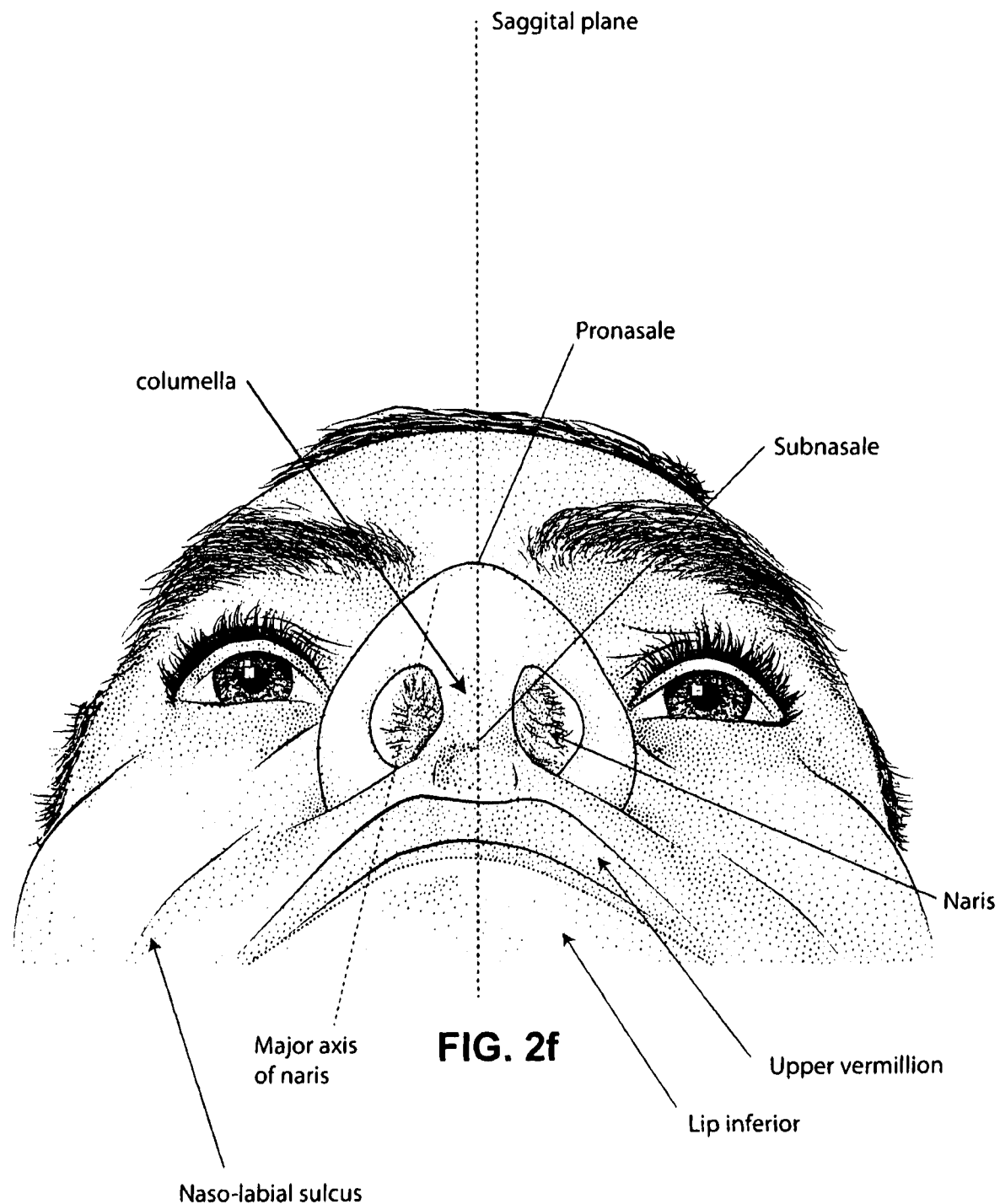

FIG. 2f shows a base view of a nose.

Figure 2I:
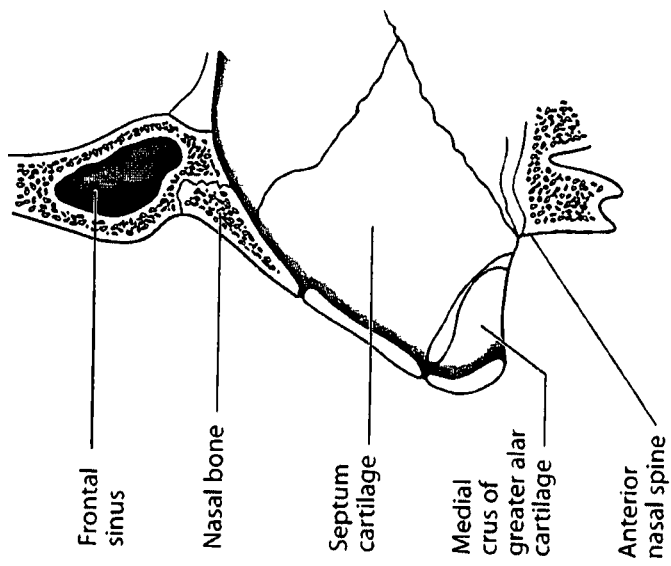
Figure 2H:
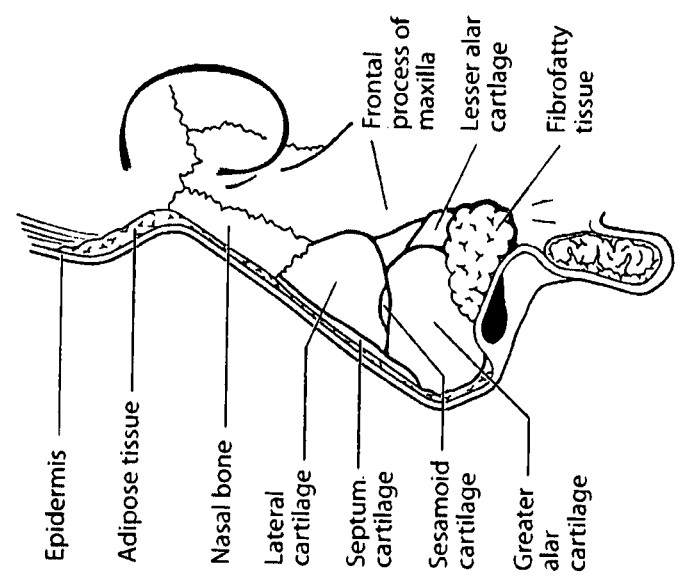
Figure 2G:
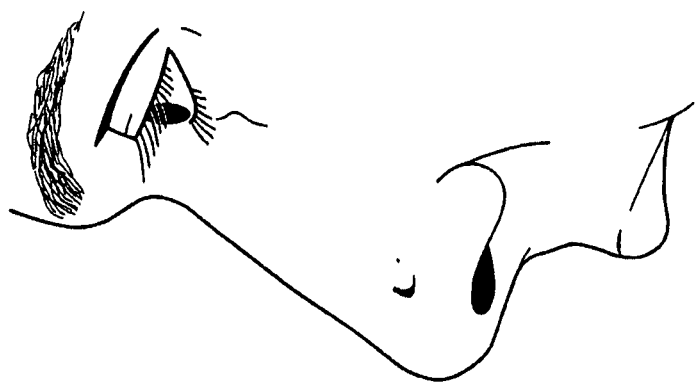

FIG. 2g shows a side view of the superficial features of a nose.

FIG. 2h shows subcutaneal structures of the nose, including the cartilaginous framework comprising the lateral cartilage, septum cartilage, greater alar cartilage, lesser alar cartilage and also shows the fibrofatty tissue.

FIG. 2i shows a medial dissection of a nose, approximately several millimeters from a sagittal plane, amongst other things showing the septum cartilage and medial crus of greater alar cartilage.

Figure 2K:
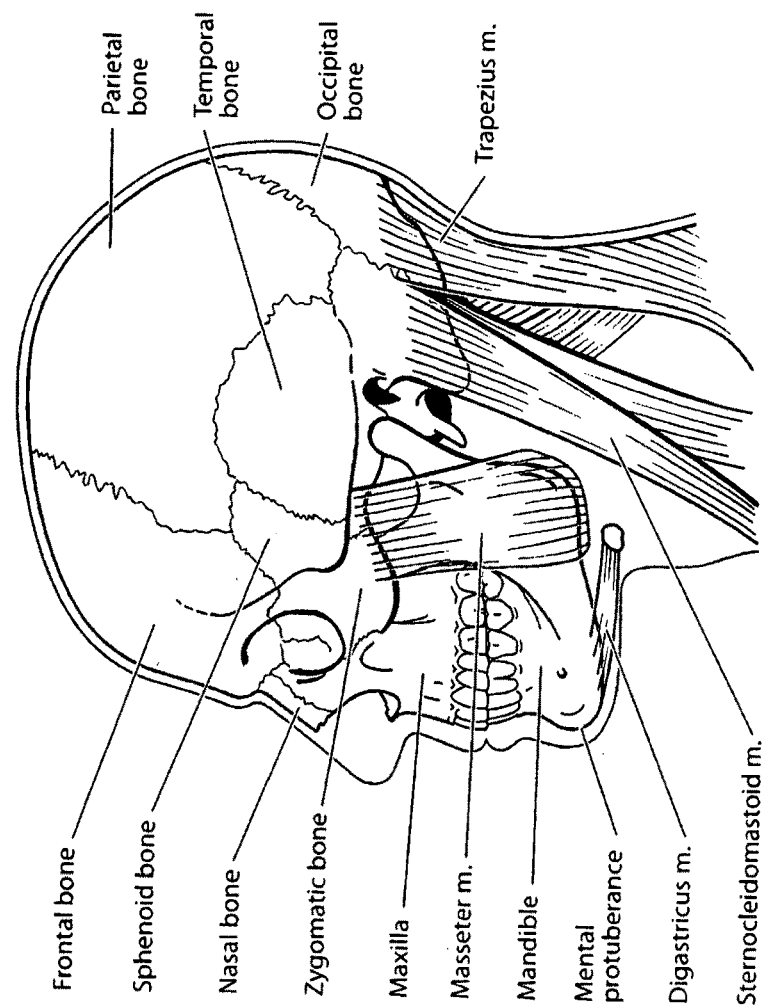
Figure 2J:
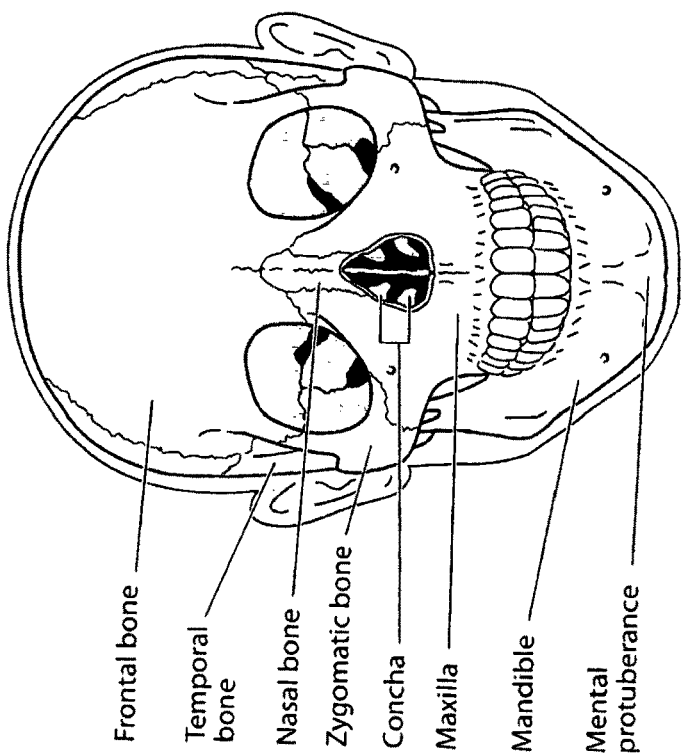

FIG. 2j shows a front view of the bones of a skull including the frontal, temporal, nasal and zygomatic bones. Nasal concha are indicated, as are the maxilla, mandible and mental protuberance.

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

4.3 Patient Interface

Figures 1, 3:
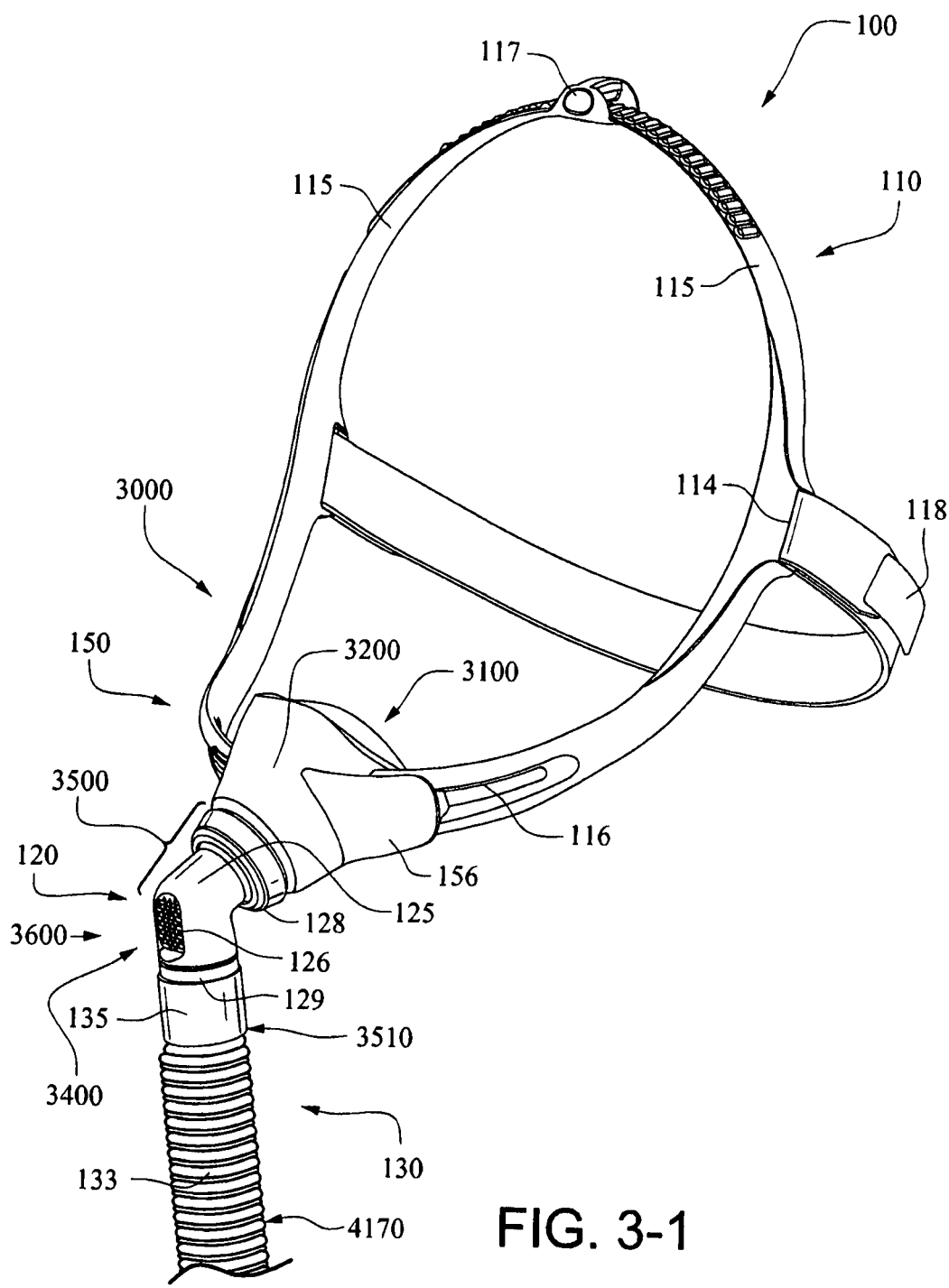

FIG. 3-1 is a perspective view of a nasal mask system according to an example of the present technology.

Figures 2, 3:
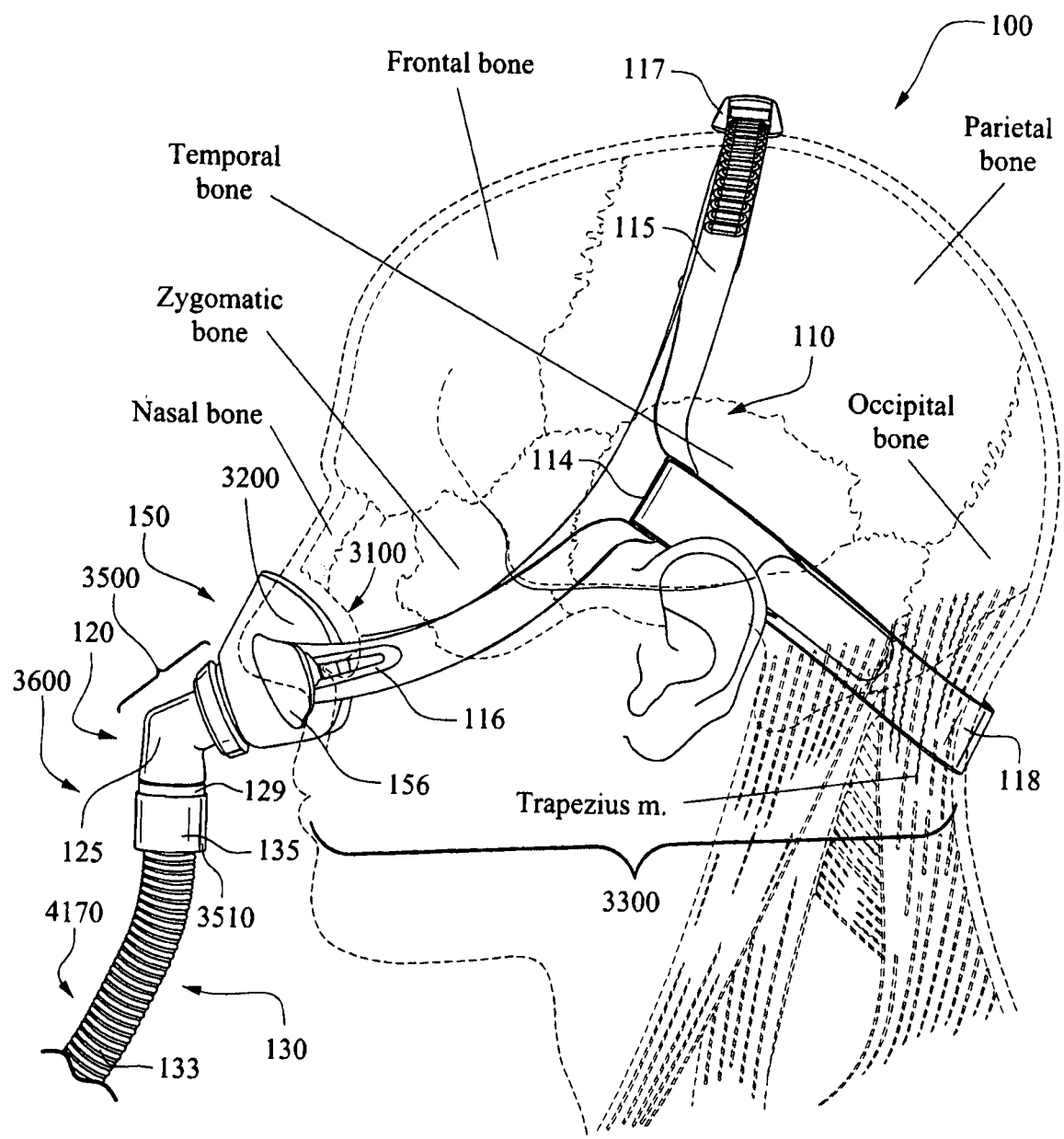
Figure 3:
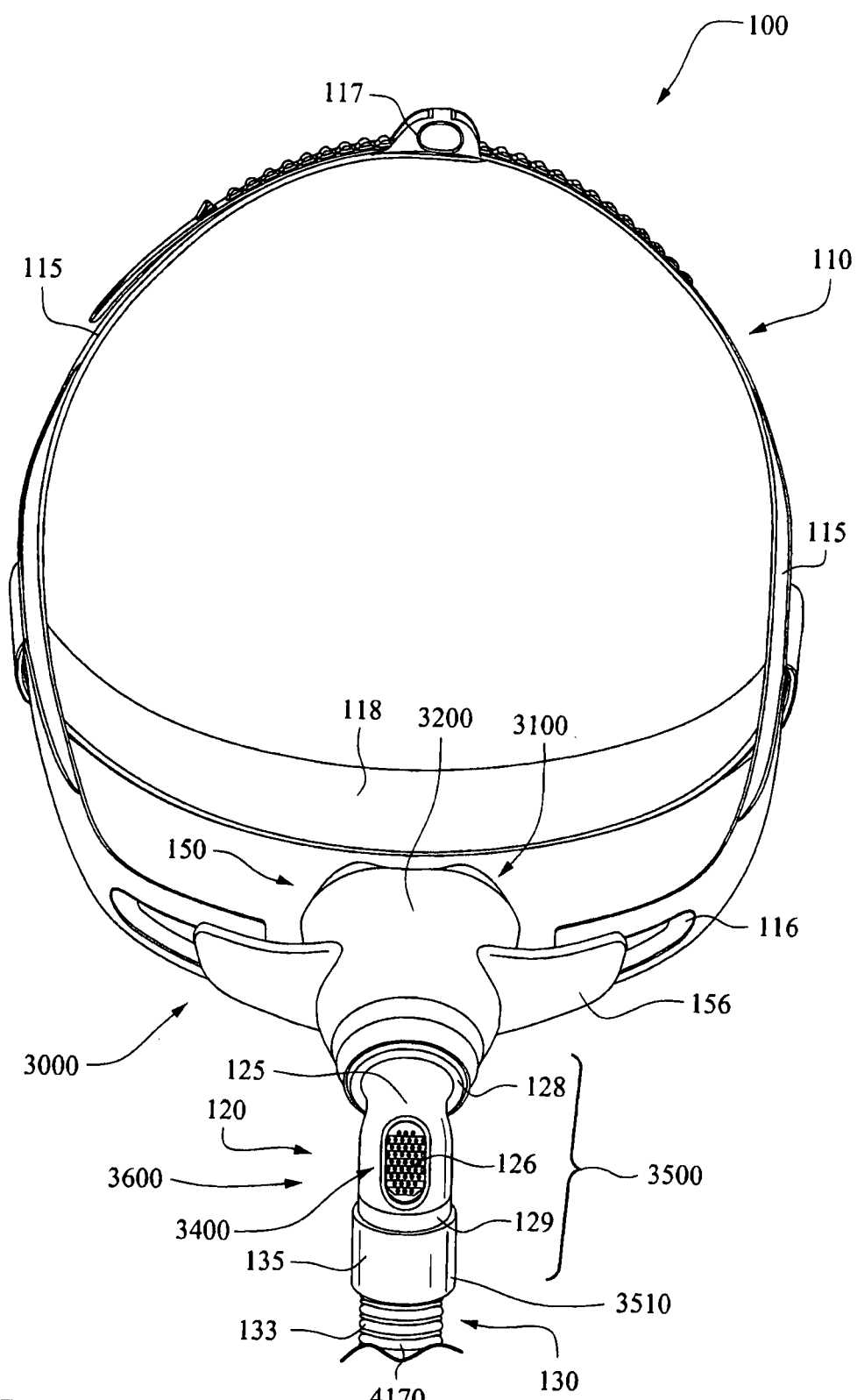

FIG. 3-2 is a side view of a nasal mask system according to an example of the present technology. The nasal mask system is shown overlaying a head to indicate the approximate relative location of the headgear in use.

FIG. 3-3 is a front view of a nasal mask system according to an example of the present technology.

Figures 3, 4:
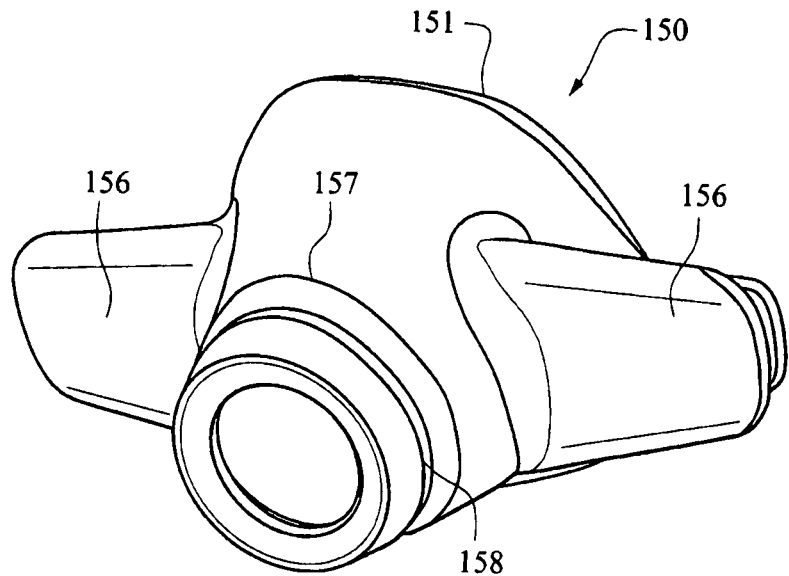

FIG. 3-4 is a perspective front view of a cushion of a nasal mask system according to an example of the present technology.

Figures 3, 4, 5:
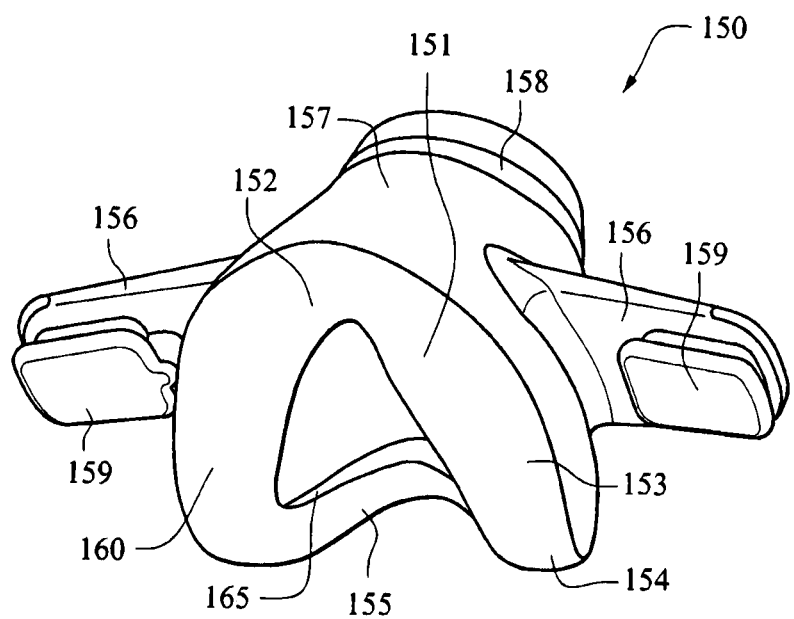

FIG. 3-5 is a perspective rear view of a cushion of a nasal mask system according to an example of the present technology.

FIG. 3-6 is a bottom view of a cushion of a nasal mask system according to an example of the present technology.

FIG. 3-7 is a top view of a cushion of a nasal mask system according to an example of the present technology.

FIG. 3-8 is a front view of a cushion of a nasal mask system according to an example of the present technology.

FIG. 3-9 is a rear view of a cushion of a nasal mask system according to an example of the present technology.

FIG. 3-10 is a cross-sectional view of the cushion of the nasal mask system of FIG. 3-9.

FIG. 3-11 is a perspective view of an elbow assembly of a nasal mask system according to an example of the present technology.

FIG. 3-12 is a rear view of an elbow assembly of a nasal mask system according to an example of the present technology.

FIG. 3-13 is a cross-sectional view of the elbow assembly of a nasal mask system of FIG. 3-12.

FIG. 3-14 is a perspective rear view of a cushion of a nasal mask system according to another example of the present technology.

FIG. 3-15 is a top view of the cushion of FIG. 3-14.

FIG. 3-16 is a bottom view of the cushion of FIG. 3-14.

FIG. 3-17 is a front view of the cushion of FIG. 3-14.

FIG. 3-18 is a cross-section view of the cushion of FIG. 3-17.

FIG. 3-19 is an enlarged view of a portion of FIG. 3-18.

FIG. 3-20 is a rear view of the cushion of FIG. 3-14.

FIG. 3-21 is a side view of the cushion of FIG. 3-14.

FIG. 3-22 is a rear view of the cushion of FIG. 3-14 showing cross-sectional lines.

FIG. 3-23 is a cross-section through line 3-23-3-23 of FIG. 3-22.

FIG. 3-24 is a cross-section through line 3-24-3-24 of FIG. 3-22.

FIG. 3-25 is a cross-section through line 3-25-3-25 of FIG. 3-22.

FIG. 3-26 is a cross-section through line 3-26-3-26 of FIG. 3-22.

FIG. 3-27 is a cross-section through line 3-27-3-27 of FIG. 3-22.

FIG. 3-28 is a cross-section through line 3-28-3-28 of FIG. 3-22.

FIG. 3-29 is a cross-section through line 3-29-3-29 of FIG. 3-22.

FIG. 3-30 is a cross-section through line 3-30-3-30 of FIG. 3-22.

FIGS. 3-31 to 3-34 are sequential views showing exemplary steps for donning a nasal mask system according to an example of the present technology.

FIG. 3-35 is a cross-sectional view showing a nasal mask system engaged with a patient's face according to an example of the present technology.

FIG. 3-36 is a cross-sectional view showing a nasal mask system engaged with a patient's face according to an example of the present technology.

FIG. 3-37 is another perspective view of the cushion of FIG. 3-14.

FIG. 3-38 shows a cushion assembly engaged with the patient's face and under pressure or inflated in use according to an example of the present technology.

FIG. 3-39 is a schematic rear view of a cushion assembly showing the sealing portions engaged with the patient's face in use according to an example of the present technology.

FIGS. 3-40-1 to 3-40-8 show various views of a cushion assembly according to another example of the present technology.

FIGS. 3-41-1 to 3-41-10 show various views of a cushion assembly according to another example of the present technology.

FIG. 3-42 is an isometric cross sectional view of a swivel elbow and connector assembly according to an example of the technology.

FIG. 3-43 is a cross sectional side view of the swivel elbow and connector assembly of FIG. 1.

FIGS. 3-44 and 3-45 are exploded isometric views of the swivel elbow and connector assembly of FIG. 3-42.

FIGS. 3-46 and 3-47 are isometric views of a double swivel elbow and connector assembly according to another example of the technology in a first position or configuration.

FIG. 3-48 is a side view of the double swivel elbow and connector assembly of FIGS. 3-46 and 3-47.

FIG. 3-49 is a side view of the double swivel elbow and connector assembly of FIG. 3-48 in a second position or configuration.

FIG. 3-50 is a side view of the transition of the double swivel elbow and connector assembly from the first position to the second position.

FIG. 3-51 is an isometric cross sectional view of the double swivel elbow and connector assembly in the first position.

FIG. 3-52 is an isometric cross sectional view of the double swivel elbow and connector assembly in the second position.

FIG. 3-53 is a cross sectional side view of the double swivel elbow and connector assembly in the first position.

Figures 3, 4, 5, 6:
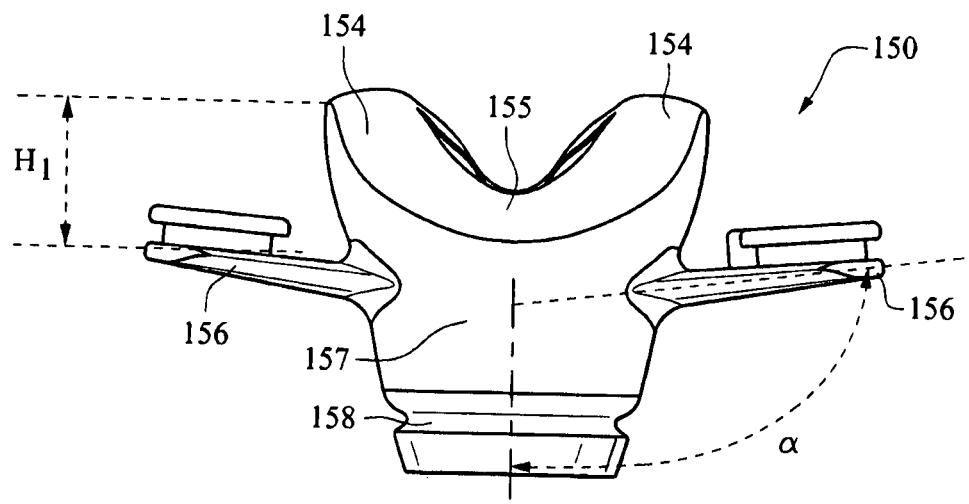
Figures 3, 4, 5, 6, 7:
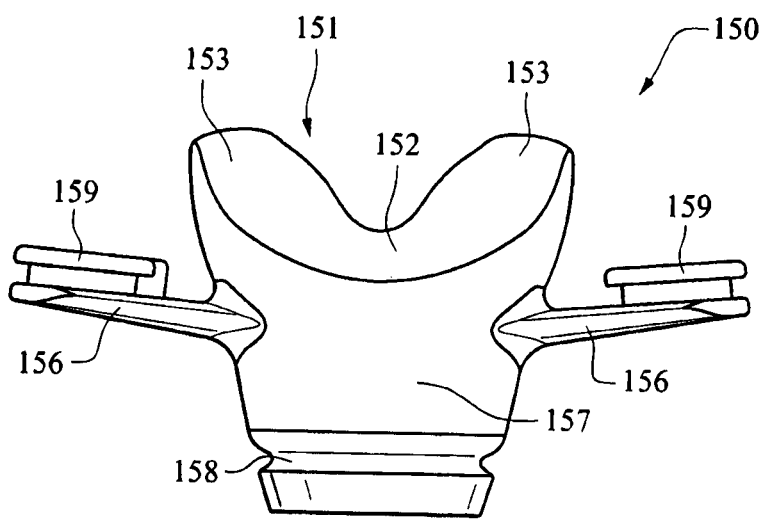
Figures 3, 4, 5, 6, 7, 8:
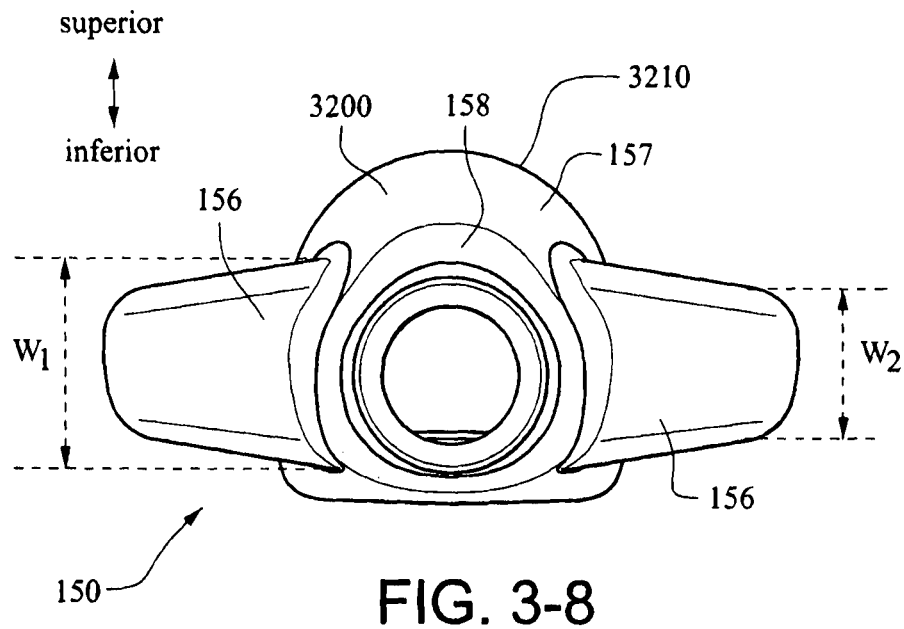
Figures 3, 4, 5, 6, 7, 8, 9:
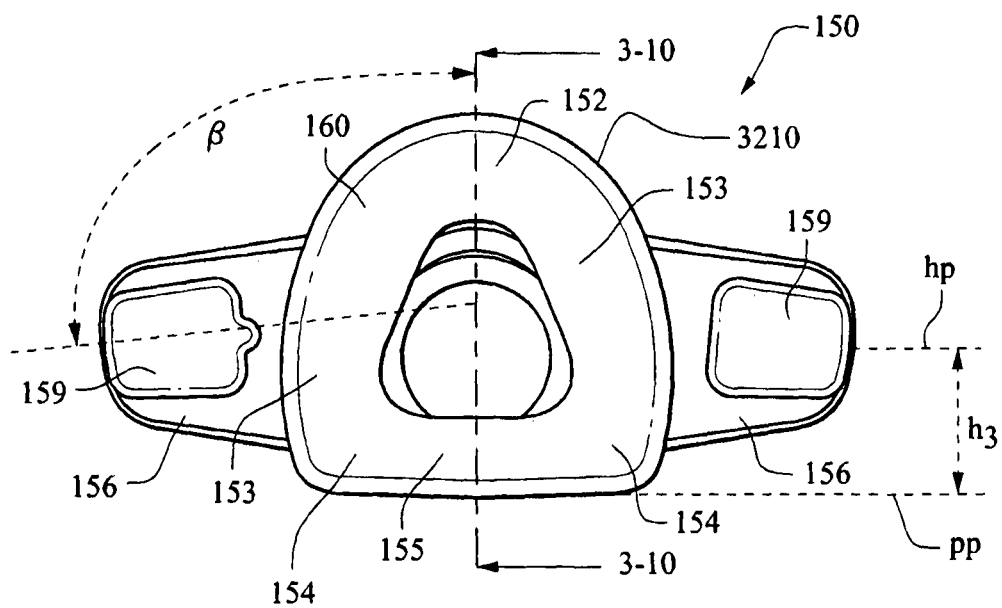
Figures 3, 4, 5, 6, 7, 8, 9, 10:
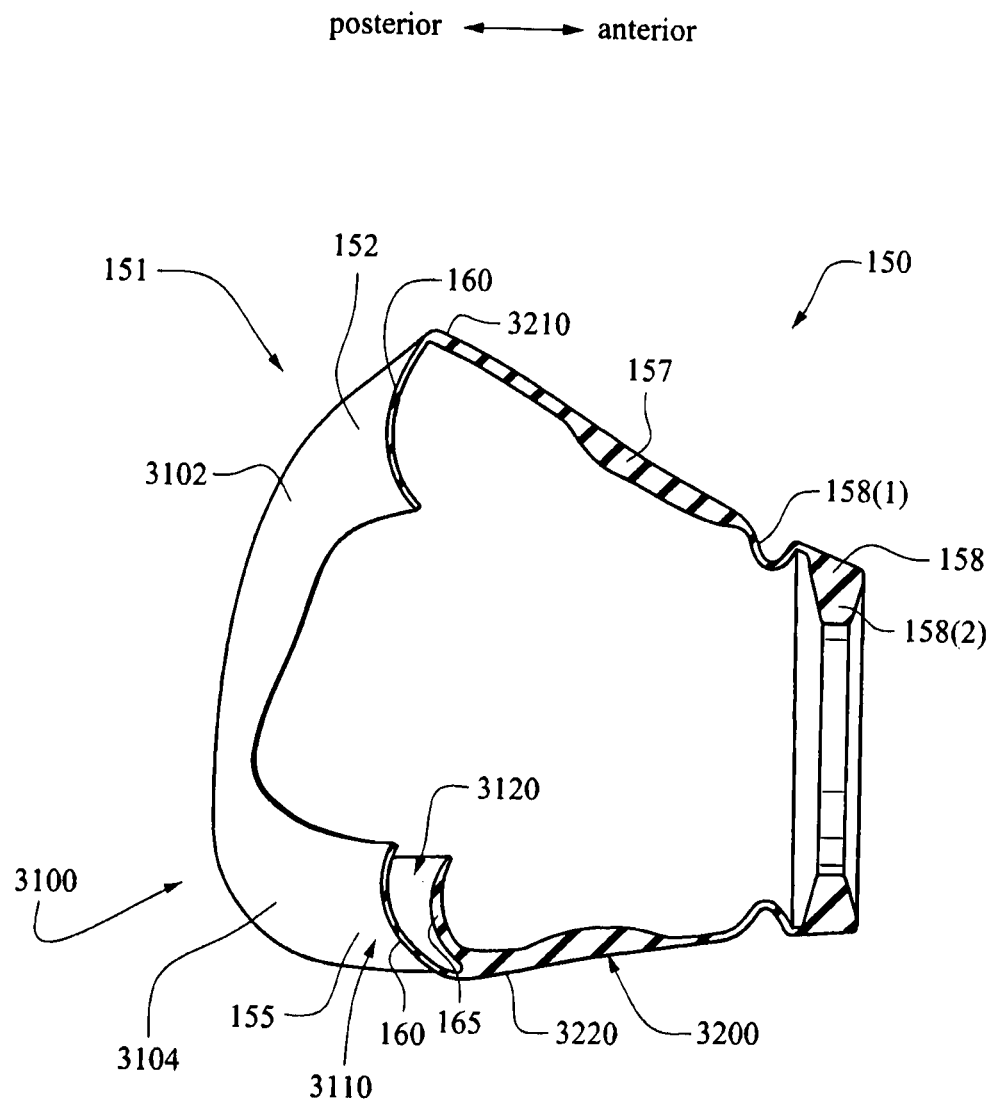
Figures 3, 4, 5, 6, 7, 8, 9, 10, 11:
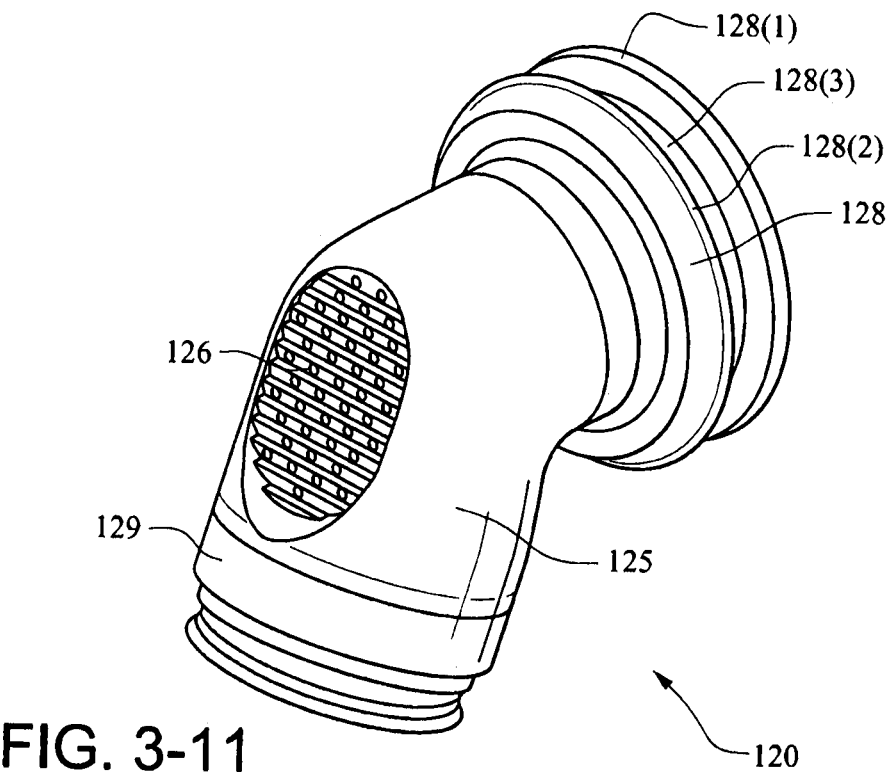
Figures 3, 4, 5, 6, 7, 8, 9, 10, 11, 12:
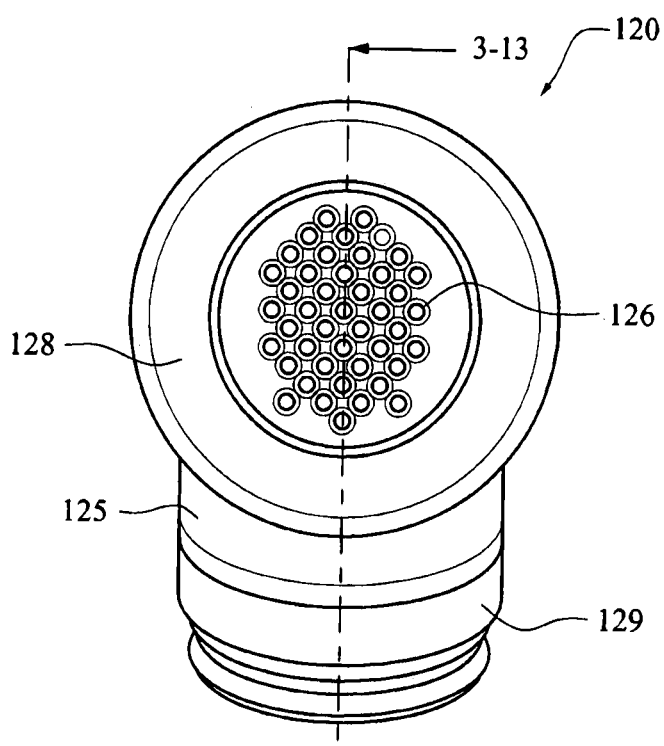
Figures 3, 4, 5, 6, 7, 8, 9, 10, 11, 12, 13:
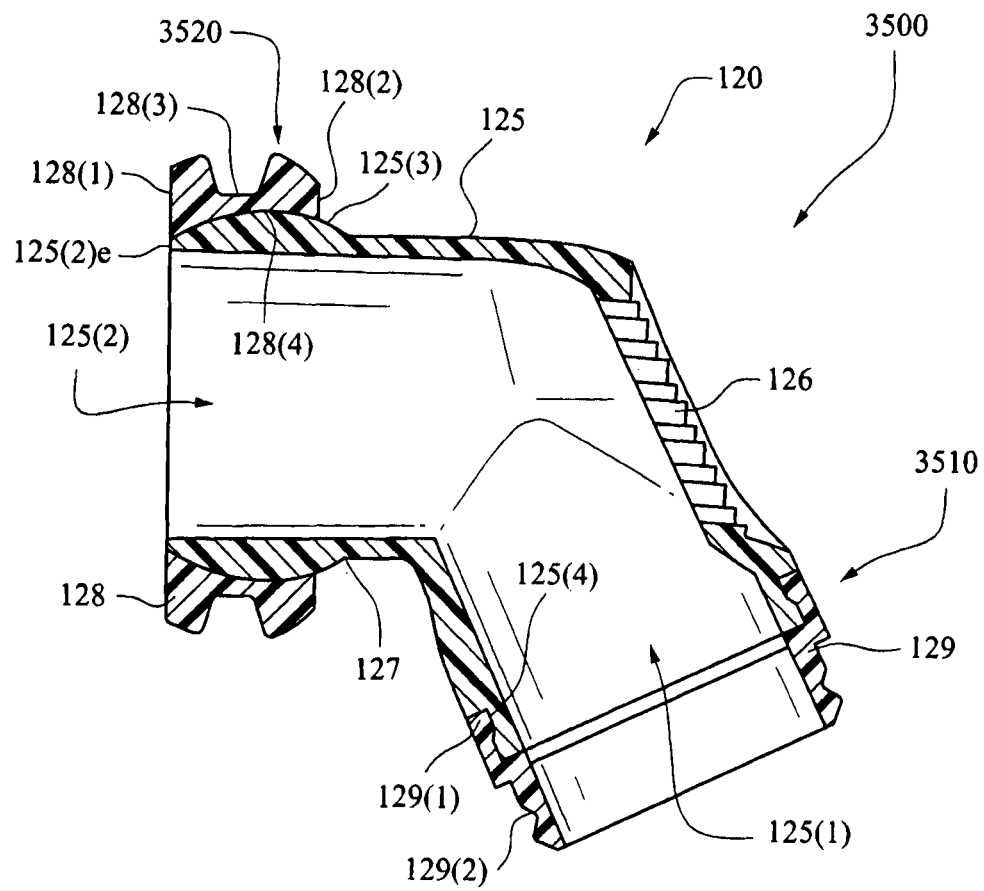
Figures 3, 4, 5, 6, 7, 8, 9, 10, 11, 12, 13, 14:
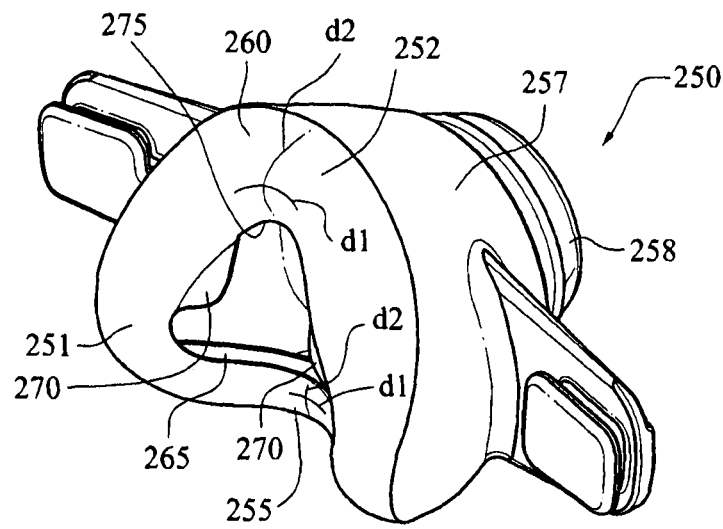
Figures 3, 4, 5, 6, 7, 8, 9, 10, 11, 12, 13, 14, 15:
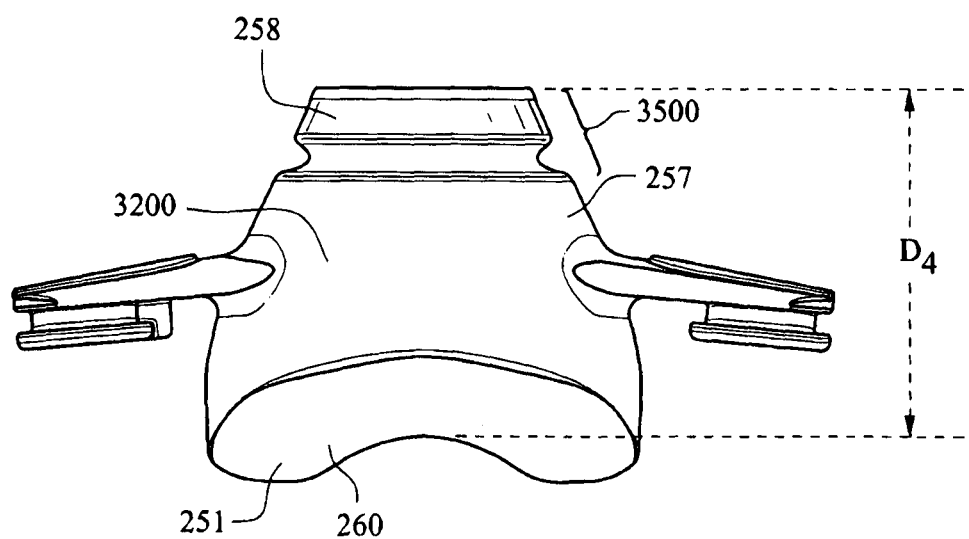
Figures 3, 4, 5, 6, 7, 8, 9, 10, 11, 12, 13, 14, 15, 16:
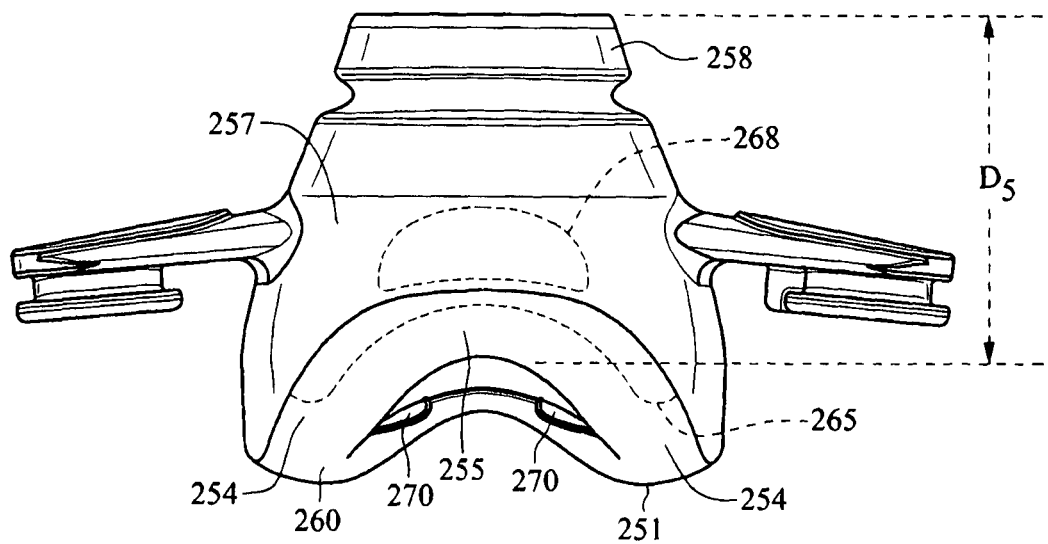
Figures 3, 4, 5, 6, 7, 8, 9, 10, 11, 12, 13, 14, 15, 16, 17:
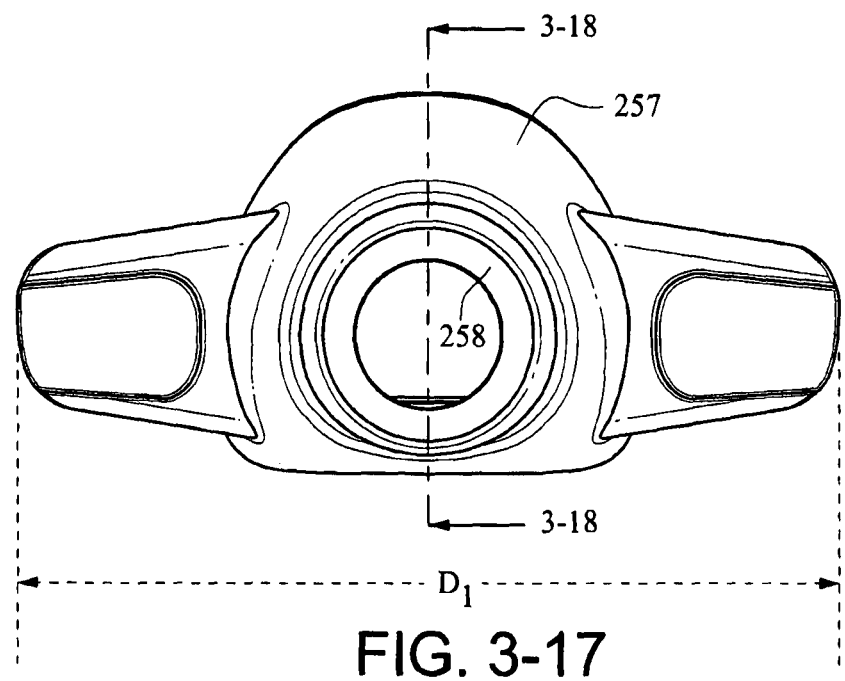
Figures 3, 4, 5, 6, 7, 8, 9, 10, 11, 12, 13, 14, 15, 16, 17, 18:
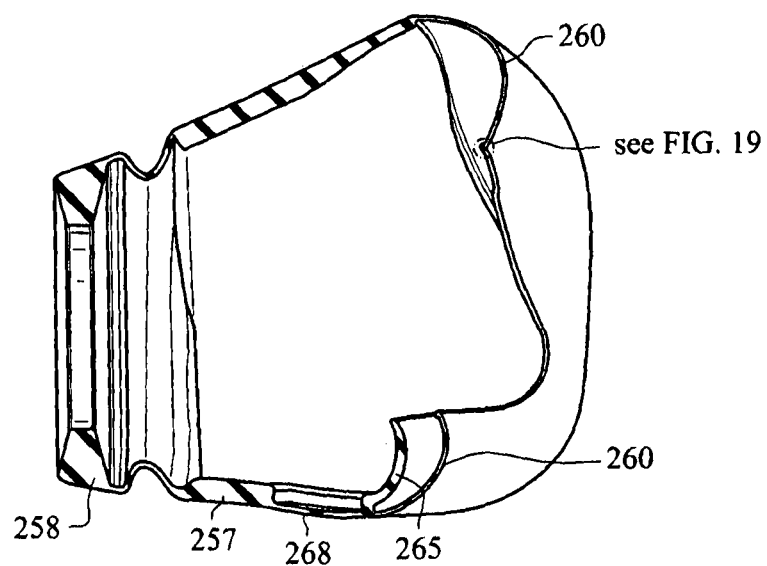
Figures 3, 4, 5, 6, 7, 8, 9, 10, 11, 12, 13, 14, 15, 16, 17, 18, 19:
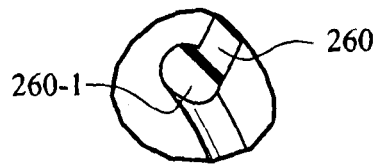
Figures 3, 4, 5, 6, 7, 8, 9, 10, 11, 12, 13, 14, 15, 16, 17, 18, 19, 20:
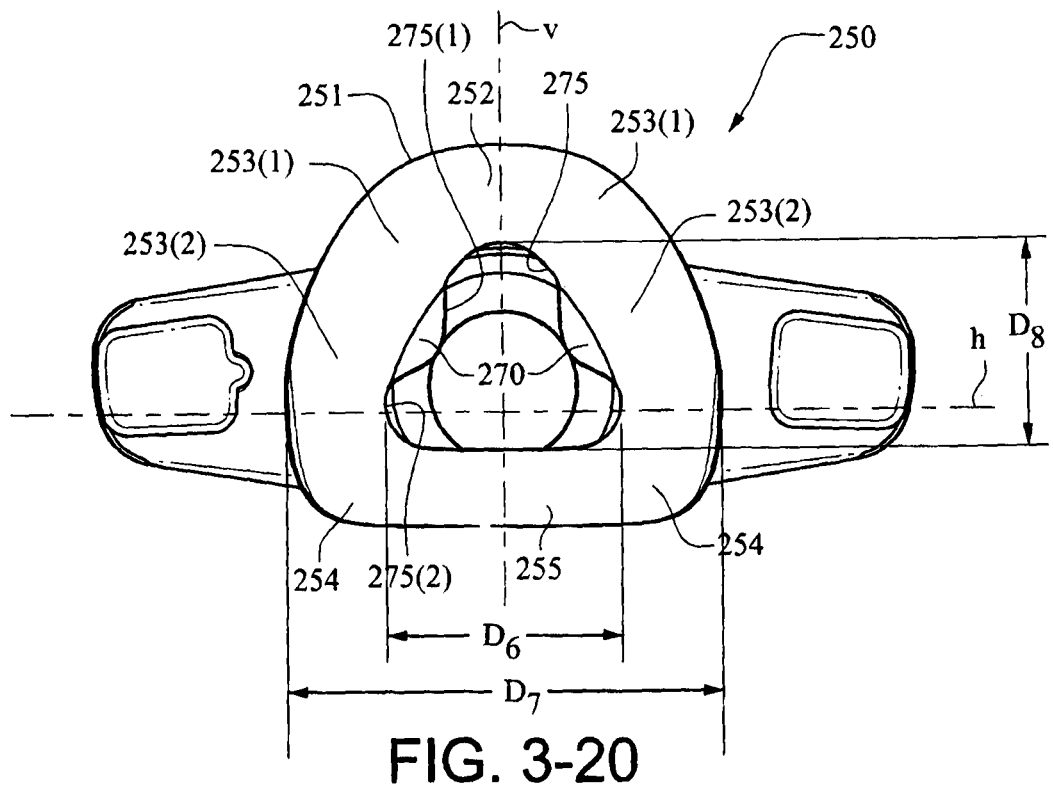
Figures 3, 4, 5, 6, 7, 8, 9, 10, 11, 12, 13, 14, 15, 16, 17, 18, 19, 20, 21:
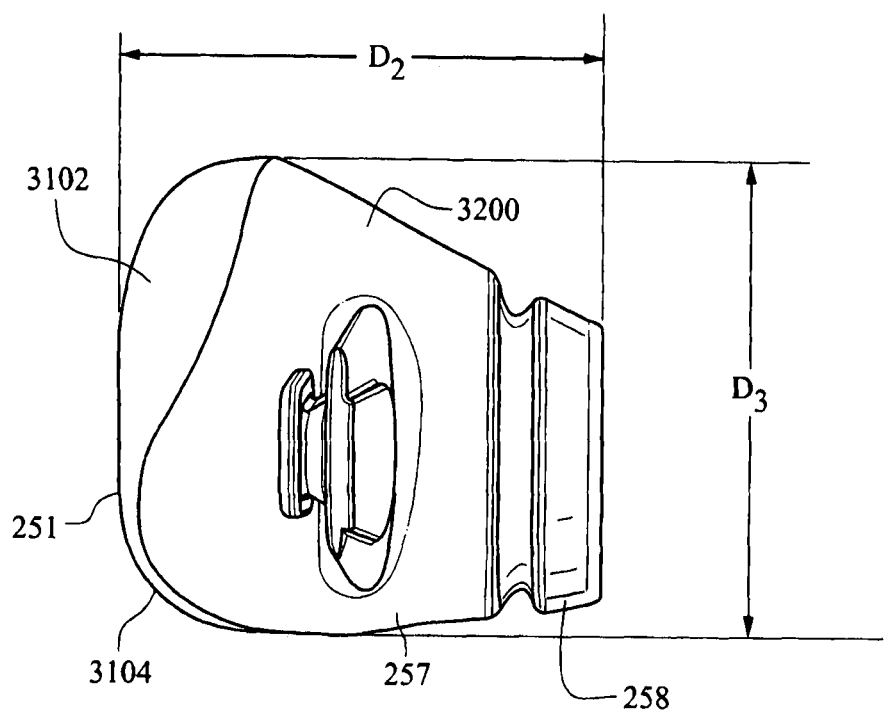
Figures 3, 4, 5, 6, 7, 8, 9, 10, 11, 12, 13, 14, 15, 16, 17, 18, 19, 20, 21, 22:
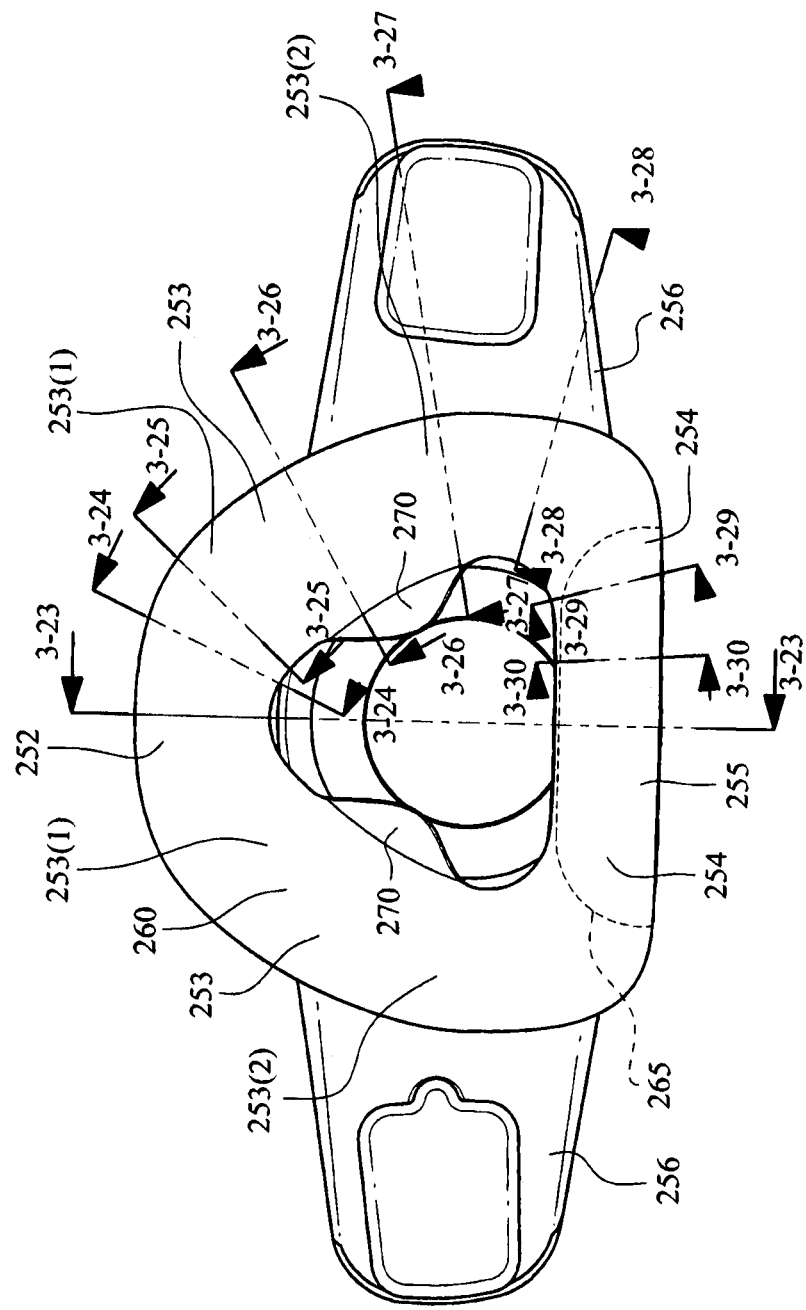
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31:
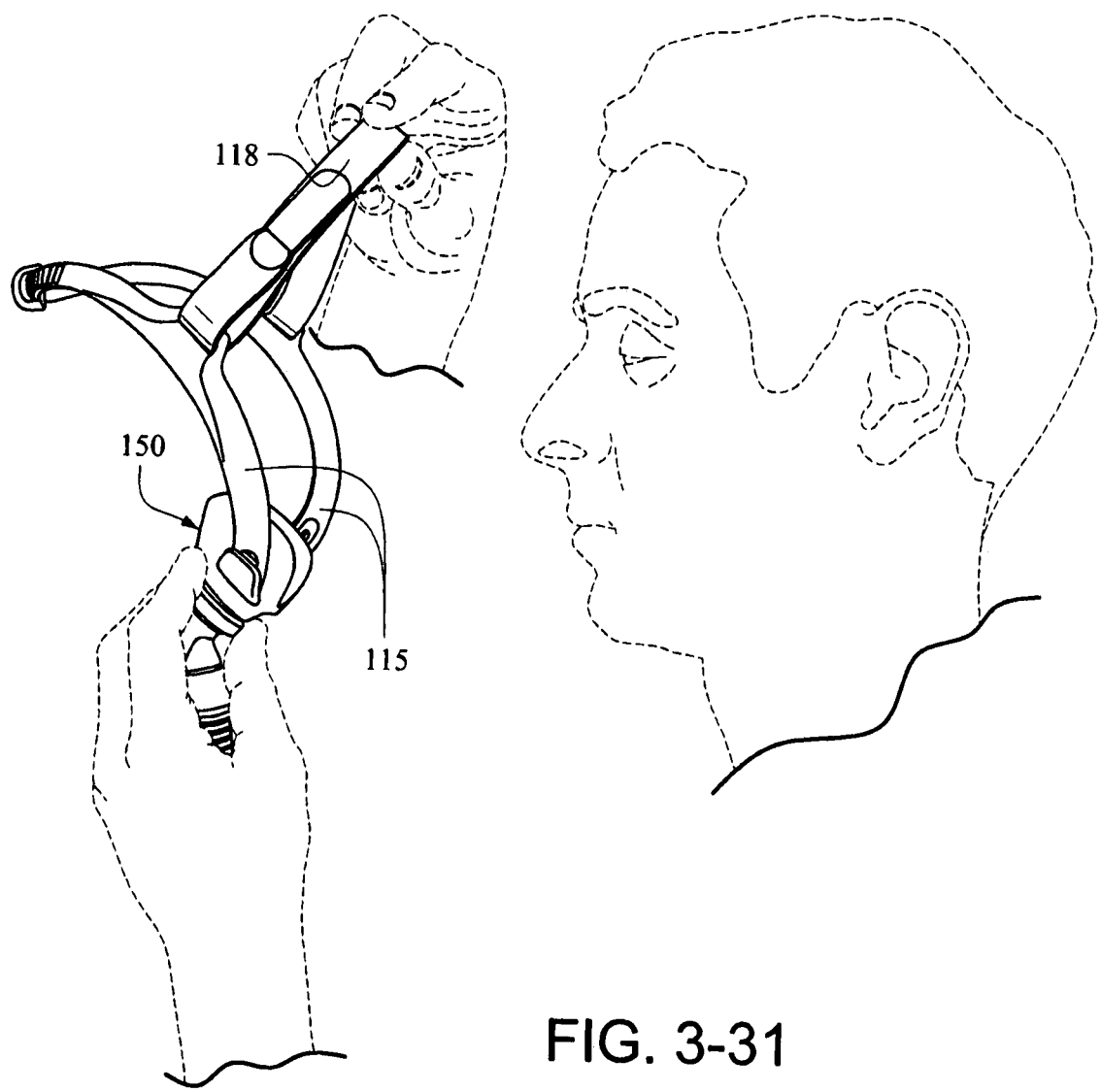
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
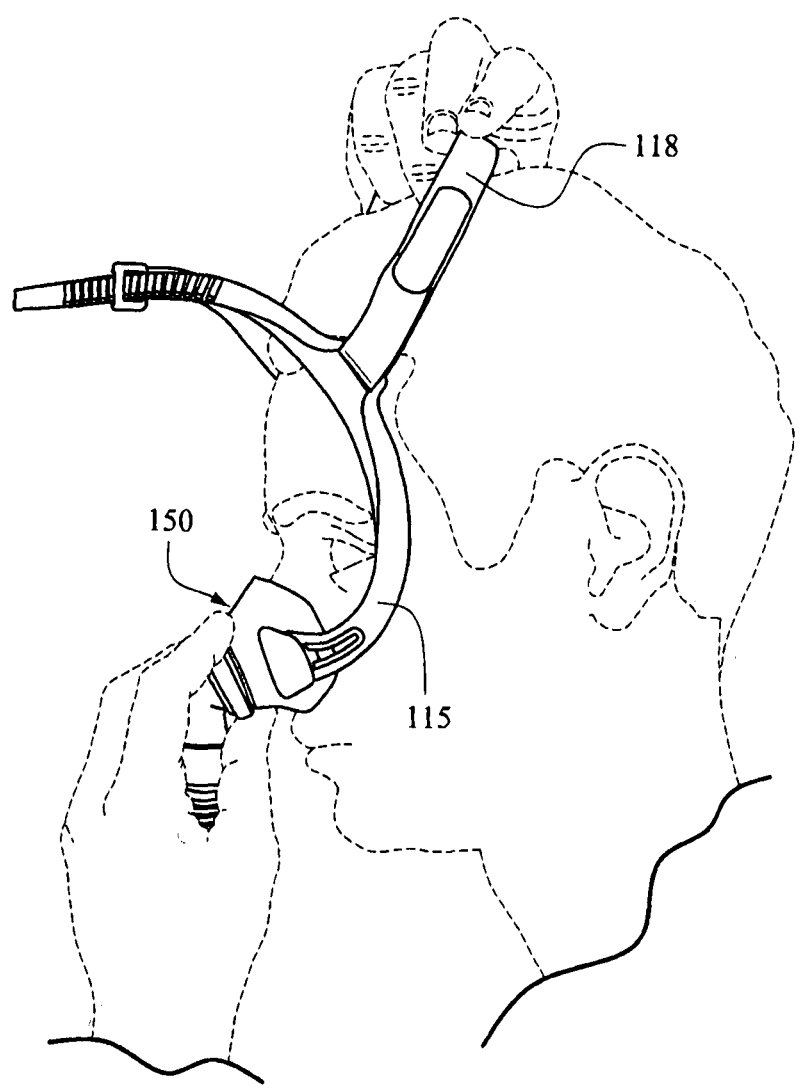
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
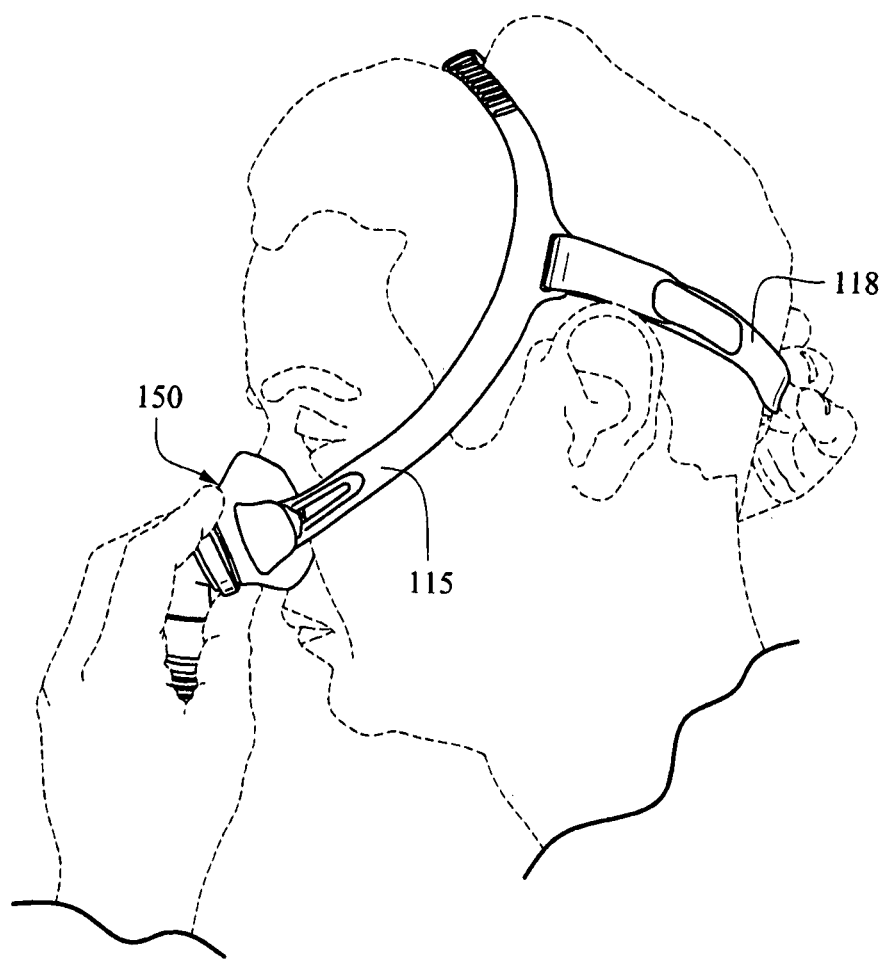
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
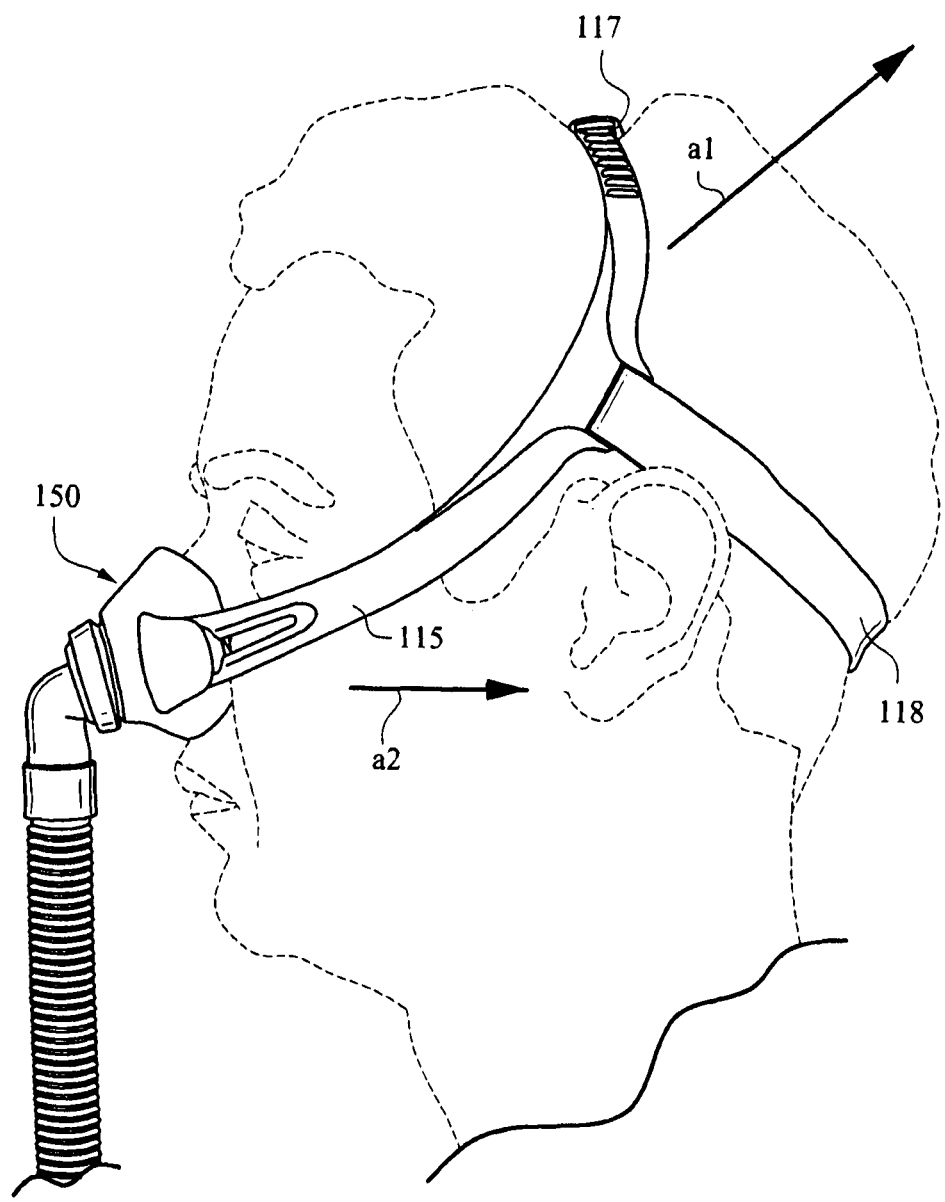
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
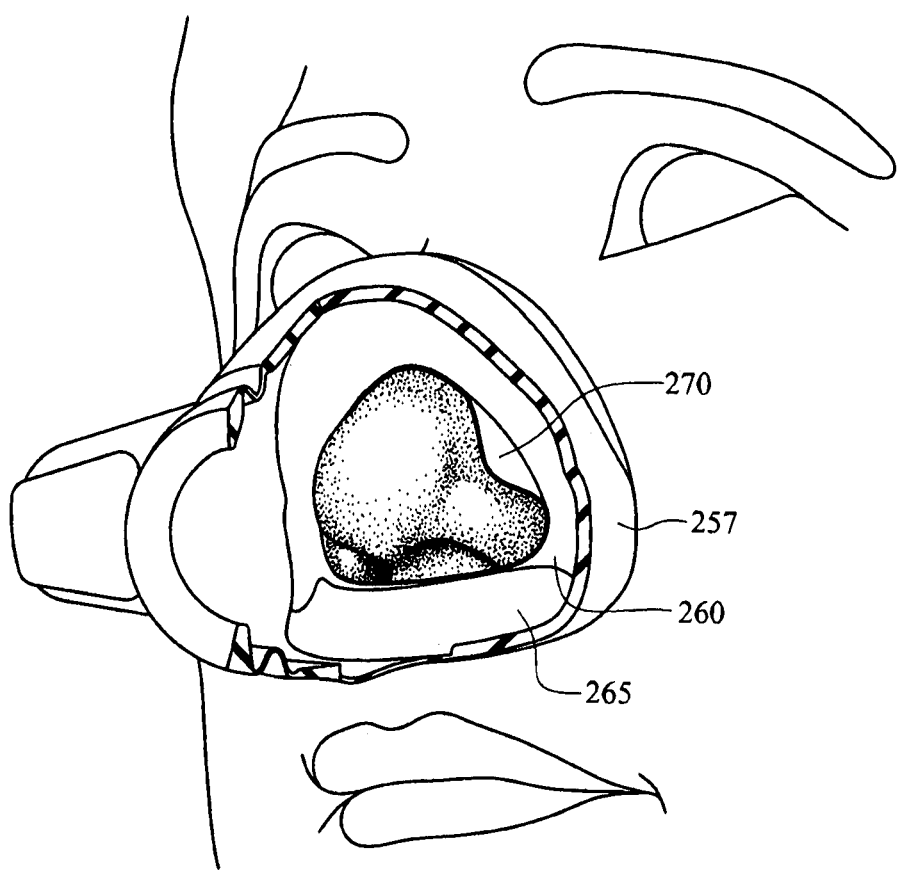
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
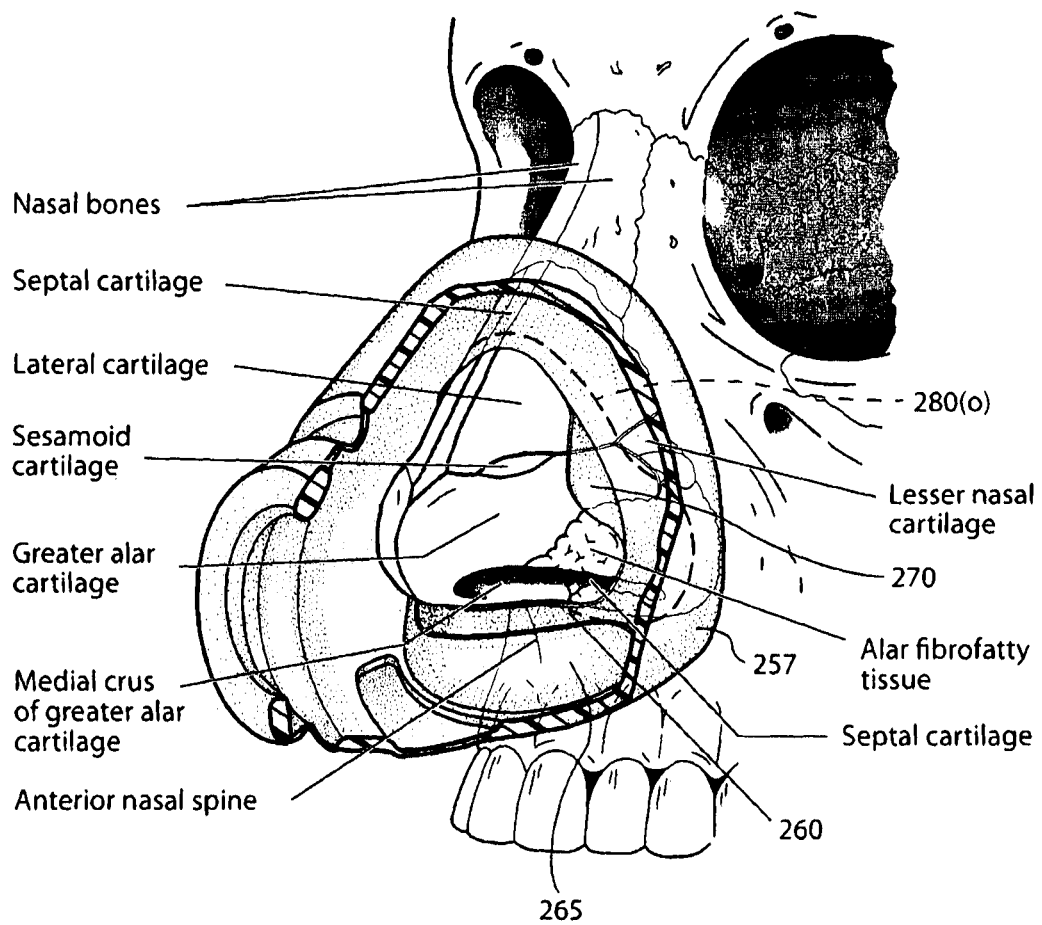
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
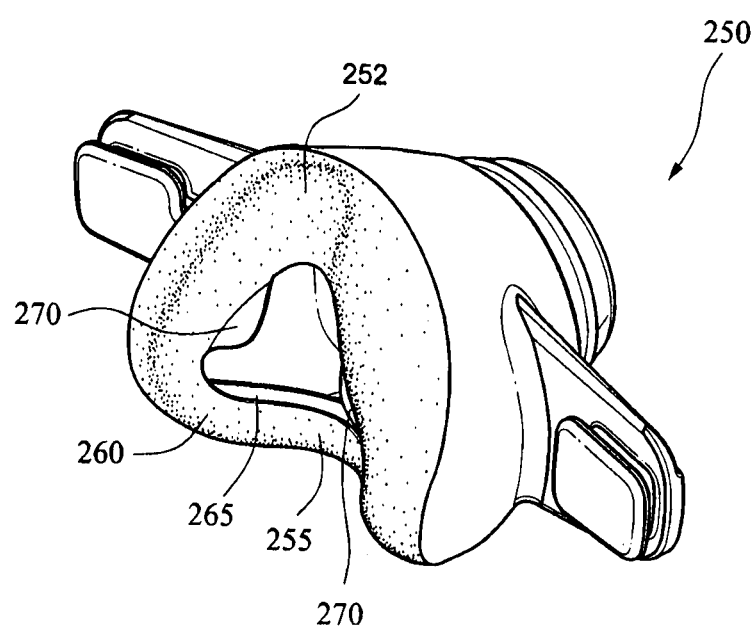
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
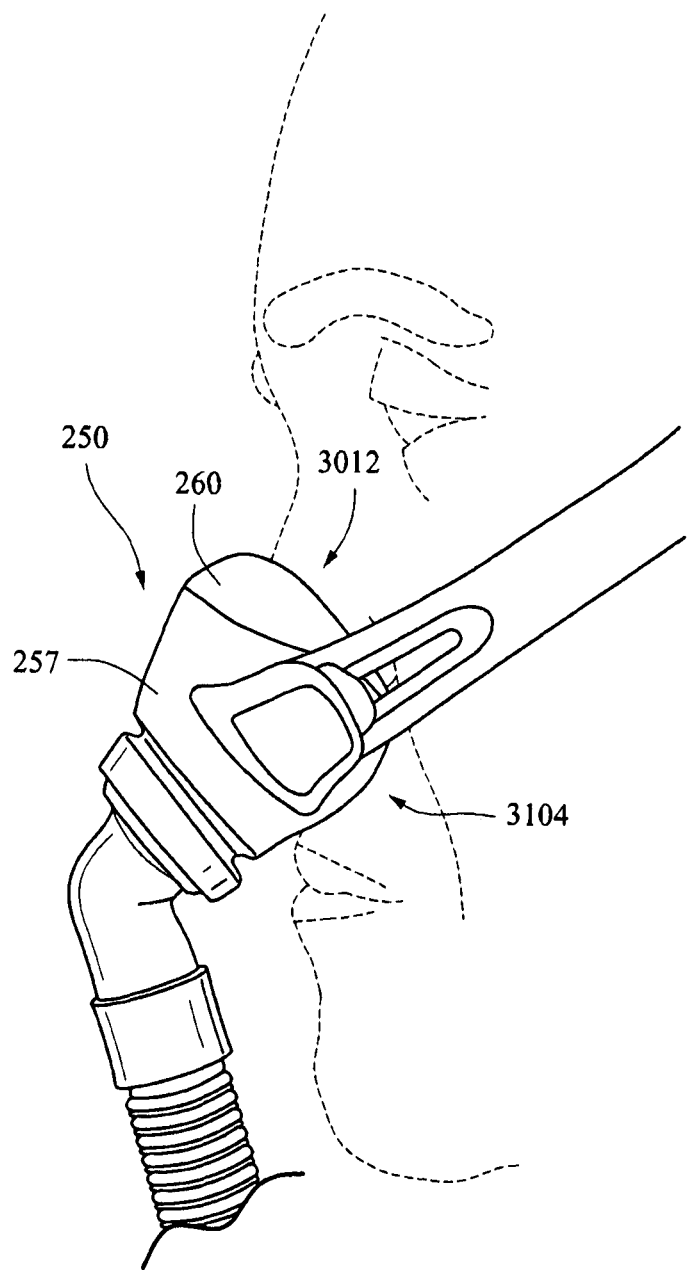
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
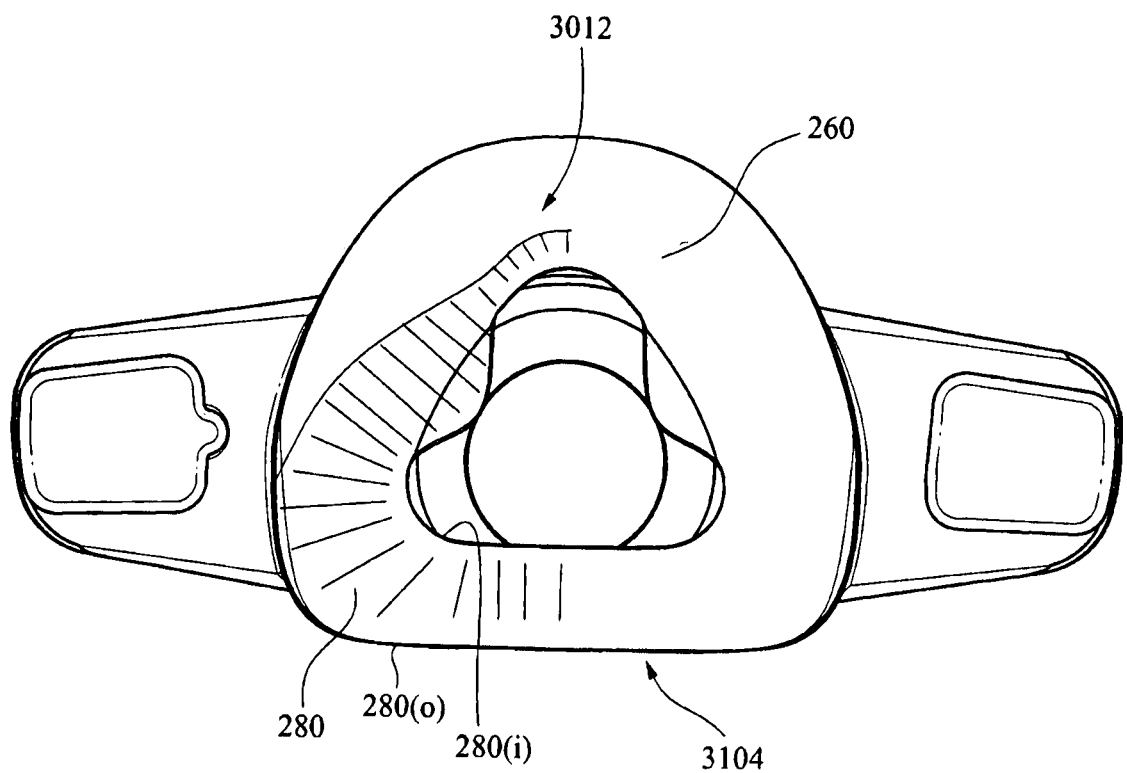
Figures 1, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
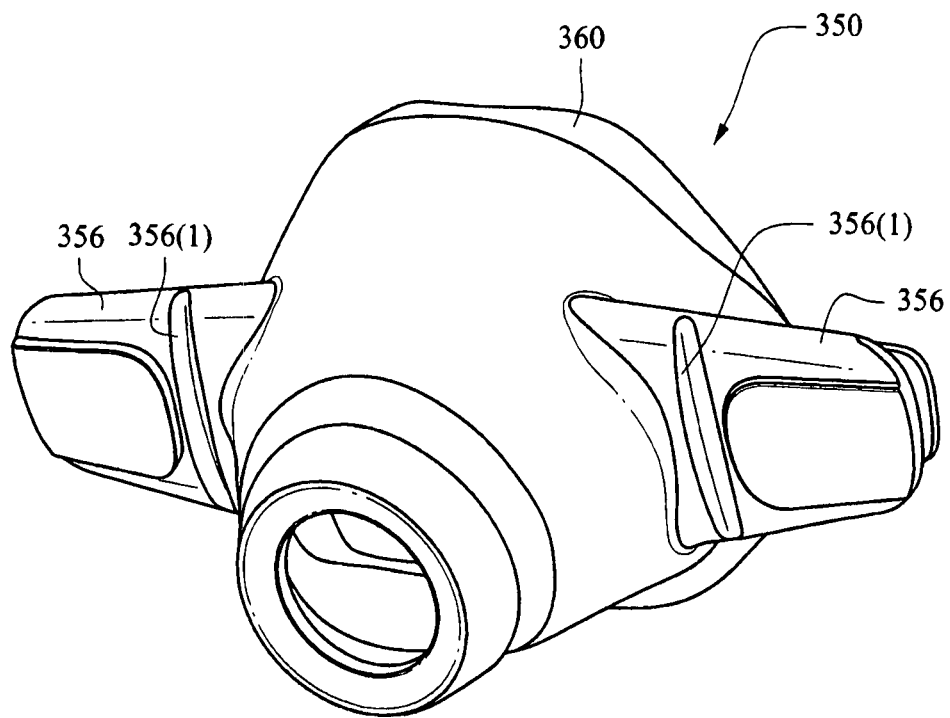
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
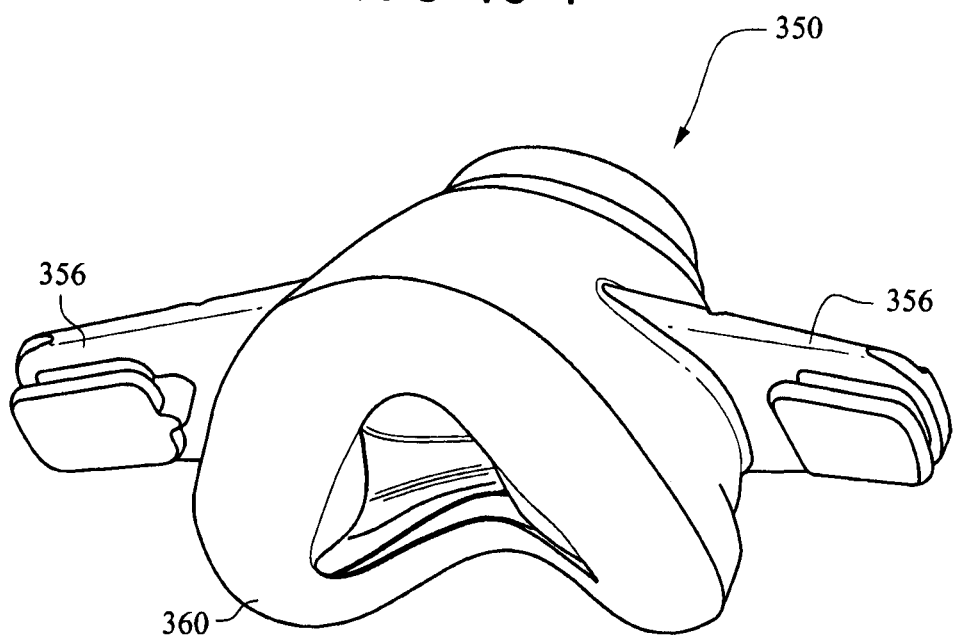
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
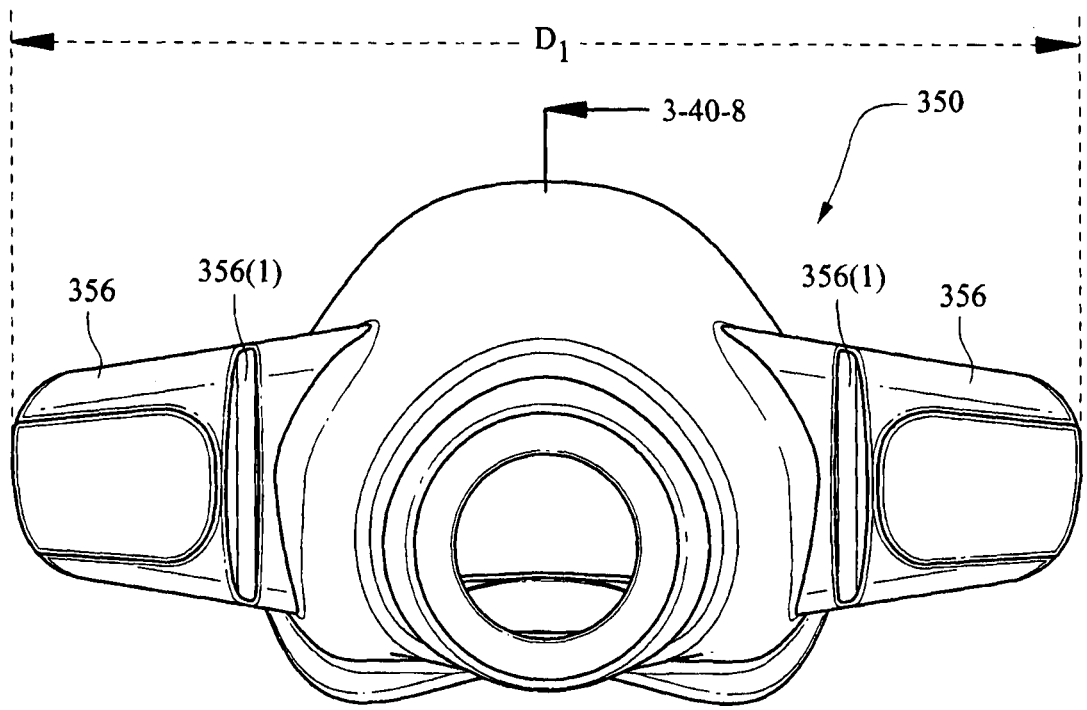
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
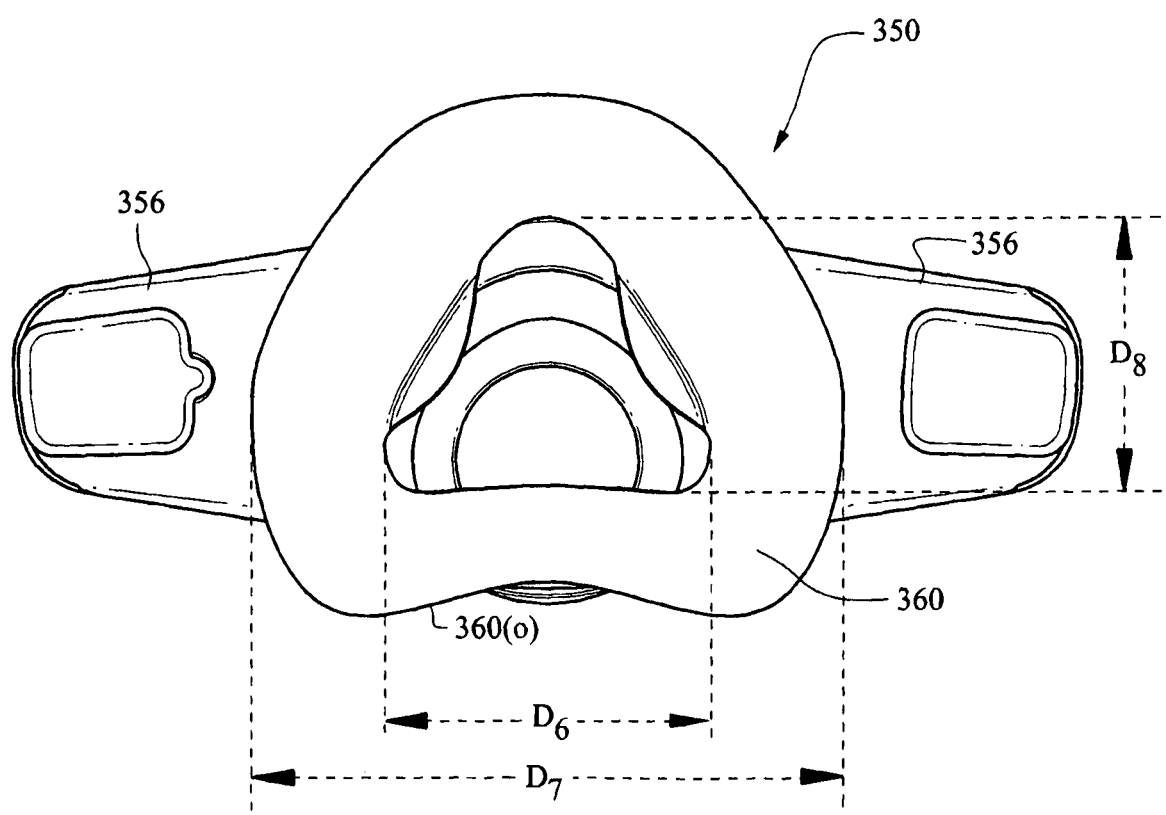
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
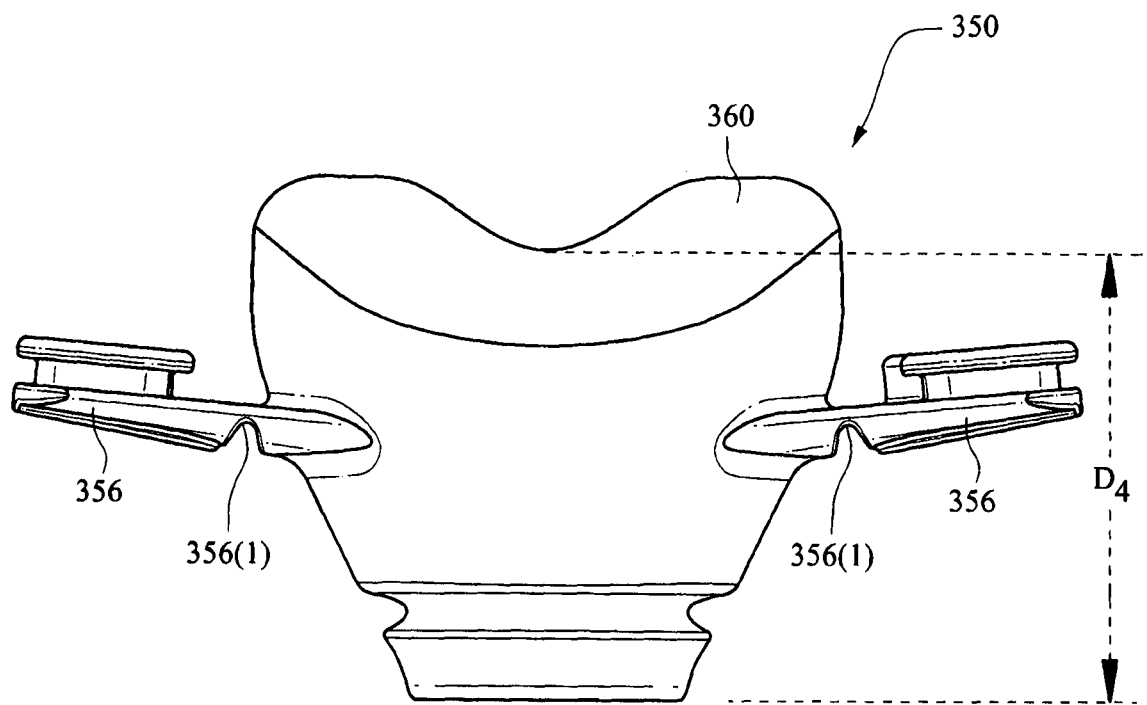
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
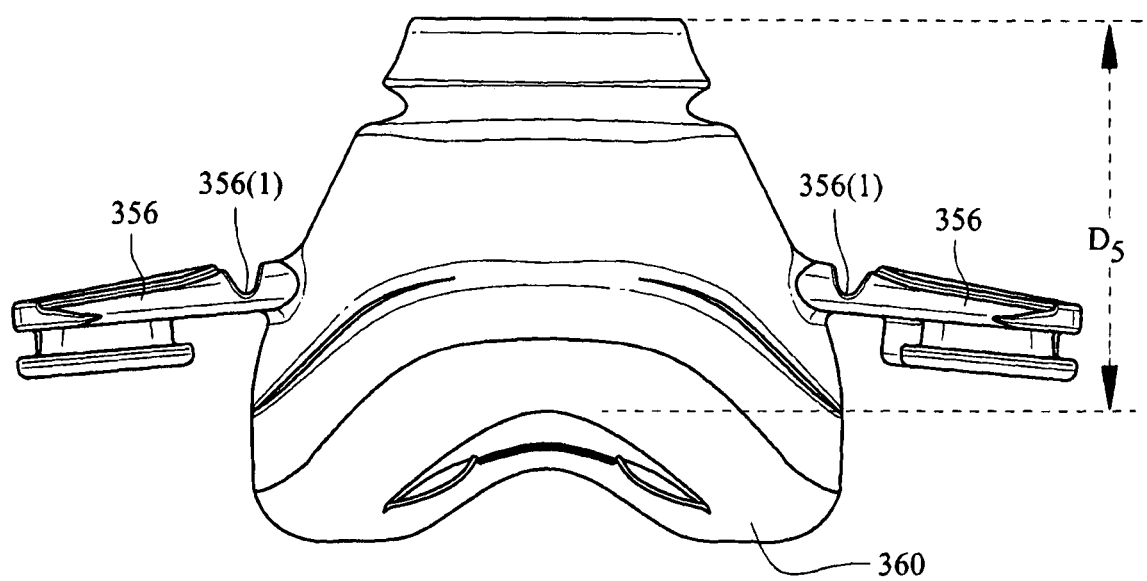
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
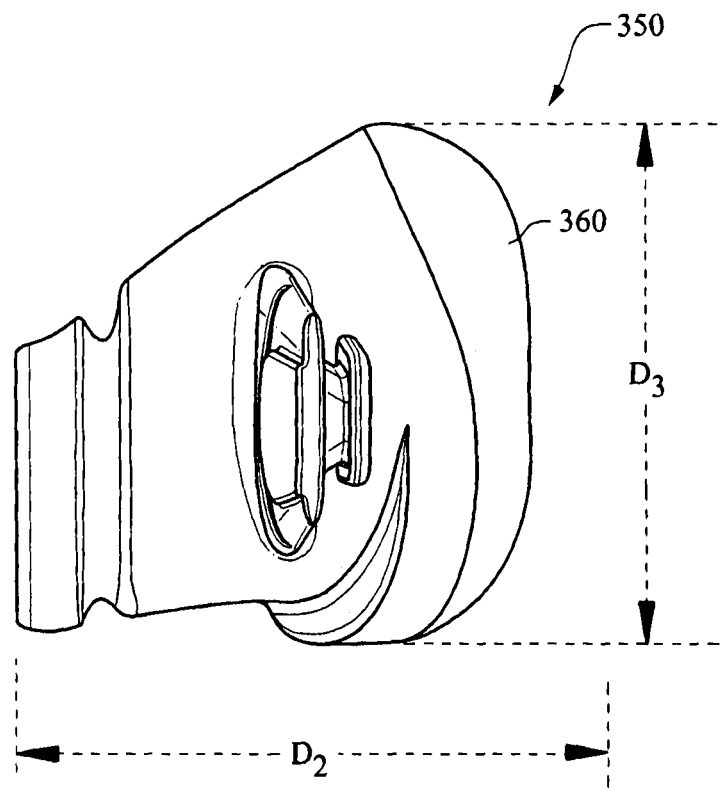
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
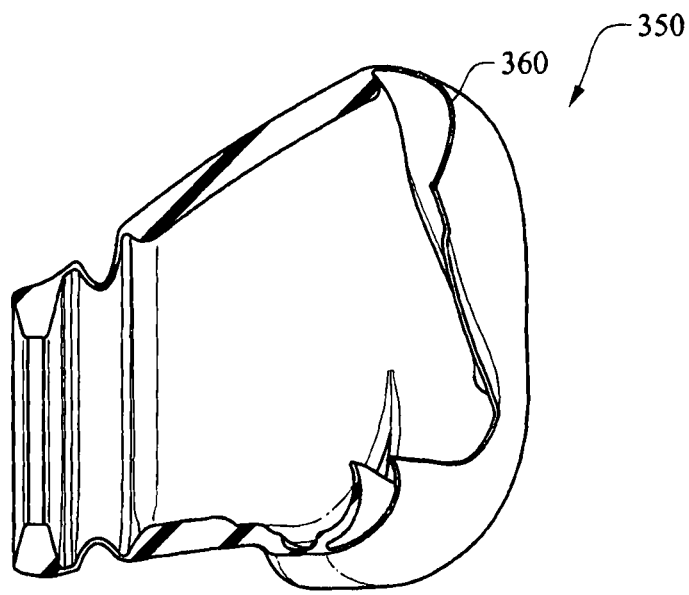
Figures 1, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
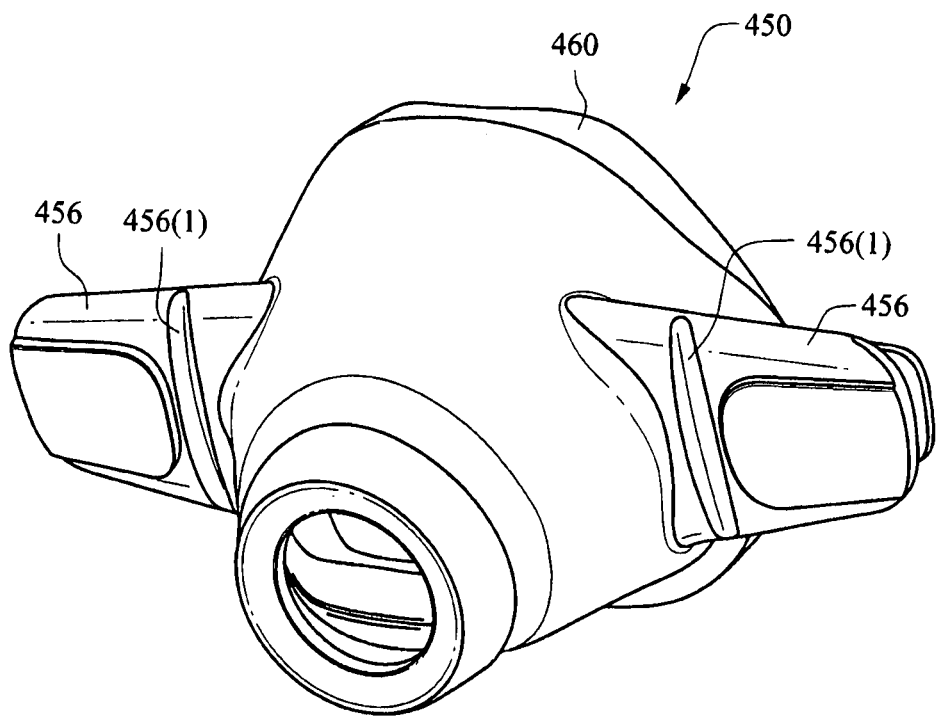
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
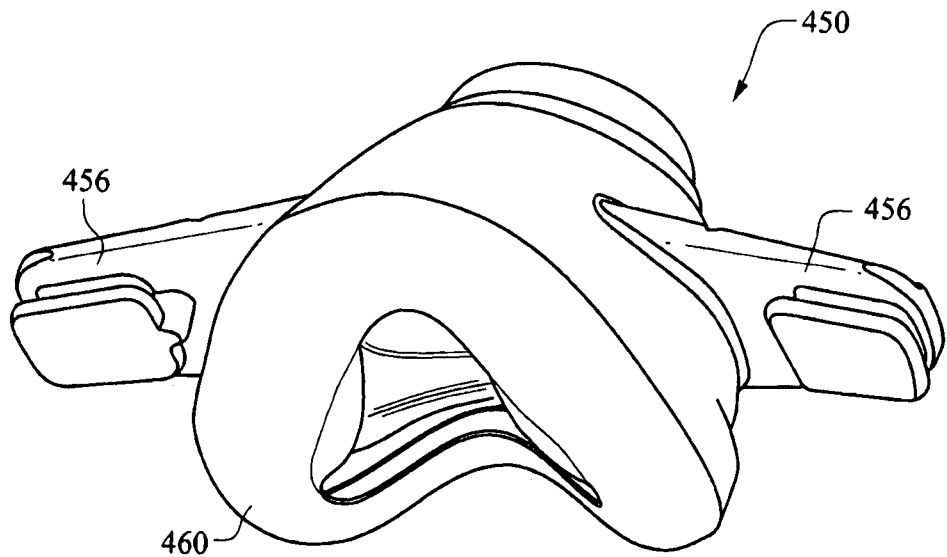
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
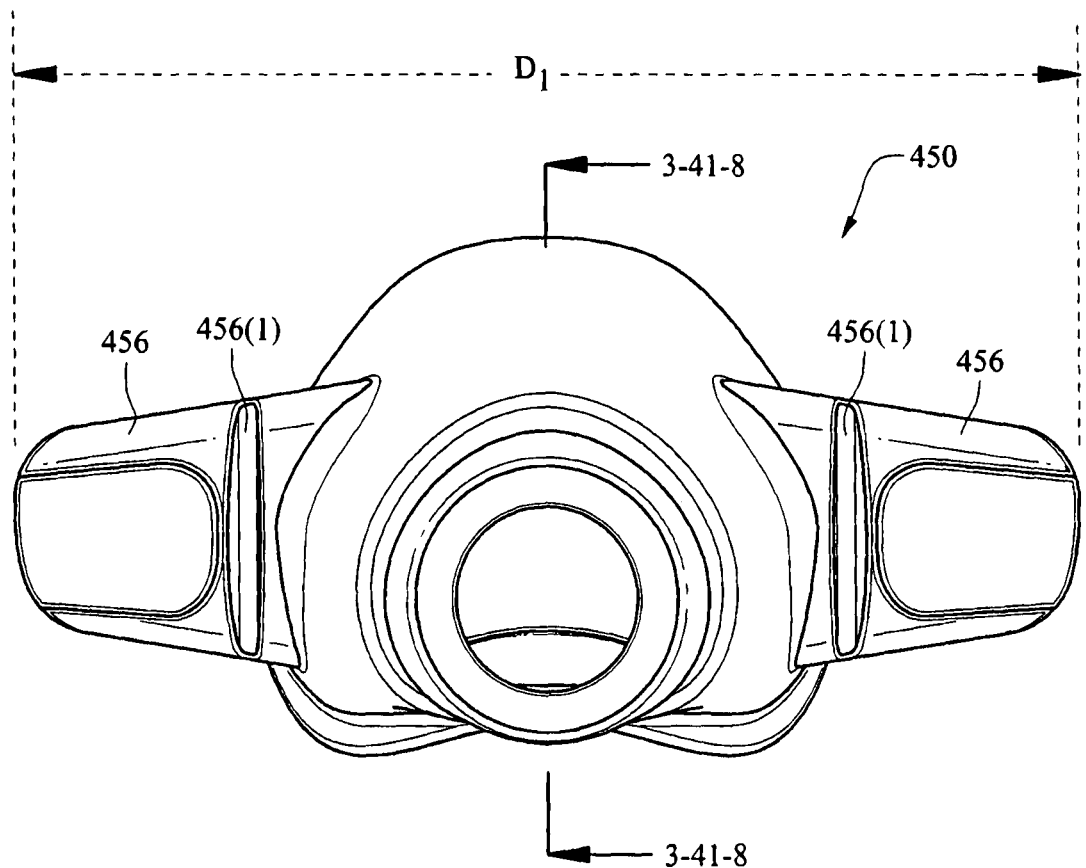
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
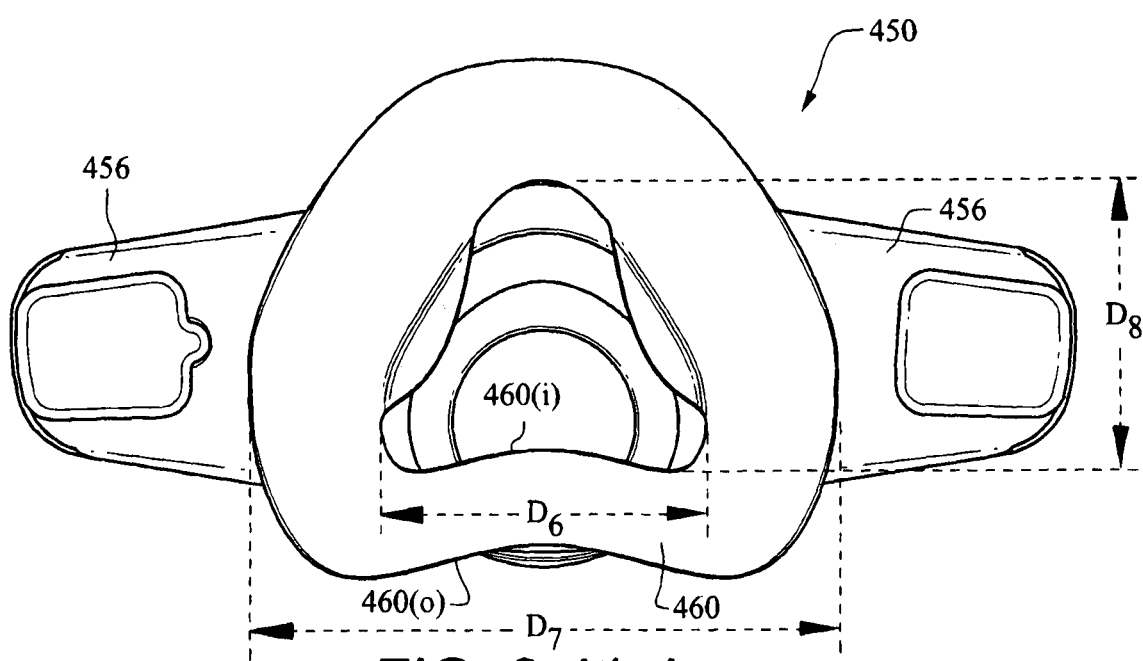
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
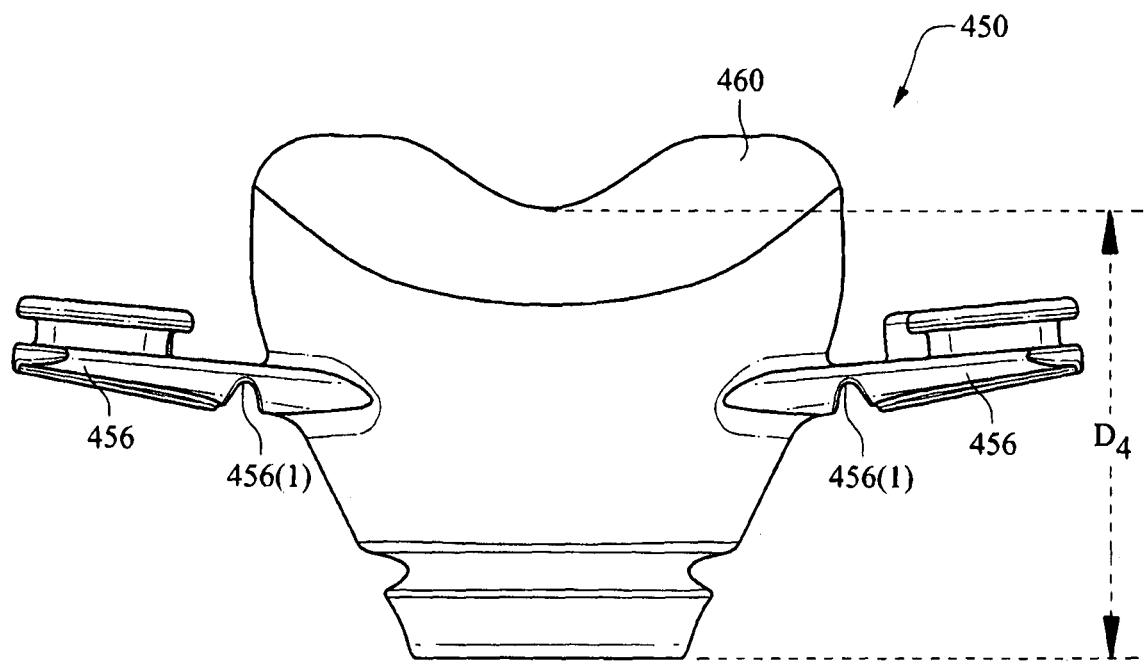
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
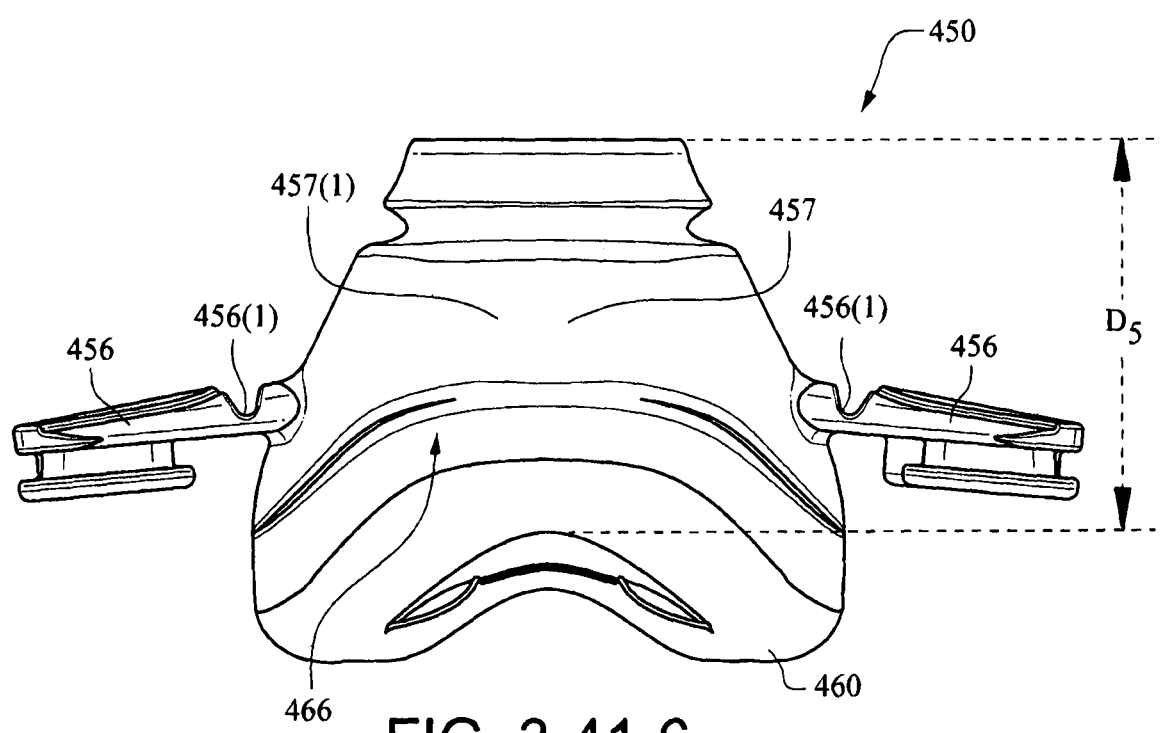
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
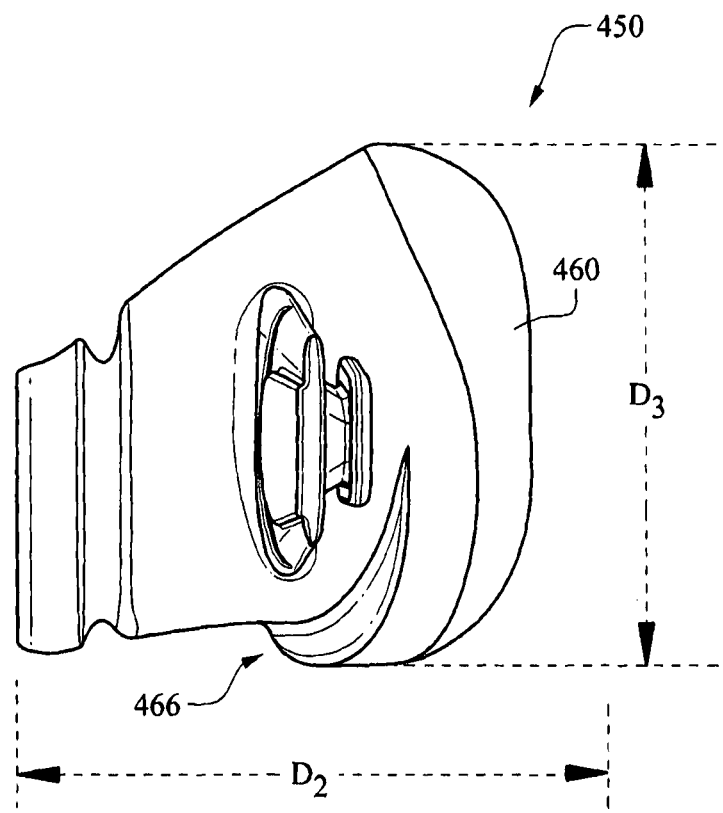
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
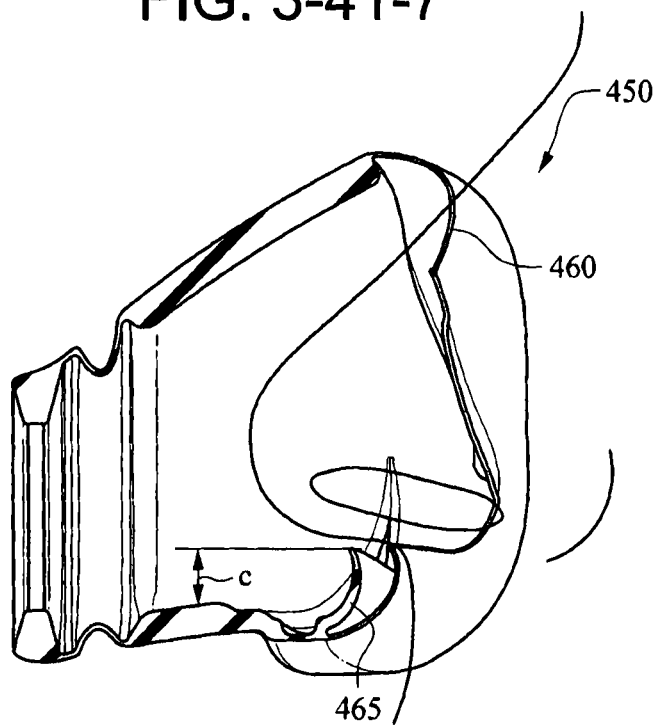
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
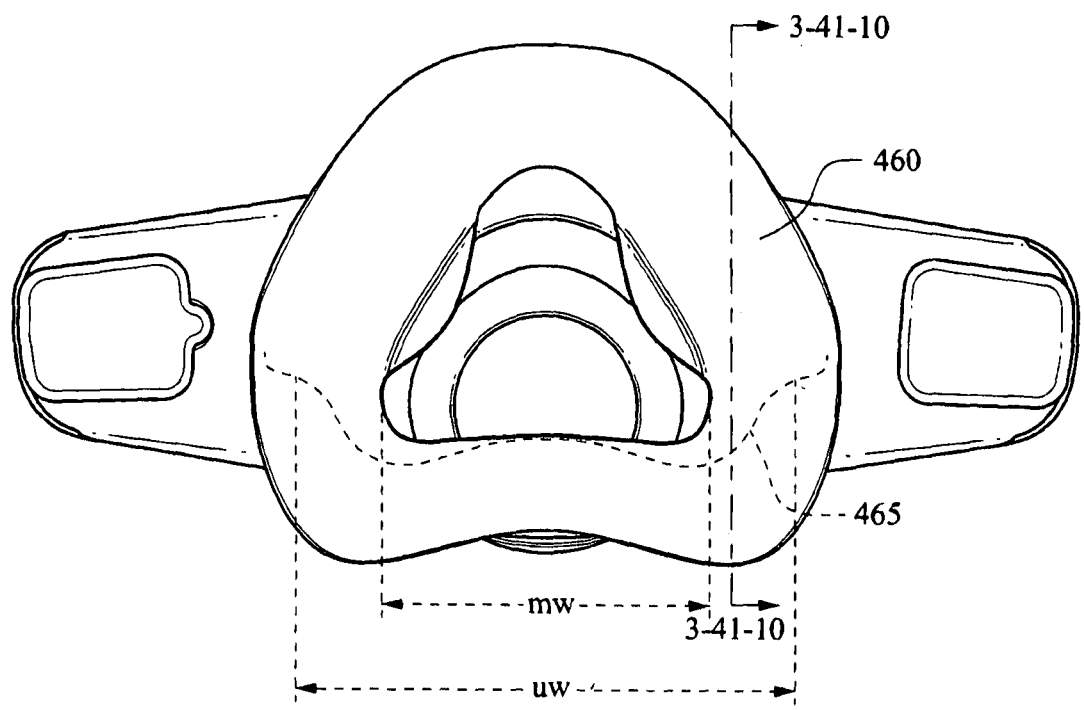
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
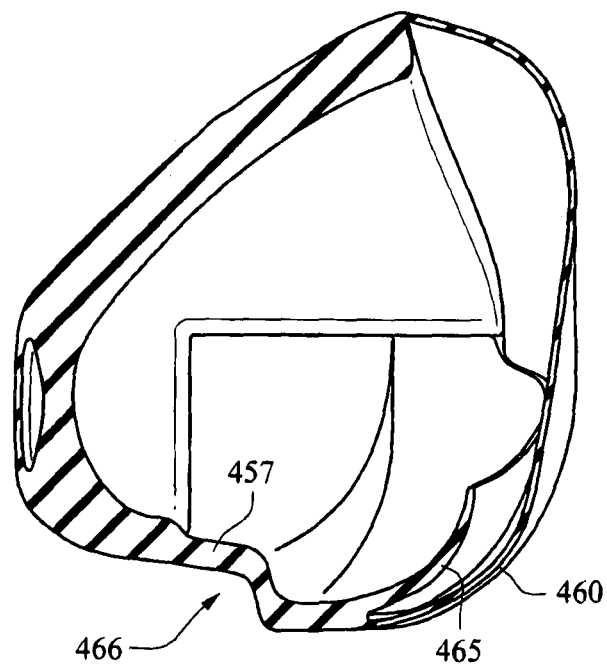
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
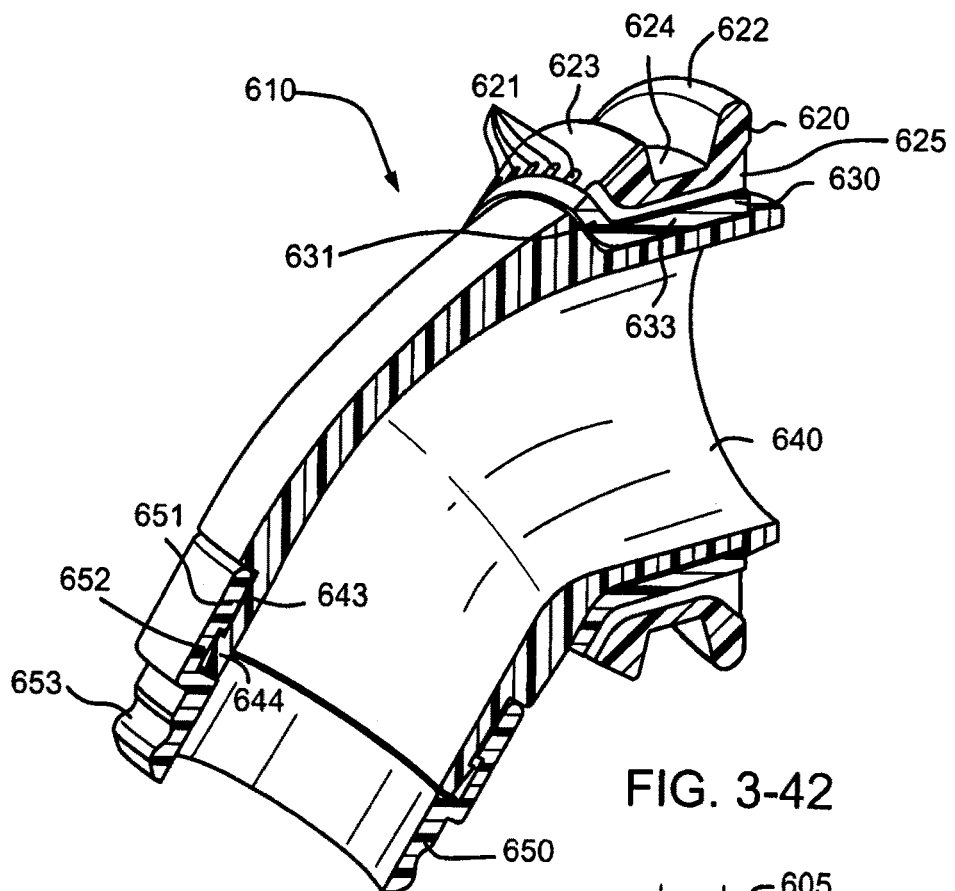
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
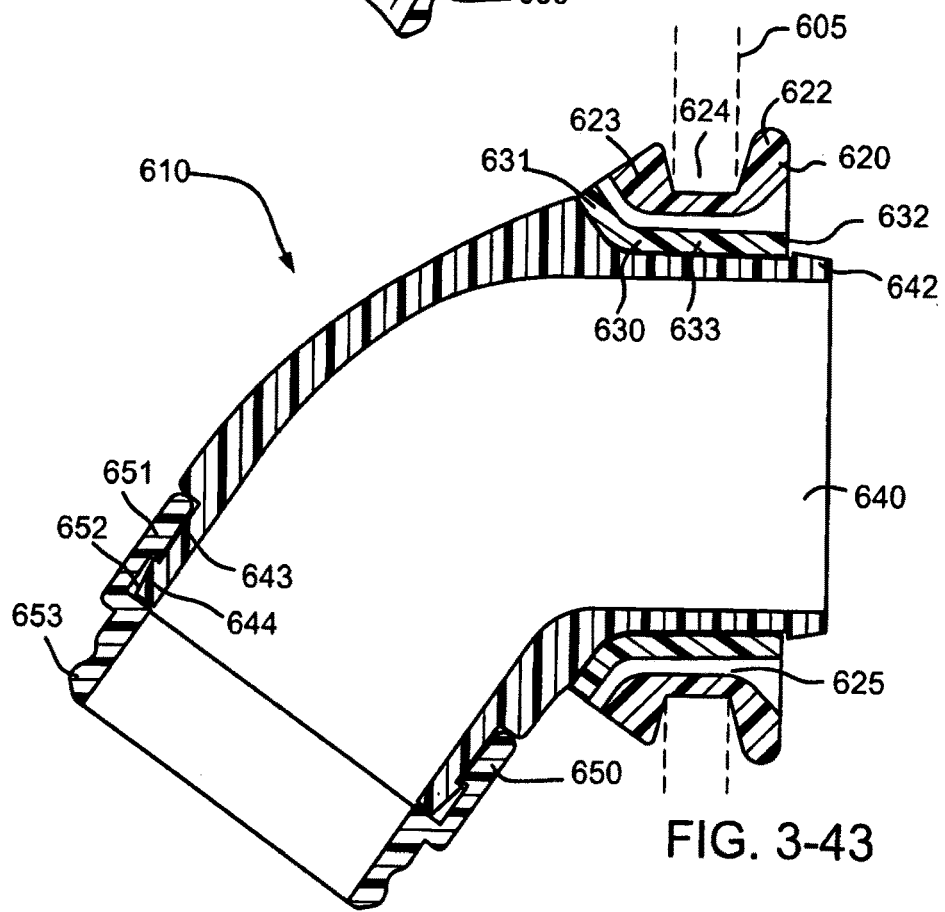
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
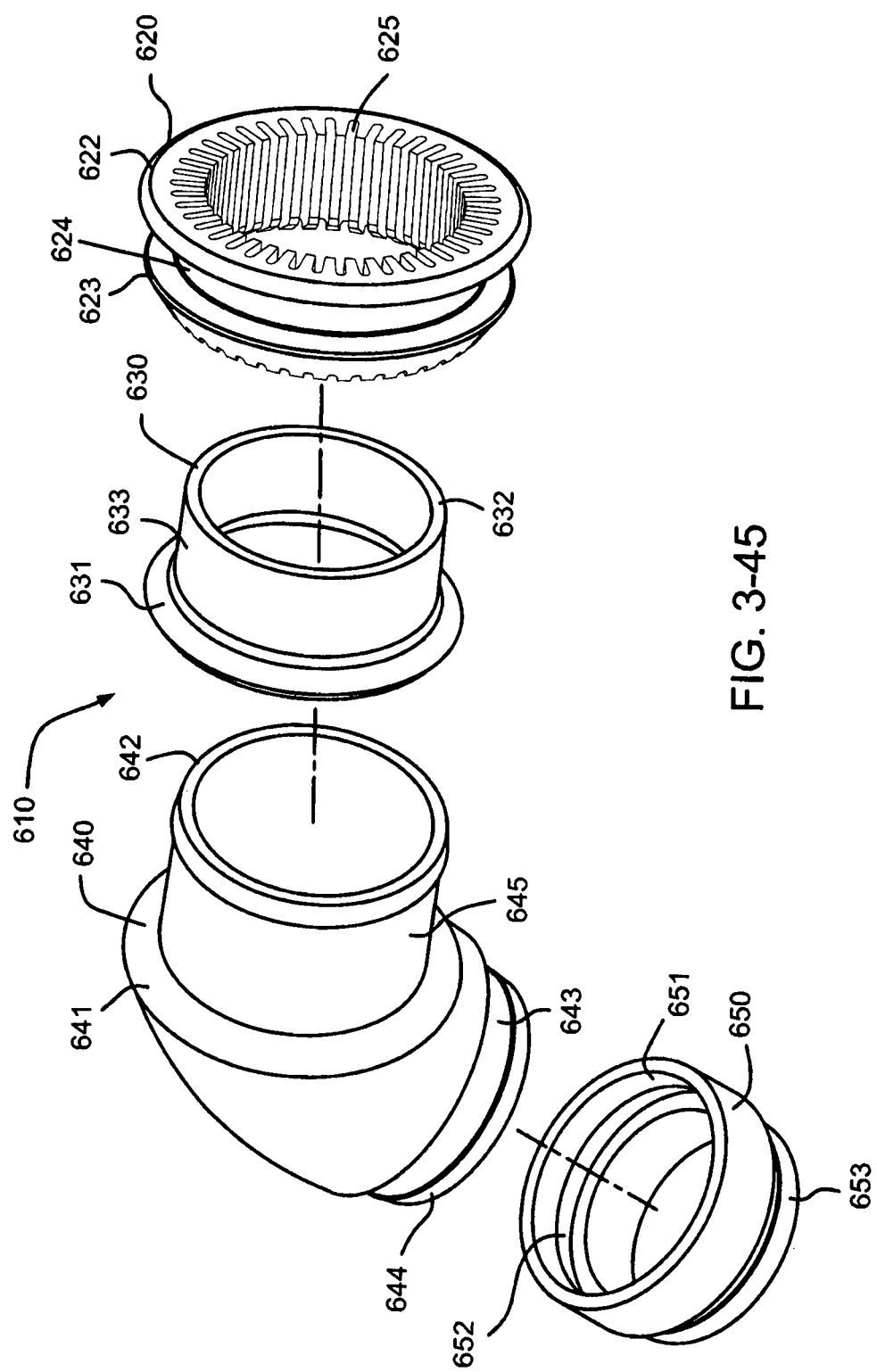
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
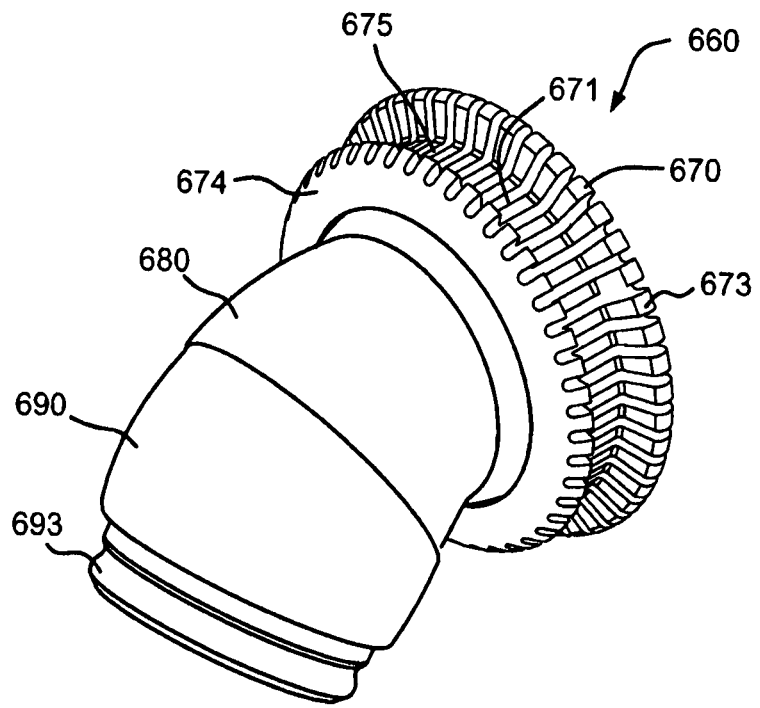
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
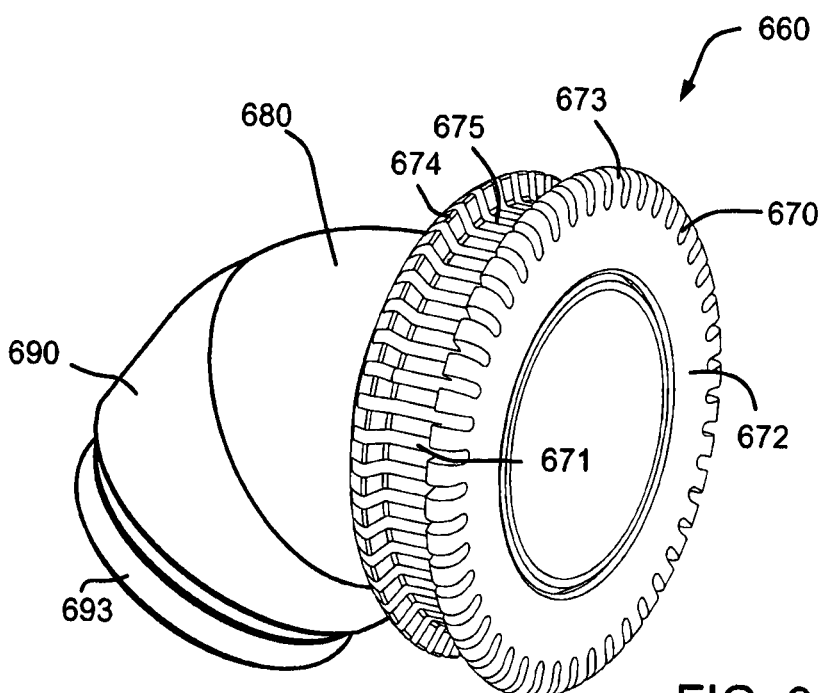
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
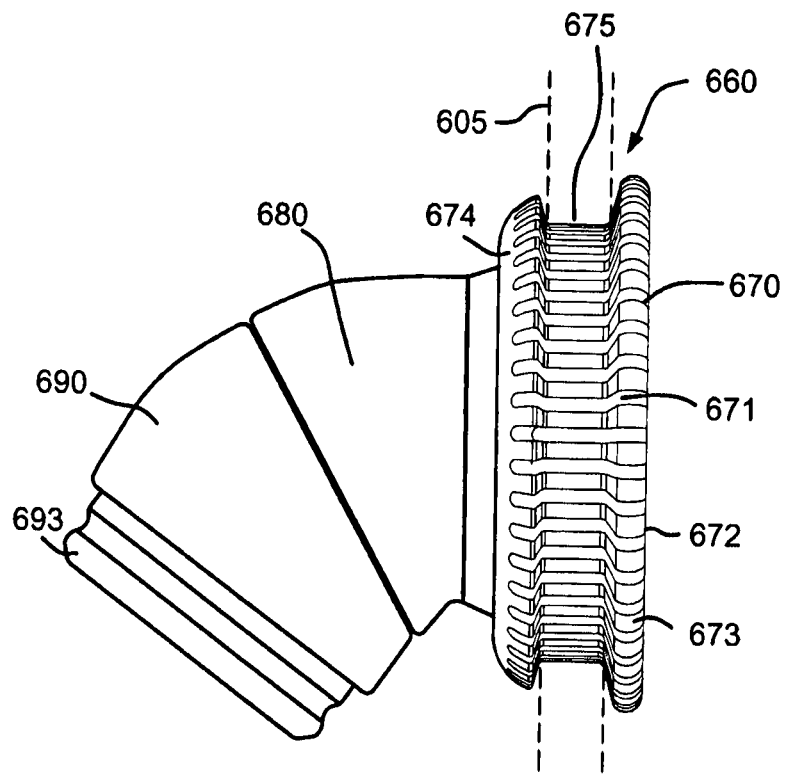
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
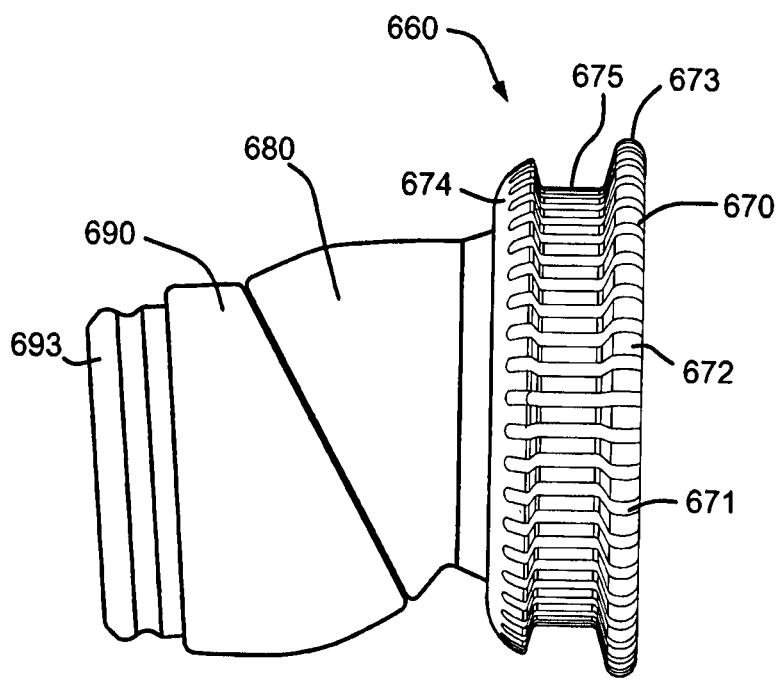
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
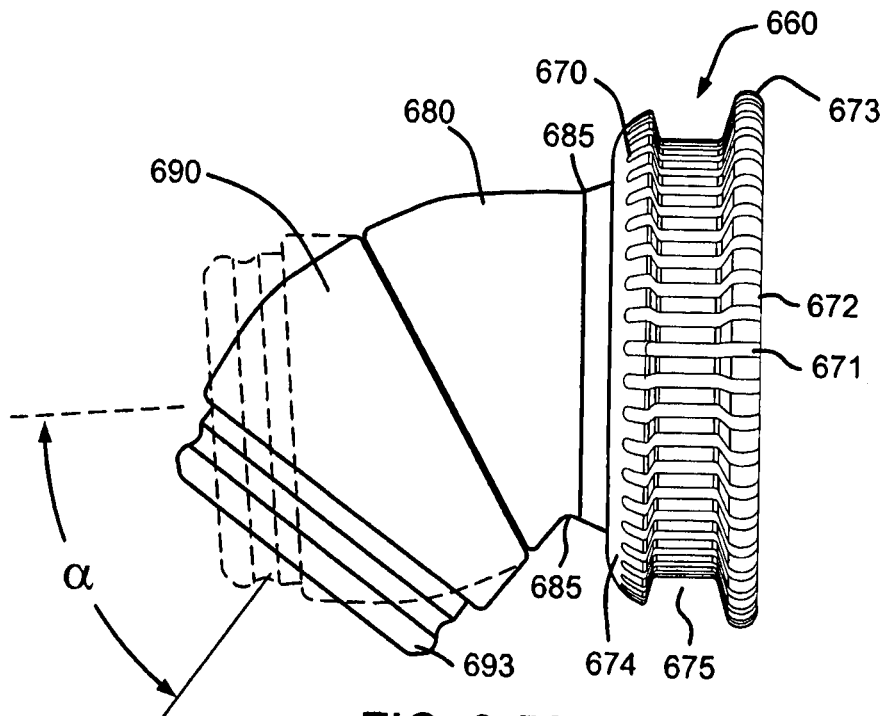
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
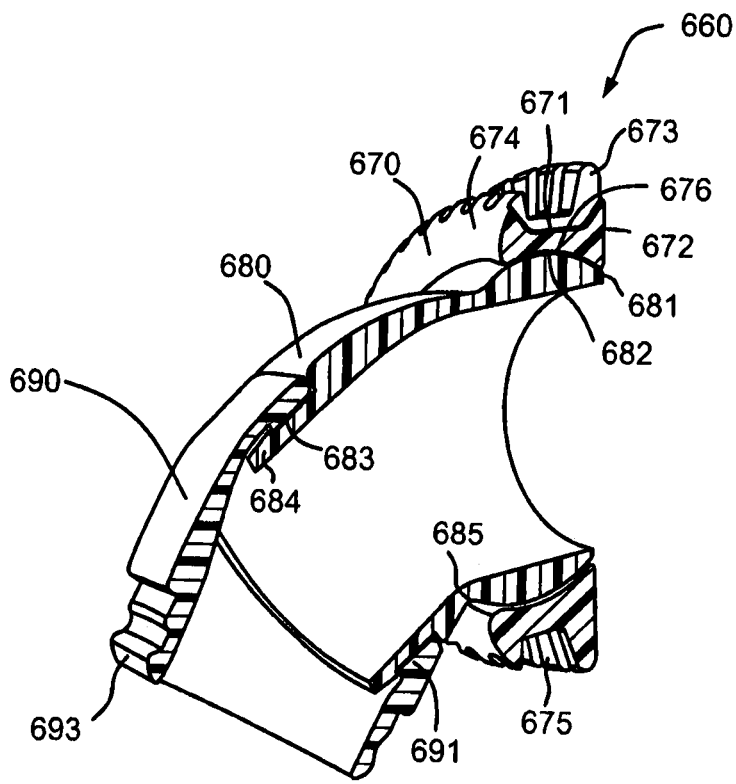
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
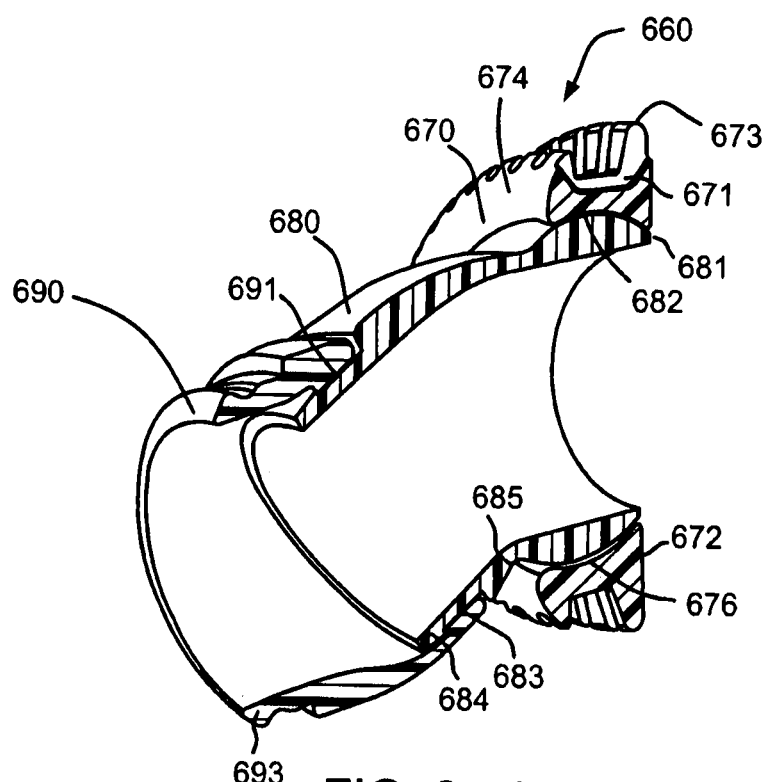
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
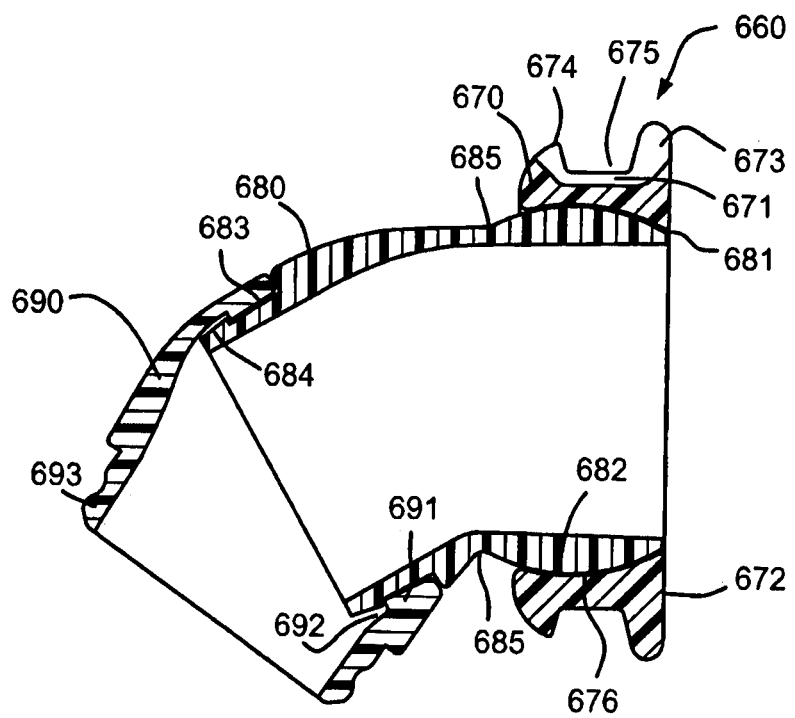
Figures 3, 54:
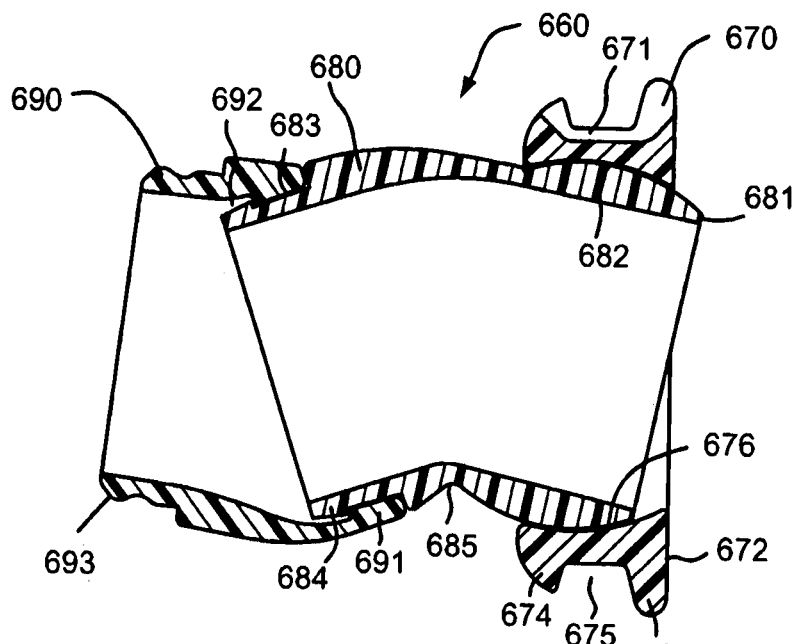

FIG. 3-54 is a cross sectional side view of the double swivel elbow and connector assembly in a third position or configuration.

Figures 3, 55:
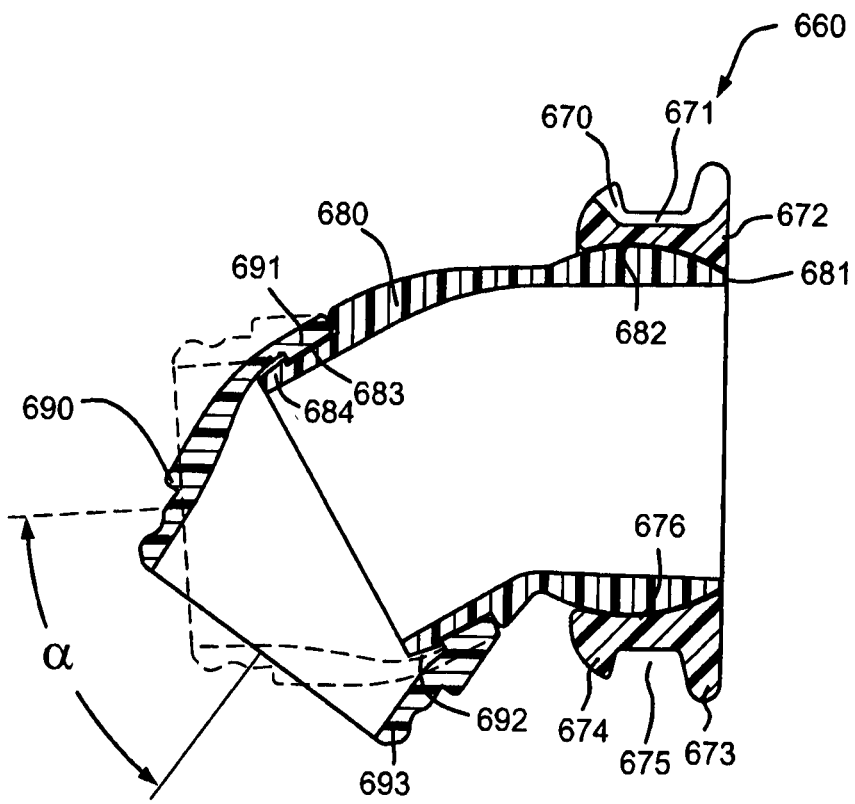

FIG. 3-55 is a cross sectional side view of the transition of the double swivel elbow and connector assembly from the first position to the second position.

Figures 3, 56:
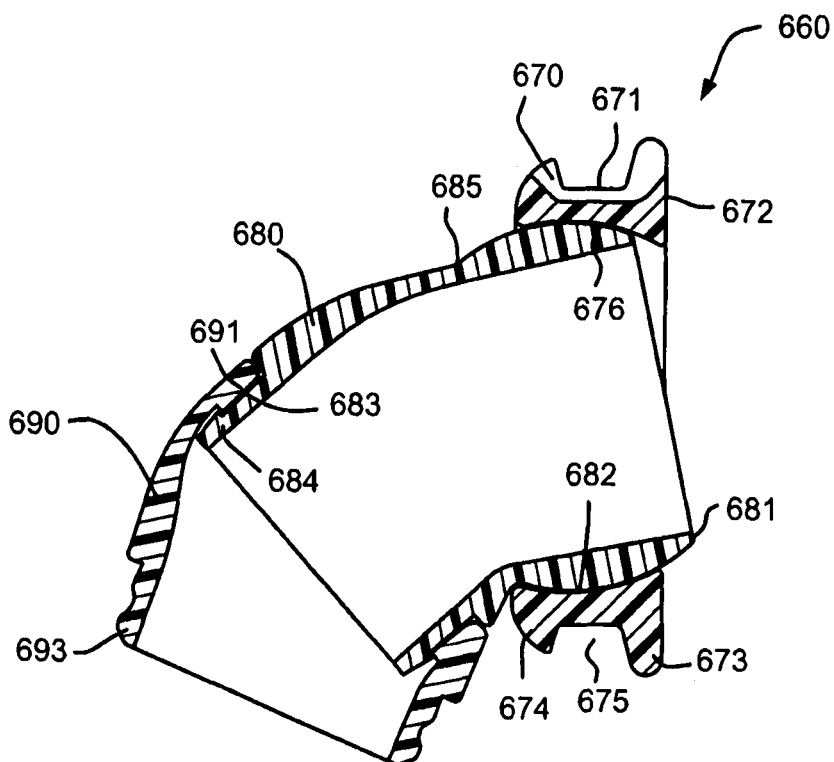

FIG. 3-56 is a cross sectional side view of the double swivel elbow and connector assembly in a fourth position or configuration.

Figures 3, 57:
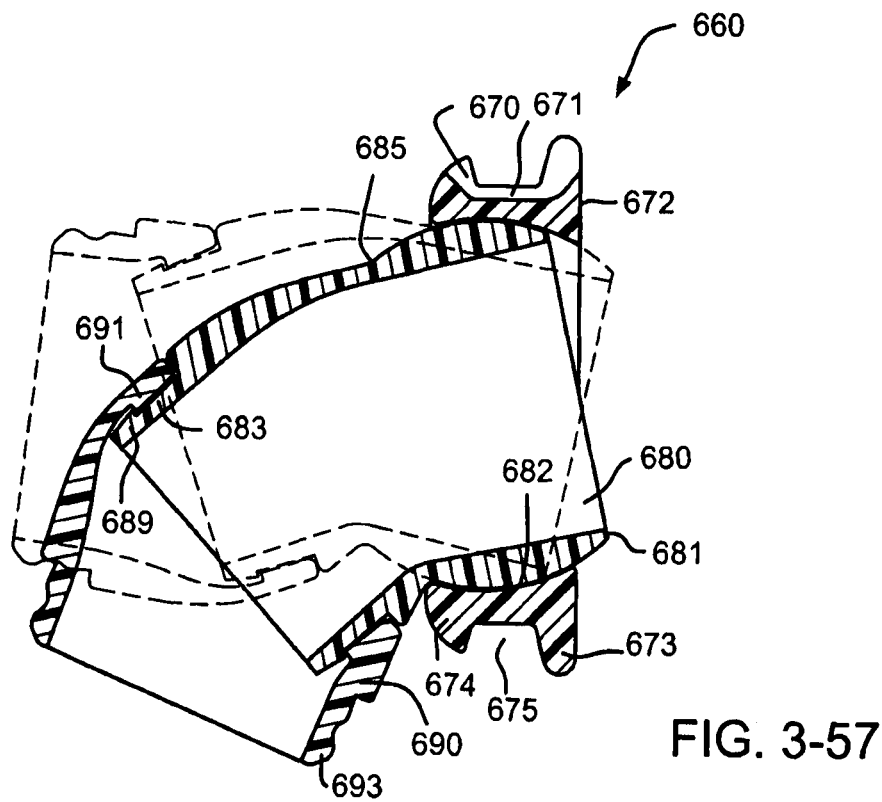

FIG. 3-57 is a cross sectional side view of the transition of the double swivel elbow and connector assembly from the third position to the fourth position.

Figures 3, 58:
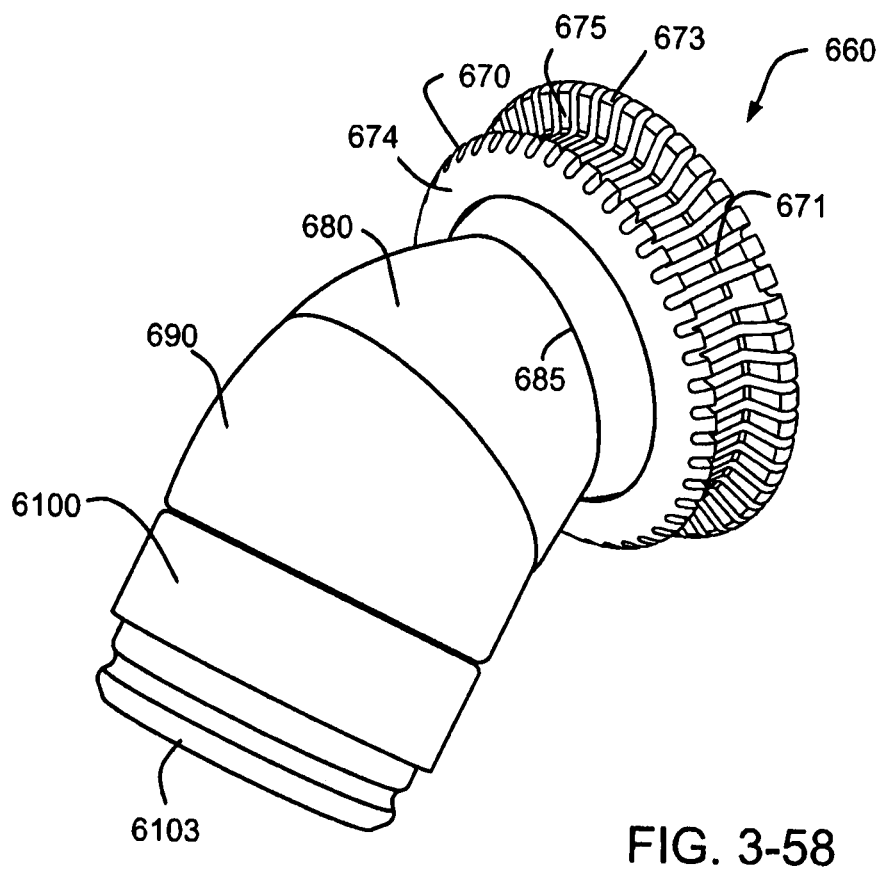
Figures 3, 59:
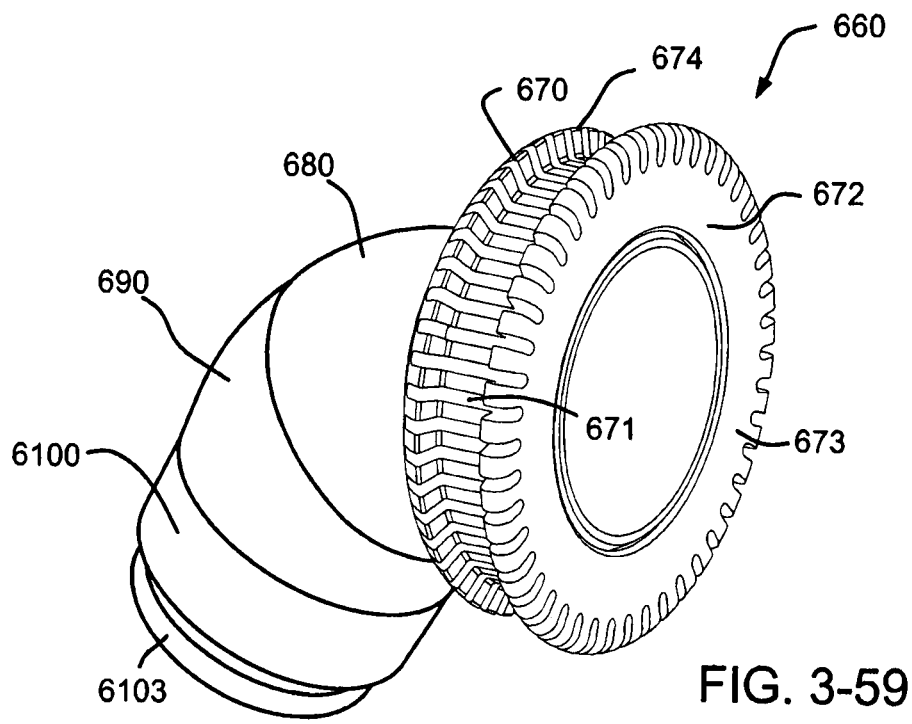

FIGS. 3-58 and 3-59 are isometric views of a triple swivel elbow and connector assembly including a second swivel cuff according to still another example of the technology in a first position or configuration.

Figures 3, 60:
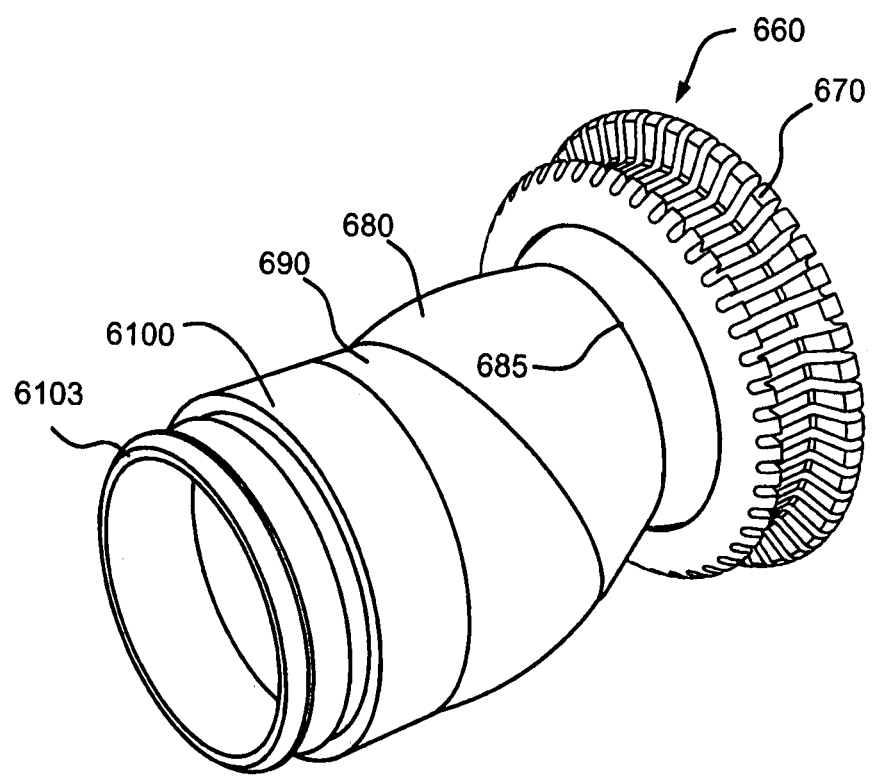

FIG. 3-60 is an isometric view of the triple swivel elbow and connector assembly of FIGS. 3-58 and 3-59 in a second position or configuration.

Figures 3, 61:
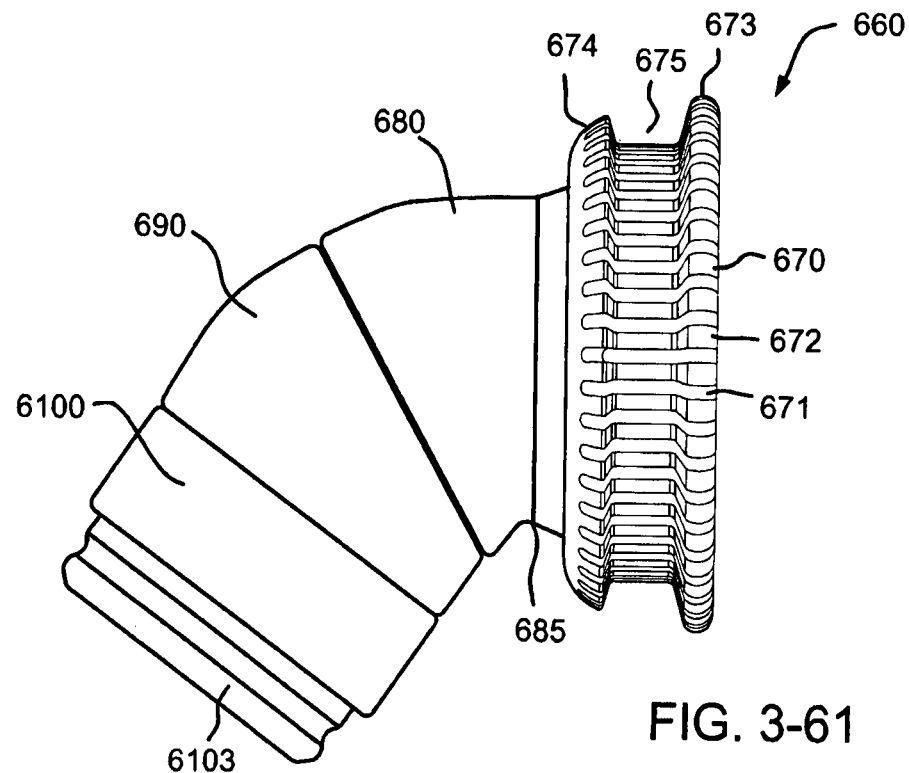

FIG. 3-61 is a side view of the triple swivel elbow and connector assembly of FIGS. 3-58 and 3-59.

Figures 3, 62:
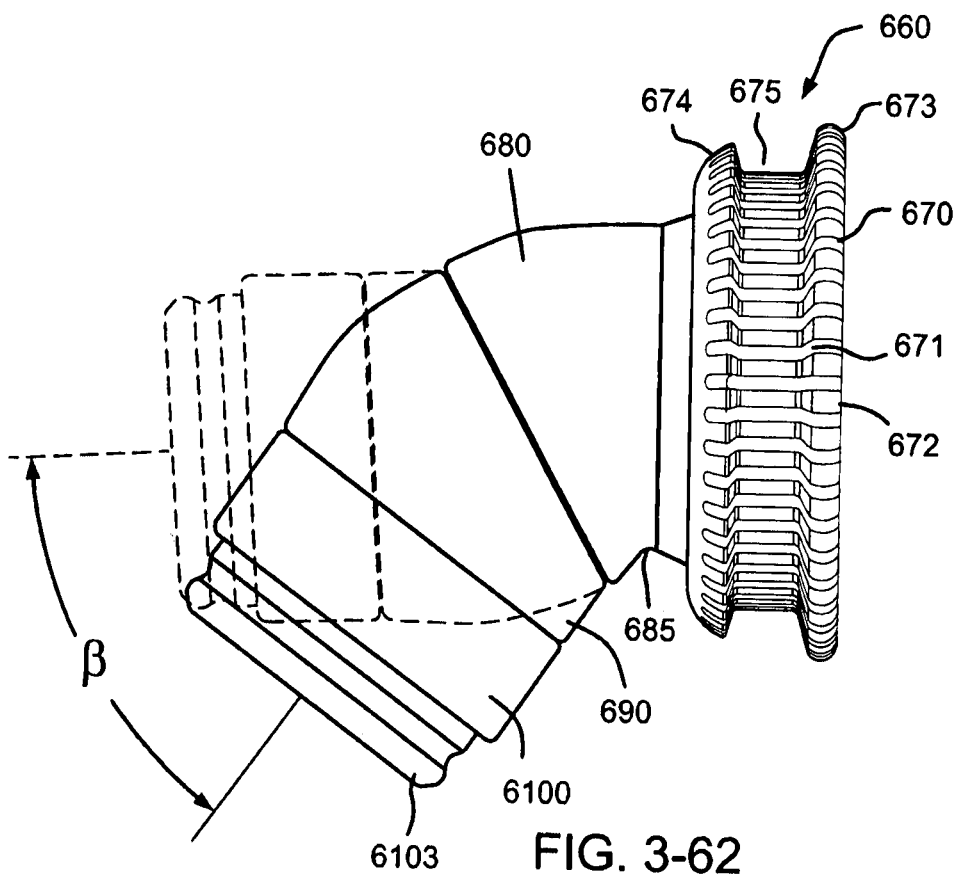

FIG. 3-62 is a side view of the transition of the triple swivel elbow and connector assembly from the first position to the second position.

Figures 3, 63:
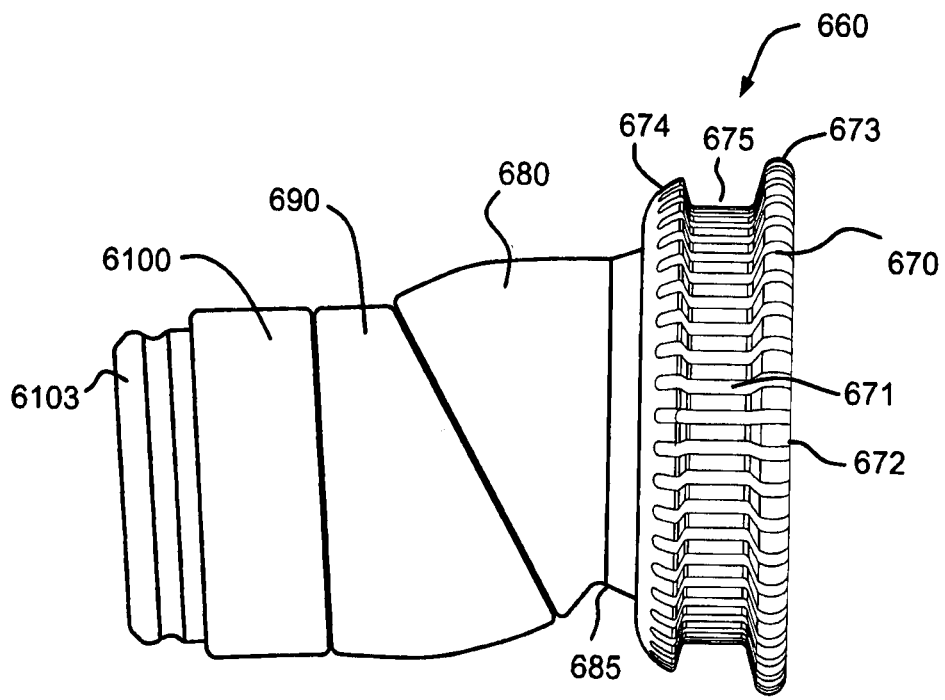

FIG. 3-63 is side view of the triple swivel elbow and connector assembly in the second position.

Figures 3, 64:
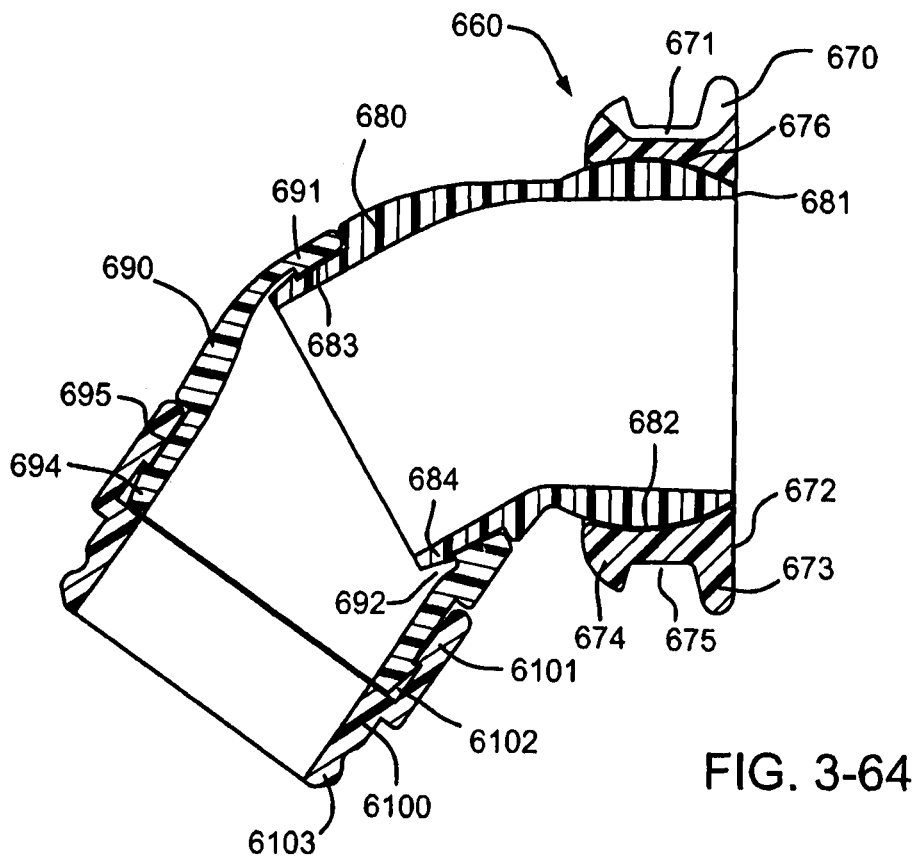

FIG. 3-64 is a cross sectional side view of the triple swivel elbow and connector assembly in the first position.

Figures 3, 65:
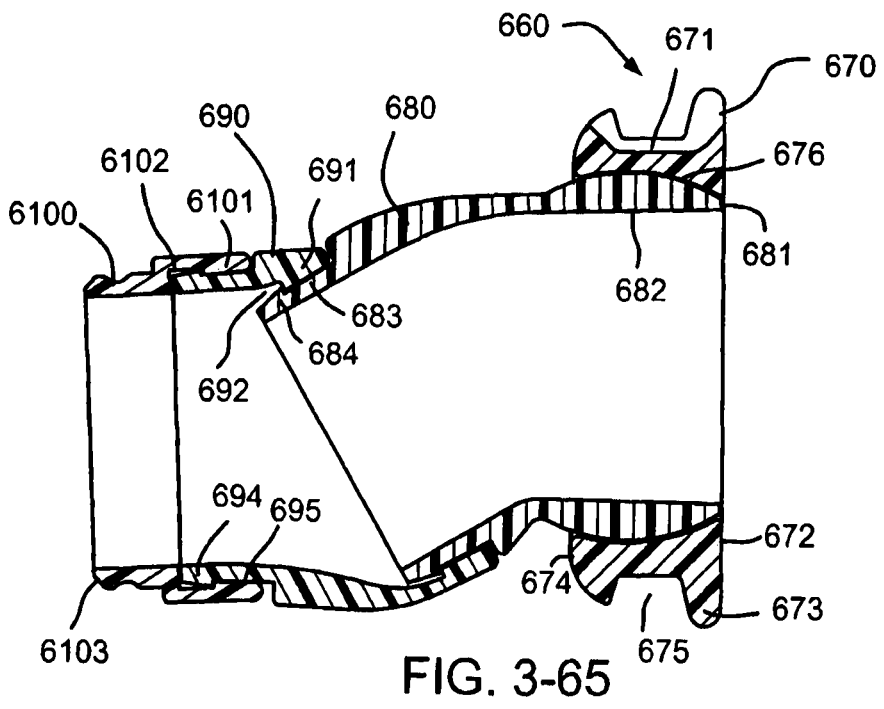

FIG. 3-65 is a cross sectional side view of the triple swivel elbow and connector assembly in the second position.

Figures 3, 66:
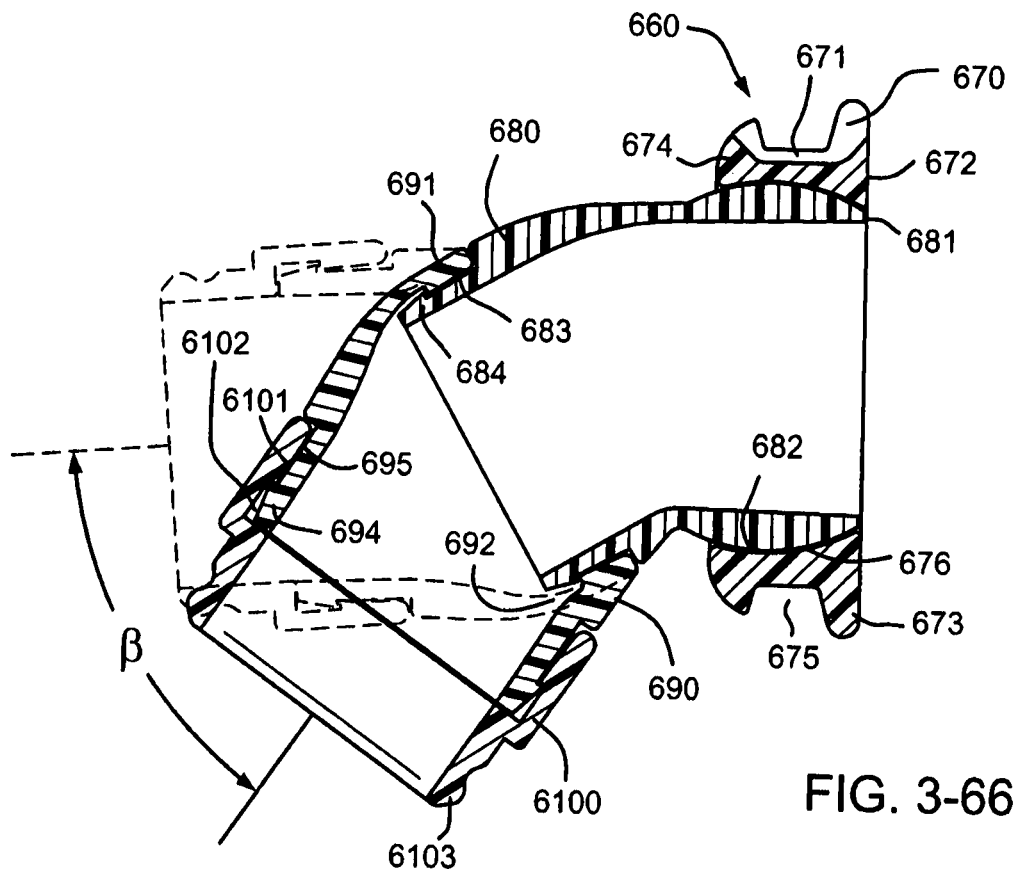

FIG. 3-66 is side view of the transition of the triple swivel elbow and connector assembly from the first position to the second position.

Figures 3, 67:
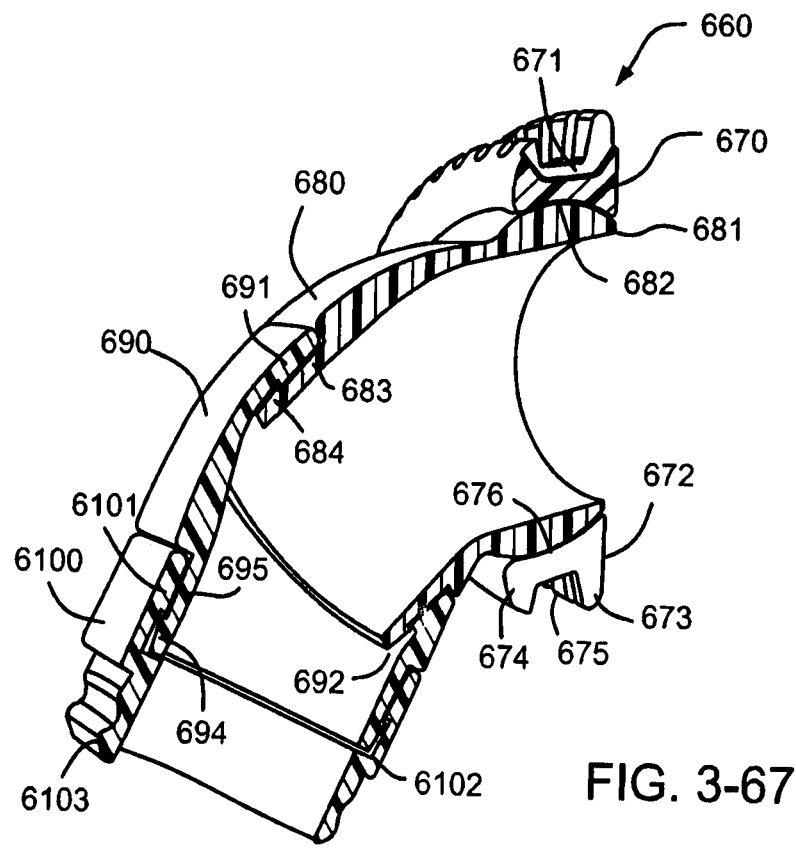

FIG. 3-67 is a cross sectional isometric view of the triple swivel elbow and connector assembly in the first position.

Figures 3, 68:
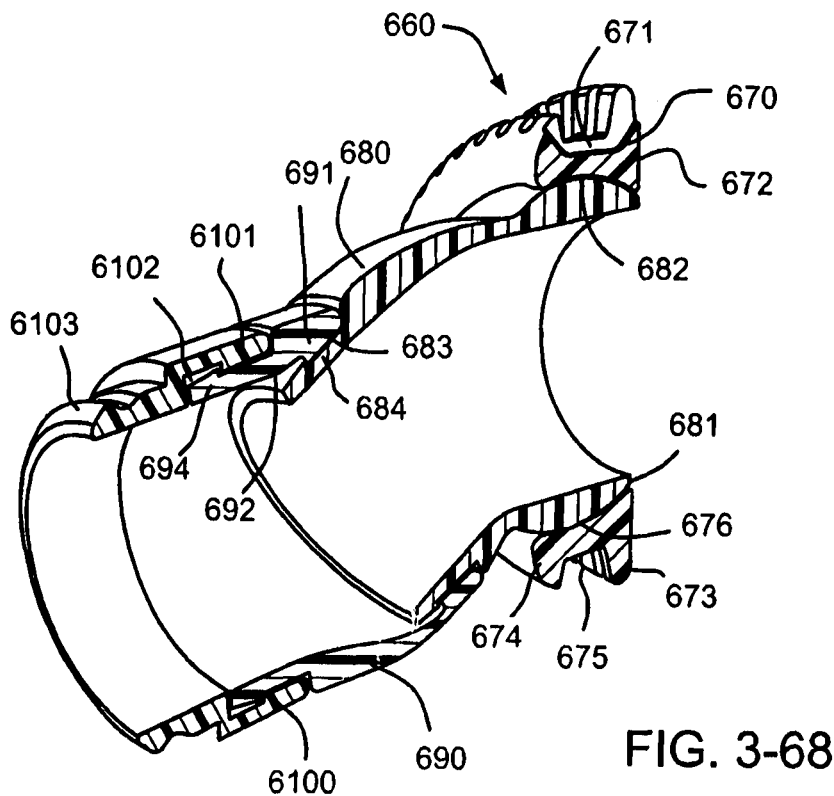

FIG. 3-68 is a cross sectional isometric view of the triple swivel elbow and connector assembly in the second position.

Figures 3, 69:
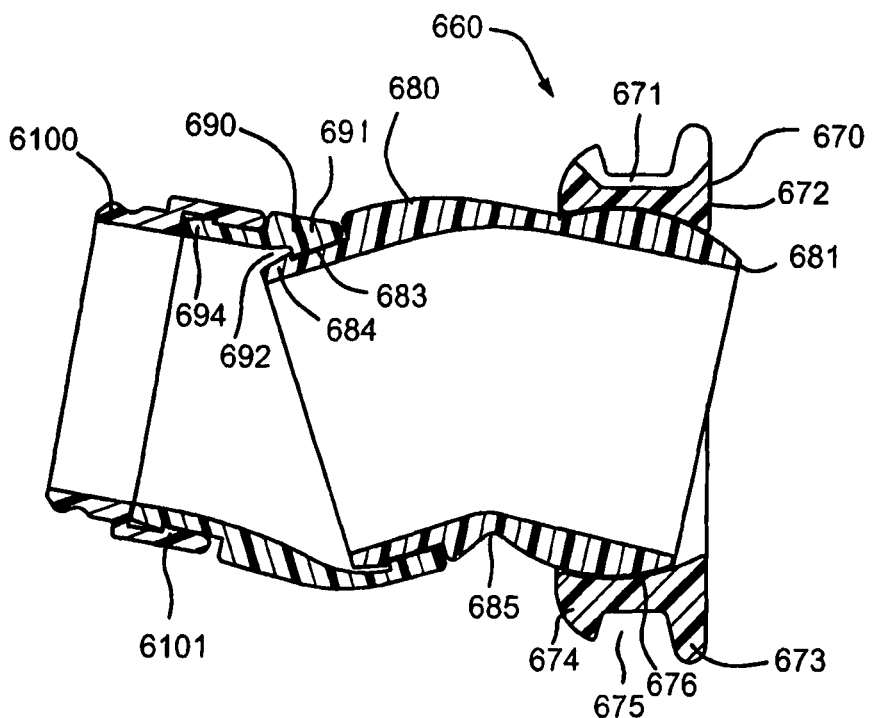

FIG. 3-69 is a cross sectional side view of the triple swivel elbow and connector assembly in a third position or configuration.

Figures 3, 70:
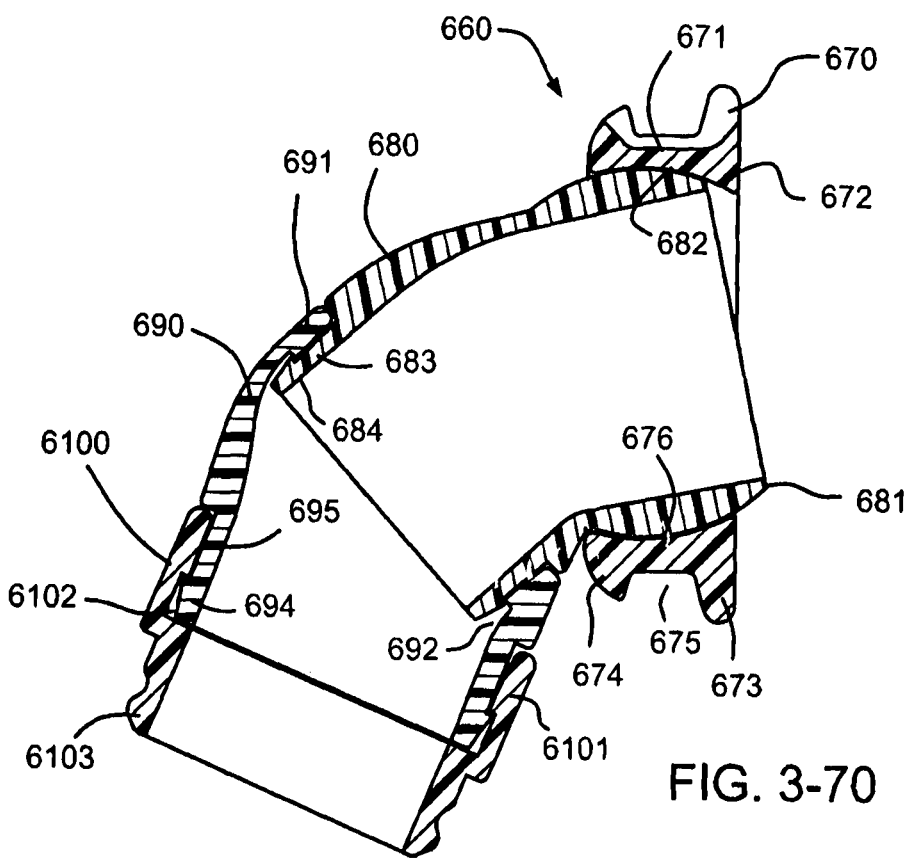

FIG. 3-70 is a cross sectional side view of the triple swivel elbow and connector assembly in a fourth position or configuration.

Figures 3, 71:
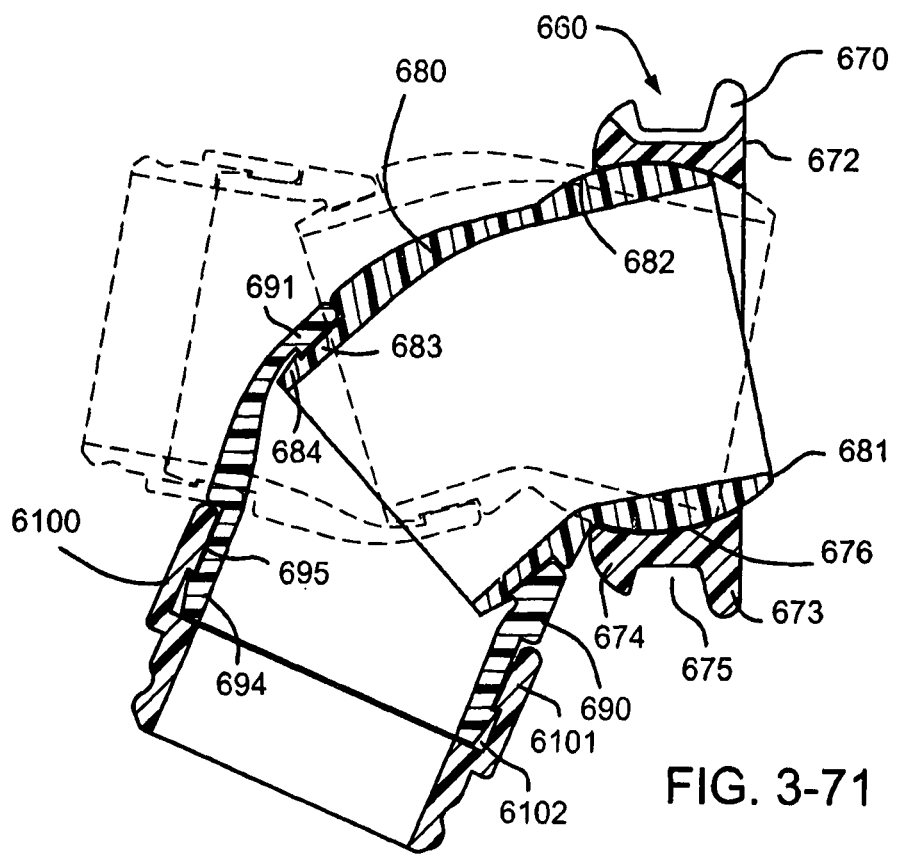

FIG. 3-71 is a cross sectional side view of the transition of the swivel elbow and connector assembly from the third position to the fourth position.

Figures 3, 72:
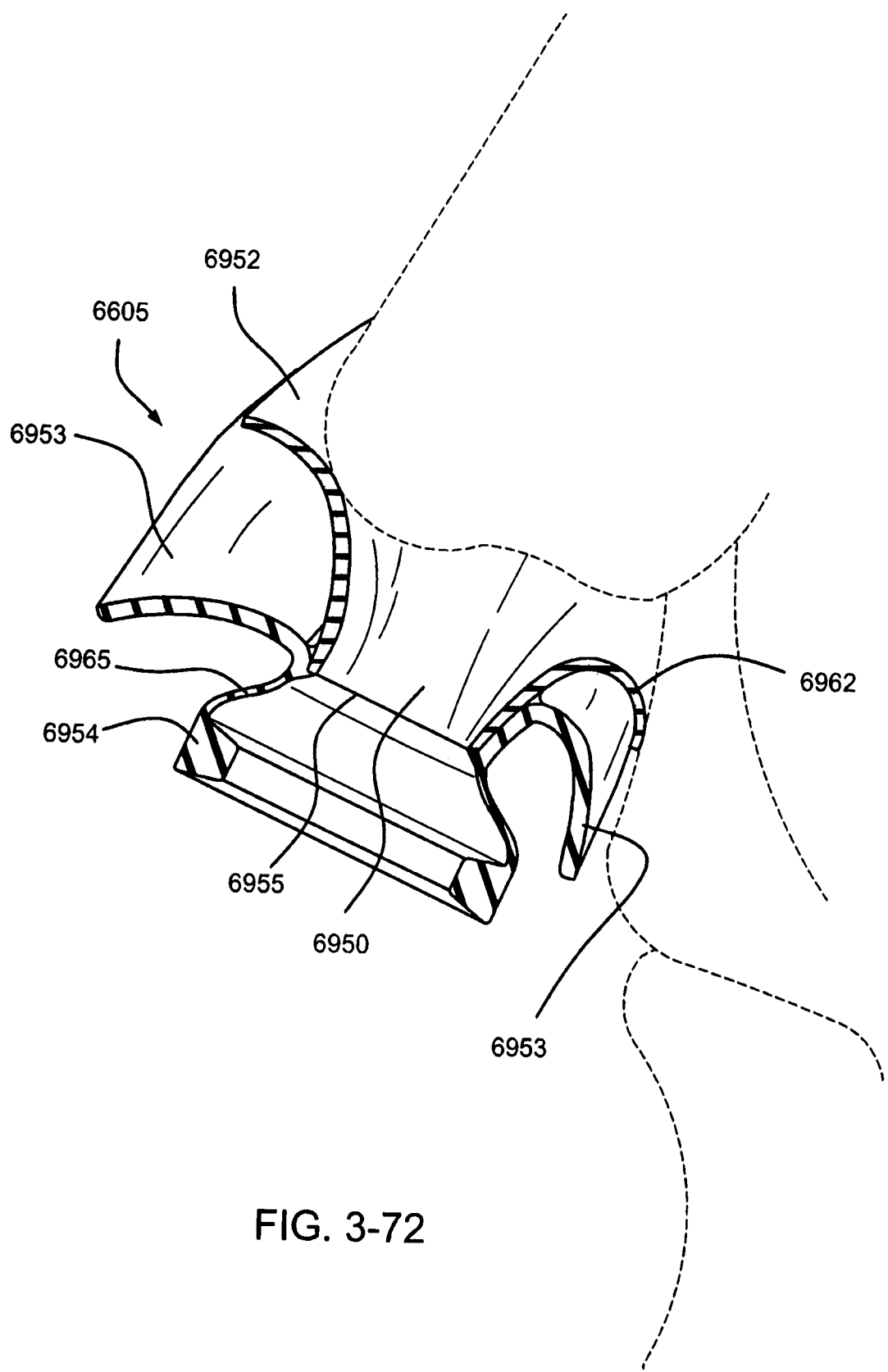

FIG. 3-72 is a cross sectional view of a patient interface structure, or cushion, usable with examples of the technology.

Figures 3, 73:
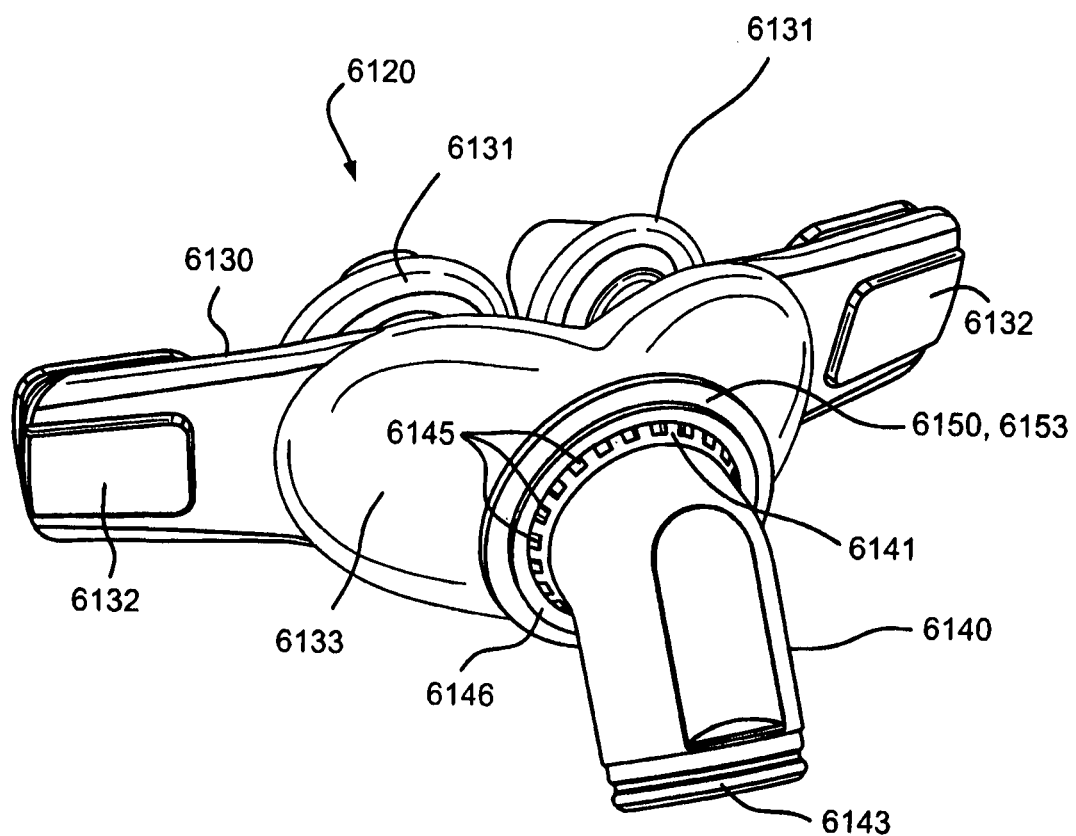

FIG. 3-73 is an isometric view of a swivel elbow and connector assembly according to an example of the technology.

Figures 3, 74:
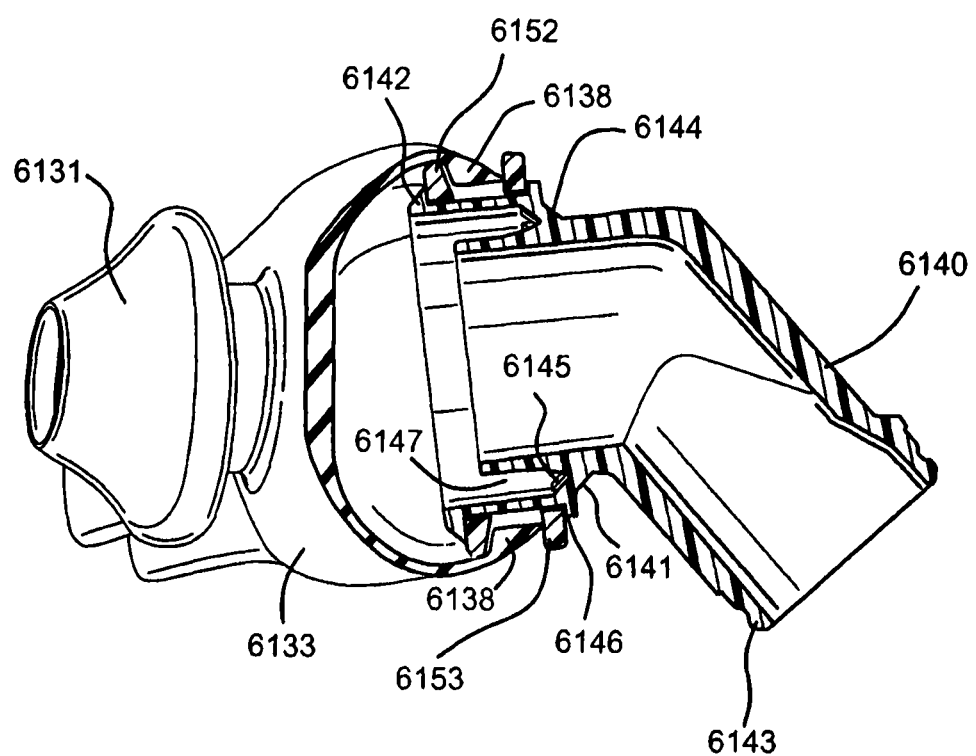

FIG. 3-74 is a partial side cross sectional view of the swivel elbow and connector assembly of FIG. 3-73.

Figures 3, 75:
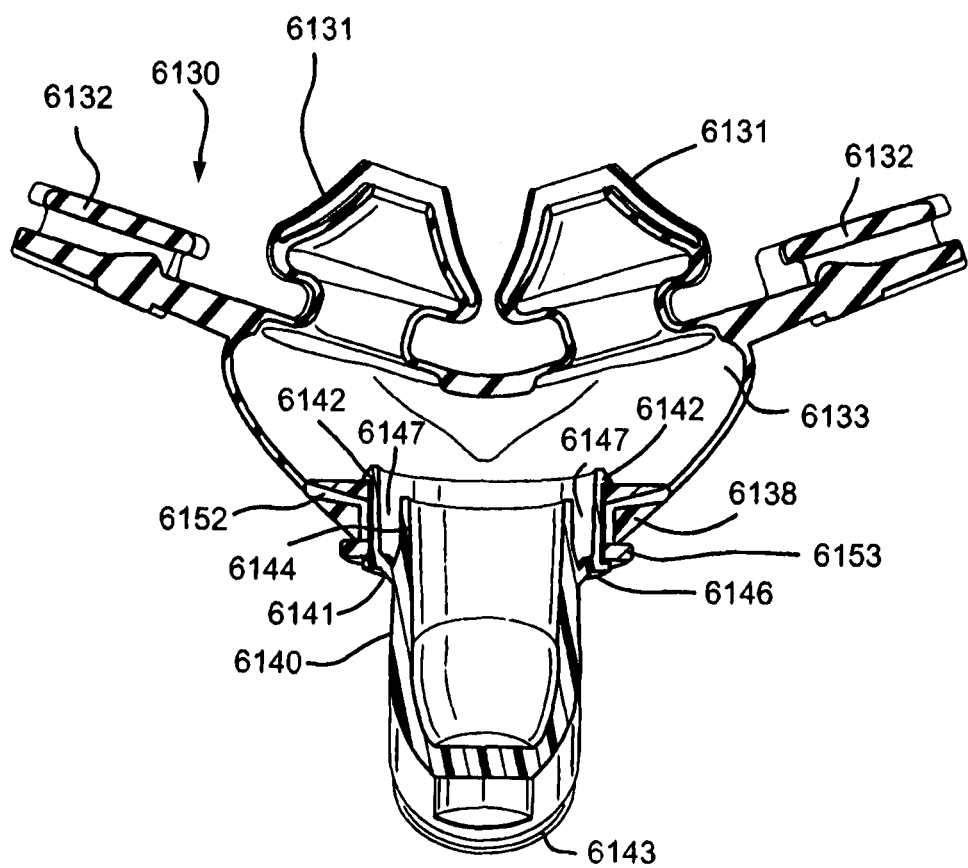

FIG. 3-75 is a top cross sectional view of the swivel elbow and connector assembly of FIG. 3-73.

Figures 3, 76:
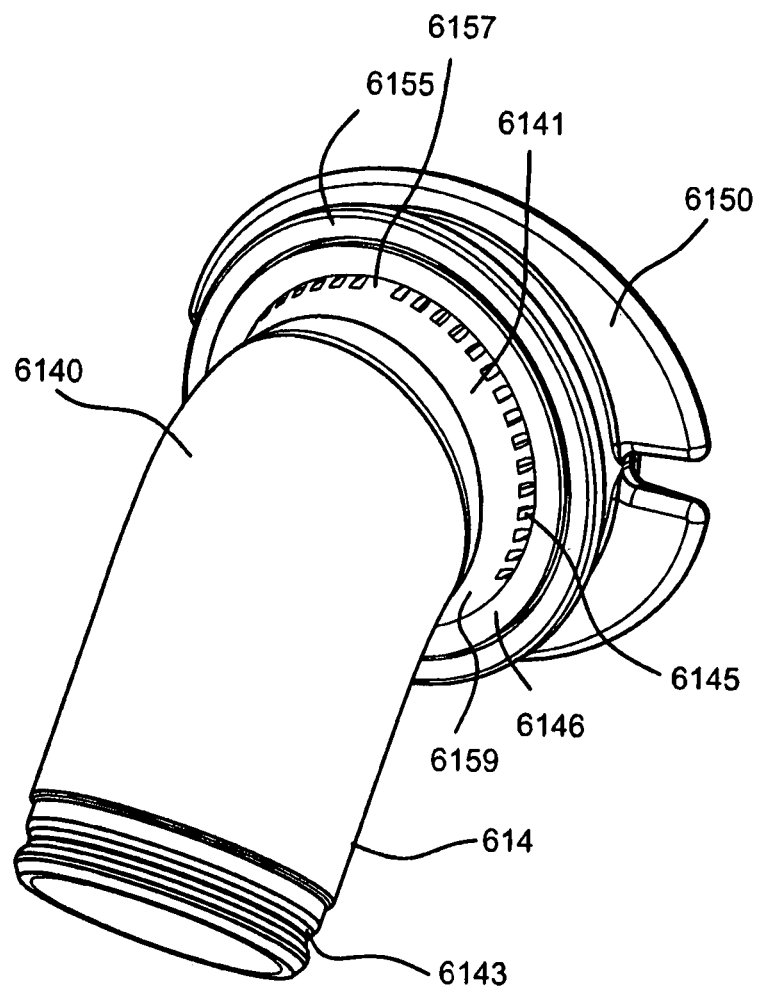

FIG. 3-76 is an isometric view of a variation of the swivel elbow and connector assembly of FIG. 3-73.

Figures 3, 77:
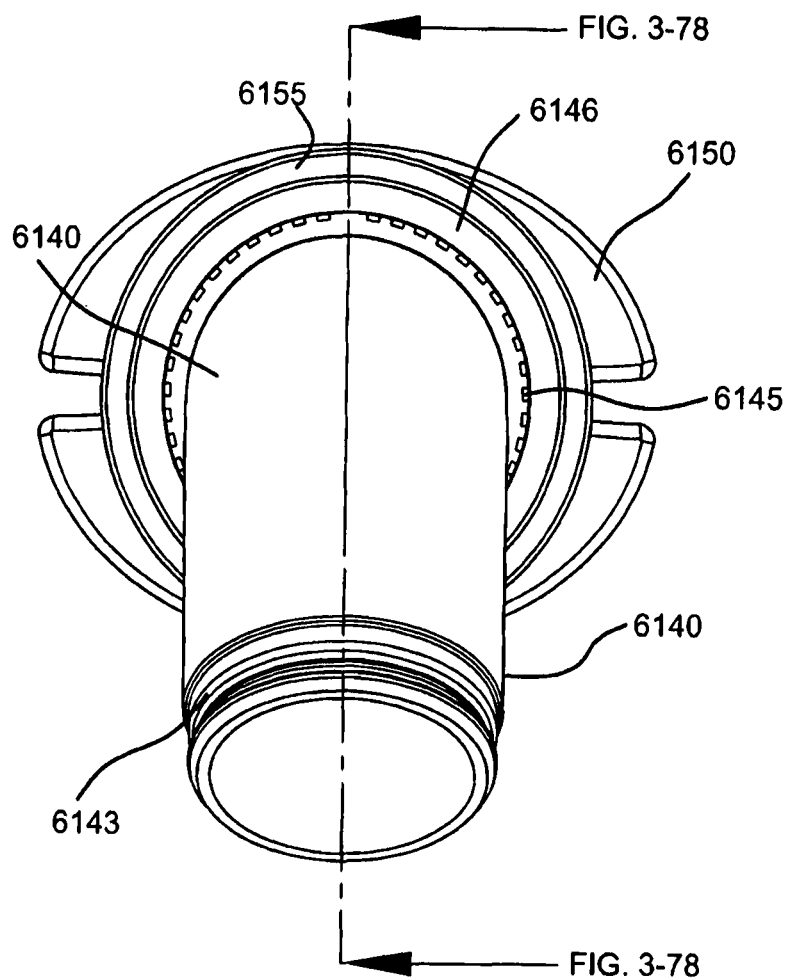

FIG. 3-77 is a front view of the swivel elbow and connector assembly of FIG. 3-76.

Figures 3, 78:
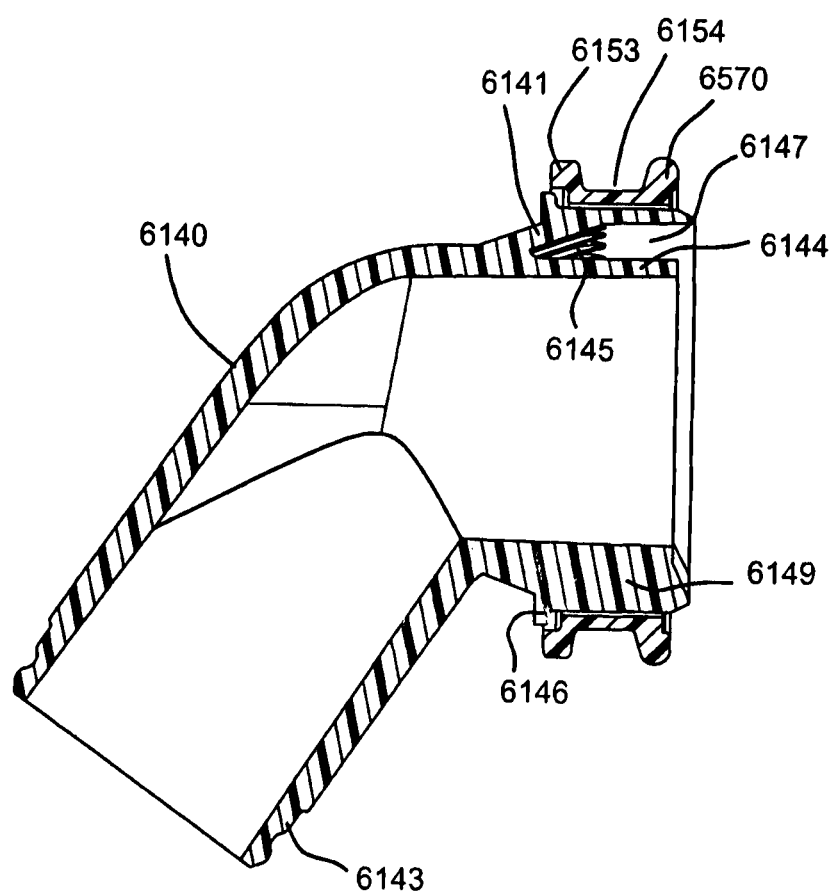

FIG. 3-78 is a cross sectional view of the swivel elbow and connector assembly of FIG. 3-76.

Figures 3, 79:
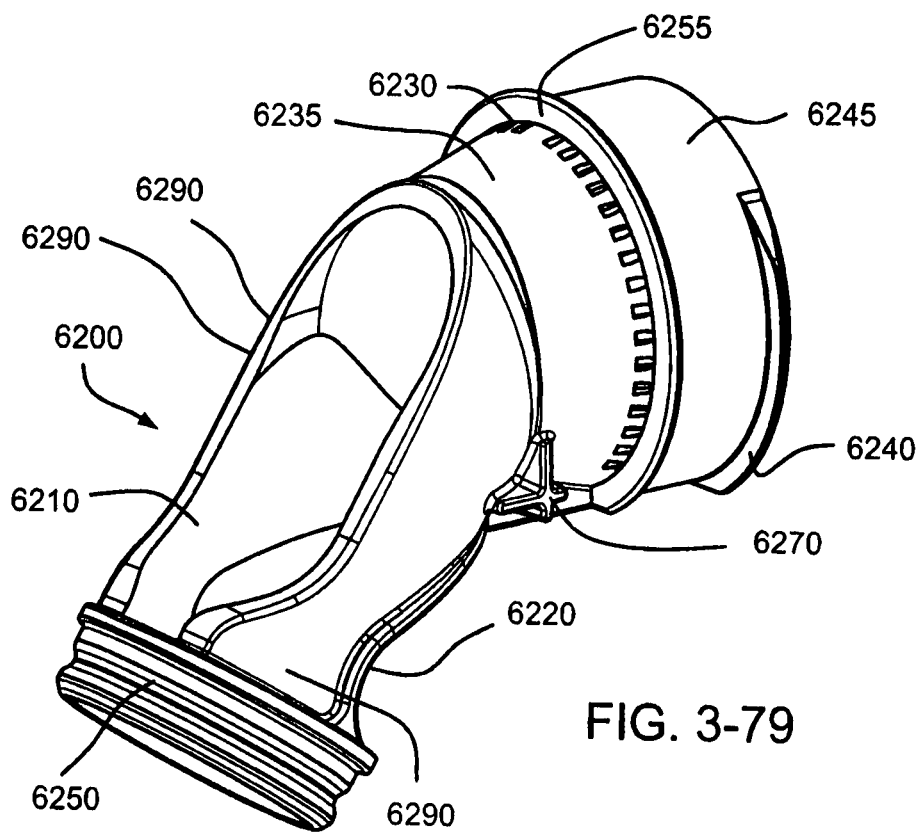

FIG. 3-79 is an isometric view of a first component of a swivel elbow and anti-asphyxia valve assembly according to an example of the technology.

Figures 3, 80:
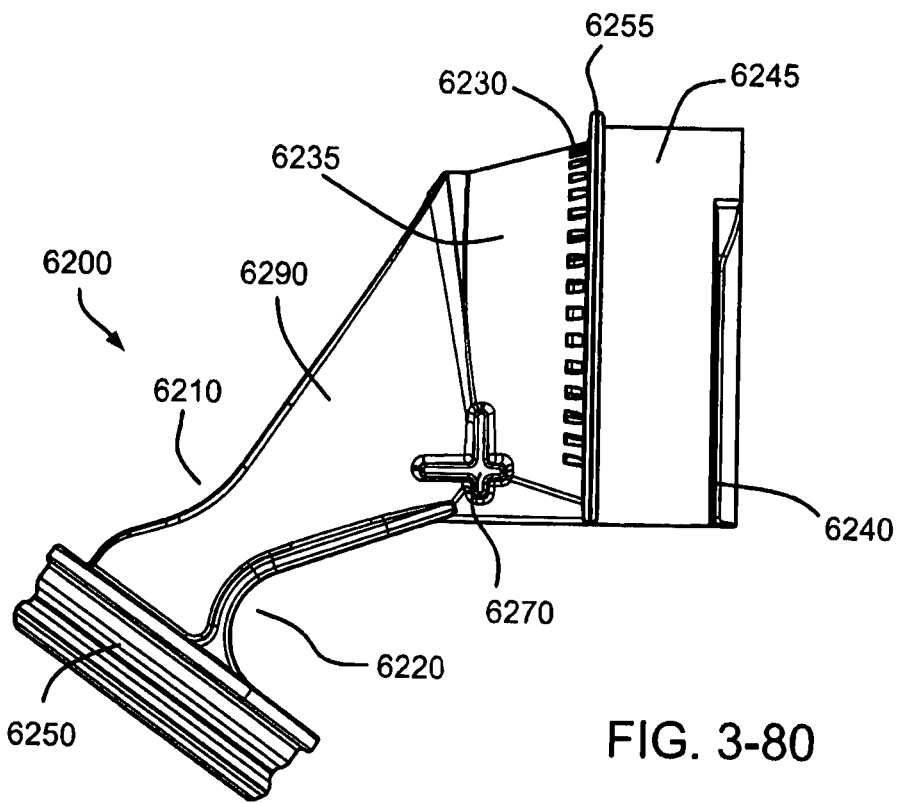

FIG. 3-80 is a side view of the first component of FIG. 3-79.

Figures 3, 81:
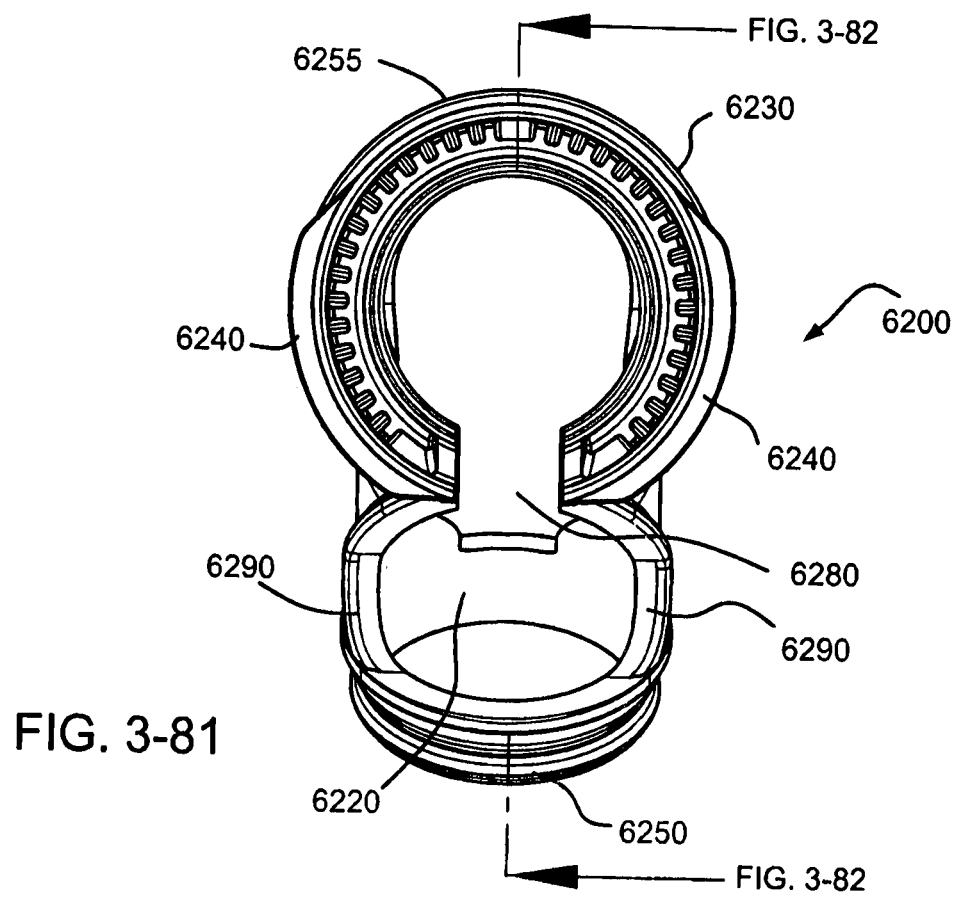

FIG. 3-81 is a rear view of the first component of FIGS. 3-79 and 3-80.

Figures 3, 82:
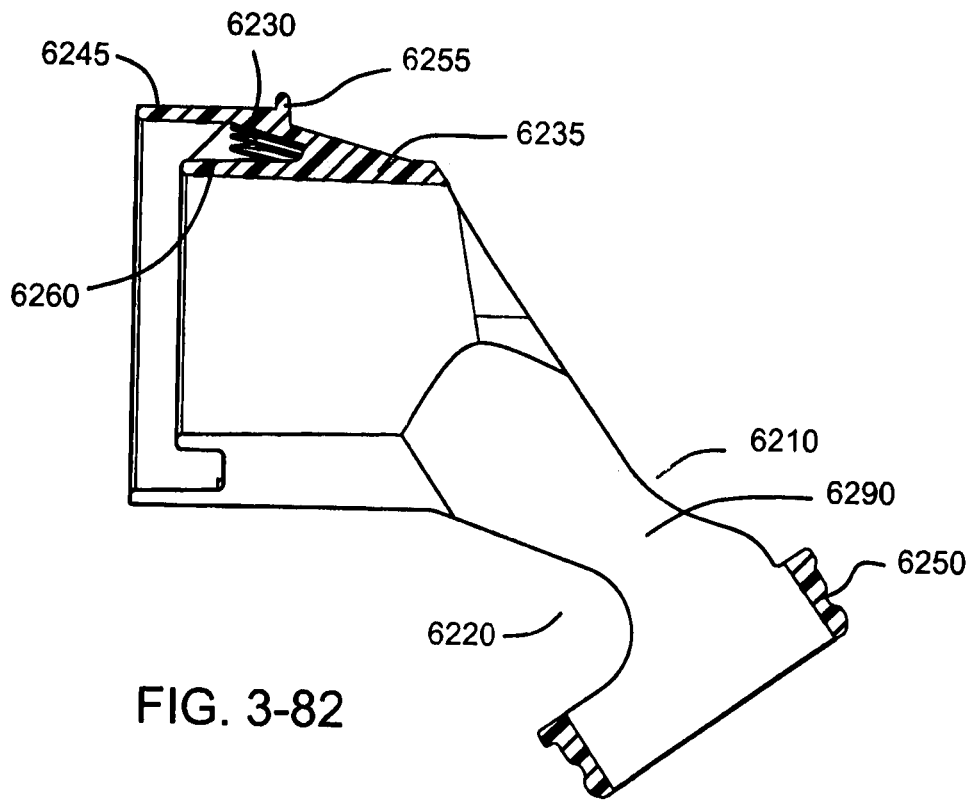

FIG. 3-82 is a cross sectional side view of the first component of FIGS. 3-79 to 3-81.

Figures 3, 83:
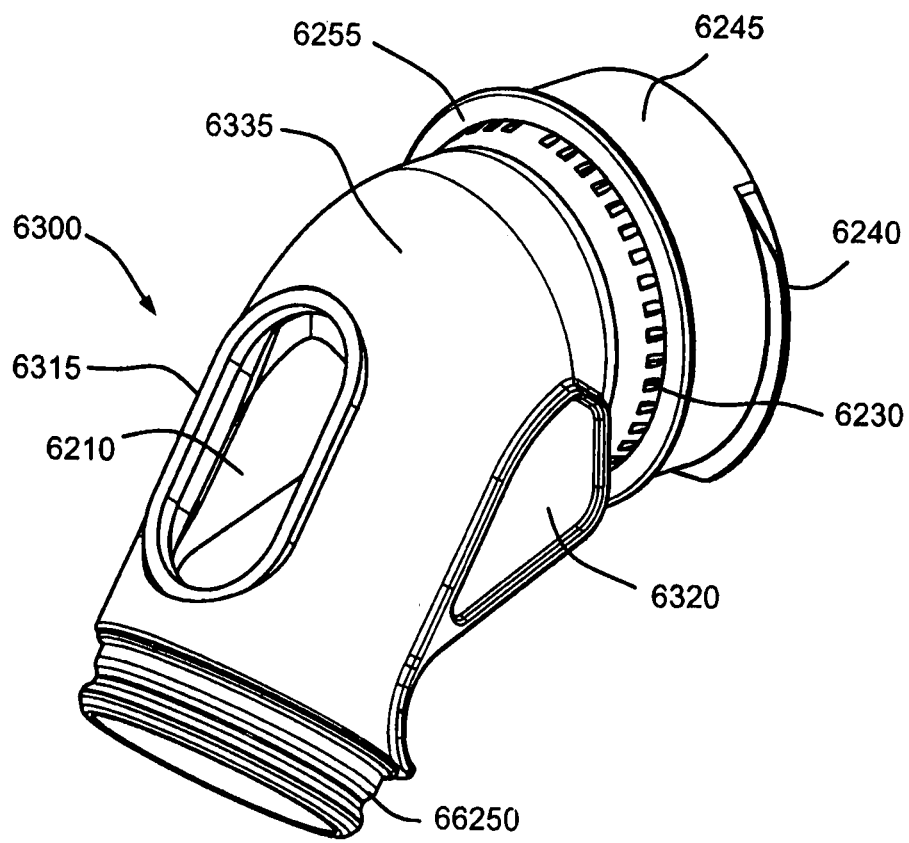

FIG. 3-83 is an isometric view of the first component and a second component of the swivel elbow and anti-asphyxia valve assembly.

Figures 3, 84:
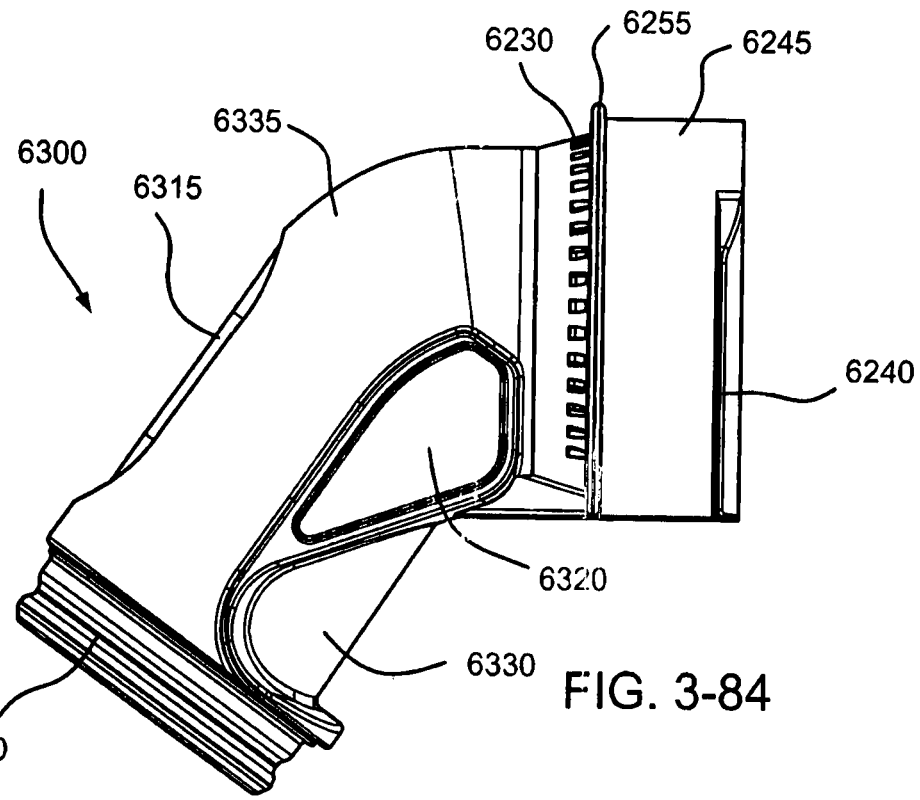

FIG. 3-84 is a side view of the swivel elbow and anti-asphyxia valve assembly of FIG. 3-83.

Figures 3, 85:
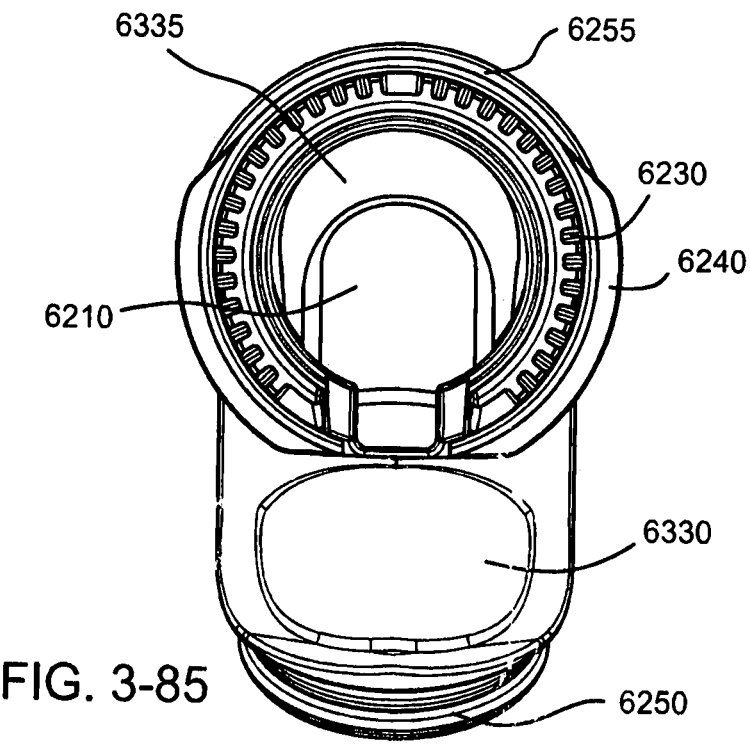

FIG. 3-85 is a rear view of the swivel elbow and anti-asphyxia valve assembly of FIGS. 3-83 and 3-84.

Figures 3, 86:
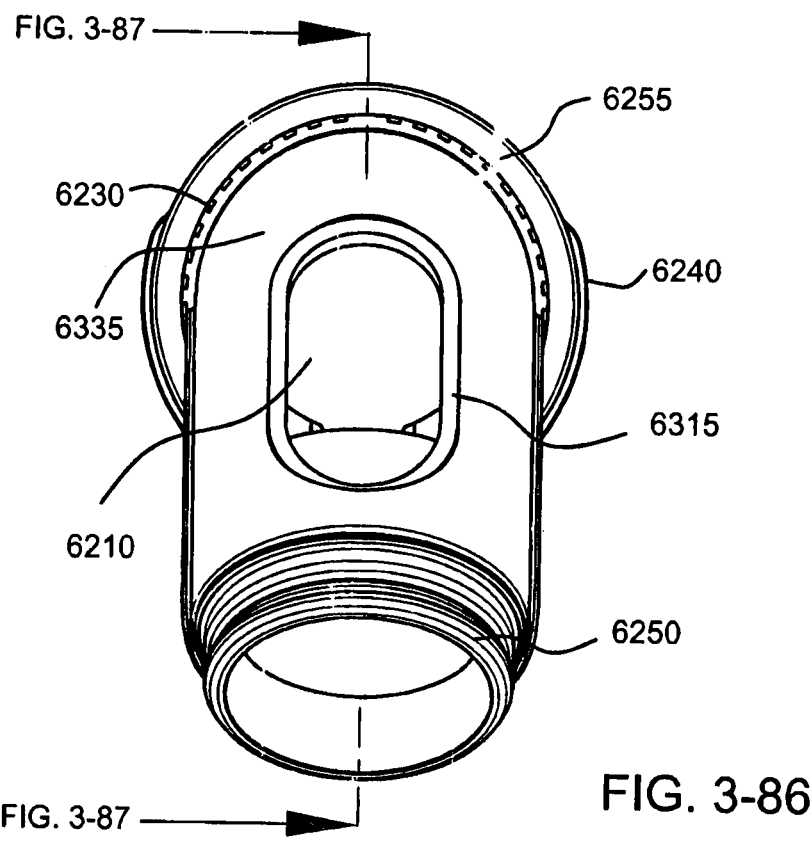

FIG. 3-86 is a front view the swivel elbow and anti-asphyxia valve assembly of FIGS. 2-83 to 3-85.

Figures 3, 87:
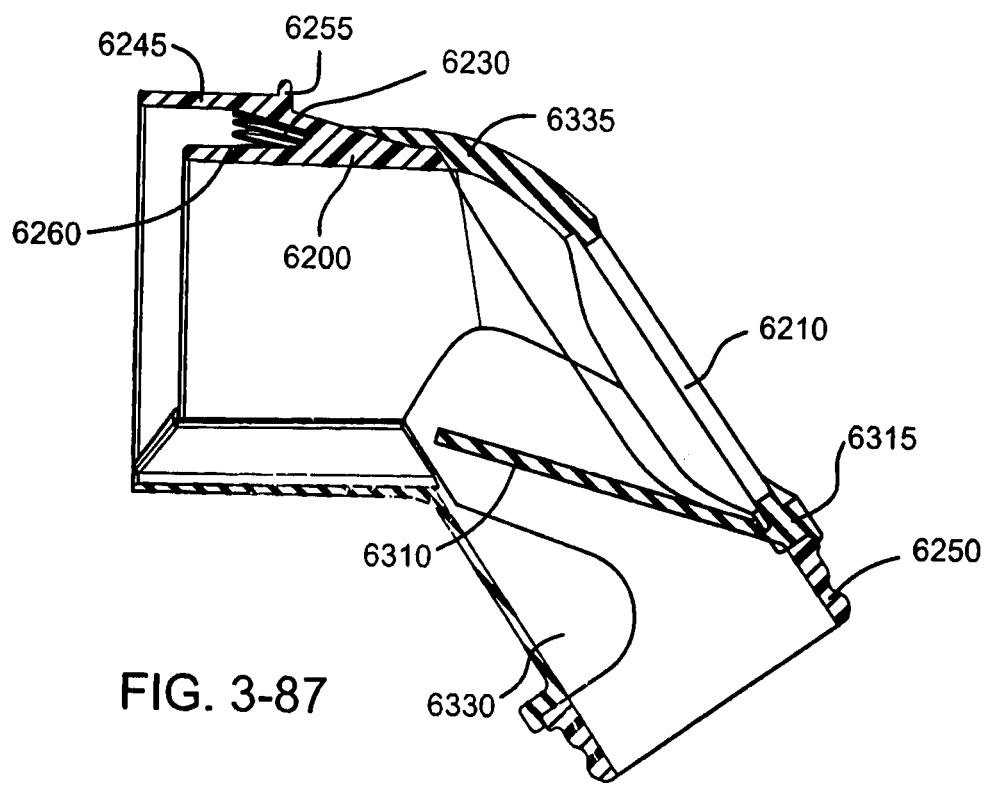

FIG. 3-87 is a cross sectional side view of the swivel elbow and anti-asphyxia valve assembly of FIGS. 3-83 to 3-86.

Figures 3, 88:
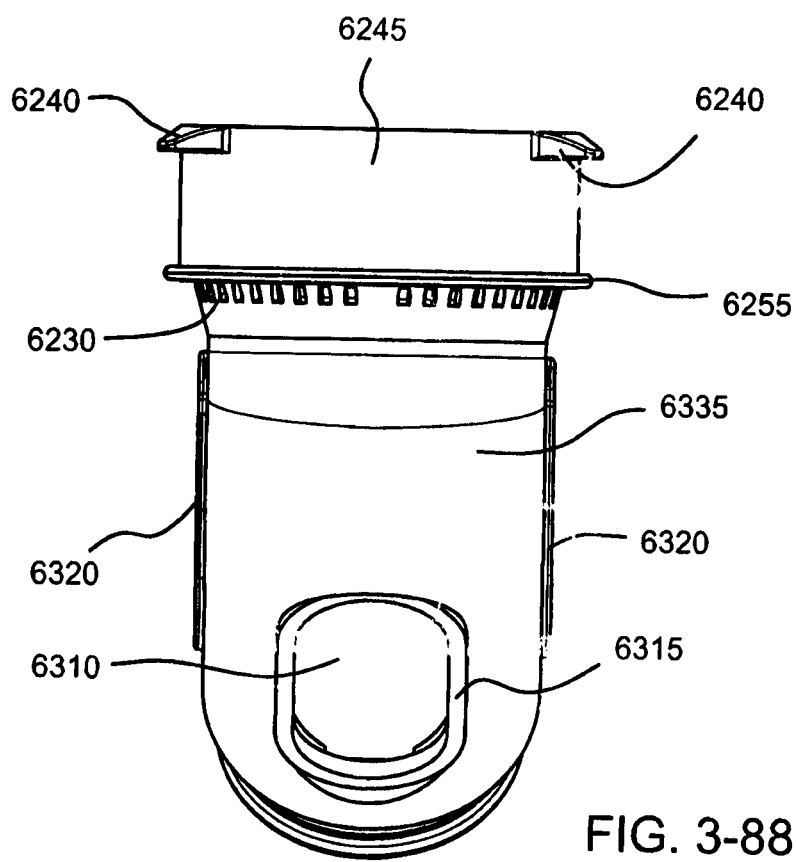

FIG. 3-88 is a top view of the swivel elbow and anti-asphyxia valve assembly of FIGS. 3-83 to 3-87.

Figures 3, 89:
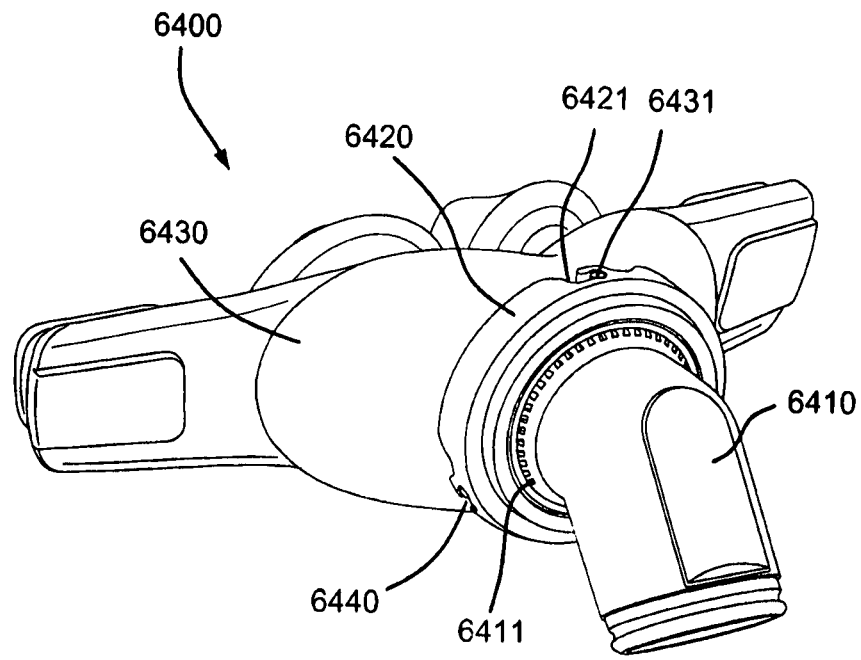

FIG. 3-89 is an isometric view of a patient interface including a swivel elbow and connector assembly according to another example of the technology.

Figures 3, 90:
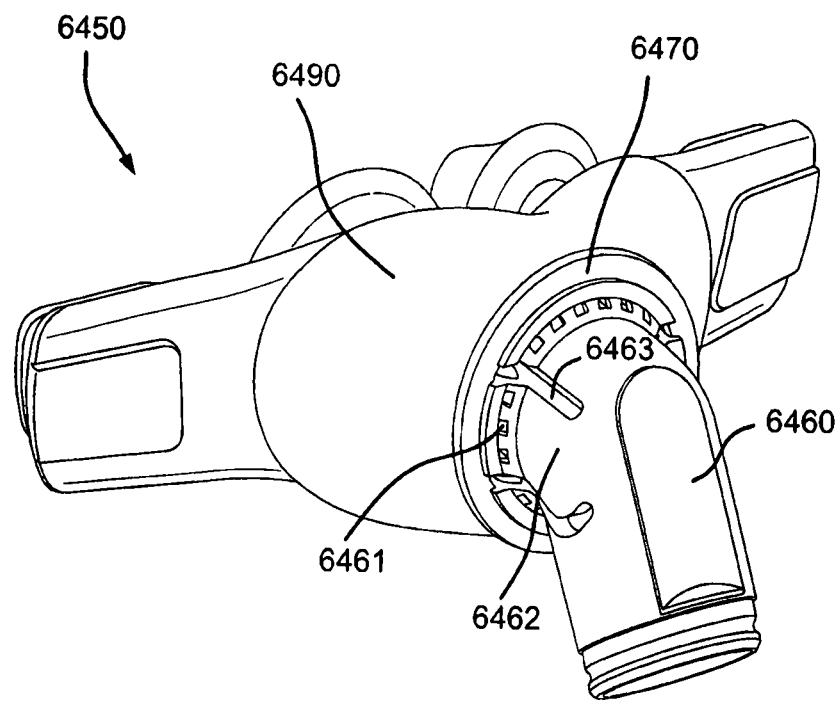

FIG. 3-90 is an isometric view of a patient interface including a swivel elbow and connector assembly according to another example of the technology.

Figures 3, 91:
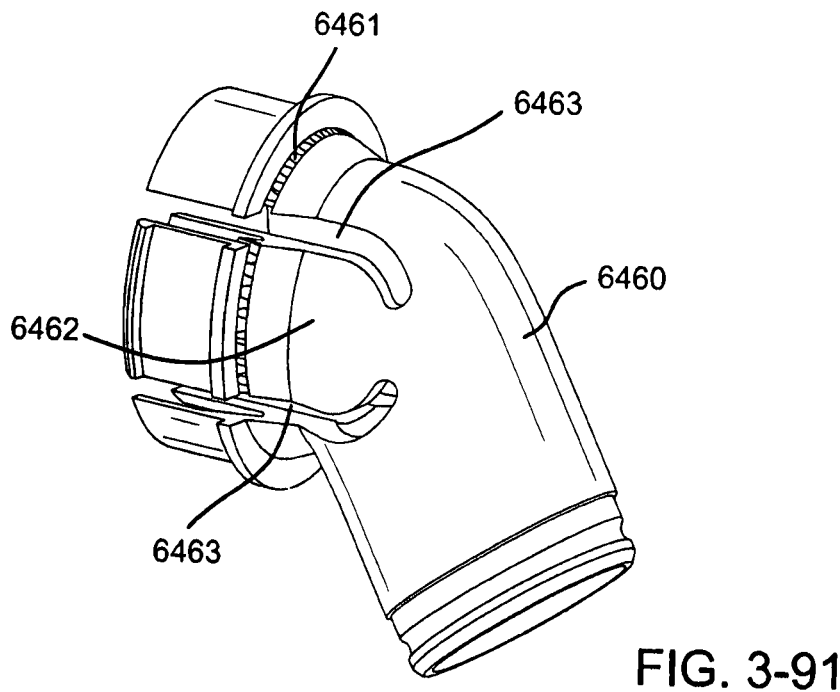

FIG. 3-91 is an isometric view of the elbow of FIG. 3-90.

Figures 3, 92:
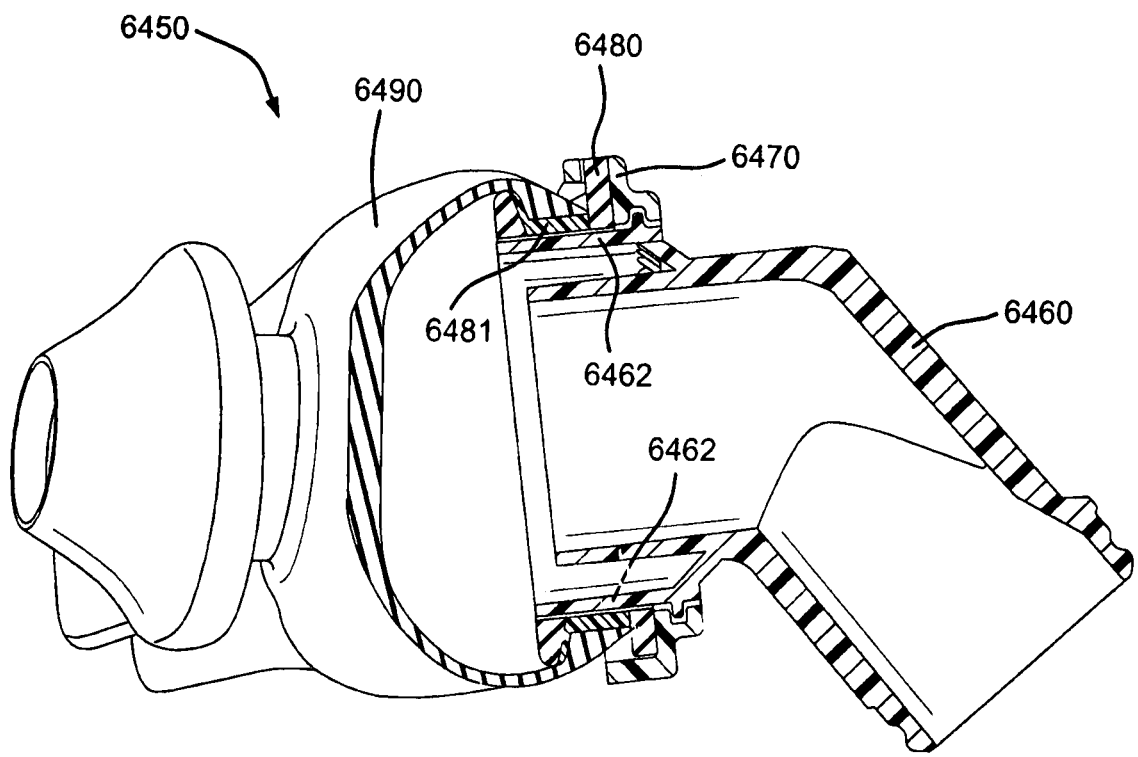

FIG. 3-92 is a cross sectional view of the patient interface of FIG. 3-90.

Figures 3, 93:
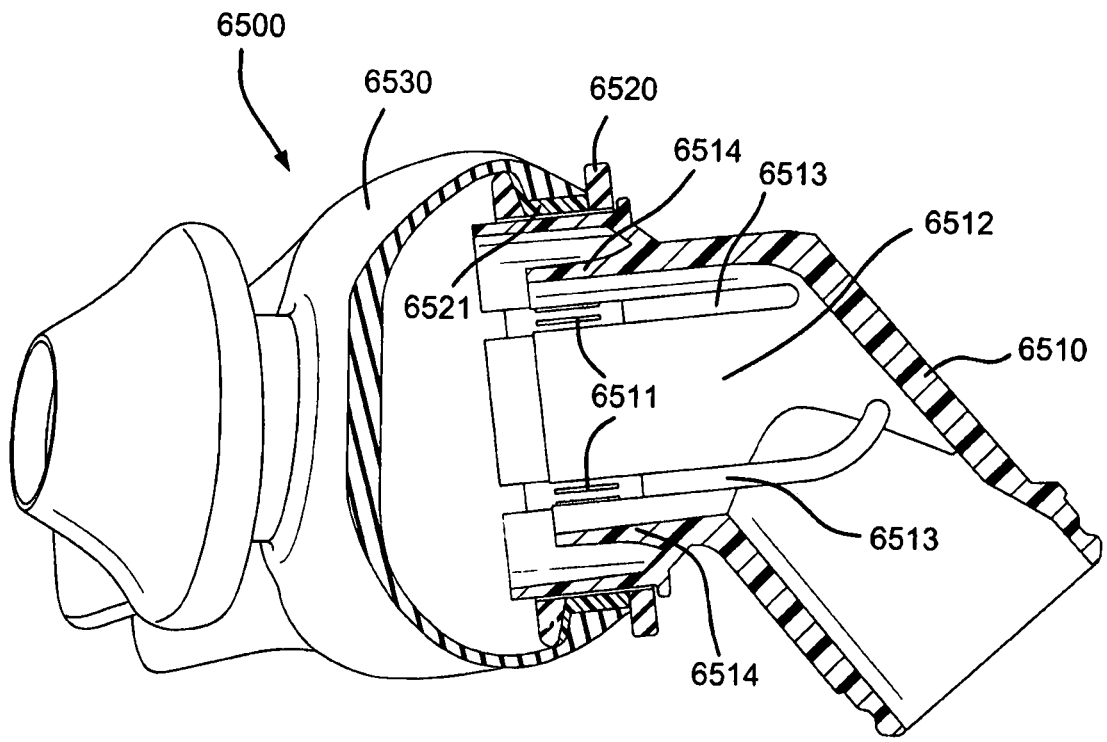

FIG. 3-93 is a cross sectional view of a patient interface including a swivel elbow and connector assembly according to another example of the technology.

Figures 3, 94:
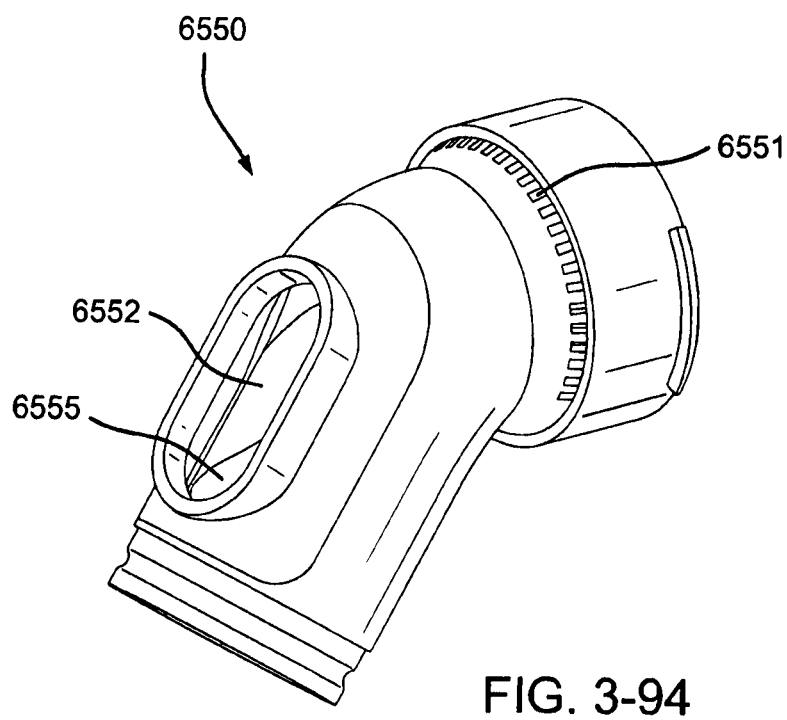

FIG. 3-94 is an isometric view of an elbow according to an example of the technology.

Figures 3, 95:
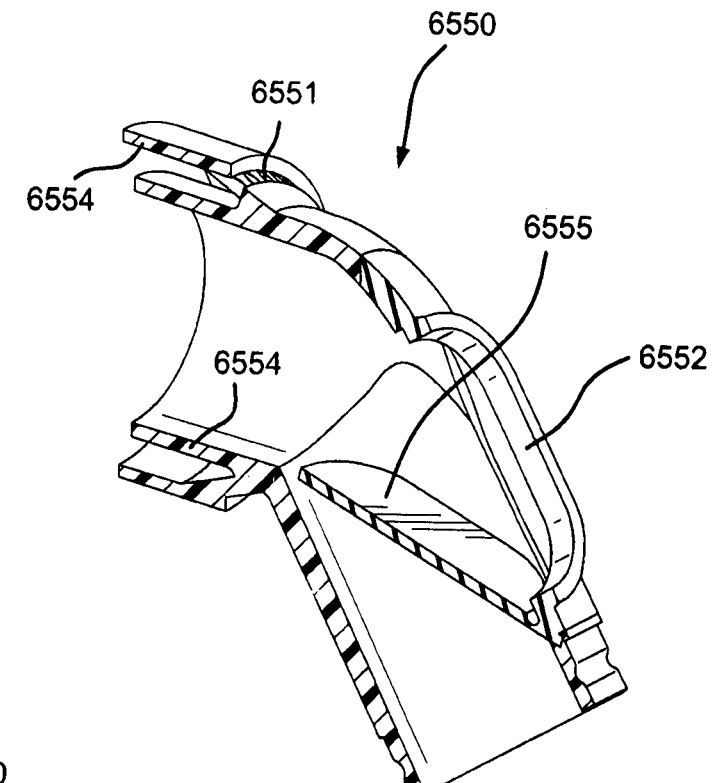

FIG. 3-95 is a cross sectional view of the elbow of FIG. 3-94.

Figures 3, 96:
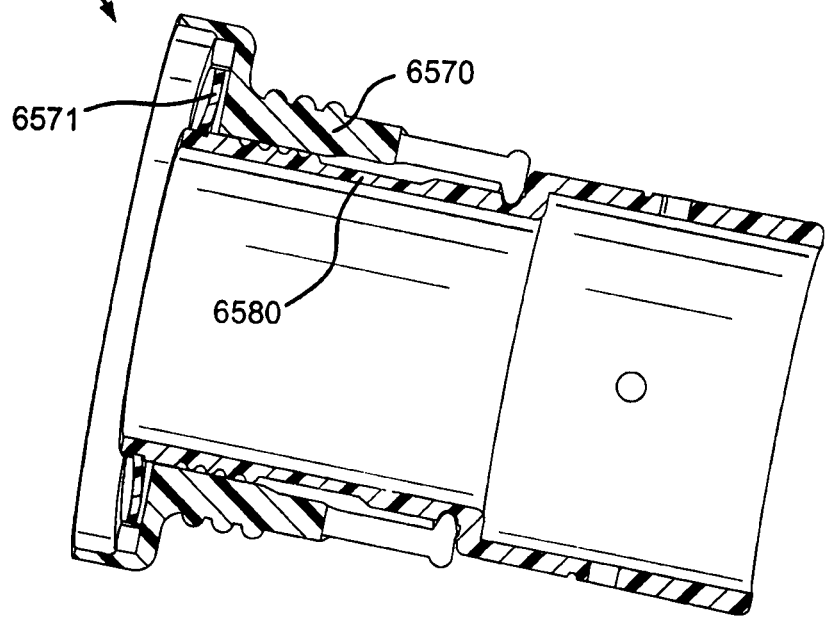

FIG. 3-96 is a cross sectional view of an elbow and tube connector assembly according to the technology.

Figures 3, 97:
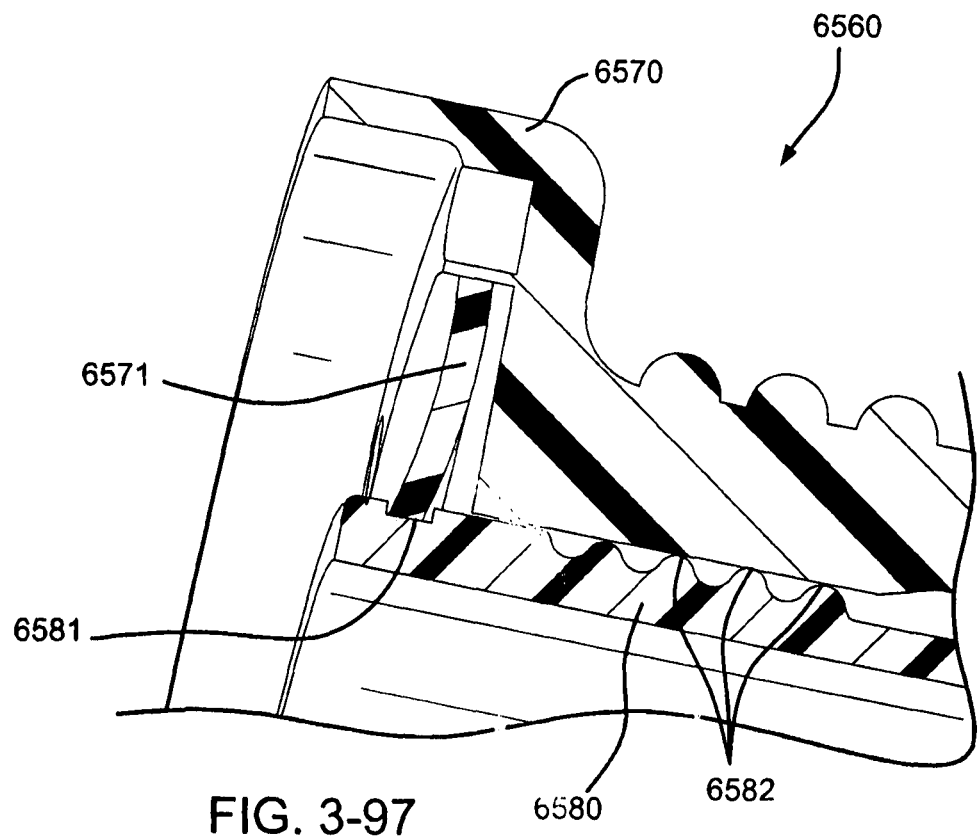

FIG. 3-97 is an enlarged view of a portion of FIG. 3-96.

Figures 3, 98:
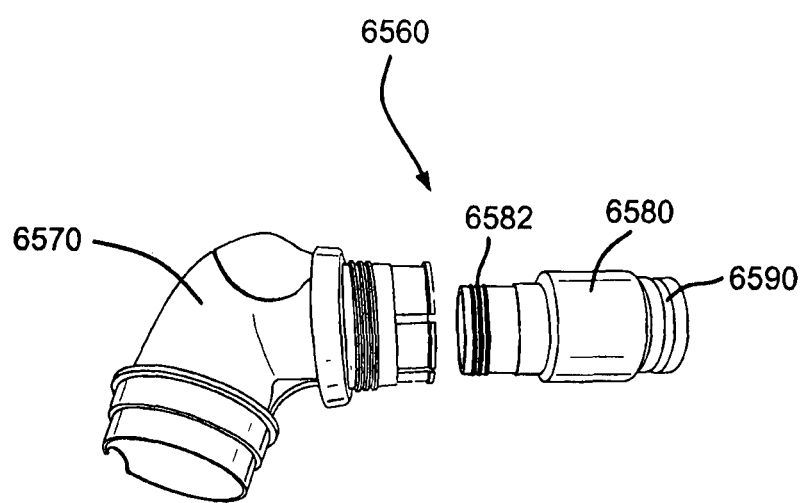

FIG. 3-98 is an exploded assembly view of the elbow and tube connector assembly of FIG. 3-96.

Figures 3, 99:
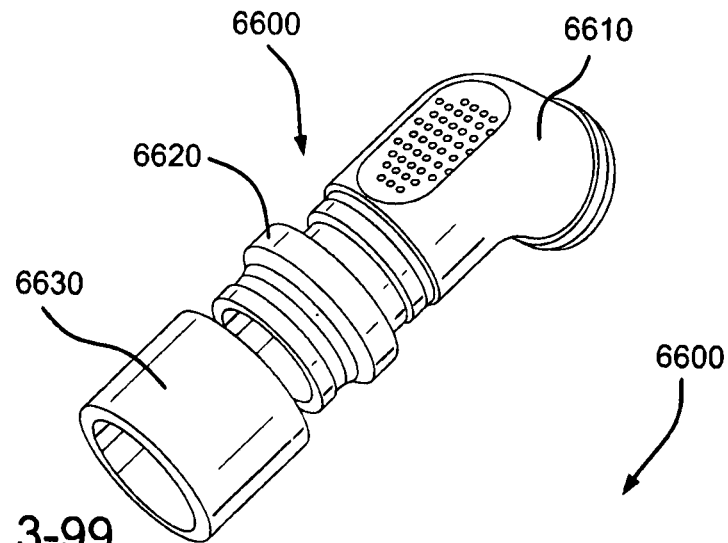

FIG. 3-99 is an exploded assembly view of an elbow and tube connector assembly according to another example of the technology.

Figures 3, 100:
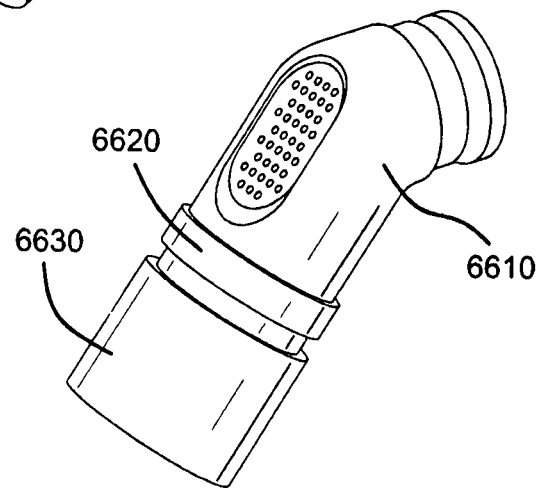

FIG. 3-100 is an assembly view of the elbow and tube connector assembly of FIG. 3-99.

Figures 3, 101:
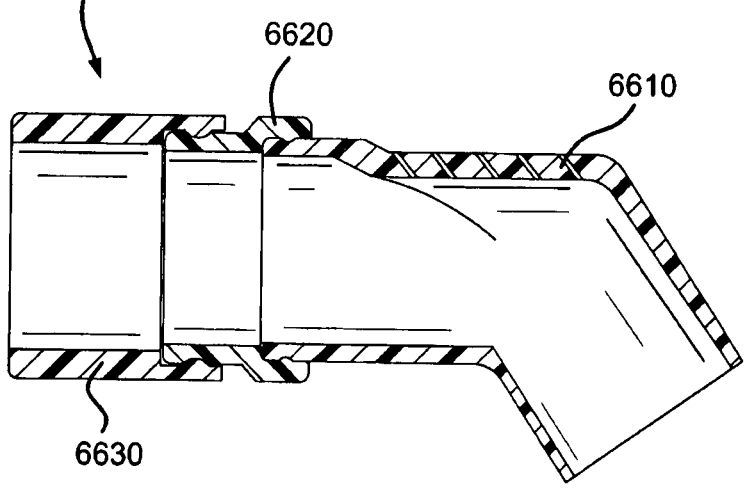

FIG. 3-101 is a cross sectional view of the elbow and tube connector assembly of FIG. 3-100.

Figures 3, 102, 103:
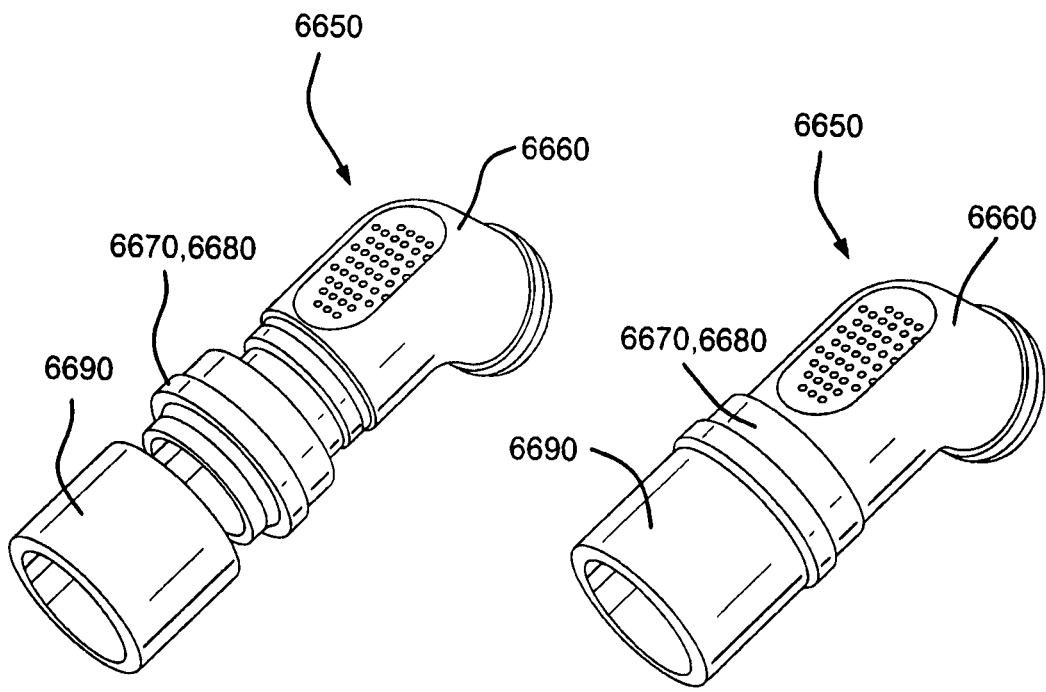

FIG. 3-102 is an exploded assembly view of an elbow and tube connector assembly according to another example of the technology.

FIG. 3-103 is an assembly view of the elbow and tube connector assembly of FIG. 3-102.

Figures 3, 104:
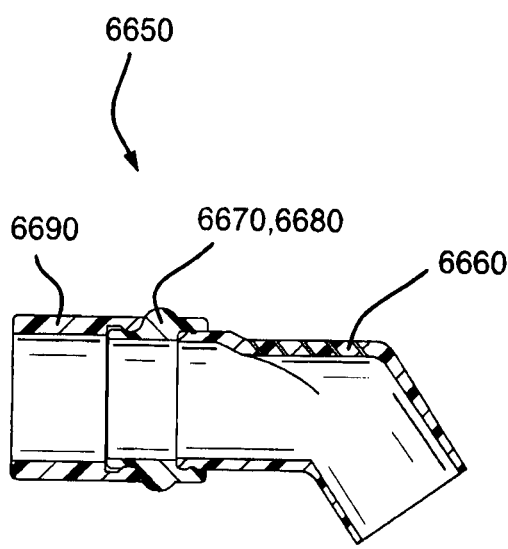

FIG. 3-104 is a cross sectional view of the elbow and tube connector assembly of FIG. 3-103.

FIG. 3-105 is an isometric view of the connector of the elbow and tube connector assembly of FIG. 3-104.

FIG. 3-106 is a cross sectional view of the connector of FIG. 3-105.

FIG. 3-107 is a cross sectional view of a tube connector assembly according to an example of the technology.

FIG. 3-108 is an isometric view of the tube connector assembly of FIG. 3-107.

Figures 3, 109A:
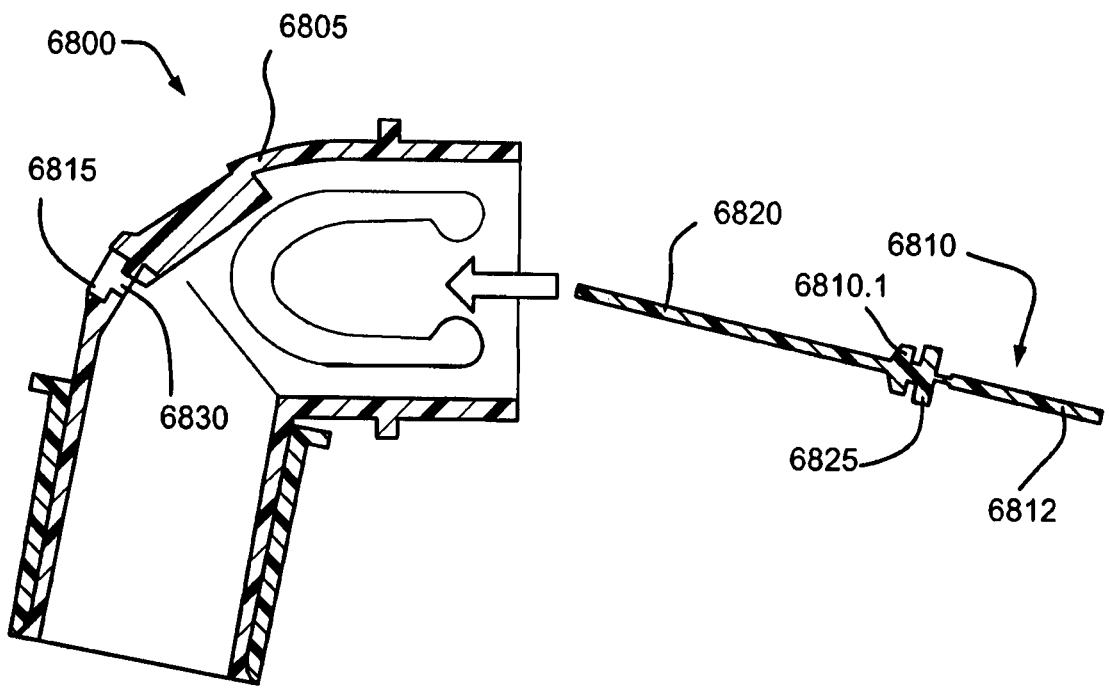
Figures 3, 109B:
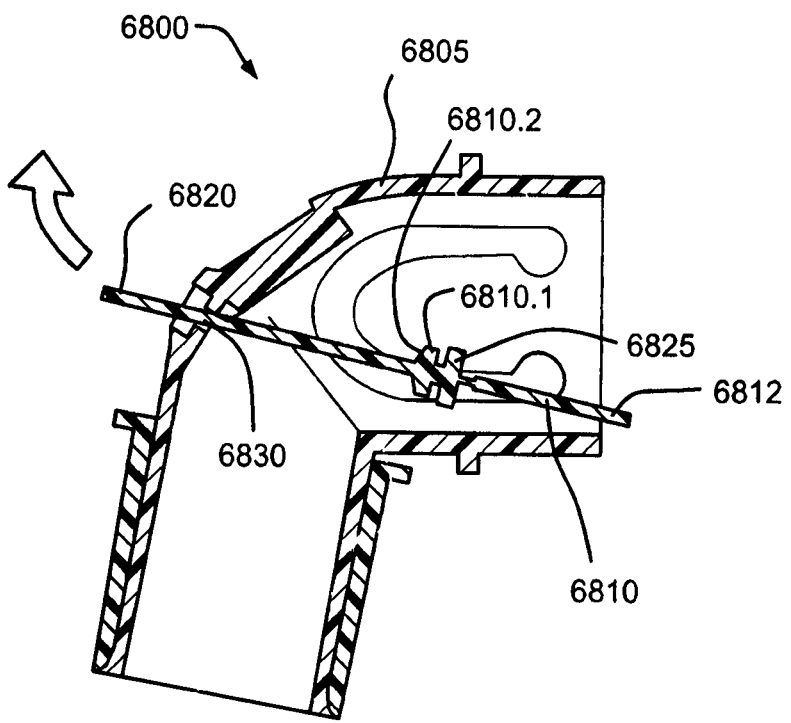
Figures 3, 109C:
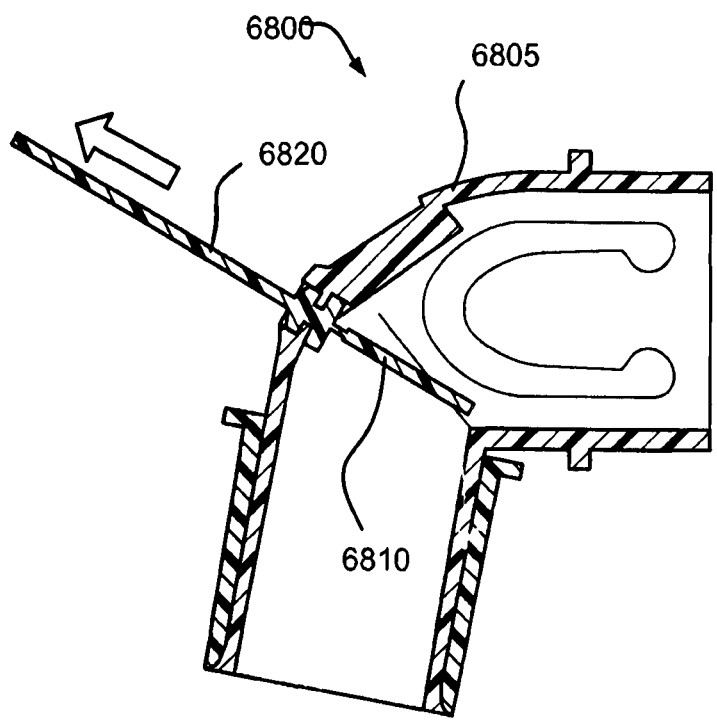

FIGS. 3-109A-D show a multi-step process for manufacturing an elbow with anti-asphyxia valve.

FIG. 3-110A shows a perspective view of a variant of the elbow.

FIG. 3-110B shows a cross section of the variant shown in FIG. 3-110A.

FIG. 3-111 shows the AAV (a variant) in isolation.

FIGS. 3-112-1 and 3-112-2 are a top view and related cross-sectional view showing a nasal mask system engaged with a patient's face according to an example of the present technology, the nasal mask system in a static sealing position.

FIGS. 3-113-1 and 3-113-2 are a side view and related cross-sectional view showing a nasal mask system engaged with a patient's face according to an example of the present technology, the nasal mask system in a static sealing position.

FIGS. 3-114-1 and 3-114-2 are a top view and related cross-sectional view showing a nasal mask system engaged with a patient's face according to an example of the present technology, the nasal mask system in a dynamic sealing position with the nasal mask system being pulled sideways.

FIGS. 3-115-1 and 3-115-2 are a side view and related cross-sectional view showing a nasal mask system engaged with a patient's face according to an example of the present technology, the nasal mask system in a dynamic sealing position with the nasal mask system being pulled upwards.

FIGS. 3-116-1 and 3-116-2 are an alternative side view and related cross-sectional view showing a nasal mask system in a dynamic sealing position with the nasal mask system being pulled upwards.

FIGS. 3-117-1 and 3-117-2 are a side view and related cross-sectional view showing a nasal mask system engaged with a patient's face according to an example of the present technology, the nasal mask system in a dynamic sealing position with the nasal mask system being pulled downwards.

FIGS. 3-118-1, 3-118-2, and 3-118-3 illustrate rotation of an elbow assembly in the X-axis, Z-axis, and Y-axis according to an example of the present technology.

Figures 3, 109D:
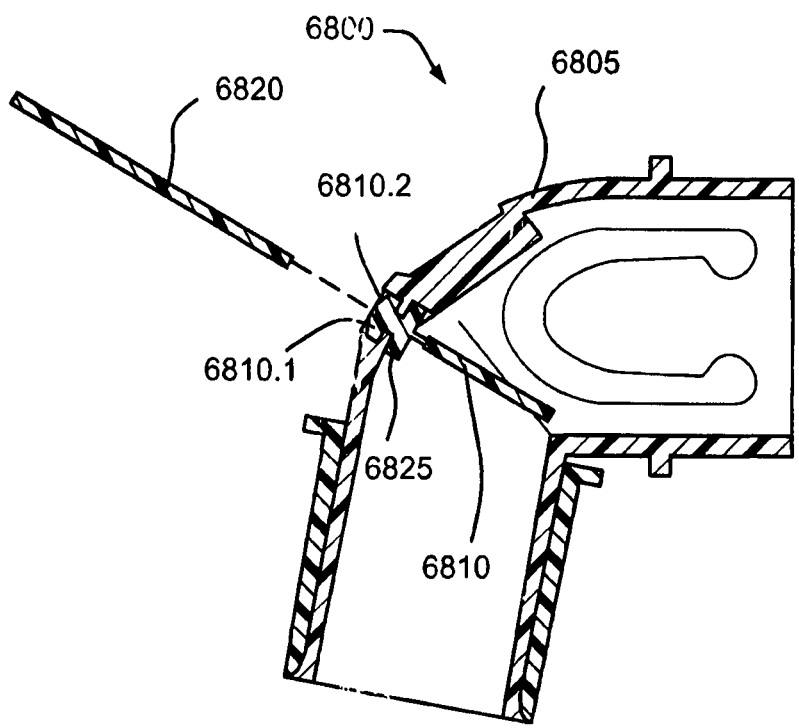
Figures 1, 3, 112:
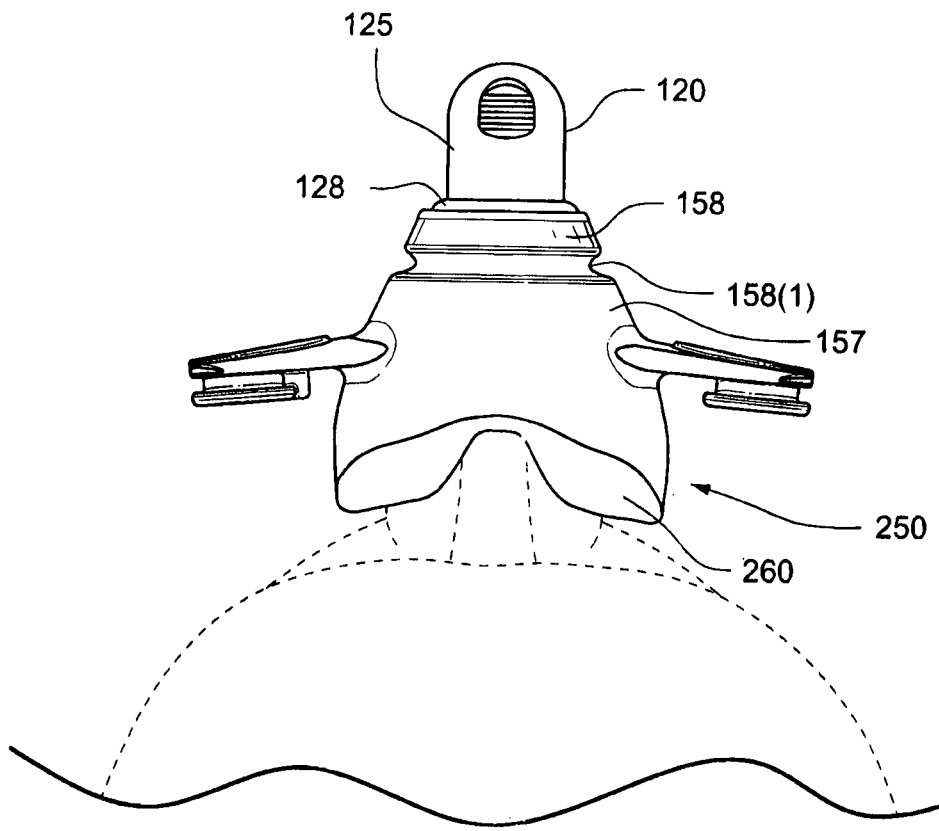
Figures 2, 3, 112:
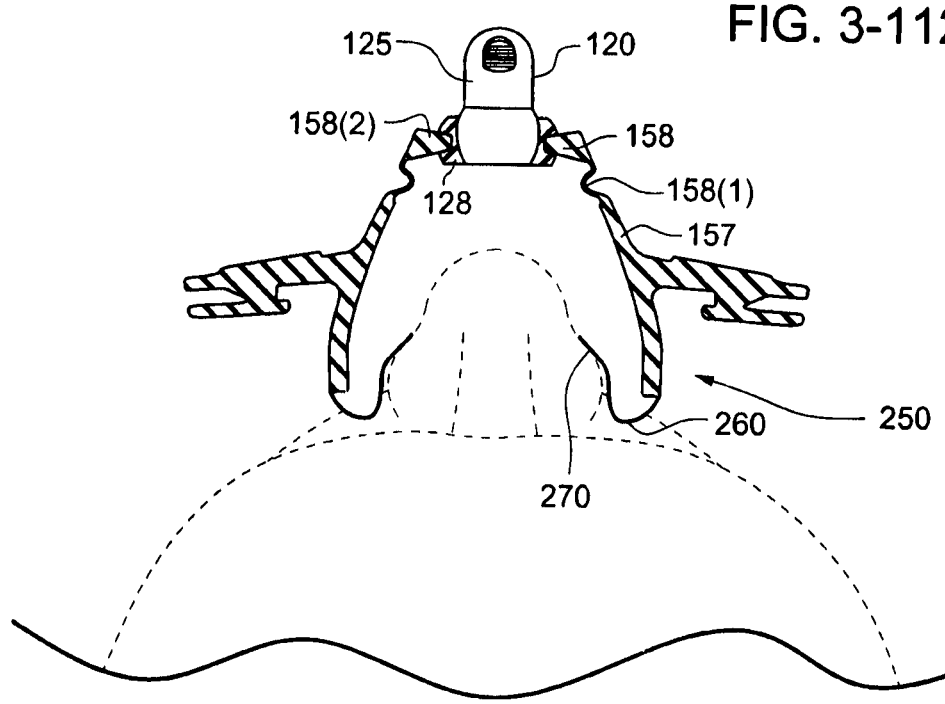
Figures 1, 3, 113:
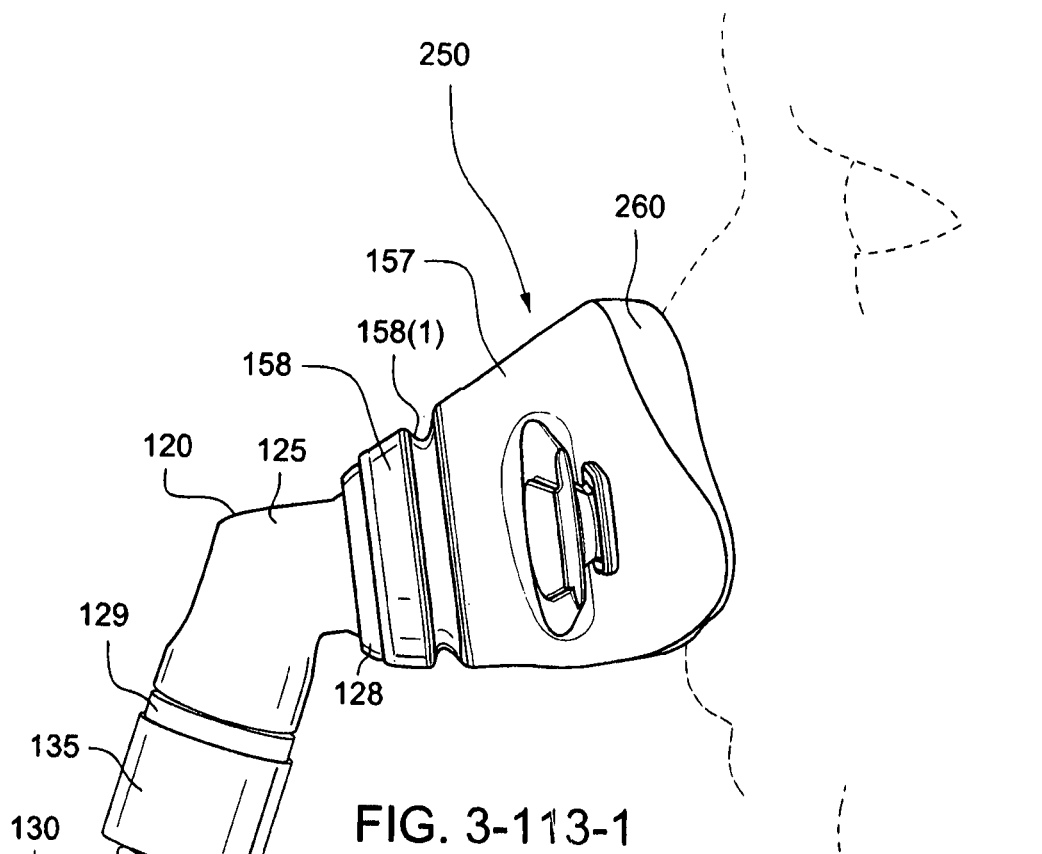
Figures 2, 3, 113:
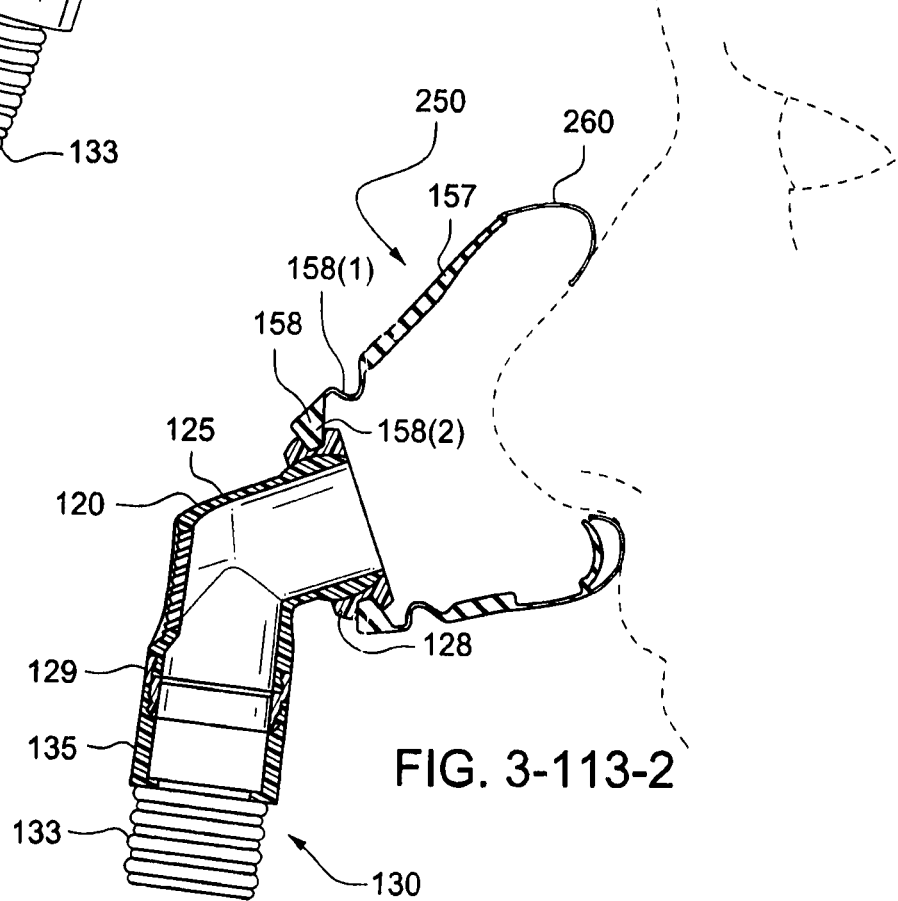
Figures 1, 3, 114:
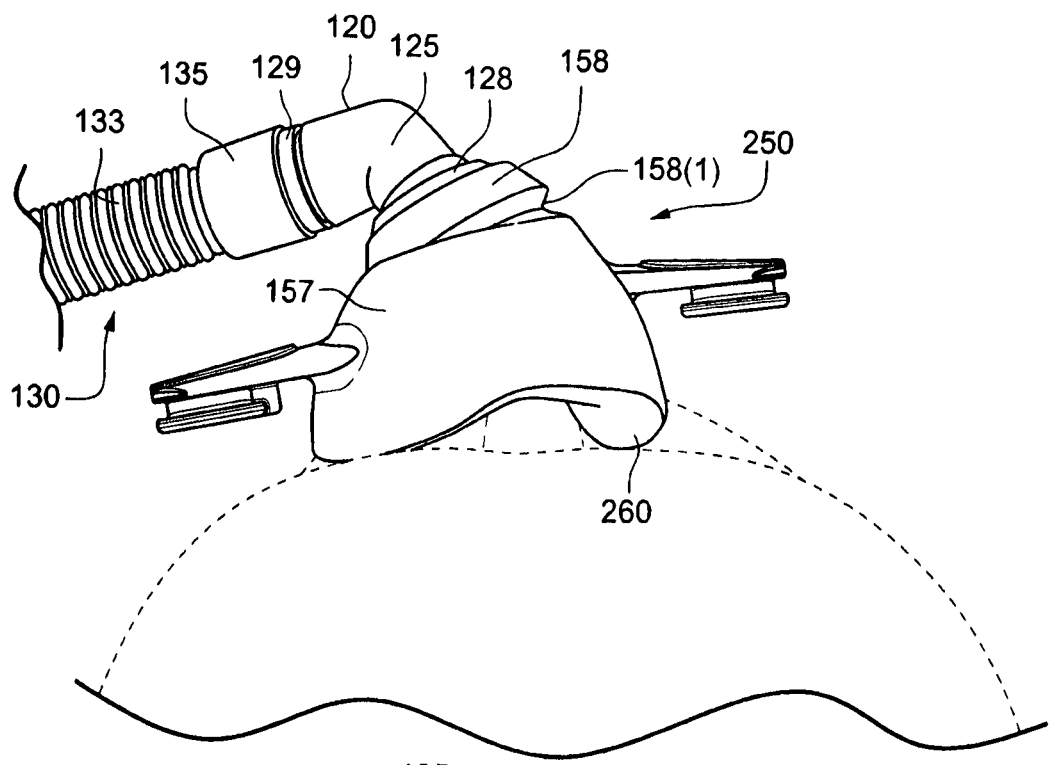
Figures 2, 3, 114:
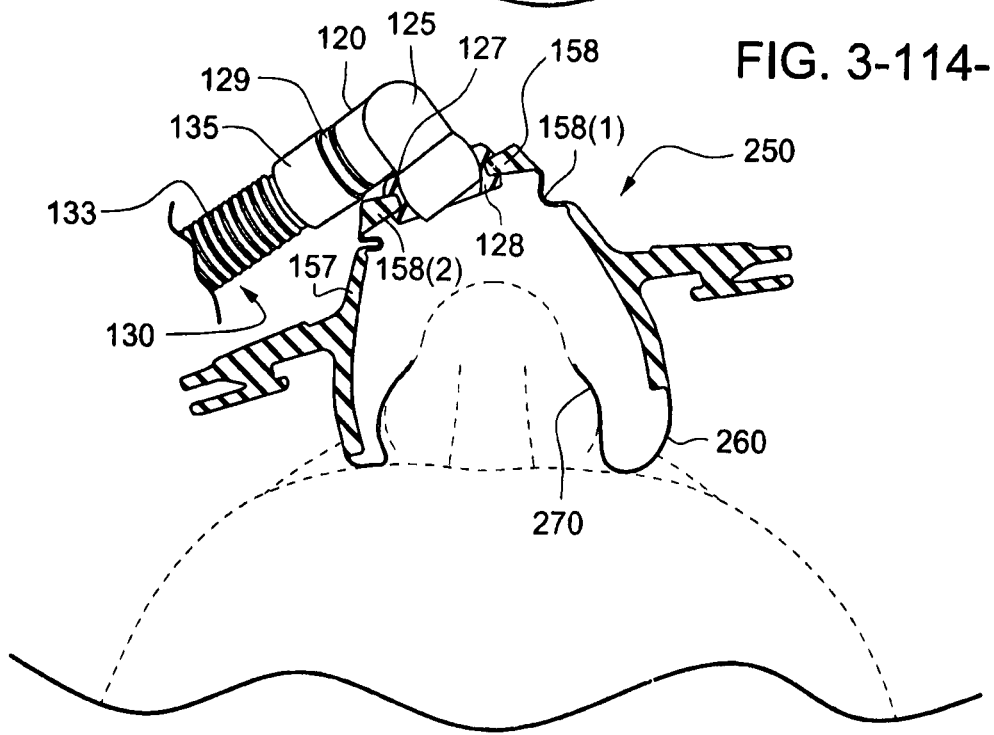
Figures 1, 3, 115:
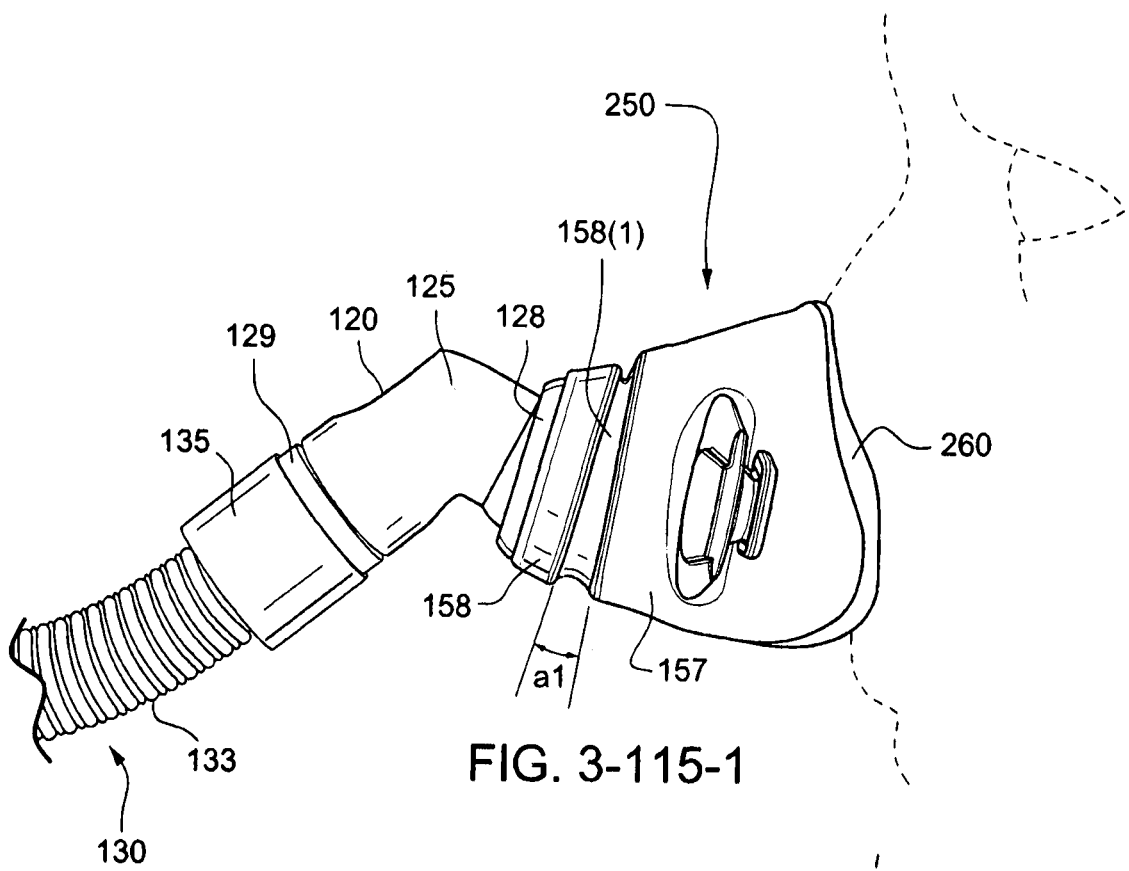
Figures 2, 3, 115:
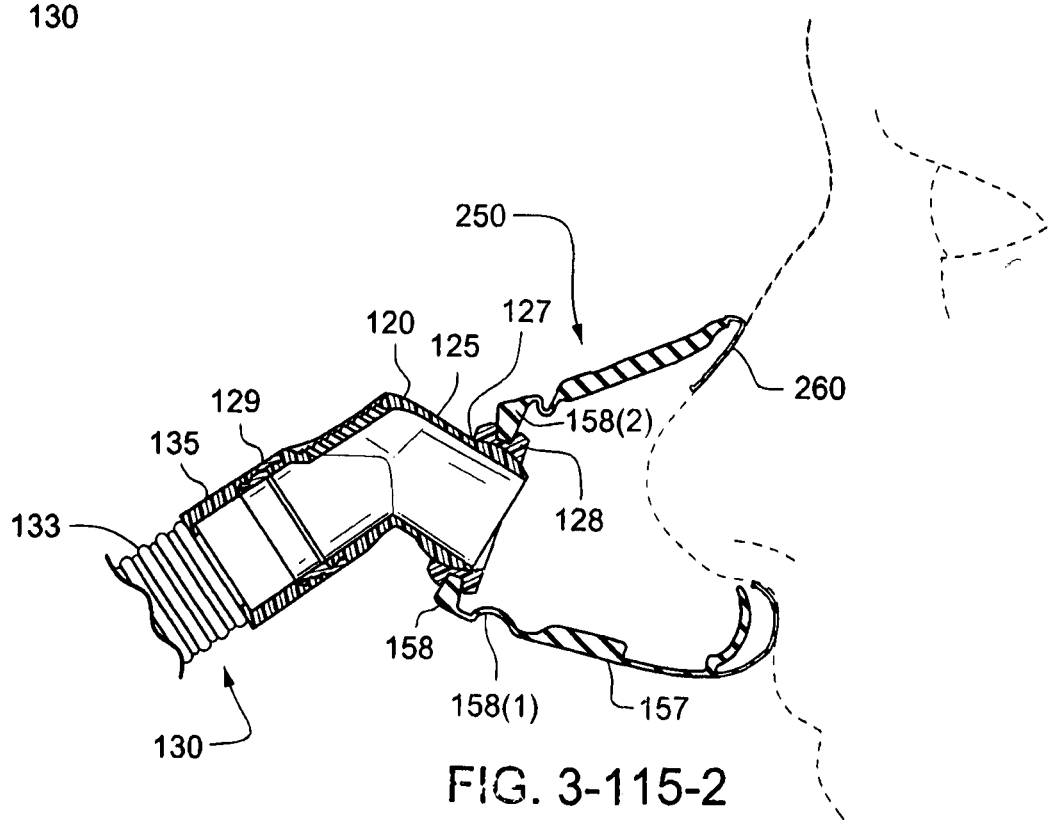
Figures 1, 3, 116:
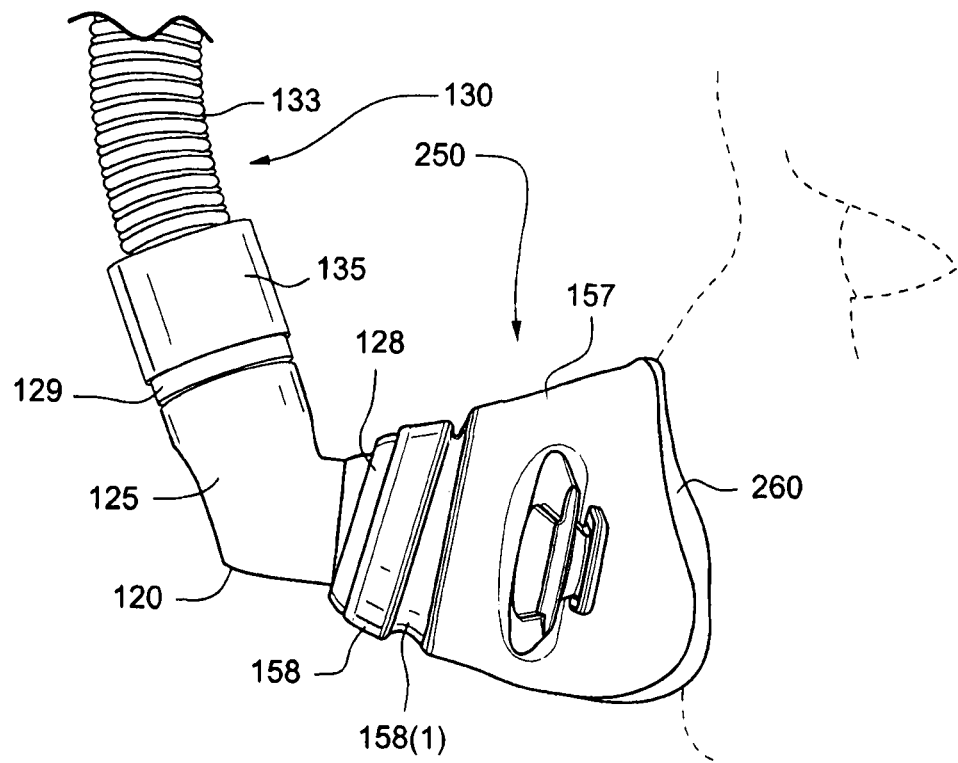
Figures 2, 3, 116:
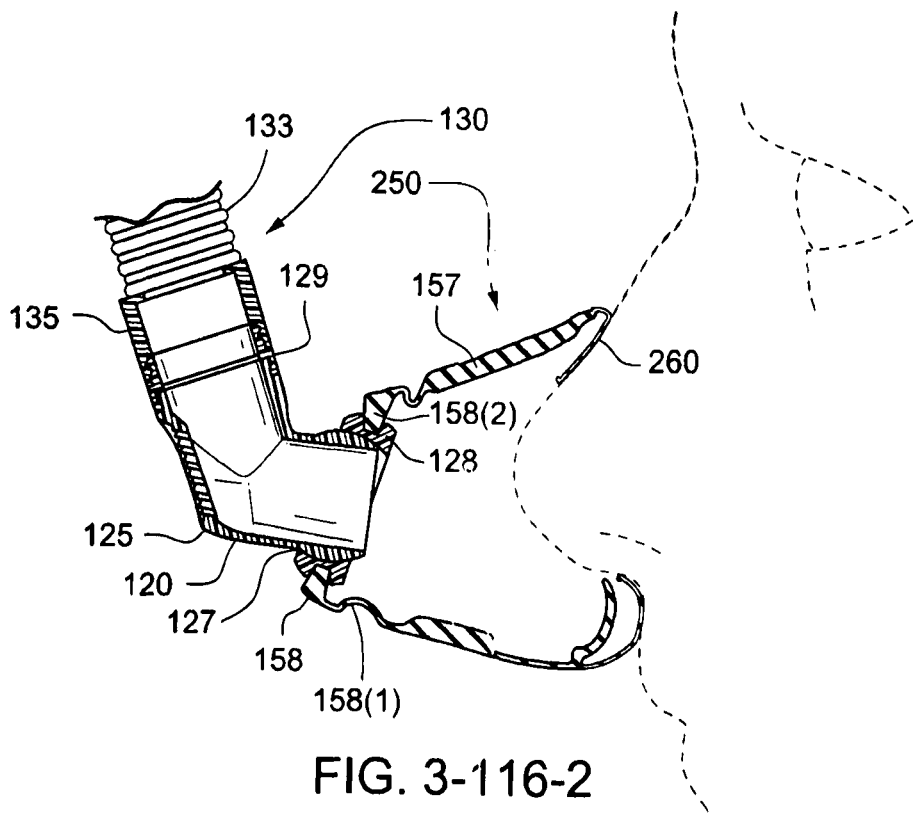
Figures 1, 3, 117:
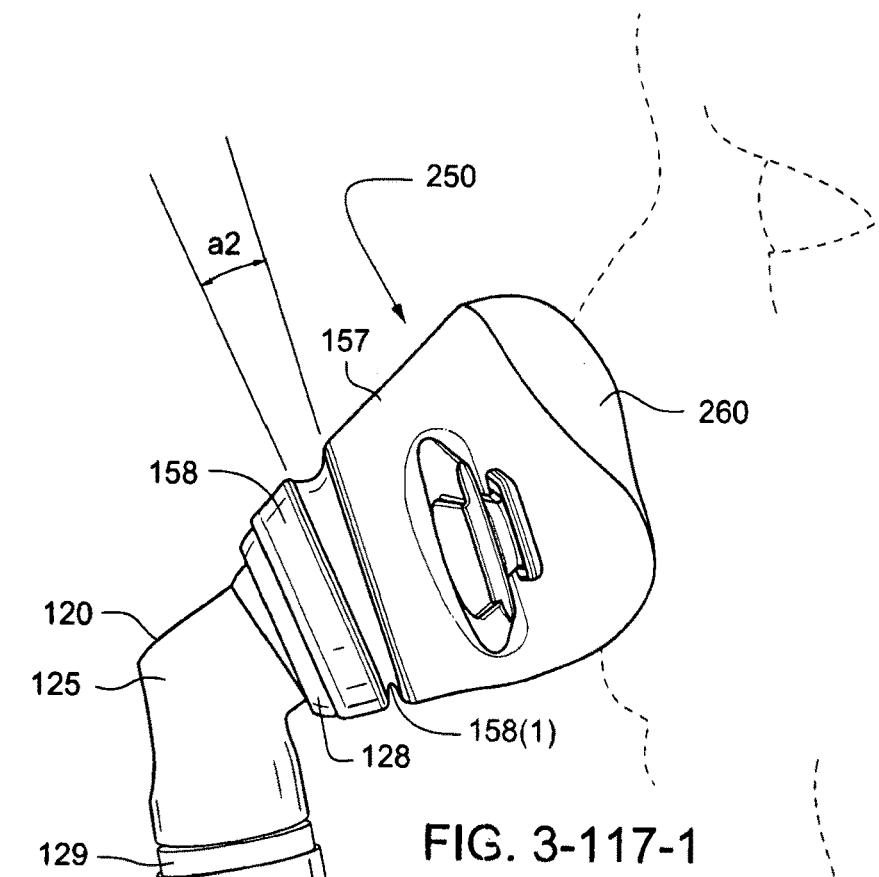
Figures 2, 3, 117:
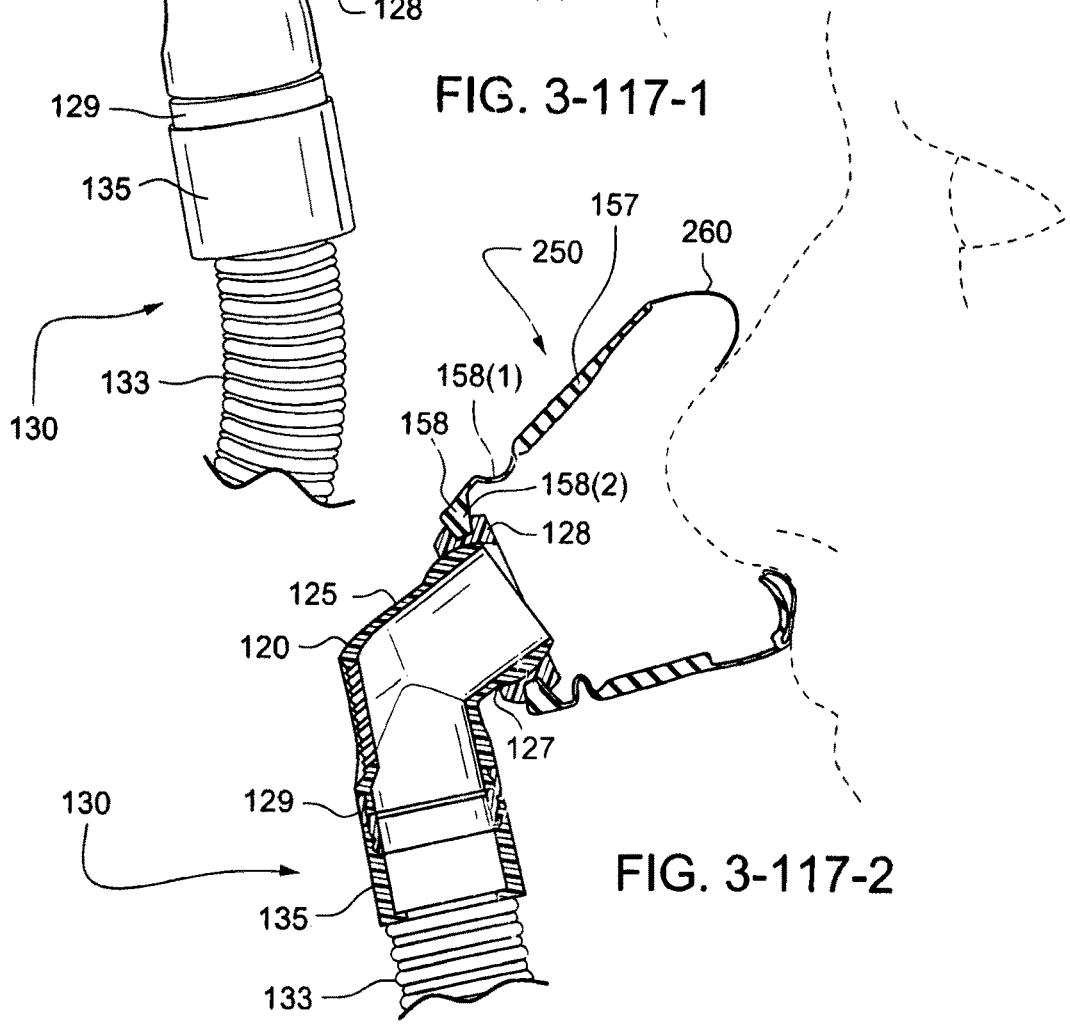
Figures 1, 3, 118:
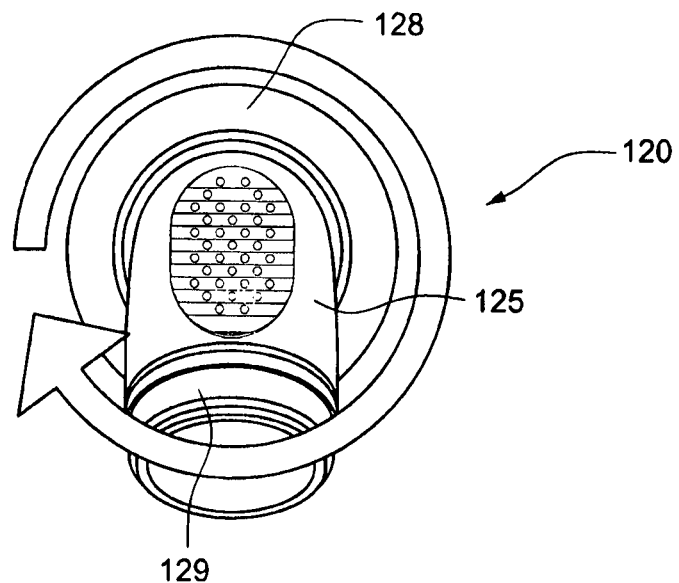
Figures 2, 3, 118:
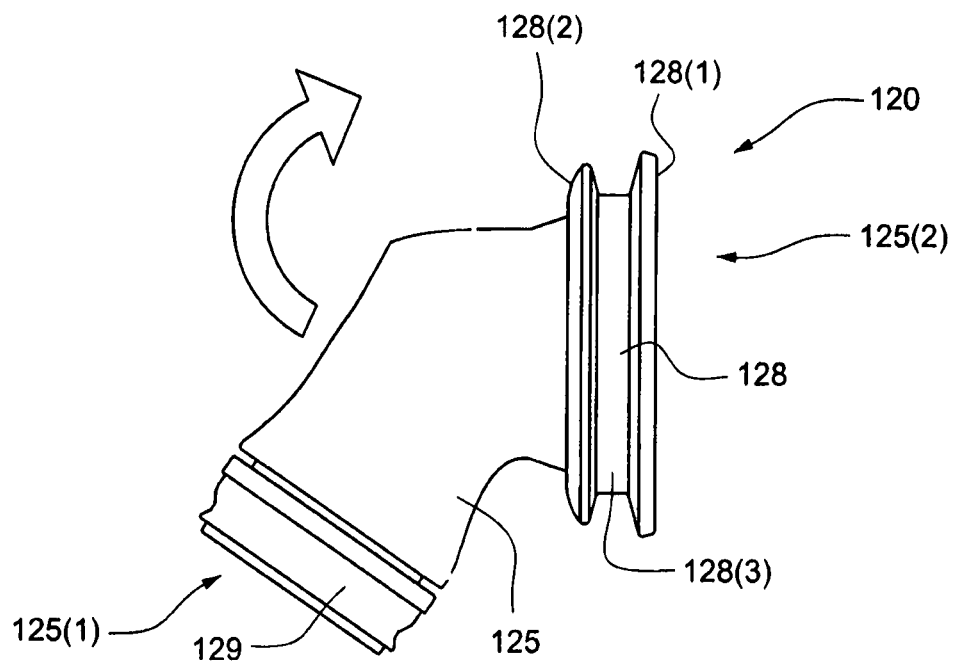
Figures 3, 118:
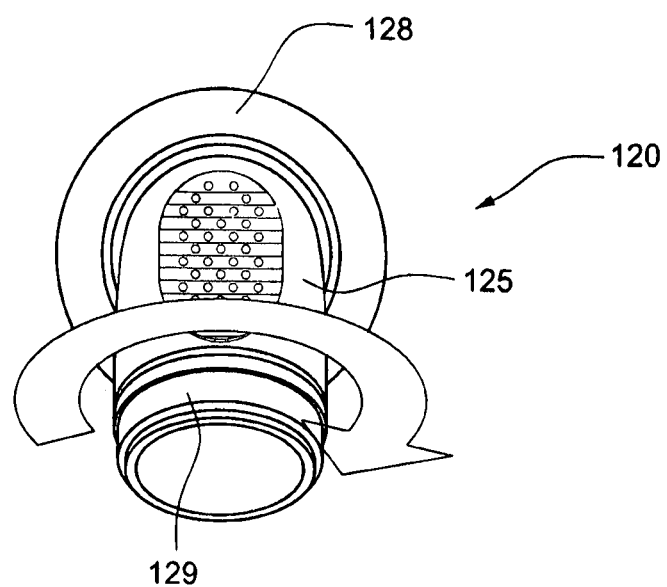
Figures 1, 3, 119:
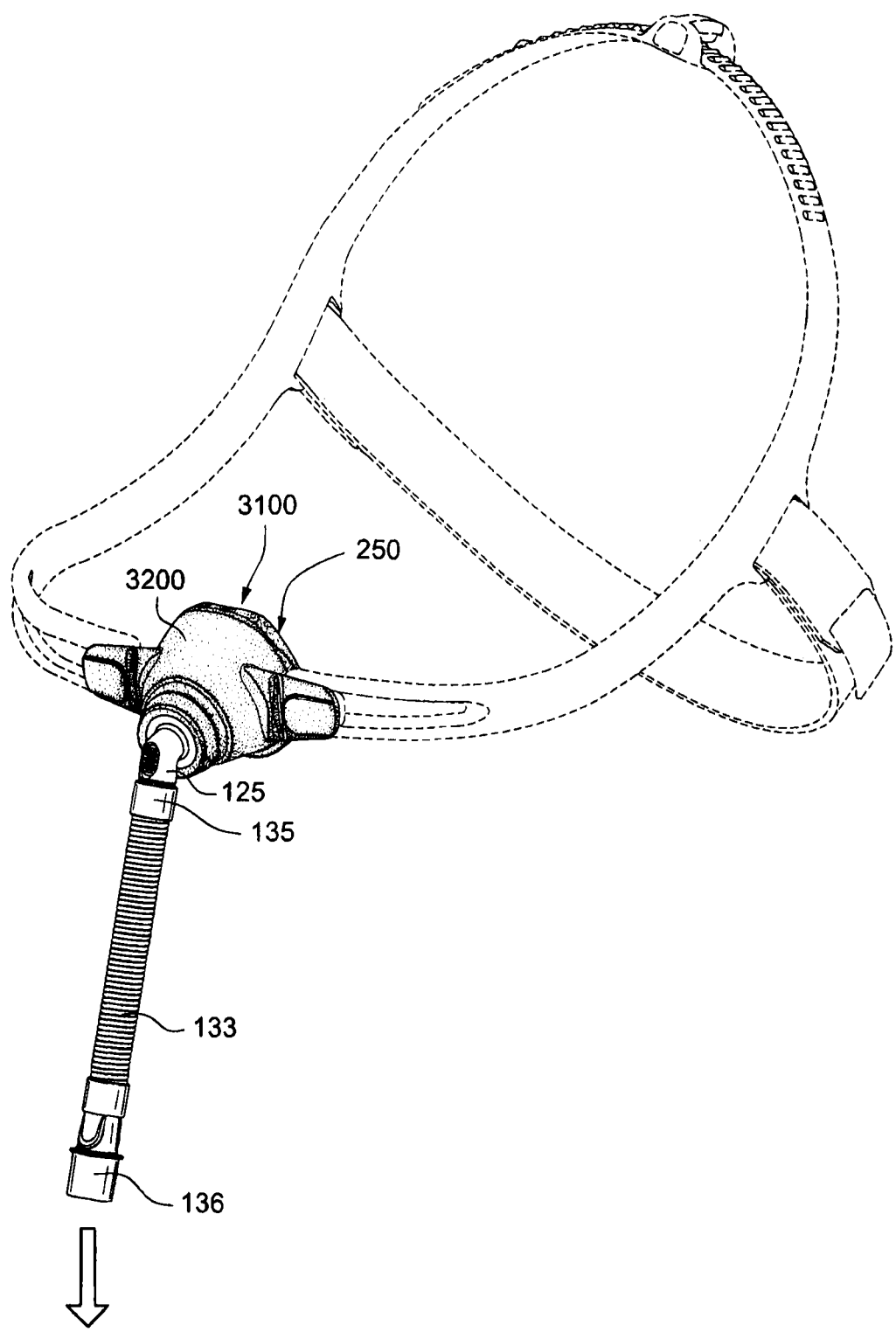
Figures 2, 3, 119:
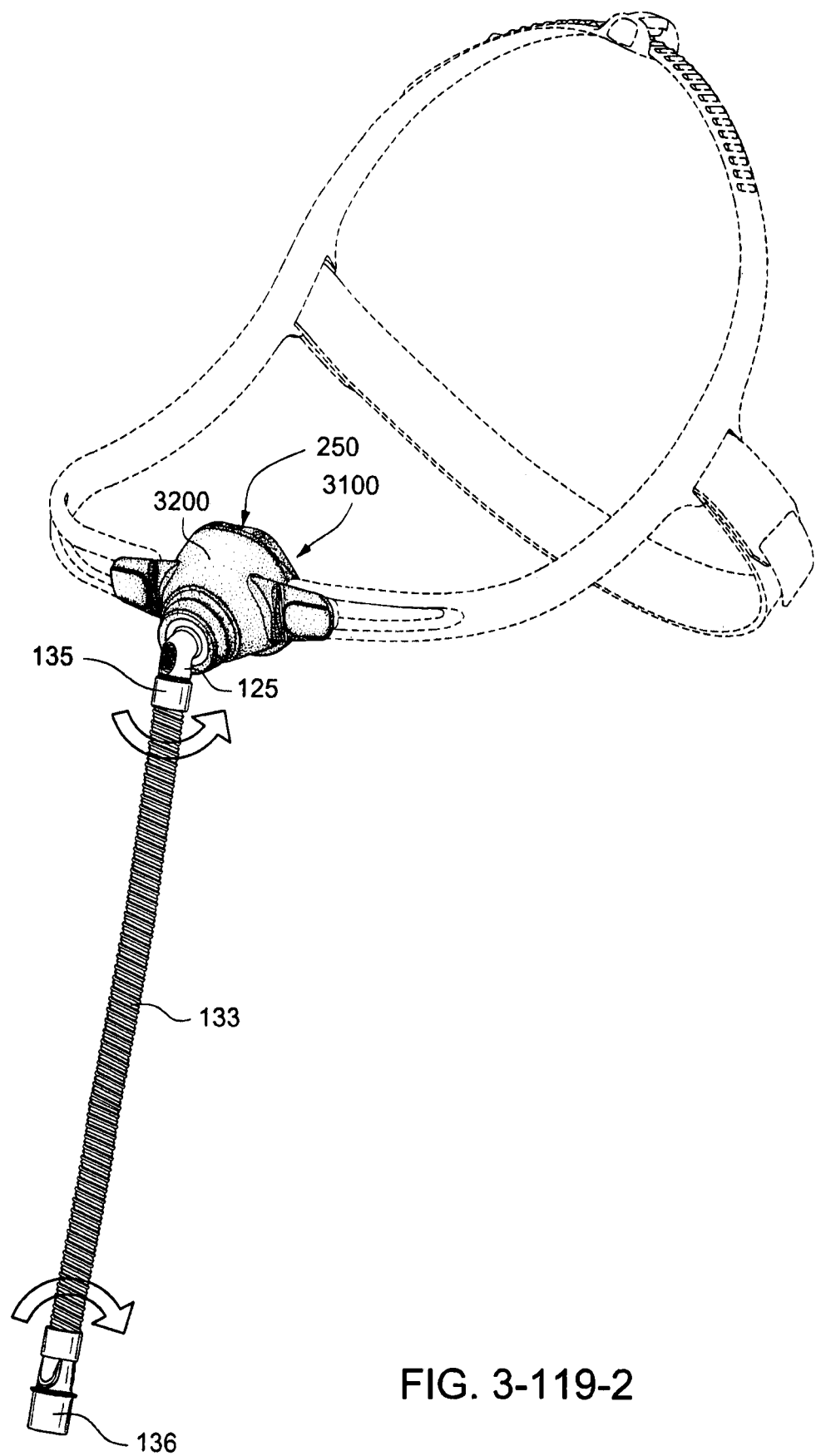

FIG. 3-119-1 is a perspective view of a nasal mask system with the short tube in a retracted position according to an example of the present technology.

FIG. 3-119-2 is a perspective view of a nasal mask system with the short tube in an extended position according to an example of the present technology.

FIGS. 3-120-1 to 3-120-4 show various views of an elbow, short tube and swivel assembly according to an example of the present technology.

Figures 1, 3, 120:
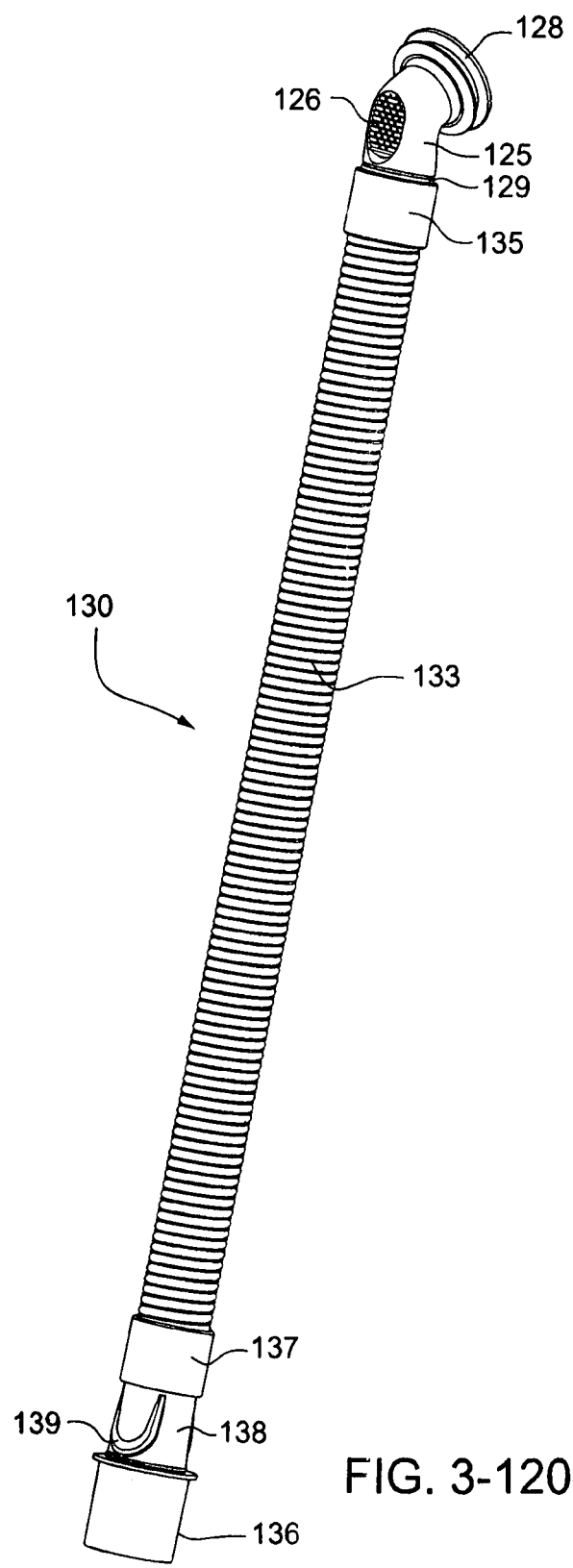
Figures 2, 3, 120:
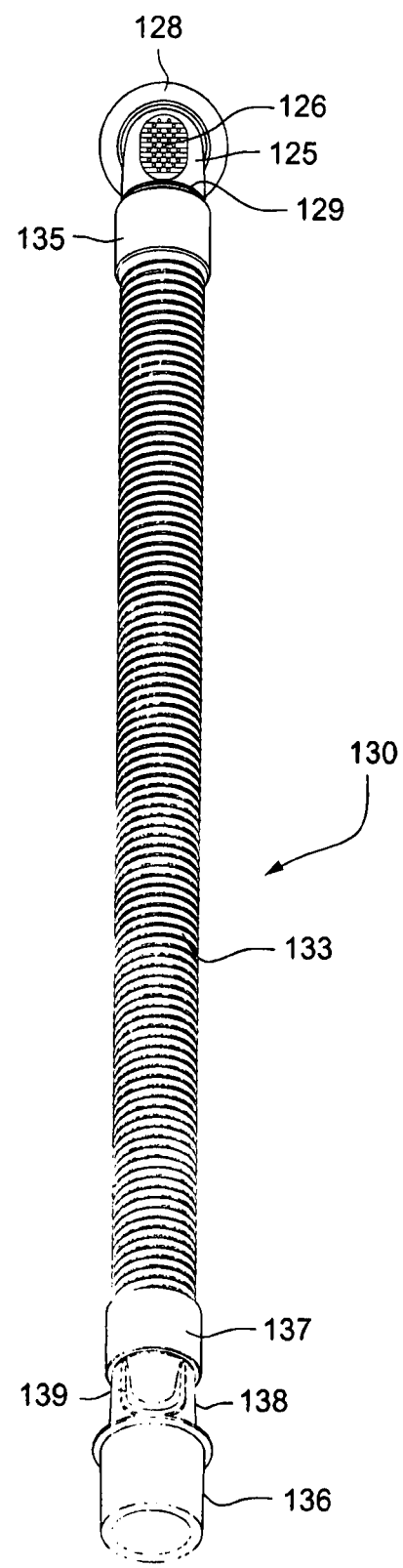
Figures 3, 120:
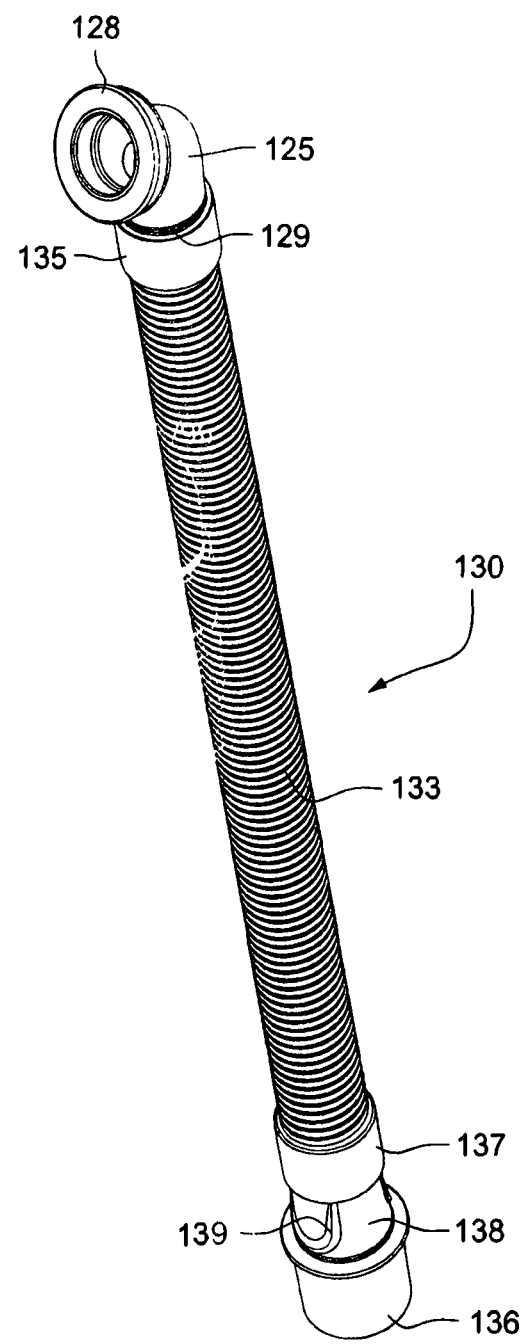
Figures 3, 4, 120:
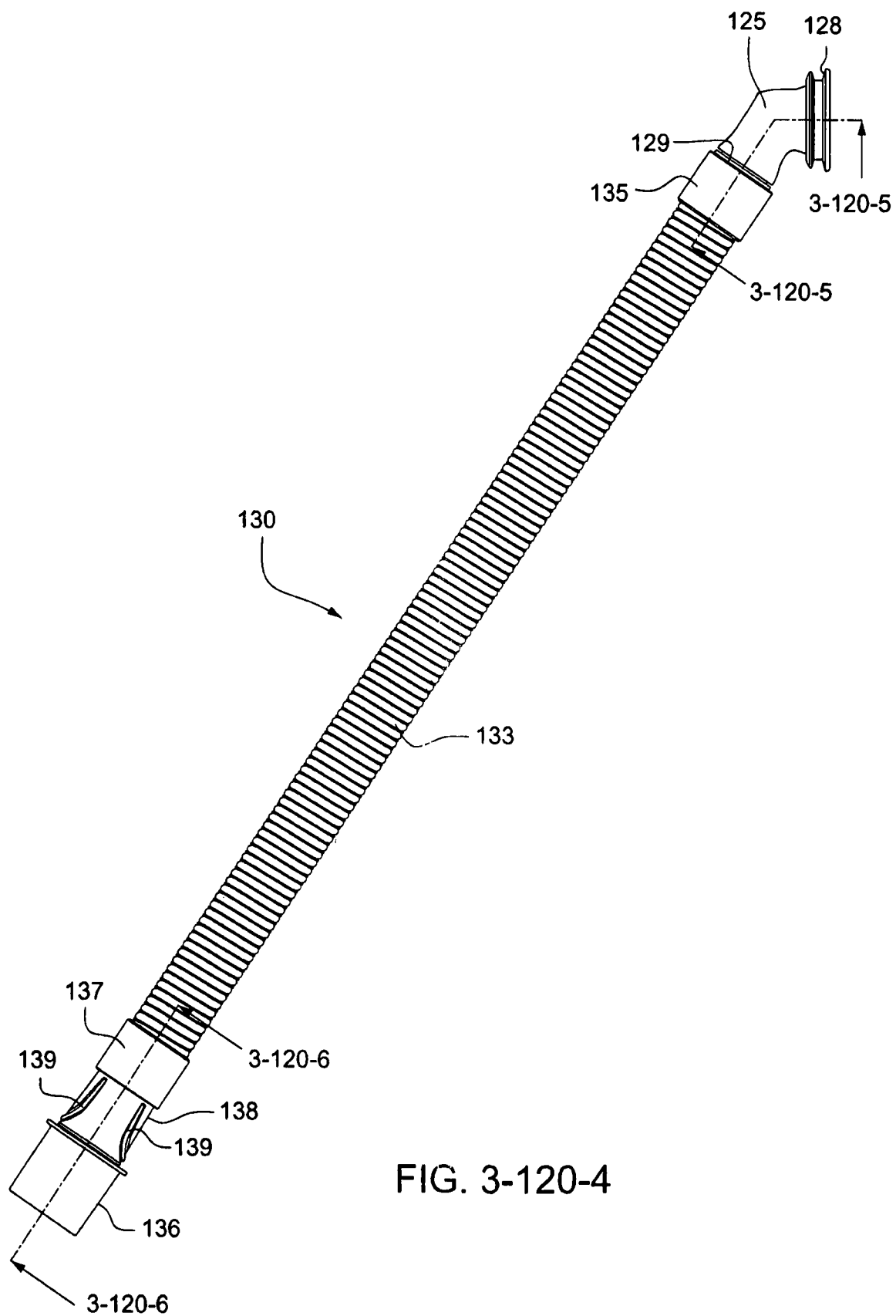
Figures 3, 5, 120:
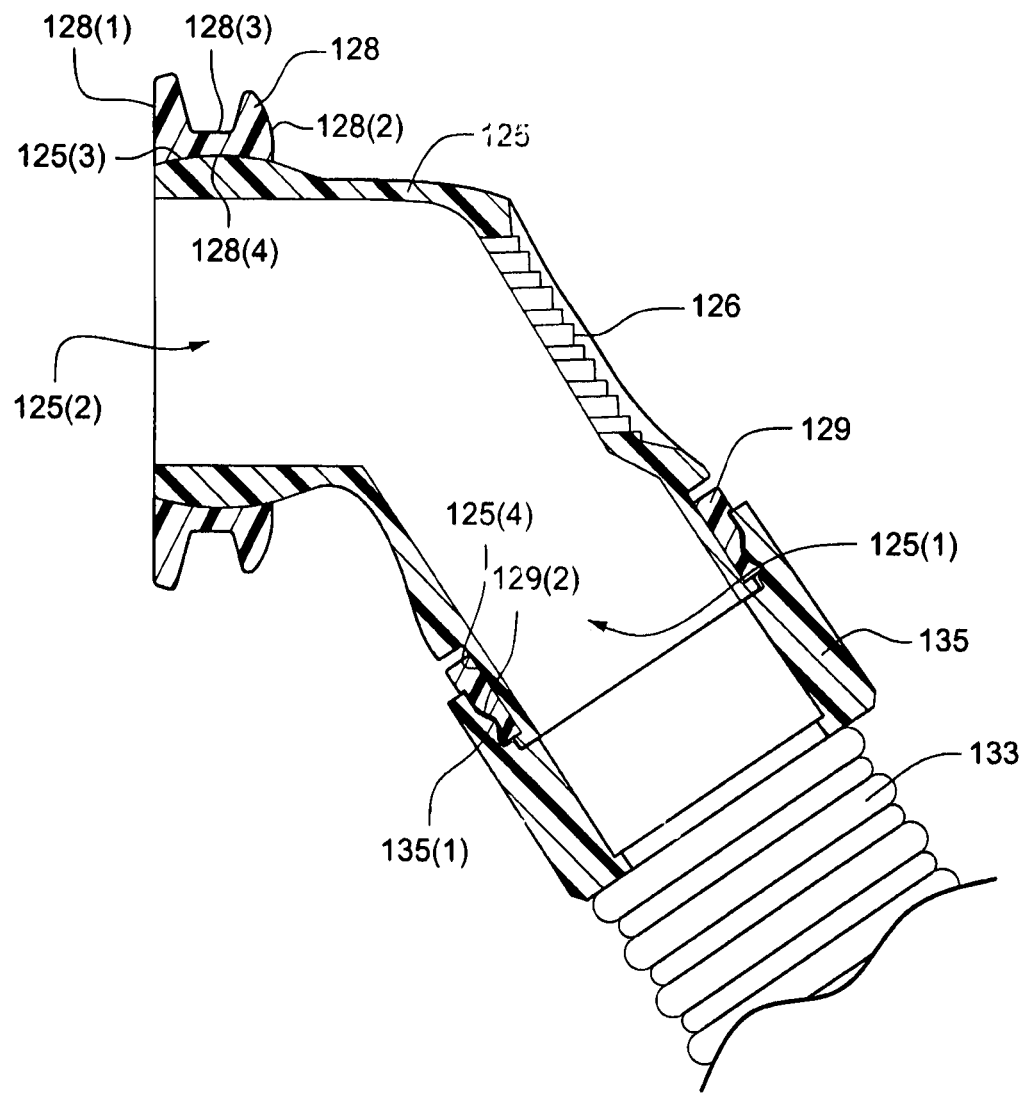
Figures 3, 6, 120:
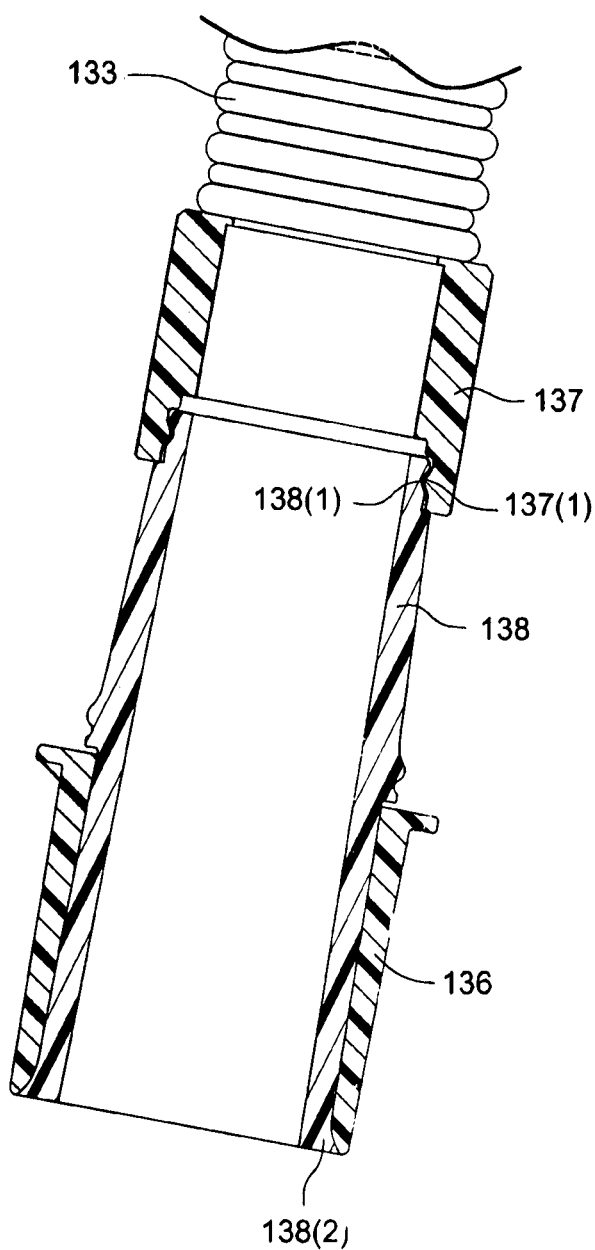

FIG. 3-120-5 shows a cross-section through line 3-120-5-3-120-5 of FIG. 3-120-4.

FIG. 3-120-6 shows a cross-section through line 3-120-6-3-120-6 of FIG. 3-120-4.

4.4 PAP Device

Figure 4A:
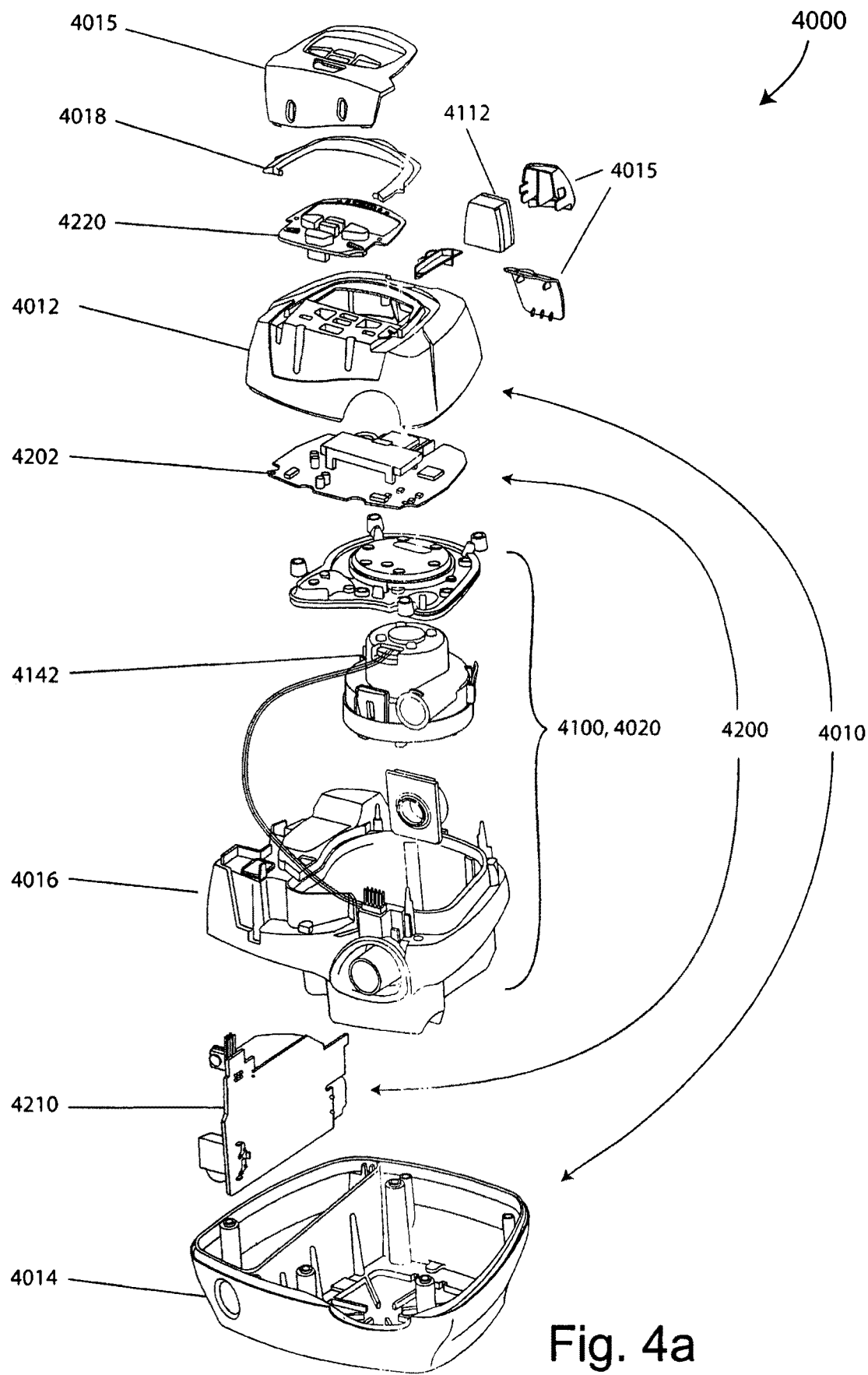

FIG. 4*a* shows a PAP device in accordance with one form of the present technology.

5 DETAILED DESCRIPTION ILLUSTRATED EXAMPLES

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to several examples which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. Hence a supply of air may correspond to a supply of gas including air and supplemental oxygen. It is also acknowledged that the PAP devices or blowers described herein may be designed to pump fluids other than air.

Examples of the technology are directed towards a nasal mask system that is easy and quick to fit (e.g., with little or no adjustment), enable reduced strap tension, is manufacturable in high volumes, provides high consumer appeal, provides comfort and seal, provides reliable quality, unobtrusive, and/or fits a large majority of the population.

One or more examples may include exemplary metrics, e.g., dimensions, angles, percentages, etc. Although specific metrics and ranges therefore may be provided, it is to be understood that these metrics and ranges are merely exemplary and other metrics and ranges are possible depending on application. For example, metrics/ranges that vary from those provided +/−10-20% may be suitable for particular applications.

The present technology is adapted to provide an arrangement or assembly between a patient interface and a tube that may be adapted to decouple tube drag forces, provide a freedom of movement for the tube to enable a patient to position the tube in a desired position without disrupting the seal, vent exhausted gases and provide a compact, unobtrusive design that is aesthetically acceptable to patients.

The venting arrangement may diffuse the exhausted air to prevent air jetting on patients or their bed partners, and to reduce noise.

The venting arrangement may cooperate with the elbow or connector assembly to further diffuse exhaled air, for example the elbow may be provided with a ridge to deflect air in a diffused manner.

The elbow may be provided with one or more swivel connectors adapted to provide more degrees of movement and aid in decoupling tube drag forces.

The elbow may be referred to as an adaptor, connector or may be described as any element attach an air delivery tube to a patient interface.

5.1.1 Nasal CPAP for OSA

In one form, the present technology comprises a method of treating Obstructive Sleep Apnea in a patient by applying nasal continuous positive airway pressure to the patient.

5.2 Patient Interface 3000

A patient interface 3000 in accordance with one aspect of the present technology comprises the following functional aspects: a seal-forming structure 3100, a plenum chamber 3200, a positioning and stabilising structure 3300 and a connection port 3600 for connection to an air circuit 4170 (e.g., see FIG. 3-2). In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

In an example, the plenum chamber 3200 and the seal forming structure 3100 are moulded in one piece. In another example they are formed as two or more separate components.

A patient interface 3000 in accordance with one form of the present technology is nasal mask system 100. As shown in FIGS. 3-1 to 3-3, nasal mask system 100 in accordance with the present technology may comprise a headgear assembly 110, an elbow assembly 120, an air delivery assembly 130 and a cushion assembly or cushion 150. FIGS. 3-4 to 3-10 show various views of the cushion assembly 150, and FIGS. 3-11 to 3-12 show various views of the elbow assembly 120.

A plenum chamber 3200 in accordance with one form of the present technology is cushion assembly 150. Cushion assembly 150 may be adapted to sealingly engage with a patient's airway, including a patient's nose. As shown in FIGS. 3-1 to 3-3, cushion assembly 150 may receive breathable gas from air delivery assembly 130 and/or elbow assembly 120, and be supported in position by headgear assembly 110.

Cushion assembly 150 may comprise a sealing region or sealing cuff 151, two headgear connectors 156, a side wall or side wall region 157 and an attachment region 158. In an example, cushion assembly 150 may be formed from a flexible elastomer or rubber.

FIGS. 3-14 to 3-30, 3-35, and 3-36-1 to 3-40-2 show various views of a cushion assembly 250 according to another example of the present technology, which is similar to the cushion assembly 150. Cushion assemblies 150, 250 are generally referred to as a compact nasal cushion in contrast to the embodiment depicted in FIG. 3-74 which is generally referred to as nasal pillows. As described below, the cushion assembly 250 includes a thinner wall section adjacent a top lip region of the sealing region of the cushion assembly 250 (e.g., to avoid excessive pressure on the patient's columella and septum). Also, each side of the nose region of the sealing region includes a wing or sealing flap adapted to form a seal on the region adjacent the junction between the nasal greater alar cartilage and the lateral nasal cartilage of the patient's nose.

In the illustrated example of FIGS. 3-14 to 3-21, $D_1$ is about 85-105 mm (e.g., about 97 mm), $D_2$ is about 35-55 mm (e.g., about 48 mm), $D_3$ is about 35-55 mm (e.g., about 44 mm), $D_4$ is about 30-50 mm (e.g., about 41 mm), $D_5$ is about 25-45 mm (e.g., about 35 mm), $D_6$ is about 20-30 mm (e.g., about 26 mm), $D_7$ is about 40-60 mm (e.g., about 50 mm), and $D_3$ is about 20-30 mm (e.g., about 23 mm). Although specific dimensions are provided, it is to be understood that these dimensions are merely exemplary and other dimensions are possible depending on application. For example, the exemplary dimensions may vary by +/−10-20% or more or less depending on application.

5.2.1 Seal-Forming Structure 3100

In one form of the present technology, a seal-forming structure 3100 provides a sealing-forming surface, and may additionally provide a cushioning function.

In an example, a seal-forming structure 3100 in accordance with the present technology is constructed from a soft, flexible, resilient material such as silicone.

In one form, the seal-forming structure 3100 comprises a sealing flange 3110 and a support flange 3120. In one form of the present technology, sealing flange 3110 includes membrane 160 of the sealing region 151 and support flange 3120 includes undercushion or backup band 165 of the sealing region 151 (e.g., see FIG. 3-10). In an example, the sealing flange 3110 comprises a relatively thin member with a thickness of less than about 1 mm, for example about 0.25 mm to about 0.45 mm that extends around the perimeter 3210 of the plenum chamber 3200. In an example, the support flange 3120 is relatively thicker than the sealing flange 3110. The support flange 3120 is disposed between the sealing flange 3110 and the marginal edge 3220 of the plenum chamber 3200, and extends at least part of the way around the perimeter 3210 of the plenum chamber 3200. The support flange 3120 is a spring-like element and functions to support the sealing flange 3110 from buckling in use. In use the sealing flange 3110 can readily respond to system pressure in the plenum chamber 3200 acting on its underside to urge it into tight sealing engagement with the face.

In one form of the present technology, seal-forming structure 3100 comprises a superior sealing portion 3102 and an inferior sealing portion 3104 (e.g., see FIGS. 3-10 and 3-21). The superior sealing portion 3102 and the inferior sealing portion 3104 are, e.g., located adjacent one another, and one region may blend into the other.

5.2.1.1 Superior Sealing Portion 3102

Superior sealing portion 3102 is constructed and arranged to form a seal on a portion of the cartilaginous framework of the nose. In an example, superior sealing portion 3102 is constructed from a relatively thin material, e.g. a flap, flange or membrane of material e.g. a thermoplastic elastomer, or a silicone rubber, and further, e.g., one that readily bends or folds in response to light finger pressure when not in use. Depending on the shape of the nose with which it is being used, a relatively narrow width of superior sealing portion 3102 may engage with nose ridge to form a seal. A relatively wider portion of superior sealing portion 3102 may engage with the skin adjacent lateral nasal cartilage to form a seal. See, e.g., FIG. 3-39.

The superior sealing portion 3102 is not designed to overlay the whole of the nose.

In an example, the superior sealing portion 3102 is constructed and arranged, e.g. by being thin and flexible, to be adaptable to different heights of nose ridge. In this way, the range of faces that will be able to get a good seal is increased.

Furthermore, for a given face and nose, the flexibility of the superior sealing portion 3102 means that a seal may be maintained should the plenum chamber 3200 may be moved, e.g. in response to movement of the air circuit 4170.

While the superior sealing portion is constructed so that it does not overlay the nasal bones in use, certain portions of the superior sealing portion may overlay some part of the nasal bones on some faces, depending on exactly how the patient interface is used and the size and shape of the particular face.

In an alternative form, the superior sealing portion is constructed and arranged to form a seal on the nasal bones in use.

5.2.1.2 Inferior Sealing Portion 3104

Inferior sealing portion 3104 is constructed and arranged to form seal on a portion of the upper lip of a patient, and to direct at least part of a sealing force to the maxilla bone of the patient. In use, part of the inferior sealing portion 3104 is located close to the subalare and the alar crest point.

In one form, inferior sealing portion is configured to avoid excessive pressure on the upper teeth or gums. In an example, the inferior sealing portion does not extend along bone (e.g., frontal process of maxilla) superiorly to the alar crest point, however it should be appreciated that in other examples it might.

Inferior sealing portion 3104 may be constructed from a single, relatively thicker flap, rim or flange of material, e.g. a silicone rubber, or thermoplastic elastomer, e.g. with a thickness of about 1 mm to 2 mm. In one form, inferior sealing portion 3104 may be constructed from a dual flap, rim or flange, for example one being relatively thin and the other being relatively thick. Alternatively, inferior sealing portion 3104 may be constructed from a gel-filled bladder.

5.2.1.3 "W" Shaped Region

FIGS. 3-40-1 to 3-40-8 show various views of a cushion assembly 350 according to another example of the present technology. In this example, the cushion assembly includes a general "W" shape in the top lip region, i.e., general "W" shape along the outer (inferior) edge 360(o) of the membrane 360 in the top lip region as best shown in FIG. 3-40-4.

FIGS. 3-41-1 to 3-41-8 show various views of a cushion assembly 450 according to another example of the present technology. This example shows a cushion assembly with a general "W" shape in the top lip region. In contrast to the example of FIGS. 3-40-1 to 3-40-8, the cushion example of FIGS. 3-41-1 to 3-41-8 includes general "W" shape along both the inner (superior) edge 460(*i*) of the membrane 460 and the outer (inferior) edge 460(*o*) of the membrane in the top lip region as best shown in FIG. 3-41-4.

In one form, the "W" portion of the top lip region is constructed and arranged so that a middle portion of the "W" may rest on the subnasale or columella in use, in the event of the seal forming portion shifting upwards (superiorly) in use, leaving clearance (e.g.; indicated by c in FIG. 3-41-8 which is between an inner edge of the undercushion 465 and an inner surface of the plenum chamber) around the respective left and right subalare.

In an example, as best shown in FIGS. 4-41-6, 3-41-7, and 3-41-10, a portion of the sealing portion may have a question-mark shaped, sickle shaped, or c-shaped cross-section. The question-mark shaped, sickle shaped, or c-shaped cross-section may provide the sealing portion with greater range of movement or flexibility towards the patient's face in use. In the illustrated example, the question-mark shaped, sickle shaped, or c-shaped cross-section is provided to a lower portion of the undercushion 465 and/or the side wall region 457, which provides a space below the lower portion of the undercushion 465 and adjacent the side wall region 457. For example, the lower portion of the undercushion 465 is radially offset towards the outside of the side wall region 457. It should be appreciated that such cross-section may be provided around the entire perimeter of the cushion or may only be provided in selected regions of the cushion, e.g., only in the top lip region. Also, the size and/or configuration of such cross-section may vary in selected regions.

In the illustrated example of FIGS. 3-40-1 to 3-40-8 and 3-41-1 to 3-41-8, $D_1$ is about 90-110 mm (e.g., about 105 mm), $D_2$ is about 40-60 mm (e.g., about 51 mm), $D_3$ is about 40-60 mm (e.g., about 51 mm), $D_4$ is about 35-55 mm (e.g., about 44 mm), $D_5$ is about 30-50 mm (e.g., about 38 mm), $D_6$ is about 25-35 mm (e.g., about 32 mm), $D_7$ is about 45-65 mm (e.g., about 58 mm), and $D_8$ is about 20-30 mm (e.g., about 26 mm). Although specific dimensions are provided, it is to be understood that these dimensions are merely exemplary and other dimensions are possible depending on application. For example, the exemplary dimensions may vary by +/−10-20% or more or less depending on application. For example, the sealing portion and aperture may be wider, e.g., $D_1$ is about 100-120 mm (e.g., about 114 mm), $D_6$ is about 40-50 mm (e.g., about 42 mm), $D_7$ is about 55-75 mm (e.g., about 68 mm), and $D_8$ is about 20-30 mm (e.g., about 24 mm). In another example, the sealing portion and aperture may be narrower, e.g., $D_1$ is about 90-110 mm (e.g., about 100 mm), $D_6$ is about 25-35 mm (e.g., about 28 mm), $D_7$ is about 45-65 mm (e.g., about 54 mm), and $D_8$ is about 20-30 mm (e.g., about 24 mm).

5.2.1.4 Sealing Region

In accordance with another form of the present technology seal forming structure 3100 comprises sealing region 151. Sealing region 151 may be adapted to interface with the patient and form a seal with the patient's airways. Sealing region 151 may include a nose ridge or nose ridge region 152, sides of the nose region 153, corners of the nose region 154 and top lip region 155. Sealing region 151 may comprise a membrane or flap type seal 160. In an example, as shown in FIGS. 3-18 and 3-19, the inner edge of the membrane 260 may includes a bead 260-1, e.g., to prevent tearing, enhance sealing along the edge. Sealing region 151 may further comprise an undercushion or backup band 165, extending around part of or the entire perimeter of the sealing region. A further aspect of the present technology is a cushion for a mask that seals at its upper extent in a region of the nose that is generally above the tip of the nose, and extends across the alar or flares of the patient's nose.

In an example, sealing region 151 may be preformed or otherwise pre-shaped so as to conform to that patient's facial topography.

Sealing Along Nasal Ridge

One aspect of the present technology relates to sealing of the sealing region in the nose ridge region. In an example, the sealing region in the nose ridge region is adapted to engage along the nasal ridge between the pronasale and sellion, and along the nasal cartilage region of the nasal ridge and below or inferior to the nasal bone. That is, the nasal mask system is constructed to have a seal-forming region that is substantially on at least part of the cartilaginous framework of the patient's nose and not on the nasal bone, i.e., seal along nasal ridge without contacting nasal bridge/skin on the nasal bone.

For example, the sealing region 151 is adapted to be positioned and seal at its upper extent in a region of the nose that is generally above the tip of the nose (i.e., above the pronasale), and extends across the alar or flares of the patient's nose, e.g., not extending over or across the bone of the patient's nose.

In an example, the sealing region 151 is positioned at its upper extent in a region of the nose that is generally close to the junction between bone and cartilage on a range of people with larger noses, and avoids impinging on the sight of people with smaller noses.

Nose Ridge Region

Nose ridge region 152 may be adapted to engage with a nose ridge of a patient. In an example, the nose ridge region may be shaped or preformed to accommodate a patient's nose ridge, for example, as best shown on FIG. 3-7, the nose ridge region may be lower (i.e., closer to the attachment region 158) than the sides of the nose region 153. Nose ridge region 152 may comprise a membrane 160 for sealing without an undercushion or backup band. In an example, such an arrangement prevents excess pressure on the sensitive nose ridge region. In an example, the membrane at the nose ridge region 152 may be relatively longer that the membrane in other regions of the seal region, for example the top lip region 155. The membrane in the nose ridge region 152 may be, for example, about 2-5 mm in length. In an example, the membrane in the nose ridge region 152 may be about 2-4 mm in length. In an example, the membrane in the nose ridge region 152 may be about 3 mm in length.

Sides of the Nose Region

Sides of the nose region 153 may be adapted to engage with the sides of a patient's nose. In an example, sides of the nose region 153 may be preformed to accommodate the sides of the patient's nose and potentially their cheeks. As best shown on FIG. 3-5, sides of nose the region 153 extends from the apex of the cushion at nose ridge region 152 to the corners of the nose region 154. The sides of nose the region 153 slopes upwardly from the nose ridge region 152 to the corners of the nose region, see for example FIG. 3-6. Sides of the nose region 153 may comprise a membrane 160 for sealing without an undercushion or backup band. In an example, such arrangement prevents excess pressure on the sides of the patient's nose or alar or flares. Excess pressure on these regions may cause the cartilage of the nose to collapse inwardly towards the septum, thereby occluding or partially occluding the patient's airway.

Corners of the Nose Region

Corners of the nose region 154 may be adapted to form a seal with the corners of the patient's nose. FIG. 3-6 shows the corners of the nose region 154 having an apex or point generally indicated by $H_1$, being the maximum height of the sealing region 151. This height is to ensure that the most force is applied to the sealing region 151 in the corners of the nose region 154, as this is a boney region of the face and is therefore less sensitive to pressure. Furthermore, this region of the patient's face is particularly difficult to seal on as the geometry of the face in this region is quite complex, so the greater the force applied to the seal in this region, the more likely a seal will form. In addition, since lower sealing forces are required on the nose ridge region and the sides of the nose region (for comfort and to avoid occlusion), the sealing region must be anchored at the corners of the nose region. Corners of the nose region 154 may comprise a membrane or membrane seal 160 and an undercushion or backup band 165. The use of both a membrane and an undercushion may ensure a higher sealing force in this region. In an example, the membrane may have a thickness about 0.1-0.5 mm, for example about 0.3 mm. In an example, the undercushion may have a thickness of about 0.3-2 mm.

Top Lip Region

Top lip region 155 may be adapted to engage the surface between the patient's top lip and base of the nose. In an example, top lip region may have a relatively shorter membrane length than the nose ridge region, for example a length of about 0.5-2.5 mm, e.g., about 1.5-2.5 mm. In an example, this shorter membrane length may be advantageous as some patient's only have a small space between their top lip and the base of their nose. As best shown in FIG. 3-10, top lip region 155 may have a membrane seal 160 and an undercushion or backup band 165. The use of both a membrane and an undercushion may ensure a higher sealing force in this region. In an example, the membrane may have a thickness about 0.1-0.5 mm, for example about 0.3 mm. In an example, the undercushion may have a thickness of about 0.3-2 mm, for example about 1.5 mm. In an example, the thickness of the undercushion may vary along the length of the top lip region, for example from about 0.3 mm at the corners of the nose region, to about 1.2 mm at the centre of the top lip region.

5.2.1.5 Seal

Use of the undercushion or back-up band enables the membrane or facial flap to be made considerably thinner than if a single unsupported flap were used. This is highly advantageous in that a thinner flap is in turn more flexible, so as to feel softer and more comfortable and more readily conform to irregularities in the facial contour. It also permits the flap to more readily respond to system pressure in the breathing chamber acting on its underside to urge it into tight sealing engagement with the face.

As noted above, the nasal mask system is constructed to have a seal-forming region that is substantially on the cartilaginous framework on the nose (i.e., not on the nasal bone), and which does not block the nose. In an example, this may be achieved by providing a compression seal (e.g., using an undercushion structure) along the patient's top lip (e.g., inferior sealing portion) and not on the patient's nose. Seal on the patient's nose (e.g., superior sealing portion) may be achieved by tension in the membrane and/or a pneumatic seal.

For example, as shown in the cushion example of FIGS. 3-14 to 3-30 and also described in the above example, the undercushion or backup band 265 is only provided in the top lip region 255 and the corners of the nose region 254 of the cushion, e.g., see FIGS. 3-16, 3-18, 3-22, 3-23, 3-29, and 3-30. That is, the sealing region includes a single layer or membrane 260 only structure in the nose ridge region 252 and sides of the nose region 253 (e.g., see FIGS. 3-18 and 3-22 to 3-28), and the sealing region includes a dual layer or membrane 260 and undercushion 265 structure in the top lip region 255 and corners of nose region 254. The dual layer structure provides a compression seal along the top lip region and corners of nose region. In contrast, the nose ridge region and sides of the nose region uses tension in the membrane (edge of the membrane stretched into sealing engagement due to tension applied to membrane) and/or pressure in the breathing chamber acting on the membrane (pneumatic seal) to provide a seal. The single layer is also provided in the nose ridge region and sides of the nose region to provide a softer and more flexible seal that avoids any potential for blocking the patient's nose, i.e., prevents excess pressure on the sides of the patient's nose or alar or flares which may cause the cartilage to collapse inwardly and potentially at least partially occlude the patient's airway.

Thus, the cushion assembly according to an example of the present technology provides different sealing mechanisms in different portions of the cushion. For example, the cushion assembly may provide one mechanism of sealing in the superior portion of the cushion (e.g., sealing by tension in the membrane and/or a pneumatic seal) and a different mechanism of sealing in the inferior portion of the cushion (e.g., compression seal). In the illustrated example, the cushion assembly provides a compression seal via a dual layer or membrane and undercushion structure. However, it should be appreciated that the compression seal may be provided by alternative structures, e.g., gel-filled or foam-filled pocket, thicker single wall (e.g., about 0.8 to 1.2 mm thick silicone).

FIG. 3-38 shows an example of the cushion assembly 250 engaged with the patient's face and under pressure or inflated in use, i.e., supply of air at positive pressure being applied to the cushion assembly 250. FIG. 3-39 shows a hatched area along the sealing portion of the cushion assembly 250 which illustrates a width or contact area 280 of the sealing portion engaged with the patient's face in use. The width or contact area includes an inner edge 280(i) (e.g., along the edge of the orifice) and an outer edge 280(o). FIG. 3-36 also shows the outer edge 280(o) of the contact area in dashed lines. As illustrated, a relatively narrow width of superior sealing portion 3102 may engage with the nose ridge to form a seal, e.g., depending on the shape of the nose with which it is being used. A relatively wider portion of superior sealing portion 3102 may engage with the skin adjacent lateral nasal cartilage to form a seal. In the inferior sealing portion 3104, substantially the entire width of the inferior sealing portion may engage the skin along the corner of nose region and top lip region to form a seal. Thus, the width or contact area of the sealing portion engaged with the patient's face in use may vary around the perimeter of the cushion assembly to form a seal.

5.2.1.6 Sealing Flap

In an example, as shown in FIGS. 3-14, 3-16, 3-20, 3-22, 3-26, 3-27, 3-35, and 3-36, each side of nose region 253 of the sealing region includes a portion 270, e.g., a wing or sealing flap, that protrudes from the edge of the membrane 260 along its inner perimeter. As best shown in FIGS. 3-35 and 3-36, each sealing flap 270 is adapted to form a seal on the region adjacent the junction between the nasal greater alar cartilage and the lateral nasal cartilage of a patient's nose (also referred to as the alar crease). The exact location of the sealing flap on a face in use may vary depending on the size and shape of the nose with which it is being used.

As illustrated, each sealing flap 270 is at least partially angled or pre-biased outwardly away from the breathing chamber of the cushion. When engaged with the patient's nose, the sealing flaps are deflected towards the breathing chamber which provides a bias for sealing in the junction noted above. That is, the shape, flexibility, and pre-bias of the sealing flaps allows the flaps to accommodate changes in curvature or contour in this junction (e.g., which tend to continually vary when the nasal alar or "flare" in use) so as to maintain seal and prevent leaks in use.

In an example, the sealing flange (including membrane 260 and sealing flap 270) defines a generally T-shaped orifice. The edge of the membrane 260 along its inner perimeter along with the edge of each sealing flap 270 along its inner perimeter cooperate to define an orifice 275 into the plenum chamber. In an example, such orifice 275 includes a general T-shape including an upper orifice portion 275(1) (along vertical axis v as viewed in FIG. 3-20) and a lower orifice portion 275(2) (along horizontal axis has viewed in FIG. 3-20) that extends generally transverse to the upper orifice portion 275(1).

As best shown in FIG. 3-14, the sealing flap 270 changes the curvature and/or angle of the edge defining the orifice 275, i.e., edge of the orifice 275 curves upwardly and outwardly away from the breathing chamber at least along the sealing flap 270.

The curvature of the cushion may vary along the patient contacting surface of the membrane 260 in different regions of the cushion, e.g., to facilitate sealing in different regions of the patient's face.

For example, as shown in FIG. 3-14, the nose ridge region 252 and the top lip region 255 each include at least a portion that is locally saddle-shaped in curvature, e.g., curves up in one direction d1 and curves down in a different direction d2. FIG. 3-37 is another view of the cushion 250 illustrating such saddle-shaped curvature in the nose ridge region 252 and the top lip region 255.

It should be appreciated that the above-noted shapes of curvature are approximate shapes and should not be limited to strict mathematical definitions of such shapes.

In addition, it should be appreciated that regions may include similar curvature shapes, but the magnitudes of such curvature may be different. For example, the nose ridge region 252 and the top lip region 255 may both include at least a portion that is locally saddle-shaped, however the magnitude of curvature in one and/or both principle directions of such saddle-shape may be different in each region.

5.2.2 Aperture

In an example, where a single mask should be used to fit about 85% of the female population, the undercushion aperture width (e.g., indicated at uw in FIG. 3-41-9 for example) is about 36 mm to about 42 mm, or about 38 mm to about 40 mm. In an example, where a single mask should be used to fit about 85% of the male population, the undercushion aperture width is about 40 mm to about 46 mm, or about 42 mm to about 44 mm. In one form, to account for nose width variations of various ethnicities, to fit up to 95% of an average population, an undercushion aperture width is about 50 mm to about 56 mm, or about 52 mm to about 54 mm.

In an example, where a single mask should be used to fit about 85% of the female population, the membrane aperture width (e.g., indicated at mw in FIG. 3-41-9 for example) is about 23 mm to about 29 mm, or about 25 mm to about 27 mm. In an example, where a single mask should be used to fit about 85% of the male population, the membrane aperture width is about 39 mm to about 45 mm, or about 41 mm to about 43 mm. In one form, to account for nose width variations of various ethnicities, to fit up to 95% of an average population, a membrane aperture width is about 49 mm to about 55 mm, or about 51 mm to about 53 mm.

5.2.3 Plenum Chamber 3200

Plenum chamber 3200 is formed in part by a side wall. In one form, the side wall includes side wall region 157 of sealing region 151. The plenum chamber has a perimeter 3210 that is shaped to conform generally to the surface contour of the face of an average person (e.g., see FIGS. 3-8 and 3-9). In use, a marginal edge 3220 of the plenum chamber 3200 is positioned in close proximity to an adjacent surface of the face (e.g., see FIG. 3-10). Actual contact with the face is provided by the seal-forming structure 3100. In an example, the seal-forming structure 3100 extends in use about the entire perimeter 3210 of the plenum chamber 3200. In an example, the plenum chamber is adapted to receive a portion of the patient's nose including the pronasale, e.g., the plenum chamber forms over and surrounds a portion of the cartilaginous framework of the nose including the pronasale.

In an example, the walls of the plenum chamber 3200 are flexible, or semi-rigid. In an example, plenum chamber 3200 does not include a rigid frame or shell. In an example, the walls of the plenum chamber 3200 are not rigid, and, e.g., the walls of the plenum chamber 3200 are not floppy. In certain forms, flexibility of the walls of the plenum chamber 3200 assists to decouple a tube drag force from disrupting a seal.

In one form, the walls of the plenum chamber 3200 are moulded from a silicone rubber. In an example, the walls of the plenum chamber 3200 are constructed from a silicone rubber with a Type A indentation hardness of about 35 to about 40, and with a thickness in the range of about 2 mm to about 4 mm. In certain forms of the present technology, the plenum chamber 3200 may have different thicknesses in different regions.

5.2.3.1 Side Wall Region

Side wall region 157 may extend between sealing region 151 and attachment region 158. Side wall region 157 may be generally conical, that is, it may have a first diameter at proximate attachment region 158 and a second diameter proximate sealing region 151, with the first diameter being less than the second diameter. Side wall region may have a thickness of about 1.5-5 mm, e.g., about 1.5-3 mm, e.g., about 2 mm. Such a thickness may provide some support to the sealing region 151, prevent the elbow assembly 120 contacting the patient's nose, and ensure that the cushion does not collapse from headgear tension when in use.

Side wall region 157 may connect or be formed with headgear connectors 156. Such an arrangement may replace the need for a rigid frame or skeleton, as the headgear connectors are arrange proximal to the sealing region 151. Headgear connectors 156 may be disposed on opposing sides of side wall 157.

5.2.3.2 Thinner Wall Section

In an example, as best shown in FIGS. 3-16, 3-18, 3-23, and 3-30, the side wall region 257 between the sealing region 251 and the attachment region 258 includes an area 268 adjacent the top lip region 255 of the sealing region that includes a thickness that is less than corresponding thicknesses adjacent the nose ridge, sides of nose, and corners of nose regions of the sealing region. That is, the area 268 includes a thinner walled cross-section adjacent the top lip region 255 of the sealing region. Such area 268 of thinner cross-section lessens the force provided by the sealing region along this section of the top lip region 255. For example, such area 268 provides less pressure along the top lip region 255 than the corners of nose region 254 (i.e., stiffer along the corners of nose region than the top lip region thereby giving rise or effecting relatively greater pressure along the corners of nose region (along the corners of the lip adjacent the alars), in order to avoid excessive pressure on the columella or septum of the patient's nose which is a more sensitive region of the patient's nose.

FIGS. 3-22 to 3-30 show exemplary cross-sectional views through various regions of the cushion assembly 250. For example, FIG. 3-23 is a cross-sectional view through the nose ridge region 252 and the top lip region 255 showing the single layer or membrane 260 only structure in the nose ridge region 252 and the dual layer or membrane 260 and undercushion 265 structure in the top lip region 255. FIG. 3-23 also shows the thinner cross-section area 268 in the side wall region 257 adjacent the top lip region 255, e.g., to avoid excessive pressure on the columella or septum. In addition, FIG. 3-23 shows the attachment region 258 including thinner wall section 258(1), e.g., to permit decoupling of tube drag forces. 3-24 and 3-25 show the single layer or membrane 260 only structure in the sides of the nose region 253. FIGS. 3-26 and 3-27 also show the single layer or membrane 260 only structure in the sides of the nose region 253 as well as at least part of the wing or sealing flap 270 that protrudes from the edge of the membrane 260. FIGS. 3-27 and 3-28 show at least part of the headgear connector 256. 3-29 and 3-30 show the dual layer or membrane 260 and undercushion 265 structure in the corners of nose region 254 and the top lip region 255. FIG. 3-30 shows the thinner cross-section area 268 in the side wall region 257 adjacent the top lip region 255.

5.2.4 Positioning and Stabilising Structure 3300

In an example, the seal-forming portion 3100 of the patient interface 3000 of the present technology is held in sealing position in use by the positioning and stabilising structure 3300.

In one form, the seal-forming portion 3100 of the patient interface 3000 of the present technology is held in sealing position via a two-point connection to a positioning and stabilising structure 3300.

In one form, the positioning and stabilising structure 3300 connects to plenum chamber 3200 via headgear connector 156.

In an example, there are only two connectors 156 to the plenum chamber 3200.

5.2.4.1 Headgear Connector

Headgear connector 156 may comprise a lug or interface 159 adapted to receive a cushion connector 116 on headgear 110. A similar arrangement is disclosed in PCT application number PCT/AU2008/001557, filed 22 Oct. 2008, which is incorporated herein by reference in its entirety.

Headgear connectors 156 may be positioned at an angle relative to the vertical axis of the sealing region 151. As best shown in FIGS. 3-6 and 3-7, headgear connectors 156 may be positioned at angle α relative to the vertical axis of the sealing region 151. In an example, angle α may be approximately 90-135°. In an example, angle α may be approximately 90-120°. In an example, angle α may be approximately 90-100°. Angle α aligns the headgear connectors in such a way so as to ensure a sealing force between the cushion and the patient is sufficient to effect a seal without causing discomfort or causing the cushion to collapse (for example, the closer angle α is to 180°, the more likely the cushion is to collapse inwardly towards the vertical axis when headgear tension is applied, thus pinching the patient's nose), particularly in the sides of the nose region 153 of sealing region 151.

In an alternative example, as best shown in FIGS. 3-40-1, 3-40-3, 3-40-5, 3-40-6, 3-41-1, 3-41-3, 3-41-5, 3-41-6, a hinge or thinner wall section 356(1), 456(1) may be provided to each headgear connector 356, 456 to enhance flexibility of the headgear connectors and allow sufficient bending in use so headgear tensioning force is not transferred to collapse the cushion inwardly, e.g., to avoid pinching of the alar under headgear tension. Also, as shown in FIG. 3-41-6, one or more wall sections 457(1) of the side wall region 457 between the lugs of the headgear connectors may be thickened, e.g., to prevent or reduce collapse of the side wall region under headgear tension.

Headgear connectors 156 may be positioned at an angle relative to the horizontal axis of the sealing region 151. As best shown in FIG. 3-9, headgear connectors 156 may be positioned at angle β relative to the horizontal axis of the sealing region 151. In an example, angle β may be approximately 90-135°. In an example, angle β may be approximately 90-120°. In an example, angle β may be approximately 90-100°. Angle β aligns the headgear connectors in such a way so as to ensure the sealing force provided by the headgear connectors 156 is distributed over the sealing region 151, with more force provided in the top lip region 155 and corners of the nose region 154, and less force provided in the nose ridge region 152. Such distribution may be more comfortable and stable.

As shown in FIG. 3-8, headgear connectors 156 may have a first width $w_1$ at a region proximal to the side wall 157, and a second width $w_2$ at its extremity, with first width $w_1$ being greater than second width $w_2$. In an example, first width $w_1$ may be about 15-50 mm. In an example, first width $w_1$ may be about 15-30 mm. In an example, first width $w_2$ may be about 20-25 mm. In an example, second width $w_2$ may be about 15-30 mm. In an example, second width $w_2$ may be about 15-25 mm. In an example, second width $w_2$ may be about 15-20 mm. First width $w_1$ ensures that the force provided by the headgear is spread from the sides of the nose region 153 to the corners of the nose region 154, and also stabilizes the cushion in the horizontal plane. Second width $w_2$ is arranged to reduce the visual bulk of the headgear connector 156 and permit connection with cushion connector 116.

Headgear connectors 156 are advantageously disposed proximal to the sealing region 151. Headgear connectors 156 are positioned at a height $H_1$ from the sealing region 151, as shown on FIG. 3-6. In an example, height $H_1$ may be approximately 10-50 mm. In an example, height $H_1$ may be approximately 10-30 mm. In an example, height $H_1$ may be approximately 10-20 mm. In an example, height $H_1$ may be approximately 20-30 mm. This arrangement ensures that headgear forces are translated directly to the sealing portion, and the sealing region is able to wrap or conform to the patient's nasal geometry.

The position and size of the headgear connectors directs the sealing force to the sealing region in such a way so as to negate or eliminate the need for a forehead support or vertical headgear strap. For example, the width of the headgear connectors proximal to the side wall stabilizes the sealing region on the patient's face. The height of the headgear connectors 156 to the sealing region 151 ensures that headgear forces are translated directly to the sealing portion, thereby eliminating the need for additional stabilization from a forehead support.

In an alternative form of the present technology, headgear connectors 156 are formed separately from the plenum chamber.

5.2.4.2 Headgear Assembly

One form of positioning and stabilising structure 3300 in accordance with the present technology is headgear assembly 110. Headgear assembly 110 may be adapted to support, stabilize and/or position the cushion assembly 150 on the patient's face.

As shown in FIGS. 3-1 to 3-3, headgear assembly 110 may comprise a pair of side straps 115, connected to a rear strap 118. Side straps 115 define a main headgear loop that may be positioned along the sides of the patient's face, across the patient's cheeks, extending between the eyes and the ears of the patient, e.g., overlaying at least a portion of the zygomatic bone, towards the crown of the patient's head where it e.g., overlays a portion of the parietal bone. Side straps 115 may have a cushion connector 116 adapted to receive a headgear connector 156 of cushion 150. Side straps 115 may have an adjustment portion 117, wherein side straps 115 interlock or otherwise connect to each other and are able to adjust in length relative to one another. Rear strap 118 extends between the side straps and may loop through a respective slot 114 provided to the side straps 115. Rear strap 118 defines a rear headgear loop that may be positioned over the back of the patient's head, e.g., engaging along or below the patient's occiput. In an example, a portion of the headgear rear strap 118 or rear headgear loop overlays or engages a point on the head below or inferior to the occipital bone, e.g. a portion of the strap lies on a portion of the trapezius muscle, adjacent the occipital bone in use. In an example, at least a portion of the rear strap 118 engages below or inferior a lower edge of the occipital bone, which lower edge helps to maintain the rear strap in position and prevent the rear strap from riding up the patient's head, e.g., prevent sliding in a superior direction. Refer to FIGS. 2i and 3-2 for location of the trapezius and an exemplary positioning of the rear strap 118 along a portion of the trapezius. In an example, the headgear straps are sufficiently stretchy or flexible, e.g., to enhance comfort and adjustability. For example, the headgear may not require length adjustment to don.

In one form, headgear assembly 110 comprises a silicone main portion and a fabric rear portion. In another form, headgear assembly 110 comprises a fabric main portion and a fabric rear portion. In another form, headgear assembly 110 comprises a silicone main portion and a silicone rear portion.

In one form, headgear assembly 110 is constructed and arranged to be substantially floppy.

In one form, headgear assembly 110 comprises a main structural tie, and a rear structural tie.

An exemplary headgear assembly 110 is disclosed in PCT application number PCT/AU2008/001557, filed 22 Oct. 2008, which is incorporated herein by reference in its entirety.

5.2.5 Vent 3400

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

In an example, the vent 3400 is located in a decoupling structure 3500, e.g. a swivel 3510. Alternatively, the vent 3400 is located in the plenum chamber 3200.

One form of vent 3400 in accordance with the present technology is vent 126. Vent 126 may permit to expiration of exhaled gases from the nasal mask system. Vent 126 may comprise a series of holes, a mesh or other arrangement adapted to permit the flow of gas. In an example, vent 126 may be sufficiently rigid to avoid collapse of the air channels that exhaust the exhaled gas. Vent 126 may be positioned on the elbow 125 or other region such as the air delivery tube assembly 130 or cushion assembly 150 (including, for example, side wall 157).

In certain forms of the present technology, the vent 3400 may be constructed from a flexible, or floppy material that is supported by a sufficiently rigid frame to avoid collapse of the air channels that exhaust the exhaled gas.

In an alternative form, the patient interface 3000 does not include a vent.

5.2.6 Decoupling Structure(s) 3500

In one form the patient interface 3000 includes at least one decoupling structure 3500, for example a swivel 3510 or a ball and socket 3520 (e.g., see FIG. 3-13). In one form, decoupling structure 3500 may be formed at least in part by attachment region 158.

5.2.6.1 Attachment Region

Attachment region 158 may be adapted to receive elbow assembly 120. Attachment region 158 may include a thinner wall section 158(1) than the side wall region 157, for example attachment region 158 may have a wall section of about 0.1-1 mm, for example about 0.2-0.8 mm, for example about 0.5 mm. In an example, the thinner wall section 158(1) is configured to permit decoupling of the tube drag forces from the sealing forces. At the opening end or aperture of the attachment region 158 is a lip portion 158(2) having a thickness of about 2 mm to 3 mm. Also, the lip portion 158(2) reduces the diameter of the opening end from the side wall region 157 of about 26 mm to 27 mm to about 18 mm to 19 mm, which is approximately a 30% reduction in diameter. The thickness and reduced diameter of the lip portion 158(2) assist with retention of the connector ring 128 of the elbow 125 with the cushion assembly 250.

5.2.7 Connection Port 3600

In one form, connection port 3600 to air circuit 4170 is made by elbow assembly 120 (e.g., see FIGS. 3-1 and 3-2).

5.2.7.1 Elbow Assembly

Elbow assembly 120 may be adapted to connect or serve as an interface between the cushion assembly 150 and the air delivery assembly 130. Elbow assembly 120 may be formed with or integral with the air delivery assembly 130, or cushion assembly 150. Elbow assembly 120 may also be adapted to permit exhaust of exhaled gases.

As shown in FIGS. 3-1 to 3-3 and 3-11 to 3-13, elbow assembly 120 may comprise an elbow 125, the elbow having a vent 126, the elbow connecting to or otherwise formed with connector ring 128. Elbow 125 may be formed with a ball joint and the connector ring 128, and may be constructed and arranged to permit rotation of the ball joint while ensuring a sufficient seal with the elbow 125 to ensure air leakage does not compromise the patient's treatment pressure. The ball joint provides a decoupling mechanism, e.g., decouple tube drag forces from sealing forces. In one embodiment, the connector ring 128 is releasably or removably detachable from the elbow 125 by pulling the connector ring 128 off the elbow 125 to facilitate thorough cleaning of all surfaces of the connector ring 128 and elbow 125. The connector ring 128 has two raised edges 128(1), 128(2) that extend outwardly from the outer circumferential surface at the distal ends of the connector ring 128, i.e., a first raised edge or first flange on a first side of the ring adjacent an interior of the cushion assembly in use and a second raised edge or second flange on a second side of the ring adjacent an exterior of the cushion assembly in use. A channel 128(3)

is defined between the two raised edges 128(1), 128(2), as shown in FIGS. 3-11 and 3-13, such channel 128(3) adapted to sealingly engage the lip portion 158(2) that defines the opening end or aperture of the attachment region 158. As shown in FIG. 3-13, the elbow 125 has a first opening 125(1) and a second opening 125(2) for directing the pressurised air through the elbow 125. The connector ring 128 is retained on the elbow 125 at the second opening 125(2) of the elbow 125, and is freely rotatable relative to the elbow 125. As shown in FIG. 3-13, the partially spherical or curved inner circumferential surface 128(4) of the connector ring 128 abuts the partially spherical, outer surface 125(3) of the elbow 125 which allows relative tilting between the connector ring 128 and elbow 125. In an example, the partially spherical surfaces of the ring 128 and the elbow 125 have approximately equal radii of curvature. As depicted in FIG. 3-13, when the centers of the connector ring 128 and second opening 125(2) of the elbow 125 are aligned, the first edge 128(1) of the connector ring 128 is co-planar to the edge 125(2)e of the second opening 125(2) of the elbow 125, i.e., annular surface provided by edge 125(2)e of the elbow 125 is flush with the annular surface provided by the first edge 128(1) of the ring 128 when the longitudinal axes of the elbow 125 and ring 128 are co-linear. Although FIG. 3-13 depicts the first edge 128(1) having substantially the same diameter as the second edge 128(2), it is possible that the first edge 128(1) may have a larger diameter than the second edge 128(2) (e.g., see FIG. 3-120-5). This may minimise inadvertent detachment of the elbow 125 to the cushion assembly 250 when the lip portion 158(2) of the attachment region 158 is retained within the channel 128(3) of the connector ring 128. When the lip portion 158(2) is engaged within the channel 128(3), it is locked into a fixed position and also unable to freely rotate relative to each other due to surface friction.

Elbow 125 may also be attached to or otherwise connected with swivel or swivel cuff 129, adapted to receive an air delivery tube assembly 130. Swivel 129 may be arranged such that it may form a seal or have a low leak with elbow 125, while still being able to freely rotate relative to elbow 125.

The swivel cuff 129 includes an annular engaging ring 129(1) that is received in an annular groove 125(4) of the elbow to rotatably connect the swivel cuff 129 to the elbow 125. The swivel cuff 129 also has a channel portion 129(2) defined on an outer circumferential surface to matingly receive a cuff or connector 135 provided to the air delivery tube assembly 130. The swivel cuff 129 and the cuff or connector of the air delivery tube assembly 130 are removably detachable from each other.

5.2.8 Forehead Support

In an example, the patient interface 3000 does not include a forehead support, however in one alternative form, a forehead support may be included.

5.2.9 Anti-Asphyxia

In one form, the patient interface 3000 includes an anti-asphyxia valve.

5.2.10 Ports

In one form of the present technology, a patient interface 3000 includes one or more ports that allow access to the volume within the plenum chamber 3200. In one form this allows a clinician to supply supplemental oxygen. In one form this allows for the direct measurement of a property gases within the plenum chamber 3200, such as the pressure.

5.2.11 Air Circuit 4170

An air circuit 4170 in accordance with one form of the present technology is air delivery assembly 130. Air delivery assembly 130 may be constructed to connect a flow generator to mask system 100. As shown in FIGS. 3-1 to 3-3, air delivery system 130 may comprise a tube 133 and a connector 135. Tube 133 may be relatively flexible. Connector 135 may be adapted to receive swivel 129 of elbow assembly 120.

5.2.12 Donning and Removing

The nasal mask system provides a small, unobtrusive mask system that is easy to don, easy to remove, is stable, comfortable, effective, provides wide-fit range, unobtrusive, easy to use, and adjustable. In addition, the nasal mask system provides a non-prong or non-pillows arrangement (i.e., nasal mask system provides nasal-type cushion that provides single orifice adapted to surround both nares in use) that does not suffer from problems of jetting effect, nor the potential discomfort associated with nasal prongs or pillows adapted to at least partially extend up the patient's nose. The nasal mask system is structured such that little or no adjustment may be needed to fit the nasal mask system to the patient's head. In an example, no forehead support is provided to the mask system, though one can be provided if desired.

In the illustrated example, the nasal mask system 100 provides a two-point connection with the cushion, i.e., two side straps 115 of the headgear assembly engage respective headgear connector 156 alongside of the cushion 150 (e.g., see FIGS. 3-1 to 3-3). The headgear assembly provides three adjustment points, e.g., adjustment portion 117 of the side straps 115 and respective adjustability of ends of the rear strap 118 with a respective slot 114 of the side straps 115. However, it should be appreciated that more or fewer adjustment points may be provided, e.g., side straps and rear strap may provide fixed length with no adjustability.

In an example, the two-point connection does not does not require engagement or disengagement of a clip in order to don or remove the mask system, i.e., no clips are provided to the mask system but they can be provided if desired. Also, the main headgear loop defined by the side straps 115 extends from an inferior anterior position to a superior posterior position, which avoids any headgear strap extending below the ears (i.e., straps do not pass inferior to the patient's ear) as described below.

FIGS. 3-31 to 3-34 provide a sequence of views to illustrate an exemplary method for fitting the nasal mask system to a patient, e.g. prior to the application of air pressure to the plenum chamber. As shown in FIG. 3-31, the patient may grasp the nasal mask system such that one hand holds the cushion assembly 150 in a manner to orient the sealing region towards the patient's face and the other hand holds the rear strap 118 in a manner to allow the main headgear loop defined by the side straps 115 to receive the patient's head. Then, as shown in FIG. 3-32, the cushion assembly is engaged with the patient's face, and the rear strap is held over the patient's head as it passes through the main headgear loop. The rear strap, along with the side straps attached thereto, may be pulled onto the patient's head until the rear strap is positioned along the back of the patient's head as shown in FIG. 3-33, i.e., straps rotated or pivoted about the cushion assembly onto the patient's head until the straps engage and self-locate onto the patient's head. Finally, as shown in FIG. 3-34, ends of the rear strap 118 and/or the adjustment portion 117 of the side straps may be adjusted as necessary to secure the nasal mask system on the patient's head.

This arrangement is simple to put on and take off as the straps do not have to be pulled down over the ears to don the mask system or pulled up over the ears to remove the mask system, i.e., headgear straps easily slid on/off over the patient's head like a cap. That is, the mask system includes headgear that may be donned and removed like a cap without interfering with the ears of the patient.

In use, the side straps 115 are arranged to pull the nasal mask system in a superior posterior direction (e.g., as indicated by the arrow a1 in FIG. 3-34), which provides less compressive force along the nose ridge region of the cushion assembly 150 which is advantageous as such region is along a more sensitive region of the patient's nose, i.e., along the cartilage of the nose (not bone) as described above. Masks with nasal-type cushions normally include headgear arrangements arranged to pull the mask along a direction that is substantially parallel to Frankfort horizontal (as indicated by the arrow a2 in FIG. 3-34) so as to provide a compressive sealing force substantially normal to the patient's face. To provide such force, the headgear arrangement includes straps that extend under the patient's ears so as to provide such force along the Frankfort horizontal direction. In the mask system according to an example of the present technology, the headgear assembly is arranged to pull the mask along the superior posterior direction, e.g., like an "under the nose" mask (e.g., pillows or cradle), which provides less compressive force along the nose ridge region while maintaining sufficient seal as noted above. Thus, the nasal mask system provides headgear that provides an effective sealing vector similar to "under the nose" masks (i.e., not parallel to Frankfort horizontal), but instead used for mask that covers part of the nose, i.e., the nasal mask system compromises sealing force strictly along the Frankfort horizontal for an over the ear headgear arrangement to facilitate donning.

5.2.13 Pivoting Adjustment of Plenum Chamber

FIG. 3-9 shows a perpendicular distance $h_3$ between a headgear connection point hp, i.e., line of headgear tension as headgear connects to the cushion assembly 150, and a pivoting point or rotation axis pp of the cushion assembly 150 on the face, i.e., the top lip. This perpendicular distance $h_3$ allows adjustment of the headgear tension to effect rotational or pivotal adjustment of the plenum chamber/cushion assembly about the pivoting point pp. As illustrated, the headgear connection point hp is superior to the pivoting point pp or point of contact of the cushion assembly with the top lip. This arrangement enables a user to rotate/pivot the cushion assembly via adjustment of headgear tension and to use only a two point headgear connection to accommodate different nose ridge geometry. In an example, increasing the perpendicular distance $h_3$ will increase the moment.

Alternative Examples of Elbow Assemblies

FIGS. 3-42 to 3-111 show elbow assemblies according to alternative examples of the technology. It should be appreciated that such elbow assemblies may be adapted for use with patient interfaces of the type described above. However, aspects of the technology may be adapted for use with other suitable interface types, e.g., nasal prongs, etc.

Swivel Elbow and Connector Assembly—Vented Connector or Ring

Referring to FIGS. 3-42 to 3-45, a swivel elbow and connector assembly 610 according to an example of the technology comprises a vented elbow connector, or ring, 620 and a swivel elbow 640. A sleeve 630 is provided between the vented elbow ring 620 and the swivel elbow 640. The sleeve 630 is provided between a first end of the swivel elbow 640 and the vented elbow ring 620. A swivel cuff 650 is provided to a second end of the swivel elbow 640 opposite the first end. The swivel cuff 650 comprises a swivel cuff annular engaging ring 651 that is received in an annular groove 643 of the swivel elbow 640 so that the swivel cuff 650 is rotatable, or swivelable, with respect to the swivel elbow 640. In one embodiment, the swivel cuff annular engaging ring 651 and connector ring 620 are made from nylon, and the elbow 640 is made from polypropylene.

The connector ring 620 and swivel cuff annular engaging ring 651 are inserted in an elbow mold. Next, the elbow 640 is molded while previously the molded connector ring 620 and molded swivel cuff annular engaging ring 651 is in the elbow mold. Since the connector ring 620 and swivel cuff annular engaging ring 651 are made from nylon their melt temperature is higher than the polypropylene molding temperature, and therefore they do not undergo plastic deformation when the elbow 640 that is made from polypropylene is molded. This process enables an accurate and snug fit between these three components 620, 651, 640 which addresses the problem of uncontrolled leak at the connection locations which has been a problem in the past. Also, it eliminates at least one post-molding assembly step usually required when attaching multiple plastic parts together, i.e., ring 620 and ring 651 are insert molded in the elbow mold at substantially the same time. The second end portion of the swivel elbow 640 also includes a tapered flange 644 that is received in an annular groove 652 of the swivel cuff 650 to secure the swivel elbow 640 to the swivel elbow 640. The swivel elbow 640 also includes an end portion 653 that is configured to be connected to an air delivery hose or conduit that is configured to deliver a flow of breathable gas generated by a flow generator, or blower.

Referring to FIG. 3-43, the vented elbow ring 620 comprises an inner flange 622 and an outer flange 623. A patient interface structure, e.g. cushion, 65 of a patient interface system may be fitted into a channel 624 of the vented elbow ring 620 defined by the flanges 622, 623. The cushion 605 may be a nasal cushion, a full face cushion, or a nasal pillows or prongs cushion. The patient interface system may also include, for example, a support structure, or frame, that supports the cushion 605; a tube, conduit, or hose configured to deliver a flow of breathable gas to the cushion; and/or a patient interface positioning and stabilizing system (e.g. headgear). It should also be appreciated that the vented elbow ring 620 may be provided in, for example, the support structure or frame.

Referring to FIG. 3-72, a cushion 605 usable with the swivel elbow and connector assembly 610 may include a sealing portion 6950 having an upper lip engagement portion 6962 that is supported by a supporting portion 6953. The sealing portion 6950 is separated from the supporting portion 6953 by a front gap in an area of a nose tip engagement portion 6952. The nose tip engagement portion 6952 is flexible and can extend downward when contacted by a patient's nose, but will be limited in how far it can extend if it reaches the supporting portion 6953. The nose tip engagement portion 6952 is extended in length from the aperture 6955 to fit nose tips of different size, so that the nose tip of different patients may engage the nose tip engagement portion at different locations. A stem 6954 supports the supporting portion 6953 and the sealing portion 6950. The cushion 605 may be as disclosed in, for example, International Application PCT/AU2010/00684 (WO 2010/139014 A1), the entire contents of which are incorporated herein by reference. However, it should be appreciated that the swivel elbow and connector assemblies disclosed herein may be used with other patient interface structures or systems, e.g. cushions, such as those disclosed in, for example, U.S. Application 61/443,623 or U.S. 2009/0044808 A1, the entire contents of each being incorporated herein by reference.

The stem 6954 may receive the vented elbow ring 620. The vented elbow ring 620 may be inserted into the aperture of the cushion 605 such that the stem 6954 is sealingly located in the channel 624 between the flanges 622, 623. The sealing portion 6950, the stem 6954, and the supporting portion 6953 may be a flexible material such as liquid silicone rubber material or another elastomeric material, e.g., TPE, gel or foam. The stem 6954 and the supporting portion 6953 may be formed together such as in a mold, and the sealing portion 6950 may be formed separately and then joined together, e.g. such as by gluing. Alternatively, the stem 6954 and the supporting portion 6953 may be formed together such as in a mold, and then the sealing portion 6950 may be bonded to the supporting portion 6953 and the stem 6954 in the mold.

The cushion 605 may comprise a flexible gusset 6965, which may include the supporting portion 6953 and the stem 6954. The supporting portion 6953 and the stem 6954 may be formed as a single unitary element. The flexible gusset 6965 may be constructed of a silicone with a hardness of about 20 to 90 Shore A, preferably about 40 Shore A. The flexible gusset 6965 could also be made from polycarbonate, polypropylene, nylon, thermoplastic elastomer (TPE), Hytrel™, etc.

Referring again to FIGS. 3-42 to 3-44, the vented elbow ring 620 comprises a plurality of vent slots 625 that extend through the inner flange 622 across the channel 624 and through the outer flange 623. As shown in FIG. 3-43, the sleeve 630 includes a sleeve flange 631 provided between a flange 641 of the swivel elbow 640 and the flange 623 of the vented elbow ring 620. As shown in FIG. 3-42, the connection of the sleeve 630 between the swivel elbow 640 and the vented elbow ring 620 provides a plurality of vents 621 for the venting of exhalation gases from the interior of the cushion 605 to the exterior of the cushion 605 through the vent slots 625.

The shape of the vent hole in one example of the present technology may be such that the cross section (e.g., round) is larger on or towards the inside (entry of air) compared to the smaller outside cross sections (e.g., diameter) where the air exits to atmosphere. Also, the exit point or region may be angled to diffuse air away from bed partner/bed clothes, e.g., not perpendicular.

A smooth transition may be provided at the vent passage to help reduce/ensure low noise providing vents along the swivel effectively increase overall length of vents, which may allow for laminar flow development, and result in less noise.

The first end portion of the swivel elbow 640 includes a tapered flange 642 that engages an annular surface 632 of the sleeve 630. A cylindrical portion 633 of the sleeve 630 extends between the sleeve flange 631 and the tapered flange 642 of the swivel elbow 640. The sleeve 630 in the swivel elbow 640 may be permanently assembled by the tapered flange 642 as shown in FIG. 3-43, although it should be appreciated that the sleeve 630 may be under molded, co molded or otherwise formed with the swivel elbow 640 to reduce assembly costs.

Referring to FIG. 3-42, the swivel elbow and connector assembly 610 may be provided with a plurality of vents 621, for example, 20-60 vents, for example 30-50 vents, for example 38 vents, 40 vents or 42 vents. The cross sectional area of the vents may vary from, for example, 0.5 mm×0.5 mm, for example, 1.0 mm×1.0 mm, or 0.7 mm×0.7 mm.

The sleeve flange 631 and the flange 641 of the swivel elbow 640 may be provided at an angle that provides for venting of the exhalation gases from the interior of the cushion 605, 360° around the swivel elbow 640 and in direction away from the face of the patient. The sleeve 630 provides good diffusivity, and the vent path is contained and easily adjustable. The formation of the vents 621 by the sleeve 630 also reduces the noise of the venting from the interior of the cushion 605.

Although the vented elbow ring 620 is shown in FIGS. 3-42 to 3-45 as circular, it should be appreciated that the vented elbow ring may be, for example, elliptical in cross section, as show in FIGS. 3-76 and 3-77.

Swivel Elbow and Connector Assembly—Vented Elbow

Referring to FIGS. 3-73 to 3-78, a swivel elbow and connector assembly 6120 according to another example comprises a swivel elbow 6140 and a connector, or ring, 6150. A cushion 6130 comprises a flexible base 6133 comprising an aperture for sealingly receiving the ring 6150. The flexible base may comprise a flange, or stem, 6138 that is configured to be received in a channel 6154 of the ring 6150 that is defined between an inner flange 6152 and an outer flange 6153. The cushion 6130 may comprise nasal pillows 6131 for sealingly engaging the nares of a patient or user and connectors 6132 for connecting the cushion 6130 to a patient interface structure positioning and stabilizing system (e.g. headgear). The cushion 6130 may be as disclosed in, for example, International Application PCT/AU2008/001557 (WO 2009/052560 A1), the entire contents of which are incorporated herein by reference. It should be appreciated that other cushions or patient interface structures may also be used with the assembly 6120, including rigid or semi-rigid patient interface support structures (e.g. frames).

The elbow 6140 includes a first end 6143 configured for connection to, for example, a delivery hose or conduit. The elbow includes a tapered flange 6142 at a second end for securing the elbow 6140 to the ring 6150. Intermediate the first and second ends, the elbow 6140 includes an angled flange 6141 having a plurality of vents 6145 spaced around the flange 6141. The flange 6141 is angled with respect to the longitudinal axis of the elbow 6140. The number and size of the vents may be as described above. It should also be appreciated that the vents 6145 may be distributed around the angled flange 6141 evenly or randomly. It should further be appreciated that the vents 6145 may not extend around the entire circumference of the angled flange 6141 of the elbow 6140, for example as shown in FIG. 3-76.

A radial flange 6146 may surround the angled flange 6141 that engages the outer flange 6153 of the ring 6150. The ring 6150 is secured between the tapered flange 6142 and the radial flange 6146. The elbow 6140 may further comprise a baffle 6144 to separate the venting portion 6147 from an incoming flow of breathable gas from the first end 6143, although it may be circular or have other shapes as well.

Referring to FIGS. 3-76 to 3-78, the ring 6150 may have an elliptical configuration (e.g. elliptical cross section). A circular radial flange 6155 may be provided on the ring 6150 to form a sealing interface with the radial flange 6146 of the elbow 6140. As also shown in FIG. 3-76, the vents 6145 may not be provided around the entire circumference of the elbow, for example the lower portion 6159 of the angled flange 6141 may not include vents 6145, and/or the angled flange 6141 may have a reinforced portion 6157 between vents 6145. As shown in FIG. 3-78, the baffle 6144 of the elbow 6140 also has an elliptical configuration that provides venting portions 6147 and non-venting portion 6149 to the elbow 6140.

Double Swivel Elbow and Connector Assembly—Vented Connector or Ring

Referring to FIGS. 3-46 to 3-57, a double swivel elbow and connector assembly 660 according to a example comprises a ball and socket connection i.e. a ball joint vented elbow ring 670, a ball joint swivel elbow 680 swivelably connected to the ball joint vented elbow ring 670, and a swivel cuff 690 swivelably connected to the ball joint swivel elbow 680. The ball joint vented elbow ring 670 includes a plurality of vent slots 671 extending around the periphery of the elbow ring 670. As shown in FIG. 3-48, the slots 671 extend through an inner flange 673 of the elbow ring 670 and through an outer flange 674 of the elbow ring 670. A cushion 605 having an aperture may be received in a channel 675 between the inner flange 673 and the outer flange 674. When the elbow ring 670 is positioned in the aperture of the cushion 605, vent holes are created between the vent slots 671 in the elbow ring 670 and the cushion 605. The cushion 605 is secured to the double swivel elbow and connector assembly 660 when the stem 6454 of the cushion is received in the channel 675 of the vented elbow ring 670. As used herein, the term "sealingly secured" means that the flow of breathable gas delivered to the patient interface system, e.g. cushion, through the swivel elbow will not pass from the interior to the exterior of the patient interface system through the vents in the absence of exhalation by the patient or wearer of the patient interface system.

Referring to FIG. 3-47, the vented elbow ring 670 includes an annular surface 672 that may be flush or in line with an annular surface 681 of the ball joint swivel elbow 680 when the double swivel elbow and connector assembly 660 is in the position or configuration shown in FIGS. 3-46 to 3-48, i.e., with the elbow pointing generally downward. As shown in FIG. 3-51, the ball joint swivel elbow 680 includes an arcuate annular, or partially spherical, outer surface 682 that is swivelably contained by an arcuate annular, or partially spherical, inner surface 676 of the vented elbow ring 670. The vented elbow ring 670 and the ball joint swivel elbow 680 thus act as a ball joint connection between the vented elbow ring 670 and the swivel elbow 680. The inner surface 676 and the outer surface 682 have radii of curvature that are approximately equal. The substantially equal radii of curvature may be achieved by molding the vented elbow ring 670 and the swivel elbow 680 together, without the vented elbow ring 670 and the swivel elbow 680 chemically bonding or mechanically bonding in the mold, e.g., by shrinkage. The inner surface 676 and the outer surface 682 are engaged essentially over the area of contact between the surfaces so that no or little gas flows between the ring 670 and the elbow 680.

The swivel elbow 680 may swivel from the position shown in FIG. 3-53, in which the annular surface 681 is flush with the annular surface 672 of the vented elbow ring 670 and the longitudinal axes of the ring 670 and the elbow 680 are co-linear, to the position shown in FIGS. 3-54, 3-56 and 3-57, in which the annular surfaces 672, 681 are not flush and the longitudinal axes are at an angle to each other. An annular junction 685 between the arcuate annular outer surface 682 of the swivel elbow 680 and the end portion of the swivel elbow 680 limits the swiveling of the elbow 680 within the vented elbow ring 670, as shown in FIGS. 3-54, 3-56 and 3-57.

Referring to FIGS. 3-51 to 3-57, the end portion of the swivel elbow 680 includes an annular groove 683 that receives a tapered annular engaging ring 691 of the swivel cuff 690. A tapered flange 684 of the swivel elbow 680 engages the tapered annular engaging ring 691 of the swivel cuff 690 to retain the swivel cuff 690 to the swivel elbow 680. As shown in FIGS. 3-53 and 3-54, the swivel cuff 690 includes an angled groove 692 that allows the swivel cuff 690 to rotate from the position shown in FIG. 3-53 to the position shown in FIG. 3-54.

Referring to FIGS. 3-50 and 3-55, the pivoting of the swivel cuff 690 allows a longitudinal axis of the double swivel elbow and connector assembly 660 to rotate through an angle $\alpha$ of, for example, 40-60°, for example 50°.

The double swivel elbow and connector assembly 660 allows for swiveling of the connection of an air delivery tube or conduit to the swivel cuff end portion 693 in two directions. For example, as shown in FIGS. 3-48 and 3-49, the swivel cuff 690 may swivel from the position shown in FIG. 3-48 to the position shown in FIG. 3-49 while the swivel elbow 680 remains in a position such that the annular surface 681 of the swivel elbow is flush with the annular surface 672 of the vented elbow ring 670. The transition from the alignment shown in FIG. 3-48 to the alignment shown in FIG. 3-49 is shown in FIG. 3-50 as a central axis of the swivel cuff 690 rotates through the angle $\alpha$ of, for example, 50°. The swiveling of the cuff 690 from the position shown in FIG. 3-48 to the position shown in FIG. 3-49 allows a short air delivery tube or conduit to straighten out thereby reducing torque forces applied to the vented elbow ring 670 and cushion 605. In other masks without this swivel, if the tube is pulled in a direction that is perpendicular to the central axis of the elbow, because the elbow has an L shaped configuration and no swivel, it cannot rotate to be in line with the tube; therefore this pulling force is directly applied to the mask and can disrupt the seal. The ball joint (or ball and socket connection) design allows the elbow and the swivel to re-align depending on the forces being exerted by the tube.

The double swivel elbow and connector assembly 660 also permits the swivel elbow 680 to swivel with respect to the vented elbow ring 670, for example, from the position shown in FIG. 3-54 to the position shown in FIG. 3-56. The pivoting or swiveling of the swivel elbow 680 is limited by the annular junction 685 between the arcuate annular outer surface 682 of the swivel elbow 680 and the end portion of the swivel elbow 680. The swivel elbow 680 may also swivel from the position shown in FIG. 3-54 to the position shown in FIG. 3-57 while the swivel cuff 690 may also pivot or swivel with respect to the swivel elbow 680.

Triple Swivel Elbow and Connector Assembly—Vented Connector or Ring

Referring to FIGS. 3-58 to 3-71, a triple swivel elbow and connector assembly 660 according to another example comprises a second swivel cuff 6100 swivelably connected to the end portion of the swivel cuff 690. The second swivel cuff 6100 comprises a tapered annular engaging ring 6101 that is received in an annular groove 695 in the end portion of the swivel cuff 690. A tapered flange 694 is provided at the end of the swivel cuff 690 to engage and retain the annular engaging ring 6101 of the second swivel cuff 6100. The second swivel cuff 6100 includes an annular groove 6102 that receives the tapered flange 694 of the swivel cuff 690. The second swivel cuff 6100 includes an end portion 6103 that is configured to receive an air delivery tube or conduit for receiving a flow of breathable gas provided by a flow generator, or blower, for delivery into a patient interface including the cushion 605.

The swivel cuff 690 and the swivel elbow 680 of the examples shown in FIGS. 3-58 to 3-71 are swivelable in the same manner as described with respect to the example disclosed in FIGS. 3-46 to 3-57. As shown in FIGS. 3-62 and 3-66, the pivoting of the swivel cuff 690 allows a longitudinal axis of the triple swivel elbow and connector assembly 660 to rotate through an angle β of, for example, 40-60°, for example 50°. Although the second swivel cuff 6100 is shown as including an annular groove 6102 that receives the tapered flange 694 of the swivel cuff 690, it should be appreciated that the second swivel cuff 6100 may be provided with an angled groove similar to the angled groove 692 of the first swivel cuff 690 to permit the second swivel cuff 6100 to swivel through an angle similar to the manner in which the swivel cuff 690 swivels with respect to the swivel elbow 680.

Swivel Elbow and Anti-Asphyxia Valve Assembly

Referring to FIGS. 3-79 to 3-88, a swivel elbow and anti-asphyxia valve assembly 6300 according to an example of the technology may be provided having a diffuse vent. The assembly may also include engagement portions, e.g. buttons or actuators, for engaging and disengaging the assembly 6300 to a patient interface, e.g. a mask. The assembly 6300 may be molded in one piece. This arrangement is advantageous as the patient is not required to dismantle the component (thereby preventing potential loss of components or misalignment when reassembling), the cost of the component may be lower, and the anti-asphyxia valve may be positioned such that it cannot be tampered with or accidentally removed.

The assembly 6300 may comprise a first elbow component, base moulding, collar or skeleton portion 6200, as shown in FIGS. 3-79 to 3-82. The skeleton portion 6200 may provide the underlying structure of the assembly 6300 to support the assembly in an open or patent position. As shown in FIG. 3-79, the skeleton portion 6200 may include vent holes 6230 adapted to permit the exit of exhausted gases from a patient interface as per previously described examples. As shown in FIG. 3-82, the skeleton portion 6200 may further comprise a baffle 6260 adapted to separate the incoming gases from the outgoing gases in the assembly 6300 as per previously described examples.

The skeleton portion 6200 may also include a first connection region 6245 comprising engagement tabs 6240 for interfacing or connecting with a patient interface, for example. The first connection region 6245 may be substantially arcuate or define a first arcuate region when viewed from the front. The skeleton portion 6200 may also include a second connection region 6250 for interfacing or connecting with a tube or swivel, for example. The skeleton portion 6200 may further include a stop 6255 to position the assembly 6300 with respect to a mask, for example, and prevent the assembly 6300 from travelling through the connection with the mask or insertion of the assembly 6300 into the mask.

The skeleton portion 6200 may be formed of a relatively rigid, or stiff, material so that the structure may remain open to permit the flow of gases. Stiffer materials may minimize the noise of the air exiting the vent holes. The skeleton portion 6200 may be formed of, for example, polycarbonate, polypropylene, or nylon. A rigid material may also assist in maintaining the assembly 6300 in an open position under certain loads, e.g. the patient lying on the assembly. A rigid material may also be easier for the user to connect and disconnect from the mask, tube and/or swivel.

As shown in FIG. 3-80, the skeleton portion 6200 may further comprise supports, arms or interconnecting regions 6290 adapted to connect the first connection region 6245 with the second connection region 6250. The supports 6290 may also form the boundaries of a first aperture 6210 and a second aperture 6220. The supports 6290 may be flexible and resilient, i.e. the supports 6290 may return to their original shape after deformation. The first aperture 6210 may be structured and arranged to receive an anti asphyxia valve or other valve. The second aperture 6220 may be structured and arranged to receive a flexible member or web. The second aperture 6220 may extend to an opening, gap or relief 6280 at the first connection region 6245, as shown in FIG. 3-81.

Referring to FIG. 3-80, the vent holes 6230, may be positioned on a surface 6235 that is generally circular or rounded to better diffuse exiting air streams. The surface 6235 may be tapered to prevent moisture build up on the elbow—this can cause vent whistle i.e. air exiting the vent holes to create a high pitched whistle-like noise. The vent holes 6230 may be scattered around the surface 6235 to diffuse the air flow. It should be appreciated that the vent holes 6230 may be uniformly spaced around the surface 6235, or provided as otherwise described herein.

The skeleton portion 6200 may further include second supports or stops 6270 adapted to receive a button or other engagement mechanism. The second supports 6270 may be adapted to transmit a force from an engagement feature or mechanism, such as a button, to the skeleton portion 6200. The second supports 6270 may also reinforce or provide a foundation for an engagement feature or mechanism, such as a button, such that when the button is pressed it does not collapse, rather it transmits a force to the skeleton portion 6200. The second supports 6270 may be an alignment feature to align the skeleton portion 6200 in a tool or mold. The second supports 6270 may form a surface for a second component, for example an over-mould, to abut or be formed against.

The skeleton portion 6200 may be over-moulded or otherwise formed with a second component (also referred to as a flexible portion or deformable region) 6335, e.g. an assembly over-mould. For example, the skeleton portion 6200 may be moulded in a first tool and then transferred to a second tool for over-moulding with the second component 6335, or could be done all in one tool. That is, second component 6335 may be chemically, mechanically or otherwise formed to the skeleton portion 6200. The second component 6335 may be formed of a relatively flexible material, such as thermoplastic elastomer (TPE), silicone, gel or other material.

The second component 6335 may include engagement portions 6320, a flexible member or web 6330, a lip 6315 and a valve member 6310. The engagement portions 6320 may be, for example, buttons, grips, tabs or other arrangements adapted to receive a pressing force or other motion from a patient or clinician. The engagement portions 6320 may be supported and/or reinforced by the second supports 6270. The engagement portions 6320 may, when pressed, squeeze towards one another thereby displacing the first supports 6290 inwards. The first supports 6290 may then deform the first connection region 6245 from a first, resting position (e.g. a circular shape) to a second, pressed position (e.g. an oval or elliptical shape). The gap or relief 6280 may be adapted to permit the first connection region 6245 to flex. This change in shape may move the engagement tabs 6240 from a first, engaged position, to a second, disengaged position. The gap or relief 6280 may form a second arcuate region, such that when combined with the first arcuate region of the first connection region 6245, the two components form a circle and hence a cylinder.

The flexible member or web 6330 may be connected to the engagement portions 6320 and also seal the second aperture 6220. The flexible member 6330 may be in the form of a membrane or other readily deformable shape, as when engagement portions 6320 are pressed, the flexible member 6330 may buckle or bend.

The lip 6315 may be formed about and positioned around the perimeter of the first aperture 6210. The lip 6315 may be adapted to prevent objects from entering the first aperture 6210. The lip 6315 may also serve as a blank off for molding elbow assembly 6300.

The valve member 6310, as shown in FIG. 3-87, may be positioned within the body of the elbow assembly 6300, i.e. between the first supports 6290. The valve member 6310 may act as an anti-asphyxia valve, i.e. when air is delivered from the second connection region 6250 to the first connection region 6245, the valve member 6310 may move into a first position (not shown) to occlude the first aperture 6210; and when there is no air being delivered from the second connection region 6250 to the first connection region 6245, the valve member 6310 may move to a second position (FIG. 3-87) that does not occlude the first aperture 6210, thereby permitting the patient to receive air from atmosphere through the first aperture 6210. The valve member 6310 may be a flap. The valve member 6310 may be integrally formed with the second component 6335, e.g. through a living hinge attached to the lip. It should be appreciated that the valve member 6310 may be formed separately from the second component 6335 and attached to the second component 6335. The valve member 6310 may be larger than the first aperture 6210, so as to occlude the first aperture 6210 when air is delivered from the second connection region 6250 to the first connection region 6245.

The valve member 6310, the lip 6315, the engagement portions 6320, and the flexible member 6330 may be formed from the same material in a single piece. Alternatively, one or more of these components may be formed separately and/or from an alternative material.

In a further example of the present technology, e.g., shown in FIGS. 3-109A to 3-111 an elbow 680 may be formed or constructed in a multi-step process, e.g., three step process, to achieve a single component with multiple functions. The elbow 6800 may comprise a skeleton or frame 6805, e.g., constructed of rigid or semi-rigid material, and adapted to communicate air flow from an air delivery tube to a mask. The skeleton 6805 may be first formed or molded in a tool. Skeleton 6805 may be constructed of a polymer such as polypropylene, polycarbonate, and nylon.

The elbow 6800 may further comprise an AAV (anti-asphyxia valve) 6810 having a flap 6812 adapted to provide the patient with access to atmospheric gas should a flow generator fail to deliver air to the mask. The AAV 6810 may be formed or molded within the skeleton 6805 or formed or molded and then subsequently assembled to the skeleton 6805. For example, as shown in FIGS. 3-109A to 3-109D, the AAV 6810 may be molded and then pulled through an opening 6815 in the skeleton. A pull tab 6820 of the AAV may enable the AAV 6810 to be pulled through the opening 6815 so as to position, retain and/or seal the AAV relative to the skeleton. The pull tab 6820 may be a sacrificial component that once utilized (e.g., pulled through the opening) it may be cut off (such that an outer surface 6810.2 of an outer flange 6810.1 is substantially flush with the elbow surface) as shown in FIG. 3-110A or otherwise removed (e.g., once an inner flange 6825 is pulled and anchored against the inner surface of the skeleton, further applied force will tear the pull tab away from the AAV, possibly assisted by a perforation(s) between pull tab and outer flange 6810.1). Alternatively the AAV 6810 may be molded in the opening 6815 and extending through the skeleton 6805 without the need for pull tab 6820. The AAV 6810 may include an inner flange 6825 to seal the AAV 6810 against the inner wall 6830 of the skeleton 6805.

The elbow 6800 may comprise a flexible component 6832 (FIG. 3-110A) adapted to secure the AAV 6810 in position and/or form one or more release buttons 6835 of the elbow 6800. For example, the flexible component 6832 may be a silicone or TPE which is molded over the skeleton 6805 to form the outer portions of the release buttons 6835, thereby allowing the release buttons 6835 to flex; and may be molded over the AAV 6810 at the opening 6830 to seal and hold the AAV 6810 in position relative to the skeleton 6805.

The arrangement may have one or more of the following advantages:

1. The AAV is sealed in position and cannot be removed from the elbow thereby preventing the patient from accidentally disassembling the AAV and thus rendering the device unsafe.
2. The flexible component can be molded in a single shot—if there was no flexible component over the AAV then the flexible component may be molded on either side of the elbow at each button. Since it is molded in a single shot, it may be more efficient and less expensive to tool
3. The elbow may be more visually appealing.

Swivel Elbow and Connector Assembly Including Cushion

Referring to FIG. 3-89, a patient interface system 6400 for delivering a flow of breathable gas to a patient may include a swivel elbow 6410, a swivel or ring or connector 6420, and a cushion 6430 for sealingly engaging the patient's airways. Although the cushion 6430 as shown includes nasal pillows or prongs or puffs, it should be appreciated that other cushions may be provided, for example a nasal cushion or a full face cushion. The swivel 6420 may be removably attachable to the cushion 6430 by a bayonet type connection 6440 that includes detents 6421 on the swivel 6420 to engage with tabs 6431 on the cushion 6430. Vents 6411 are provided between the elbow 6410 and the swivel 6420. The vents 6411 may include slots provided on the elbow surface to create venting gaps between the elbow 6410 and the swivel 6420. It should be appreciated that the slots may be provided in the swivel instead of the elbow, or that slots may be provided in both the elbow and the swivel.

Referring to FIGS. 3-90 to 3-92, according to another example a patient interface system 6450 may include a swivel elbow 6460, a swivel or ring or connector 6470, and a cushion 6490. The swivel 6470 may be connected to a ring 6480 that is attached to the cushion 6490 at 6481. The ring 6480 may be permanently or removably attached to the cushion 6490. For example, the cushion 6490 may be overmoulded to the ring 6480 or the cushion 6490 and the ring 6480 may be attached by adhesive. As another example, the cushion 6490 and the ring 6480 may be press fit together.

The elbow 6460 may be removably attached to the swivel 6470 or the elbow may be permanently attached to the swivel 6470. The elbow 6460 may have flexible buttons 6462 provided between grooves 6463 formed in the elbow 6460. The buttons 6462 may be pressed or flexed to connect and disconnect the elbow 6460 from the swivel 6470.

Vents 6461 are provided between the elbow 6460 and the swivel 6470. The vents 6461 may include slots provided on the elbow surface to create venting gaps between the elbow 6460 and the swivel 6470. It should be appreciated that the slots may be provided in the swivel instead of the elbow, or that slots may be provided in both the elbow and the swivel.

Referring to FIG. 3-93, a patient interface system 6500 according to another example may include a swivel elbow 6510, a swivel or ring or connector 6520, and a cushion

6530. The cushion 6530 may be permanently or removably connected to the swivel 6520 at 6521. The elbow 6510 may be press fit to the swivel 6520 and be releasable by pressing buttons 6512 provided between grooves 6513 as per grooves 6463. Grooves 6463 are made air tight by either being thinned regions of material or an over-molded second material (e.g., TPE, silicone). The elbow 6510 may further include slots 6511 to vent exhaled gases and a baffle 6514 to reduce noise and increase exhaust gas washout.

Referring to FIGS. 3-94 and 3-95, an elbow 5550 according to an example of the technology may include slots 6551 to vent exhaled gases and a baffle 6554 to reduce noise and increase exhaust gas washout. An aperture 6552 may be provided in the elbow 6550 to permit the patient to breathe in the event that the flow of breathable gas is interrupted or stopped. An AAV flap 6555 is provided to close the aperture 6552 when a flow of breathable gas is in the elbow 6550 (i.e. the flow of breathable gas biases the flap 6555 into a closed position to cover the aperture 6552). As shown in FIGS. 3-94 and 3-95, the AAV flap 6555 is in the open position. The elbow 6550 may be moulded from, for example, a rigid material to improve vent flow noise and to prevent the slots 6551 from occluding. The AAV flap 6555 may be formed of, for example, a flexible material to enable movement of the AAV flap 6555 from the open to the closed position under the influence of the flow of breathable gas.

Elbow and Tube Connector Assembly

Referring to FIGS. 3-96 to 3-98, an elbow and tube connector assembly 6560 may include an elbow 6570 and a tube connector 6580 that clips into the inner surface of the elbow 6570. Clipping the tube connector 6580 into the elbow 6570 reduces the overall visual bulk of the assembly 6560 and may also create a tube-specific fitting such that only tubes 6590 provided by a certain manufacturer or provided can be used with the elbow 6570.

The elbow 6570 may include a lip or flexible element 6571 adapted to engage with an outer surface, e.g. a groove, 6581 of the tube connector 6580 to ensure a more robust seal. The tube connector 6580 may also include a series of ridges 6582 adapted to engage with the inner surface of the elbow 6570, thereby causing a seal, while avoiding increased friction between the tube connector 6580 and the elbow 6570 to permit rotation of the components relative to one another.

Straight Swivel for Elbow and Tube Connection

Referring to FIGS. 3-99 to 3-101, a tube and elbow connector assembly 6600 may include a swivel elbow 6610, a tube connector 6630 and a swivel or connector or ring 6620. The assembly 6600 may be used to connect the elbow 6610, such as the elbow disclosed in, for example, U.S. 2010/0307502 A1, the entire contents of which are incorporated herein by reference, to a short retractable tube, having a length of, for example 150 mm, such as disclosed in, for example, U.S. 2009/0078259 A1, the entire contents of which are incorporated herein by reference. The assembly 6600 may reduce rotational/torque forces between the tube and the elbow. For example, as disclosed in U.S. 2010/0000534 A1, a patient interface system may include a "pillow cushion" that is adhesively applied to the patient's face. As the patient interface system has no headgear, it therefore has little to no resistance to rotational forces being applied to the pillow cushion. The patient interface system may include a decoupling gusset, a ring elbow and a short, retractable tube attached to the elbow. A longer tube, e.g. a 2 m tube, may be connected to the short, retractable tube by a swivel. As the short, retractable tube is stretched, it may rotate almost a full revolution. This in turn rotates the elbow and distorts the pillow cushion and may pull the prongs or pillows out of the nose. In the patient interface of U.S. 2010/0000534 A1, the short, retractable tube assembly is designed to be 'semi-permanent' and have minimal leak through the tube-elbow interface. As such, there is no ability to rotate at the short, retractable tube and elbow interaction site and the elbow acts as a solid fixture and increases the torque onto the cushion.

By altering the location of the swivel in the patient interface system, for example by placing the swivel between the short, retractable tube and the elbow, all the rotational forces of both the longer tube and the short, retractable tube would be rotationally decoupled from the cushion.

By copying the geometry of the external surface of the elbow, and the internal surface of the short tube cuff and offsetting each by, for example, 0.2 mm, preferably 0.1 mm, there would be clearance between both parts. As the tube is stretched and starts to rotate, the surface with the least resistance will swivel. The swivel may either 'fuse' (i.e. not rotate) on one side, and rotate 100% on the other, or take up 50% of the rotation on either side so that the cushion would only experience a tensile force.

Referring to FIGS. 3-102 to 3-106, a tube and elbow connector assembly 6650 according to another example includes an elbow 6660 connectable to a tube or tube cuff 6690 by a swivel component 6670, 6680 made by, for example, overmoulding a first swivel component 6680 over a second swivel component 6670 in a mould assembly to form a freely rotating swivel in a smaller footprint, i.e. minimising the extension of the elbow length. The internal geometry of the cuff 6690 and the external geometry of the elbow 6660 were replicated to ensure a tight fit with no leak, yet the shrinkage of the in-mould assembly would allow a smooth rotation. The swivel components 6670, 6680 form a two part swivel moulded as one.

Referring to FIGS. 3-107 and 3-108, a tube cuff-to-tube cuff connector 6700 assembly may also provide a swivel configured to join cuffs 6710, 6730 of short tubes with no multiplication of the torque forces. A cuff connector 6720 may be provided between two short tubes of, for example, 150 mm in length, rather than one 300 mm tube with 100% clockwise torque force. The cuff connector 6720 connects the two short tubes, and each the two short tubes may be wound in different directions, (i.e. 50% clockwise, 50% anti-clockwise) to cancel each other's torque out.

Static and Dynamic Sealing Positions

FIGS. 3-112-1 to 3-112-2 and 3-113-1 and 3-113-2 are exemplary views showing the cushion assembly 250 with the membrane 260 engaged with the patient's face in a static sealing position. FIG. 3-36-2 also shows the sealing flaps 270 engaged with the junction between the nasal major alar cartilage and the lateral nasal cartilage of the patient's nose as noted above.

FIGS. 3-114-1 to 3-117-2 show the cushion assembly 250 in various dynamic sealing positions as the cushion assembly 250 adjusts to accommodate external forces applied to the cushion assembly, e.g., tube drag forces and tube torque applied to the cushion assembly 250. As illustrated, the thinner wall section provided to the attachment region 158 of the cushion assembly, the ball joint mechanism and the swivel provided to the elbow assembly 120, and the flexibility provided by the membrane 260 and sealing flaps 270 permit sideways, upwards, and/or downwards forces to be applied by the elbow assembly while ensuring a sufficient seal of the cushion assembly with the patient's face.

In the illustrated example, the patient interface is provided with a decoupling system having multiple decoupling structures to permit decoupling of tube torque and/or tube drag forces from the sealing forces applied by the cushion assembly 250 to the patient's face. That is, the decoupling structures function together to absorb and/or displace forces applied by the air delivery tube so such tube forces do not adversely affect the sealing force provided by the cushion assembly 250 and forces provided by the headgear tension.

Decoupling Gusset

The thinner wall section 158(1) (e.g., also referred to as a decoupling gusset or a decoupling wall) provided to the attachment region 158 of the cushion assembly provides sufficient flexibility and durability to allow the attachment region 158 to tilt, pivot or move relative to the side wall region 157. The thickness of the wall of the decoupling gusset 158(1) is thinner than its adjacent walls of the cushion assembly 250. Sufficient clearance is provided between the decoupling gusset 158(1) and the connector ring 128 supported by the attachment region 158, e.g., to prevent connector ring 128 and/or elbow 125 from piercing through the decoupling gusset 158(1) when tilting of the elbow 125 exceeds a predetermined angle. In one embodiment, the attachment region 158 has a width of about 6 mm to 7 mm, and the decoupling gusset 158(1) has a width of about 3 mm to 4 mm. The decoupling gusset 158(1) functions in a similar manner as a spheroidal joint because it enables relative motion around an indefinite number of axes between two components which have one common center.

Ball and Socket Joint/Spheroidal Joint

The ball and socket joint provided by the elbow 125 and ring 128 allows for extra degrees of freedom of movement (i.e., in two planes) to permit rotation of the elbow 125 and provide a decoupling structure. For example, the ball and socket joint not only allows for full 360° rotation in the X-axis (see FIG. 3-118-1) but also adds an extra 30-40°, e.g., 35°, of rotational movement/tilt in the Z-axis (see FIG. 3-118-2). As a result, the elbow 125 can pivot, swivel, and/or rotate with respect to the ring 128 so that pulling forces (e.g., sideways, upwards, and downwards as shown in FIGS. 3-114-1 to 3-117-2) and/or torque forces applied to the elbow 125 are not directly applied to the cushion assembly 250 and do not disrupt the seal with the patient.

The pivoting or swiveling of the elbow 125 relative to the ring 128 is limited by annular junction 127 between the partially spherical, outer surface 125(3) of the elbow 125 and the end portion of the elbow 125 (e.g., see FIG. 3-13). When the elbow 125 reaches this pivot or swivel point (e.g., annular junction 127 engages the edge 128(2) (see FIG. 3-13) of the ring 128), pulling forces are transferred to the decoupling gusset 158(1) which deforms or pivots as described above to allow further pivoting to permit decoupling of tube drag. The type of deformation for the decoupling gusset 158(1) is typically compressive on one circumferential side and stretching on the opposing circumferential side.

In an example, as shown in FIG. 3-115-1, a maximum angle a1 accommodated by the decoupling gusset 158(1) when the elbow 125 is tilted upwards relative to the cushion assembly 250 is about 9-10°, e.g., before deformation of the side wall region 157 of the cushion assembly 250 starts to occur.

In an example, as shown in FIG. 3-117-1, a maximum angle a2 accommodated by the decoupling gusset 158(*l*) during downwards tilting is about 13-15°, e.g., before deformation of the side wall region 157 of the cushion assembly 250 starts to occur.

Swivel

The swivel or cuff swivel 129 is provided to the lower end or base of the elbow 125 and connects to the air delivery tube assembly 130 e.g., short tube. As illustrated, the air delivery tube assembly 130 includes a tube 133 and a connector 135 adapted to receive swivel 129. As shown in FIG. 3-13, the swivel cuff 129 comprises a swivel cuff annular engaging ring 129(1) that is received in an annular groove 125(4) of the swivel elbow 125 so that the swivel cuff 129 is rotatable, or swivelable, with respect to the swivel elbow 125. The swivel cuff 129 allows for full 360° rotation in the Y-axis (see FIG. 3-118-3), which provides a decoupling structure to decouple the connection with the air delivery tube assembly 130.

Short Tube

In an example, as shown in FIGS. 3-119-1 and 3-119-2, the air delivery tube assembly 130 may be in the form of a short tube arranged to interconnect the patient interface with tubing communicated with the PAP device.

As shown in FIGS. 3-120-1 to 3-120-6, the short tube includes tube 133, end cuff or connector 135 provided to one end of the tube 133 and adapted to receive swivel 129, and end cuff or connector 137 provided to the opposite end of the tube 133 and adapted to receive swivel 136. The swivel 136 is adapted to engage the tubing communicated with the PAP device 4000.

The tube 133 is in the form of a helical tube which generates torque when the short tube is moved from its neutral state or original, retracted position (FIG. 3-119-1) to an extended position (FIG. 3-119-2). The tube 133 has a helical coil comprised of a plurality of adjacent coils each separated by a width and has an outer surface defining a coil diameter. The tube 133 also has a web of material coaxial to the helical coil that is attached, e.g., integrally bonded, to the helical coil. The helical coil and web of material may be made from a thermoplastic material such as TPE or TPU.

The end cuffs 135, 137 are overmolded to respective ends of the tube 133. The end cuffs 135, 137 are permanently connected to the tube 133. On the inner circumferential surface of the end cuffs 135, 137 are circular ridges to matingly receive and form a rotational relationship with components such as the elbow 125 and cuff connector 6720.

In the example shown in FIG. 3-120-5, the swivel cuff 129 is in the form of a swivel cuff annular engaging ring that is received in an annular groove or channel 125(4) provided to the end of elbow 125 to provide a rotatable connection with the elbow 125. The swivel cuff annular engaging ring 129 includes an annular groove or channel 129(2) along an outer circumferential surface to matingly receive the circular ridge 135(1) of the end cuff 135, e.g., snap-fit connection. The end cuff 135 is removably detachable from the swivel cuff annular engaging ring 129.

As shown in FIG. 3-120-6, the swivel 136 is provided to a tube connector 138 structured to connect the swivel 136 to the end cuff 137 of the tube 133. As illustrated, one end of the tube connector 138 includes an annular groove or channel 138(1) along an outer circumferential surface to matingly receive the circular ridge 137(1) of the end cuff 137, e.g., snap-fit connection. The end cuff 137 is removably detachable from the tube connector 138. The opposite end of the tube connector 138 rotatably supports the swivel 136 to allow the swivel to rotate 360° with respect to the tube connector 138. The opposite end may include an outwardly tapered edge 138(2) to retain the swivel 136 to the tube connector 138.

As shown in FIGS. 3-120-1 to 3-120-4, the exterior surface of the tube connector 138 may include finger grips 139 to facilitate manual attachment and detachment of the tube connector 138 and swivel 136 thereof to and from the tube 133 as well as tubing communicated with the PAP device 4000. As illustrated, such finger grip 139 may be a generally U-shaped protrusion provided on opposing sides of the tube connector 138. In example, raised branding and/or raised features may be provided within each U-shaped protrusion to assist in providing grip to the tube connector 138.

The swivel 129 provided to the elbow 125, as well as the swivel 136 provided to the end of the tube 133, are able to rotate up to 180° or more in order to absorb or redirect such torque such that it has little to no effect on the cushion assembly 250. In an example, the swivel 129 may rotate about 30° with minimal extension of the short tube 133, about 120° with intermediate extension of the short tube 133, and about 180° or more with full extension of the short tube. Both ends of the tube 133 are able to rotate 360° by virtue of the proximal swivel 129 and distal swivel 136. Elongation of the tube 133 causes the helical coil of the tube 133 to twist. This tendency to twist is fully absorbed by both swivels 129, 136 and the tube 133 is easily and freely rotatable relative to the swivels 129, 136 without noticeable frictional resistance when the tube 133 is elongated from its neutral state (see direction arrow on FIG. 3-119-1). Therefore, elongation of the tube 133 does not transmit tube torque forces to components connected downstream from the tube 133 such as the elbow 125, seal-forming structure 3100 or a plenum chamber 3200. Specifically, elongating the tube 133 in a direction parallel to the longitudinal axis of the tube 133 does not result in immediate rotation (and preferably, little to no rotation) of the elbow 125, which would typically be in the clockwise or anti-clockwise direction corresponding to the chirality (left or right handedness) of the helical coil of the tube 133.

In a typical scenario, a patient may don the patient interface 3000 and be sitting up prior to sleeping. The PAP device 4000 may be positioned on a bed side table next to the bed that the patient is seated on. Due to gravity, the tube 133 tends to elongate and the elbow 125 rotates to a downward position such that the first opening 125(1) of the elbow 125 faces the ground. The swivels 129, 136 decouple the rotation of the tube 133 when elongation occurs. When the patient falls asleep on their back or on their side facing away from the PAP device 4000, the ball and socket joint of the elbow 125 and swivels 129, 136 decouple tube drag forces. The angle of the elbow 125 is particularly suited in positions where the longitudinal axis of the tube 133 is perpendicular to the Frankfort horizontal direction. In a small proportion of the time, if the patient is sleeping on their side and faces the PAP device 4000, the elbow 125 is tilted up due to the tube 133 aligning and positioning itself to be co-linear with the opening end of the attachment region 158. When the elbow 125 has exceeded its maximum tilting range, the decoupling gusset 158(1) deforms to absorb the tube drag forces before the side wall region 157 of the cushion assembly 150 starts to deform and destabilise from the tube drag forces. A patient interface 3000 having a non-elbowed component (straight component) with a ball and socket joint is unlikely to experience tube drag forces when the patient is sleeping on their side facing the PAP device 4000, however would experience tube drag forces in every other position. Therefore, an elbow 125 with a ball and socket joint is preferable for the majority of the time and majority of positions that the patient is in when they are receiving therapy instead of a non-elbowed component with ball and socket joint.

The decoupling system generally includes the ball and socket elbow 125, decoupling gusset 158(1) and tube 133 with dual swivel connections. In the embodiment where there is headgear assembly 110 with two-point connection to the cushion assembly 250 providing only two sealing vectors, the decoupling system is capable of minimising the impact of tube drag forces affecting stability without over-tightening of the headgear tension. In other words, any loss of stability caused by the type of headgear used is at least partially compensated by the decoupling system. This widens the range of headgear that could be used with the patient interface 3000 including unobtrusive headgear (with very little surface contact with the patient's face) without requiring a high and possibly uncomfortable level of headgear tension to maintain a seal.

PAP Device 4000

A PAP device 4000 in accordance with one aspect of the present technology comprises mechanical and pneumatic components, electrical components and is programmed to execute one or more algorithms. In an example, PAP device has an external housing, e.g., formed in two parts, an upper portion 4012 of the external housing, and a lower portion 4014 of the external housing. In alternative forms, the external housing may include one or more panel(s) 4015. In an example, the PAP device 4000 comprises a chassis 4016 that supports one or more internal components of the PAP device 4000. In one form a pneumatic block is supported by, or formed as part of the chassis 4016. The PAP device 4000 may include a handle 4018.

In an example, pneumatic path of the PAP device 4000 comprises an inlet air filter 4112, an inlet muffler, a controllable source of air at positive pressure (e.g., a blower 4142), and an outlet muffler. One or more pressure sensors and flow sensors are included in the pneumatic path.

In an example, pneumatic block comprises a portion of the pneumatic path that is located within the external housing.

In an example, the PAP device 4000 has an electrical power supply 4210, one or more input devices 4220, a processor, a pressure device controller, one or more protection circuits, memory, transducers, data communication interface and one or more output devices. Electrical components may be mounted on a single Printed Circuit Board Assembly (PCBA) 4202. In an alternative form, the PAP device 4000 may include more than one PCBA 4202.

The processor of the PAP device 4000 is programmed to execute a series of algorithm modules in use, e.g., including pre-processing transducer signals module, a therapy engine module, a pressure control module, and further e.g., a fault condition module.

5.3 Glossary

In certain forms of the present technology, one or more of the following definitions may apply. In other forms of the present technology, alternative definitions may apply.

5.3.1 General

Air: Air will be taken to include breathable gases, for example air with supplemental oxygen.

Positive Airway Pressure (PAP): PAP treatment will be taken to mean the application of a supply of air or breathable gas to the entrance to the airways at a pressure that is positive with respect to atmosphere. In one form, the pressure will be continuously positive (CPAP) and e.g., approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms the pressure will be a number of centimeters, e.g. about 5-15 cm of water pressure higher during inhalation than exhalation, and provide ventilatory support. In some forms, the pressure will vary between different respiratory cycles of the patient, for example being increased in response to detection of indications of partial upper airway obstruction, and decreased in the absence of indications of partial upper airway obstruction.

5.3.2 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises e.g. the nasal bones, the frontal process of the maxillae and the nasal part of the frontal bone.

(nose) Cartilaginous framework: The cartilaginous framework of the nose comprises, e.g., the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the nails. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.3.3 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.3.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.3.5 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

5.3.6 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow or air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. In an example, the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane, e.g., in the context of a sealing portion and/or face-contacting portion, will be taken to mean a typically thin element that has, e.g., substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: In an example, a shell will be taken to mean a curved structure having bending, tensile and compressive stiffness, for example, a portion of a mask that forms a curved structural wall of the mask. In an example, compared to its overall dimensions it is relatively thin. In some forms, a shell may be faceted. In an example, such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, e.g., independently, e.g., under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components, e.g., comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

5.3.7 Terms Used in Relation to Patient Interface

Floppy: A quality of a material, structure or composite that is the combination of features of:

Readily conforming to finger pressure.

Unable to retain its shape when caused to support its own weight.

Not rigid.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

5.4 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used or as being an example to construct a component, obvious alternative materials with similar properties may be used as a substitute.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

6 REFERENCE SIGNS LIST 100 mask system
110 headgear assembly
114 respective slot
115 side straps
116 cushion connector
117 adjustment portion
118 rear strap
120 elbow assembly
125 elbow
125(1) first opening
125(2) second opening
125(2)(e) edge
125(3) partially spherical, outer surface
125(4) annular groove
127 annular junction
128 connector ring
128(1) first raised edge
128(2) second raised edge
128(3) channel
128(4) curved inner circumferential surface
129 swivel cuff
129(1) annular engaging ring
129(2) channel portion
130 air delivery tube assembly
133 tube
135 connector
136 distal swivel
150 cushion assembly
151 sealing region
152 nose ridge region
153 sides of the nose region
154 corners of the nose region
155 top lip region
156 headgear connectors
157 side wall region
158 attachment region
158(1) decoupling gusset
158(2) lip portion
159 lug or interface
160 membrane
165 undercushion or backup band
250 cushion assembly
251 sealing region
252 nose ridge region
253 sides of the nose region
254 corners of nose region
255 top lip region
256 headgear connector
257 side wall region
258 attachment region
260 membrane
260-1 bead
265 undercushion
268 thinner cross-section area
270 sealing flap
275 orifice
275(1) upper orifice portion
275(2) lower orifice portion
280 width or contact area
280(i) inner edge
280(o) outer edge
350 cushion assembly 356 headgear connector
356(1) thinner wall section
360 membrane
450 cushion assembly
456 headgear connector
456(1) thinner wall section
457 side wall region
457(1) wall sections
460 membrane
465 undercushion
605 cushion
610 swivel elbow and connector assembly
620 connector ring
621 vents
622 inner flange
623 outer flange
624 channel
625 vent slots
630 sleeve
631 sleeve flange
632 annular surface
633 cylindrical portion
640 swivel elbow
641 flange
642 tapered flange
643 annular groove
644 tapered flange
650 swivel cuff
651 swivel cuff annular engaging ring
652 annular groove
653 end portion
660 swivel elbow and connector assembly
670 elbow ring
671 vent slots
672 annular surface
673 inner flange
674 outer flange
675 channel
676 inner surface
680 ball joint swivel elbow
681 annular surface
682 arcuate annular outer surface
683 annular groove
684 tapered flange
685 annular junction
690 swivel cuff
691 tapered annular engaging ring
692 angled groove
693 swivel cuff end portion
694 tapered flange
695 annular groove
1000 patient
3000 patient interface
3100 seal forming structure
3102 superior sealing portion
3104 inferior sealing portion
3110 sealing flange
3120 support flange
3200 plenum chamber
3210 perimeter
3220 marginal edge
3300 positioning and stabilising structure
3400 vent
3500 decoupling structure
3510 swivel
3520 ball and socket
3600 connection port
4000 pap device
4012 upper portion
4014 lower portion
4016 chassis
4018 handle
4112 inlet air filter
4142 blower
4170 air circuit
4202 pcba
4210 electrical power supply
4220 input devices
5000 humidifier
5550 elbow
6100 second swivel cuff
6101 tapered annular engaging ring
6102 annular groove
6103 end portion
6120 swivel elbow and connector assembly
6130 cushion
6132 connectors
6133 flexible base
6140 swivel elbow
6141 angled flange
6142 tapered flange
6143 first end
6144 baffle
6145 vents
6146 radial flange
6147 venting portions
6150 ring
6152 inner flange
6153 outer flange
6154 channel
6155 circular radial flange
6157 reinforced portion
6159 lower portion
6200 skeleton portion
6210 first aperture
6220 second aperture
6230 vent holes
6235 surface
6240 engagement tabs
6245 first connection region
6250 second connection region
6255 stop
6260 baffle
6270 second supports
6280 gap or relief
6290 first supports
6300 elbow assembly
6310 valve member
6315 lip
6320 engagement portions
6330 flexible member
6335 second component
6400 patient interface system
6410 swivel elbow
6411 vents
6420 swivel
6421 detents
6430 cushion
6431 tabs
6440 bayonet type connection
6450 patient interface system
6454 stem
6460 swivel elbow
6461 vents 6462 flexible buttons
6463 grooves
6470 swivel
6480 ring
6490 cushion
6500 patient interface system
6510 swivel elbow
6511 slots
6512 buttons
6513 grooves
6514 baffle
6520 swivel
6530 cushion
6550 elbow
6551 slots
6552 aperture
6554 baffle
6555 aav flap
6560 elbow and tube connector assembly
6570 elbow
6571 lip or flexible element
6580 tube connector
6582 ridges
6590 tubes
6600 tube and elbow connector assembly
6610 swivel elbow
6620 swivel
6630 tube connector
6650 tube and elbow connector assembly
6660 elbow
6670 second swivel component
6680 first swivel component
6690 cuff
6710 cuff
6720 cuff connector
6730 cuff
6800 elbow
6805 skeleton
6810 aav
6810.1 outer flange
6810.2 outer surface
6812 flap
6815 opening
6820 pull tab
6825 inner flange
6830 inner wall
6832 flexible component
6835 release buttons
6950 sealing portion
6952 nose tip engagement portion
6953 supporting portion
6954 stem
6955 aperture
6962 upper lip engagement portion
6965 flexible gusset

What is claimed is:

1. A patient interface configured to deliver a flow of air at a positive pressure with respect to ambient air pressure to an entrance to a patient's airways including at least the entrance of a patient's nares while a patient is sleeping, to ameliorate sleep disordered breathing, the patient interface comprising:
a retractable tube for delivering the flow of air to the patient interface from a flow generator, the retractable tube being stretchable from a neutral retracted position to an extended position during which stretching the tube has a tendency to rotate, resulting in rotational movement of the retractable tube when the retractable tube is stretched;
a cushion assembly comprising:
a seal-forming structure including a sealing flange constructed and arranged to form a seal with a region of a patient's face surrounding the entrance to the patient's airways,
wherein the seal-forming structure further includes a support flange constructed and arranged to support the sealing flange, and
wherein the support flange includes a cross-sectional thickness that is thicker than a cross-sectional thickness of the sealing flange; and
a plenum chamber pressurizable to a therapeutic pressure above ambient air pressure, the support flange being provided inside the plenum chamber,
wherein the plenum chamber includes an attachment region configured to fluidly couple to the retractable tube,
wherein the plenum chamber further includes a side wall region extending between the seal-forming structure and the attachment region,
wherein the side wall region includes a cross-sectional thickness that is thicker than the cross-sectional thickness of the sealing flange,
wherein the attachment region includes a lip portion structured and arranged to assist with retention of the retractable tube,
wherein the lip portion includes a cross-sectional thickness that is thicker than the cross-sectional thickness of the side wall region,
wherein the attachment region further includes a decoupling fold structured and arranged to allow the attachment region to move relative to the side wall region to permit decoupling from tube drag applied by the retractable tube,
wherein the decoupling fold includes a cross-sectional thickness that is thinner than the cross-sectional thickness of the support flange, the decoupling fold having a first part attached to the attachment region and a second part attached to the side wall, the second part having a diameter that is larger than a diameter of the first part,
wherein the seal-forming structure and the plenum chamber comprise a one piece molded construction,
wherein the seal-forming structure and the plenum chamber comprise an elastomeric material,
wherein the plenum chamber further comprises a pair of headgear connectors structured and arranged to provide a direct two-point connection to headgear, each of the pair of headgear connectors disposed on a respective side of the side wall region and formed as part of the one piece molded construction, and
wherein each of the pair of headgear connectors includes a thinner wall section to enhance flexibility and bending relative to the side wall region;
a swivel elbow and connector assembly comprising:
a ring configured to be sealingly secured by the lip portion of the attachment region of the cushion assembly, the ring having a partially spherical inner surface; and
a swivel elbow in fluid communication with the seal-forming structure, the swivel elbow configured to rotatably engage the ring to allow a rotational engagement in a plurality of axes, the swivel elbow comprising a partially spherical outer surface circumferentially surrounding an outer portion of the swivel elbow;

the partially spherical outer surface configured to sealingly engage with the partially spherical inner surface to form a ball and socket joint to allow the rotational engagement, the ball and socket joint configured to prevent any intentional gas venting between the swivel elbow and ring when the swivel elbow rotates in the plurality of axes; and a decoupling system for decoupling tube drag forces when the retractable tube is stretched and moved relative to the cushion assembly, the decoupling system including:

a first decoupling component to decouple the rotational movement of the retractable tube when the retractable tube is stretched from the neutral retracted position to the extended position, the first decoupling component comprising a first swivel cuff and a second swivel cuff provided to each respective end of the retractable tube;

a second decoupling component to decouple movement of the retractable tube relative to the cushion assembly, the second decoupling component comprising said swivel elbow and connector assembly provided to the cushion assembly; and a third decoupling component to decouple movement of the retractable tube relative to the cushion assembly, the third decoupling component comprising the decoupling fold, wherein the seal-forming structure includes a nose ridge region, side of nose regions, corner of nose regions, and a top lip region, and wherein the support flange is only provided in the top lip region and the corner of the nose regions.

2. The patient interface according to claim 1, wherein the ring comprises a first side adapted to be located in the plenum chamber of the cushion assembly and a second side adapted to be located exterior to the plenum chamber of the cushion assembly when the ring is secured by the lip portion.

3. The patient interface according to claim 2, wherein the ring comprises a first flange on the first side and a second flange on the second side, the first and second flanges defining a channel that sealingly engages to the attachment region of the cushion assembly when the ring is secured by the lip portion.

4. The patient interface according to claim 3, wherein the ring terminates at an edge of the second flange.

5. The patient interface of claim 1, further comprising a swivel cuff annular engaging ring that is received in an annular groove of the swivel elbow, the swivel cuff annular engaging ring configured to be in rotatable engagement with the retractable tube for delivering the flow of air to the patient interface.

6. The patient interface according to claim 5, wherein the swivel cuff annular engaging ring is rotatably connected to the swivel elbow.

7. The patient interface according to claim 5, wherein the swivel cuff annular engaging ring has a channel portion defined on an outer circumferential surface to matingly receive a first swivel cuff provided to the retractable tube.

8. The patient interface according to claim 7, wherein the retractable tube includes a first end connected to the first swivel cuff.

9. The patient interface according to claim 8, wherein the retractable tube comprises a second end connected to the second swivel cuff, the second swivel cuff configured to swivelably and releasably connect to a second component.

10. The patient interface according to claim 9, wherein the second swivel cuff includes an annular engaging ring defined on an inner surface of the second swivel cuff configured to be matingly received within an annular groove of the second component.

11. The patient interface according to claim 9, wherein the second component is a cuff connector for connecting to another tube.

12. The patient interface according to claim 9, wherein the retractable tube is freely rotatable relative to the swivel elbow and connector assembly and freely rotatable relative to the second component when the retractable tube is stretched, and rotational force from stretching of the retractable tube is contained between the first and second swivel cuffs.

13. The patient interface according to claim 1, wherein an annular surface provided by an edge of the swivel elbow is flush with an annular surface provided by an edge of the ring when longitudinal axes of the swivel elbow and the ring are co-linear.

14. The patient interface according to claim 1, wherein the swivel elbow comprises an annular junction configured to limit swiveling of the swivel elbow by engaging a second annular surface of the ring.

15. The patient interface according to claim 1, further comprising a vent having a plurality of holes configured to permit flow of gases from an interior to an exterior of the patient interface.

16. The patient interface according to claim 15, wherein the vent is positioned on the swivel elbow.

17. The patient interface according to claim 1, wherein the decoupling fold includes an inwardly extending fold.

18. The patient interface according to claim 1, wherein the cross-sectional thickness of the sealing flange is less than about 1 mm.

19. The patient interface according to claim 1, wherein the cross-sectional thickness of the side wall region is about 1.5-2 mm.

20. The patient interface according to claim 1, wherein the cross-sectional thickness of the lip portion is about 2-3 mm.

21. The patient interface according to claim 1, wherein the cross-sectional thickness of the decoupling fold is about 0.1-1 mm.

22. The patient interface according to claim 1, wherein the cross-sectional thickness of the decoupling fold is thinner than the cross-sectional thickness of the side wall region.

23. The patient interface according to claim 1, wherein the side wall region provides flexibility to assist decoupling from tube drag.

24. The patient interface according to claim 1, wherein one or more wall sections of the side wall region between the pair of headgear connectors is thickened to prevent collapse of the side wall region under headgear tension.

25. The patient interface according to claim 1, wherein the swivel elbow and connector assembly further comprises a swivel cuff rotatably engaged with the swivel elbow, and the swivel cuff is rotatable through an angle relative to the swivel elbow and into at least one position in which the swivel cuff and the swivel elbow provide a straight or horizontal flow path.

* * * * *